US011352432B2

(12) United States Patent
Fischer et al.

(10) Patent No.: US 11,352,432 B2
(45) Date of Patent: Jun. 7, 2022

(54) ANTIBODIES SPECIFICALLY BINDING TO HUMAN IL-1R7

(71) Applicant: MAB DISCOVERY GMBH, Neuried (DE)

(72) Inventors: Stephan Fischer, Weilheim (DE); Karsten Beckmann, Vaterstetten (DE)

(73) Assignee: MAB DISCOVERY GMBH, Neuried (DE)

( * ) Notice: Subject to any disclaimer, the term of this patent is extended or adjusted under 35 U.S.C. 154(b) by 0 days.

(21) Appl. No.: 16/492,381

(22) PCT Filed: Mar. 9, 2018

(86) PCT No.: PCT/EP2018/055934
§ 371 (c)(1),
(2) Date: Sep. 9, 2019

(87) PCT Pub. No.: WO2018/162724
PCT Pub. Date: Sep. 13, 2018

(65) Prior Publication Data
US 2021/0130478 A1 May 6, 2021

(30) Foreign Application Priority Data
Mar. 9, 2017 (EP) .................................... 17160191

(51) Int. Cl.
*C07K 16/28* (2006.01)
*A61K 39/00* (2006.01)

(52) U.S. Cl.
CPC .... *C07K 16/2866* (2013.01); *A61K 2039/505* (2013.01); *C07K 2317/24* (2013.01); *C07K 2317/565* (2013.01); *C07K 2317/71* (2013.01)

(58) Field of Classification Search
None
See application file for complete search history.

(56) References Cited

FOREIGN PATENT DOCUMENTS

| | | | |
|---|---|---|---|
| EP | 3241845 | A1 | 11/2017 |
| WO | 2007117577 | A2 | 10/2007 |
| WO | 2017/191325 | A1 | 11/2017 |
| WO | 2018/206565 | A1 | 11/2018 |
| WO | 2018/206565 | A9 | 11/2018 |

OTHER PUBLICATIONS

Data sheet for antibodies MAB 118 and MAB 1181 from R&D Systems. Accessed 2021 (Year: 2021).*
Communication Pursuant to Article 94(3) EPC, issued for Application No. 18711275.0, dated Oct. 8, 2020.
International Search Report and Written Opinion in PCT/EP2018/055934, dated Jul. 19, 2018. 15 pages.
Satoko, Takei et al. "Soluble interluekin-18 receptor complex is a novel biomarker in rheumatoid arthritis". Arthritis Research and Therapy, Biomed Central, London, GB. vol. 13, No. 2, Mar. 24, 2011. XP21097573.
C. Wu et al: 11 IL-I8 Receptor-Induced Changes in the Presentation of IL-18 Binding Sites Affect Ligand Binding and Signal Transduction 11. The Journal of Immunology, vol. 170, No. 11, Jun. 1, 2003 (Jun. 1, 2003). pp. 5571-5577, XP55473567.
Hamasaki T et al: 11 Human Anti-Human IL-18 Antibody Recognizing the IL-18-Binding Site 3 with IL-18 Signaling Blocking Activity 11. Journal of Biochemistry, Oxford University Press, GB, vol. 138, No. 4, Jan. 1, 2005 (Jan. 1, 2005), pp. 433-442, XP002998456, ISSN: 0021-924X, DOI: 10.1093/JB/MVI148 p. 434.
Wei Hui et al: 11 Structural basis for the specific recognition of IL-18 by its alpha receptor 11. FEBS Letters, Elsevier, Amsterdam, NL, vol. 588, No. 21, Sep. 26, 2014 (Sep. 26, 2014), pp. 3838-3843, XP029081288, ISSN: 0014-5793, DOI: 10.1016/J.FEBSLET.2014.09.019 p. 3841.
Maria A. Argiriadi et al: 11 Unusual Water-mediated Antigenic Recognition of the Proinflammatory Cytokine Interleukin-18 11. Journal of Biological Chemistry,vol. 284, No. 36, Jun. 24, 2009 (Jun. 24, 2009), pp. 24478-24489, XP55473580.
Debets et al.; IL-18 Receptors, Their Role in Ligand Binding and Function: Anti-IL-1RAcPL Antibody, a Potent Antagonist of IL-18; J Immunol 2000; 165:4950-4956; 8 pages.
Office Action issued in JP Application No. 548412/2019; dated Nov. 2, 2021; 9 pages.

* cited by examiner

*Primary Examiner* — Elly-Gerald Stoica
(74) *Attorney, Agent, or Firm* — Meunier Carlin & Curfman LLC

(57) ABSTRACT

The present invention relates to monoclonal antibodies that specifically bind to human IL-1 R7, or a fragment or derivative thereof or a polypeptide that contain at least a portion of said antibody that is sufficient to confer specific IL-1 R7 binding to the polypeptide. The invention also relates to the use of said antibodies in the treatment of a IL-18 mediated disease and pharmaceutical compositions comprising a pharmaceutically acceptable carrier and a therapeutically effective amount of the antibody according to the invention.

15 Claims, 74 Drawing Sheets

Specification includes a Sequence Listing.

Fig.1: IL-18 functional assay

| Antibody comprising SEQ ID NO. | % Inhibition |
|---|---|
| | |
| 1 | 51 |
| 2 | 31 |
| 3 | 47 |
| 4 | 61 |
| 5 | 38 |
| 6 | 53 |
| 7 | 38 |
| 8 | 56 |
| 9 | 67 |
| 10 | 40 |
| 11 | 40 |
| 12 | 35 |
| 13 | 83 |
| 14 | 81 |
| 15 | 81 |
| 16 | 80 |
| 17 | 76 |
| 18 | 73 |
| 19 | 69 |
| 20 | 69 |
| 21 | 68 |
| 22 | 66 |
| 23 | 66 |
| 24 | 66 |
| 25 | 65 |
| 26 | 65 |
| 27 | 64 |
| 28 | 64 |
| 29 | 64 |
| 30 | 63 |
| 31 | 63 |
| 32 | 62 |
| 33 | 61 |
| 34 | 61 |
| 35 | 61 |
| 36 | 60 |

| | |
|---|---|
| 37 | 59 |
| 38 | 59 |
| 39 | 58 |
| 40 | 58 |
| 41 | 58 |
| 42 | 58 |
| 43 | 58 |
| 44 | 58 |
| 45 | 58 |
| 46 | 58 |
| 47 | 57 |
| 48 | 57 |
| 49 | 57 |
| 50 | 56 |
| 51 | 56 |
| 52 | 56 |
| 53 | 55 |
| 54 | 55 |
| 55 | 54 |
| 56 | 53 |
| 57 | 53 |
| 58 | 53 |
| 59 | 53 |
| 60 | 53 |
| 61 | 53 |
| 62 | 52 |
| 63 | 52 |
| 64 | 52 |
| 65 | 52 |
| 66 | 52 |
| 67 | 52 |
| 68 | 52 |
| 69 | 52 |
| 70 | 52 |
| 71 | 51 |
| 72 | 51 |
| 73 | 51 |
| 74 | 51 |
| 75 | 51 |
| 76 | 50 |
| 77 | 50 |
| 78 | 50 |
| 79 | 49 |

Fig. 1 continued

| | |
|---|---|
| 80 | 49 |
| 81 | 49 |
| 82 | 49 |
| 83 | 49 |
| 84 | 48 |
| 85 | 48 |
| 86 | 48 |
| 87 | 48 |
| 88 | 48 |
| 89 | 47 |
| 90 | 47 |
| 91 | 47 |
| 92 | 47 |
| 93 | 46 |
| 94 | 46 |
| 95 | 46 |
| 96 | 46 |
| 97 | 46 |
| 98 | 45 |
| 99 | 44 |
| 100 | 44 |
| 101 | 44 |
| 102 | 44 |
| 103 | 44 |
| 104 | 44 |
| 105 | 43 |
| 106 | 43 |
| 107 | 43 |
| 108 | 43 |
| 109 | 42 |
| 110 | 42 |
| 111 | 41 |
| 112 | 40 |
| 113 | 40 |
| 114 | 40 |
| 115 | 40 |
| 116 | 40 |
| 117 | 40 |
| 118 | 40 |
| 119 | 39 |
| 120 | 39 |
| 121 | 39 |
| 122 | 39 |

Fig. 1 continued

| | |
|---|---|
| 123 | 38 |
| 124 | 38 |
| 125 | 38 |
| 126 | 38 |
| 127 | 38 |
| 128 | 37 |
| 129 | 37 |
| 130 | 37 |
| 131 | 37 |
| 132 | 37 |
| 133 | 37 |
| 134 | 37 |
| 135 | 37 |
| 136 | 36 |
| 137 | 36 |
| 138 | 36 |
| 139 | 36 |
| 140 | 36 |
| 141 | 36 |
| 142 | 36 |
| 143 | 36 |
| 144 | 35 |
| 145 | 35 |
| 146 | 35 |
| 147 | 35 |
| 148 | 35 |

Fig. 1 continued

Fig. 2: Human IL-1R7 cell binding assay (ELISA)

| Antibody comprising SEQ ID NO. | huIL-1R7 cell binding [RFU] |
|---|---|
| | |
| 1 | 12.903 |
| 2 | 14.648 |
| 3 | 17.510 |
| 4 | 18.504 |
| 5 | 19.829 |
| 6 | 20.251 |
| 7 | 24.765 |
| 8 | 25.976 |
| 9 | 26.476 |
| 10 | 47.924 |
| 11 | 48.160 |
| 12 | 58.449 |
| 13 | 67.915 |
| 14 | 50.759 |
| 15 | 56.624 |
| 16 | 29.914 |
| 17 | 71.403 |
| 18 | 56.507 |
| 19 | 57.687 |
| 20 | 31.360 |
| 21 | 38.962 |
| 22 | 51.505 |
| 23 | 50.686 |
| 24 | 64.195 |
| 25 | 36.555 |
| 26 | 38.634 |
| 27 | 60.801 |
| 28 | 44.941 |
| 29 | 69.938 |
| 30 | 42.692 |
| 31 | 38.023 |
| 32 | 65.085 |
| 33 | 17.107 |
| 34 | 59.030 |
| 35 | 28.709 |
| 36 | 27.354 |
| 37 | 23.011 |
| 38 | 37.396 |

| | |
|---|---|
| 39 | 30.918 |
| 40 | 28.485 |
| 41 | 47.104 |
| 42 | 16.341 |
| 43 | 30.161 |
| 44 | 42.632 |
| 45 | 26.640 |
| 46 | 47.293 |
| 47 | 49.083 |
| 48 | 20.434 |
| 49 | 50.424 |
| 50 | 22.059 |
| 51 | 31.851 |
| 52 | 19.848 |
| 53 | 79.715 |
| 54 | 96.595 |
| 55 | 20.187 |
| 56 | 44.484 |
| 57 | 43.264 |
| 58 | 36.995 |
| 59 | 24.391 |
| 60 | 48.323 |
| 61 | 59.157 |
| 62 | 46.023 |
| 63 | 29.570 |
| 64 | 38.390 |
| 65 | 42.332 |
| 66 | 35.234 |
| 67 | 55.576 |
| 68 | 65.166 |
| 69 | 11.984 |
| 70 | 19.718 |
| 71 | 33.511 |
| 72 | 39.729 |
| 73 | 64.593 |
| 74 | 38.242 |
| 75 | 83.116 |
| 76 | 23.463 |
| 77 | 67.049 |
| 78 | 14.660 |
| 79 | 53.431 |
| 80 | 41.557 |
| 81 | 11.804 |

Fig. 2 continued

| | |
|---|---|
| 82 | 29.560 |
| 83 | 33.940 |
| 84 | 21.988 |
| 85 | 59.234 |
| 86 | 19.746 |
| 87 | 49.949 |
| 88 | 76.365 |
| 89 | 45.822 |
| 90 | 35.079 |
| 91 | 25.967 |
| 92 | 29.207 |
| 93 | 52.651 |
| 94 | 15.504 |
| 95 | 54.093 |
| 96 | 66.847 |
| 97 | 26.006 |
| 98 | 22.957 |
| 99 | 62.325 |
| 100 | 31.282 |
| 101 | 17.960 |
| 102 | 86.461 |
| 103 | 32.510 |
| 104 | 40.902 |
| 105 | 41.297 |
| 106 | 83.735 |
| 107 | 44.685 |
| 108 | 39.988 |
| 109 | 46.222 |
| 110 | 26.031 |
| 111 | 41.050 |
| 112 | 106.377 |
| 113 | 25.496 |
| 114 | 21.527 |
| 115 | 23.000 |
| 116 | 16.328 |
| 117 | 21.861 |
| 118 | 81.681 |
| 119 | 117.009 |
| 120 | 50.871 |
| 121 | 24.927 |
| 122 | 19.215 |
| 123 | 50.495 |
| 124 | 53.319 |

Fig. 2 continued

| | |
|---|---|
| 125 | 59.346 |
| 126 | 68.256 |
| 127 | 42.916 |
| 128 | 37.228 |
| 129 | 31.738 |
| 130 | 47.299 |
| 131 | 51.247 |
| 132 | 42.927 |
| 133 | 47.112 |
| 134 | 18.015 |
| 135 | 31.848 |
| 136 | 32.341 |
| 137 | 19.839 |
| 138 | 24.275 |
| 139 | 29.812 |
| 140 | 52.968 |
| 141 | 55.354 |
| 142 | 43.919 |
| 143 | 22.693 |
| 144 | 28.274 |
| 145 | 60.346 |
| 146 | 41.318 |
| 147 | 41.482 |
| 148 | 64.473 |

Fig. 2 continued

Fig. 3: Human IL-1R5 cell binding assay (ELISA)

| Antibody comprising SEQ ID NO. | huIL-1R5 cell binding [RFU] |
|---|---|
| | |
| 1 | 104 |
| 2 | 16 |
| 3 | 56 |
| 4 | 56 |
| 5 | 23 |
| 6 | 461 |
| 7 | 2 |
| 8 | 30 |
| 9 | 105 |
| 10 | 13 |
| 11 | 151 |
| 12 | 405 |
| 13 | 1 |
| 14 | 6 |
| 15 | 90 |
| 16 | 114 |
| 17 | 1 |
| 18 | 3 |
| 19 | 36 |
| 20 | 87 |
| 21 | 19 |
| 22 | 110 |
| 23 | 2 |
| 24 | 12 |
| 25 | 17 |
| 26 | 369 |
| 27 | 9 |
| 28 | 319 |
| 29 | 143 |
| 30 | 5 |
| 31 | 58 |
| 32 | 24 |
| 33 | 26 |
| 34 | 54 |
| 35 | 85 |
| 36 | 20 |
| 37 | 173 |
| 38 | 6 |

| | |
|---|---|
| 39 | 10 |
| 40 | 16 |
| 41 | 11 |
| 42 | 13 |
| 43 | 153 |
| 44 | 65 |
| 45 | 8 |
| 46 | 77 |
| 47 | 32 |
| 48 | 293 |
| 49 | 149 |
| 50 | 41 |
| 51 | 7 |
| 52 | 12 |
| 53 | 4 |
| 54 | 88 |
| 55 | 14 |
| 56 | 57 |
| 57 | 14 |
| 58 | 12 |
| 59 | 28 |
| 60 | 34 |
| 61 | 48 |
| 62 | 101 |
| 63 | 8 |
| 64 | 26 |
| 65 | 17 |
| 66 | 106 |
| 67 | 153 |
| 68 | 129 |
| 69 | 700 |
| 70 | 0 |
| 71 | 22 |
| 72 | 16 |
| 73 | 248 |
| 74 | 46 |
| 75 | 28 |
| 76 | 36 |
| 77 | 69 |
| 78 | 700 |
| 79 | 10 |
| 80 | 12 |
| 81 | 41 |

Fig. 3 continued

| | |
|---|---|
| 82 | 90 |
| 83 | 9 |
| 84 | 12 |
| 85 | 22 |
| 86 | 19 |
| 87 | 118 |
| 88 | 31 |
| 89 | 7 |
| 90 | 10 |
| 91 | 51 |
| 92 | 4 |
| 93 | 2 |
| 94 | 47 |
| 95 | 50 |
| 96 | 9 |
| 97 | 27 |
| 98 | 24 |
| 99 | 5 |
| 100 | 135 |
| 101 | 43 |
| 102 | 17 |
| 103 | 3 |
| 104 | 0 |
| 105 | 17 |
| 106 | 63 |
| 107 | 11 |
| 108 | 9 |
| 109 | 40 |
| 110 | 12 |
| 111 | 130 |
| 112 | 23 |
| 113 | 94 |
| 114 | 67 |
| 115 | 43 |
| 116 | 27 |
| 117 | 27 |
| 118 | 36 |
| 119 | 10 |
| 120 | 4 |
| 121 | 16 |
| 122 | 16 |
| 123 | 6 |
| 124 | 34 |

Fig. 3 continued

| | |
|---|---|
| 125 | 139 |
| 126 | 369 |
| 127 | 11 |
| 128 | 11 |
| 129 | 6 |
| 130 | 243 |
| 131 | 118 |
| 132 | 13 |
| 133 | 5 |
| 134 | 20 |
| 135 | 23 |
| 136 | 98 |
| 137 | 183 |
| 138 | 22 |
| 139 | 6 |
| 140 | 0 |
| 141 | 22 |
| 142 | 2 |
| 143 | 32 |
| 144 | 810 |
| 145 | 1 |
| 146 | 20 |
| 147 | 29 |
| 148 | 39 |

Fig. 3 continued

Fig. 4: Sequences (amino acids in one letter code)

| SEQ ID NO. | HC VR |
|---|---|
| 1 | QSLEESGGRLVTPGTPLTLTCTISGIDLSAYAINWVRQAPGKGLEWIGGIANNGPTYYANWAKGRFTISKISTTVDLKITSPTTEDTATYFCARFPPGTNGGTDYFNIWGPGTLVTVSL |
| 2 | QSVEESGGRLVTPGTPLTVTCTVSGFSLSGYDMNWVRQAPGKGLEWIGMIYPNSGTNYATWAKGRFTISKTPTTVALKITSPTTEDTATYFCARDSGWGAFDPWGPGTLVTISS |
| 3 | QSLEESGGRLVTPGTPLTLTCTVSGFSLSTYAISWVRQAPGKGLEWIGGISNSGTTYYASWAKGRFTISKISTTVDLKITSPTTEDTATYFCARFPPGSNSGTDYFNIWGPGTLVTVSL |
| 4 | QSLEESGGRLVTPGTPLTLTCTASGFSLSGLVVSWVRQAPGKGLEWIGVIGKSGNTYYASWAKGRFSISKTSSTTVDLKIASPTTEDTATYFCGRNISGSAVWGPGTLVTVSL |
| 5 | QSLEESGGDLVKPGASLTLTCTASGFSFSSSYYMCWVRQAPGKWLEWIACIYAGSSGSTYYASWAKGRFTVSKTSSTTVTLEMTSLTAADTATYFCARDLGAGYAGYGYASDFNLWGPGTLVTVSS |
| 6 | QSLEESGGRLVTPGTPLTLTCTVSGFSLSIYAISWVRQAPGKGLEWIGGIGNNGIIHYANWAKGRFTSSKISTTVDLKITSPTTEDTATYFCARFPPGSNSGTDYFNIWGPGTLVTVSL |
| 7 | QSLEESGGDLVKPGASLTLTCTASGFSFSSSYYMCWVRQAPGKGLEWIGCIYGGSSGKTWYASWAKGRFTISKTSSTTVTLQMTSLTAADTATYFCARDNYDWYFNLWGPGTLVTVSS |
| 8 | QSLEESGGRLVTPGTPLTLTCTVSGFSLSMYAINWVRQAPGKGLEWIGGIANNGPTYYASWAKGRFTISKISTTVDLRITSPTTEDTATYFCARFPPGSNSGTDYFNIWGPGTLVTVSL |
| 9 | QSLEESGGDLVKPGASLTLTCKASGFDLSSYYYMCWFRQAPGKGPEWIACIYADDATTYYATWAKGRFTVSITSSTTVTLQMPSLTAADTATYFCARRDADYVGFIWAYYFNLWGPGTLVTVSS |
| 10 | QSVEESGGRLVTPGTPLTLTCTVSGIDLSRNAMSWVRQAPGKGLEWIGIIRNTGTTWYASWAKGRFTISKTSTTVDLKITSPTTEDTATYFCARGNPGWASTWGPGTLVTVSS |
| 11 | QEQLVESGGGLVQPGASLTLTCKTSGFSFSDNYAMCWVRQAPGKGLEWIACIYVGSGSTYYASWAQGRFTISKTSSTTVTLQMTSLTAADTATHFCARGVVIGNAYSMAHFSLWG |

| | |
|---|---|
| | SGTLVTVSS |
| 12 | QSLEESGGGLVKPGASLTLTCTASGFSFSSGYYMCWVRQAPGKGLEWIGCIYTSSGSTYYASWAKGRFTISKTSSTTVTLQMTSLTAADTATYFCARRLNYVTYPAYGYGYFNLWGPGTLVTVSS |
| 13 | QEQLEESGGDLVKPGASLTLTCTASGFSFNGNYYICWVRQAPGKGLEWIACIYAGSSGSTYYASWAKGRFTISKTSSTTVTLQMTSLTAADTATYFCVRDKPAGGSSYTLWGPGTLVTVSS |
| 14 | QEQLEESGGDLVKPGASLTLTCTASGFSFSRSYYMCWVRQAPGKGLEWIACIYAGSSDSTYYASWAKGRFTISKTSSTTVTLQMTSLTAADTATYFCARGGGIIYTQNLWGPGTLVTVSS |
| 15 | QSLEESGGDLVKPGASLTLTCTASGFSFVSMYWMCWVRQAPGKGLEWIACIYTGSSGKTHYASWAKGRSTISKTSSTTVTLQMTSLTAADTALYSCARAGSVGYGYDTAYFNLWGPGTLVTVSS |
| 16 | QSVEESGGRLVTPGTPLTLTCTVSGFSLNSYDMSWVRQAPGKGLEYIGIIYDSGSTYYANWAKGRFTIAKTSTTVDLKITSPTTEDTATYFCARTLNTLPFNIWGPGTLVTVSL |
| 17 | QEQLEESGGGLVQPEGSLTLTCTASGFSFSSSYWICWVRQAPGKGLEWIACIAAGSGSTYYASWAKGRFTISKTSSTTVTLQMTSLTAADTATYFCARDLGDDGYAYGLWGPGTLVTVSS |
| 18 | QSLEESGGVLVKPGASLTLTCTASGIDFSSSYYICWVRQAPGKGLEWIACIYAGSSGSTYYASWAKGRFTISKTSSTTVTLQMTSLTAADTATYFCARGTGSSHYTSNLWGPGTLVTVSS |
| 19 | QEQLVESGGGLVQPEGSLTLTCTASGFSFSDGYWMCWVRQAPGKGLEWIGCIYTGPGGTFYASWAKGRFTISKTSSTTVTLQLNSLTAADTATYFCARDLNGADSGSALWGPGTLVTVSS |
| 20 | QSVEESGGRLVTPGTPLTLTCTASGFSLSSYAMSWVRQAPGKGLEWIGIIHYSGYTAYASWAKGRFTISKTSTTVDLKITSPTTEDTATYFCARGGDADNFYYNIWGPGTLVTVSL |
| 21 | QEQLKESGGGLVTPGGTLTLTCTASGFTISNYQMTWVRQAPGKGLEYIGFIKADGSAYYANWAKGRFTISRTSTAVTLSLTTPTTGDTATYFCARDFYAGSSGNVNGDIWGPGTLVTVSL |

Fig. 4 continued

| | |
|---|---|
| 22 | QSLEESGGRLVTPGTPLTLTCTVSGFSLNMYAINWVRQAPGKGLEWIGGIATNGIIHYASWVKGQFTISKISTTVDLKITSPTTEDTATYFCTRFPPGSNGGTAYFNIWGPGTLVTVSL |
| 23 | QSVEESGGRLVTPGTPLTLTCTVSGFSLSNYDMNWVRQAPGKGLEWIGMIYPNSGTNYASWAKGRFTISKTPTTVALKITSPTTEDTATYFCARDSGWGAFDPWGPGTLVTVSS |
| 24 | QSVEESGGRLVTPGTPLTLTCTVSGFSLSNYDMNWVRQAPGKGLEWIGMIYPNGGTNYATWAKGRFTISKTPTTVALKITSPTTEDTATYFCARDSGWGAFDPWGPGTLVTVSS |
| 25 | QSVEESGGRLVTPGTPLTLTCTVSGIDLSSNAMIWVRQAPGKGLEWIGIIYASDSTYYATWAKGRFTISKTSTTVDLRMTSLTTEDTATYFCARGYSDIDIWGPGTLVTVSL |
| 26 | QSLEESGGRLVTPGTPLTLTCTVSGFSLSMYTINWVRQAPGKGLEWIGGIATHGIIHYASWVKGRFTISKISTTVDLKITSPTTEDTATYFCARFPPGSNGGTAYFNIWGPGTLVTVSL |
| 27 | QSVEESGGRLVTPGTPLTLTCTASGFSLSSNSISWVRQAPGKGLEWLGIISSSGSTYYASWAKGRFTISKASSTTVDLKITSPTTEDTATYFCAKGLGRGEYTSNDAFDPWGPGTLVTVSS |
| 28 | QSLEESGGDLVKPGASLTLTCTASGFSFTSTYWMSWVRQAPGKGPEWIGCIVTGRGNTYYANWAKGRFTISKTSSTTVTLQMTSLTAADTATYFCARGSSDEIALDLWGQGTLVTVSS |
| 29 | QSVEESGGRLVAPGTPLTLTCTVSGFSLNNYALSWVRQAPGKGLEYIGFINIIHGAYYASWAKGRFTISKTSTTVDLKITSPTTEDTATYFCARGPYYVGSEYVFDPWGPGTLVTVSS |
| 30 | QSLEESGGRLVTPGGSLTLTCTVSGIDLSSHATSWVRQAPGKGLEWIGFIKTGGSAYYASWAKGRFTISKTSATVDLKITSPTTEDTATYFCASMFYAGDSGHYLHLWGPGTLVTVSS |
| 31 | QSVEESGGGLVTPGGPLTLTCTVSGFSLSTYGVSWVRQAPGKGLEWIGYINTGGSASYATWAKGRFTISKTSTTVDLKITSPTTEDTATYFCAANNLWGPGTLVTVSS |
| 32 | QSLEESGGDLVKPGASLTLTCTASGFSFSSNYYICWVRQAPGKGLEWIACIYTGSTGSTYYASWAKGRFTISKTSSTTVTLQMTSLTAADRATYFCARGGYSYGGAVSLWGPGTLVTVSS |
| 33 | QSVEESGGRLVTPGTPLTLTCTVSGFSLTTYAMTWVRQAPGKGLEWIGIISNSGATAYASWAKGRFTISKTSTTVDLKITTPTTEDTATYFCARGRSGGWDALDPWGPGTLVTVSS |
| 34 | QEQLEESGGDLVKPEGSLTLTCTASGFSFSSSYWICWVRQAPGKGLEWIACIGTSSTISYYASWAKGRFTISKTSSTTVTLRMTSLTAADTATYFCAREDYAGGTDYYFRLWGPGTLVT |

Fig. 4 continued

| | |
|---|---|
| | VSS |
| 35 | QSVEESGGRLVTPGTPLTLTCTVSGFSLNNYAMSWVRQAPGKGLEWIGIIHYSGYIAYA NWAKGRFTISKTSTTVDLKITSPTTEDTATYFCARGGDADNFYYNIWGPGTLVTVSL |
| 36 | QEQLKESGGGLVTPGGTLTLTCTASGFTISNYQMTWVRQAPGKGLEYIGFIKPGGSAYY ASWAKGRFTISRTSTTVTLKLTSPTTGDTATYFCARDFYAGSSGNVNGDIWGPGTLVTV SL |
| 37 | QSLEESGGDLVKPGASLTLTCTASGFSFSSTYWACWVRQAPGKGLEWIACIDGGSSGIT GYANWAKGRFTLSRTSSTAVTLQMTSLTAADTATYFCARELDYFNLWGPGTLVTVSS |
| 38 | QEQLKESGGGLVTPGGTLTLTCTASGFTISSYQMTWVRQAPGKGLEYIGFINTGGSAYY ASWAKGRFTISRTSTTVDLIITSPTTGDTATYFCARDFYAGSSGNVNGDIWGPGTLVTV SL |
| 39 | QSLEESGGDLVKPGASLTLTCTASGFSFSSSYYMCWVRQAPGKGLEWIACIYAGSSGST YYASWAKGRFTISKTSSTTVTLQMTSLTAADTATYFCARGAGSNGDFNLWGPGTLVTV SS |
| 40 | QSLEESGGDLVKPGASLTLTCKASGFDFSSNYYMCWVRQAPGKGLEWIACIYTGSSGS TYYASWAKGRFTISKTSSTTVTLQMTSLTAADRATYFCARGAGSYGGAVRLWGPGTLV TVSS |
| 41 | QSLEESGGDLVKPEGSLTLTCTASGFSFSSSYYMCWVRQAPGKGLEWIACIHAGSSGA AYYATWAKGRFTISKASSTTVTLHMTSLTAADTATYFCVRDGYDDYGDPFNLWGPGTL VTVSS |
| 42 | QSVEESGGHLVTPGTPLTLTCTVSGFSLSNWIMSWVRQAPGEGLEWIGIITTSGNTYYA SWAKGRFTISKTSTTVDLKITSPTTEDTATYFCARISAGSDSYIIDNIWGPGTLVTVSL |
| 43 | QSLEESGGDLVKPGASLTLTCTASGFSLSSTYSMCWVRQAPGKGLEWVACIYTGSSGG TYYASWAKGRFTISKTSSTTVGLKMTSLTAADTATYFCARDAGNSGYYINLWGPGTLVT VSS |
| 44 | QSLEESGGDLVKPGASLTLTCTASGFDFSSGYDMCWVRQAPGKGLELIACIYTVNDNT WYASWAKGRFTISKTSSTTVTLQMTSLTAADTATYFCARLYKLWGPGTLVTVSS |
| 45 | QSLEESGGDLVKPGASLTLTCTASGIYFSSTYYTCWVRQAPGKGLEWIACIVDGSSGNT YYASWAKGRFTISKSSSTTVTLQMTSLTVADTATYFCGRPYVGYGYATDLWGPGTLVT |

Fig. 4 continued

| | |
|---|---|
| | VSS |
| 46 | QSVEESGGRLVTPGTPLTLTCTVSGFSLSSAAMGWVRQAPGKGLEYIGYISTSGTPYYASWVNGRFTISKTSTTVDLKITSPTTEDTATYFCARDSYAGDYAFNLWGPGTLVTVSS |
| 47 | QSVEESGGRLVTPGTPLTLTCTVSGFSLNSYDMSWVRQAPGKGLEYIGIIYNSGTTYYANWAKGRFTIAKTSTTVNLKITSPTTEDTATYFCARTHNTLPFYIWGPGTLVTVSL |
| 48 | QSLEESGGDLVKPEGSLTLTCTASGFSFSSTYWICWVRQAPGKGLEWIACIYTDSSTSTYYASWAKGRFTISKTSSTTVTLQMTSLTAADTATYFCARGSGGSDYFNLWGPGTLVTVSS |
| 49 | QEELVESGGGLVQPEGSLTLTCTASGFSFSSSYWICWVRQAPGKGLEWIACIVGGGGVNTYYANWAKGRFTISKTSSTTVTLEMTSLTVADTATYFCARDLGADGYAYHLWGPGTLVTVSS |
| 50 | QELVESGGGLVQAGESLKLSCKASGIDFSSDGISWVRQAPGKGLKWIAFIYPGVGITHYAHSVKGRLTISSDNAQNTVFLQMTSLTASDTATYFCVRDPIYDDYGGRLDLWGQGTLVTVSS |
| 51 | QSLEESGGRLVTPGTPLTLTCTVSGFSLSSYAISWVRQAPGKGLEWIGGVANNGITNYASWARGRFTISKISTTVDLKIISPTTEDTATYFCARFPPGSNGGTDYFNIWGPGTLVTVSL |
| 52 | QSVEESGGRLVTPGTPLTLTCTVSGIDLSSNALGWVRQAPGKGLEYIGYISTGGSAYYATWVNGRFTISKTSTTVDLKMTSLTAADTATYFCARDSYAGDYAFNLWGPGTLVTVSS |
| 53 | QSLEESGGRLVTPGTPLTLTCTVSGFSLNSYDMSWVRQAPGKGLEYIGIIYDSGSTYYASWAKGRFTIAKTSTTVDLKITSPTTEDTATYFCARARNTLPFNIWGPGTLVTVSL |
| 54 | QSVEESGGRLVTPGTPLTLTCTVSGIDLSNYAMGWVRQAPGKGLEWIGVISSNGGTVYANWAKGRFTISKVSTSVPLKITSPTTEDTATYFCARGLYSASGWSYCFDIWGPGTLVTVSL |
| 55 | QSVEESGGRLVTPGGSLTLTCTVSGIDLSVYAMSWVRQAPGKGLEWIGIITFSGNTYYASWAKGRFTISKTSTTVDLKITSPATGDTATYFCARFDFLVGLTYAGVLWGPGTLVTVSS |
| 56 | QSVEESGGRLVTPGTPLTLTCAVSGFSLSTYGVSWVRQAPGKGLEWIGYINIYGRTYYANWAKSRFTISKTSTTVDLKMTSPTTEDTATYFCARNGASGTYYSSLYIWGPGTLVTVSL |
| 57 | QSLEESGGRLVTPGTPLTLTCTVSGFSLSMYAINWVRQAPGKGLEWIGGIANNGPTYYASWAKGRFTISKISTTVDLKITSPTTEDTATYFCARFPPGSNSGTDYFNIWGPGTLVTVSL |

Fig. 4 continued

| | |
|---|---|
| 58 | QSVEESGGRLVTPGTPLTLTCTVSGIDLSRYAMSWVRQAPGKGLEYIGIISSSGNSYYASWAKGRFTISKASTTVDLKITVPTTEDTATYFCVGGSGWDLWGQGTLVTVSS |
| 59 | QSLEESGGRLVTPGGSLTLTCTVSGIDLSSYAMGWVRQAPGKGLEYIGIISSGLTYYASWAKGRFTISKTSTTVDLKMTSLTTEDTATYFCARGLGAASATWDIWGPGTLVTVSL |
| 60 | QSLEESGGDLVKPGASLALTCTASGFSFSSSYWICWVRQAPGKGLEWIACINFGRSGNIYYARWAKGRFTISKTSSTTVTLQMTSLTAADTATYFCARDKAGDSYYFNLWGPGTLVTVSS |
| 61 | QSLEESGGRLVTPGTPLTLTCTASGFSLNNYYMTWVRQAPGEGLEYIGFIDPYSSPYYASWAKGRFTISRTSTTVDLKISSPTAEDTATYFCARGVAVGDIWGPGTLVTVSL |
| 62 | QSLEESGGRLVTPGTPLTLTCTVSGIDLSSYHMSWVRQAPGKGLEWIGVIYGSGSAWYASWAKGRFTISKTSTTVDLKITSPTTEDTATYFCVRGILVSDLWGPGTLVTVSS |
| 63 | QQQLEESGGGLVKPEGSLTLTCKASGFDFSTIPMCWVRQAPGKGLEWIACIYPDYGDTFYATWAKGRFTISKTSSTTVTLQMTSLTVADTATYFCARGPIMVVSPSYFNFWGPGTLVTVSS |
| 64 | QSLEESGGDLVQPGASLTLTCTASGFIFSDNYAMCWVRQAPGKGLEWIACIFGSSGSIAYATWAKGRFTISKTSSTTVTLQMTSLAAADTATYFCARSYYSGGYKYVYVFDLWGPGTLVTVSS |
| 65 | QEQLVESGGGLFQPGGSLTLTCTASGFTISSYHMGWVRQAPGEGLEYIGFITTTGGSYYASWARGRFTISKTSTTVDLKMTSLTAADTATYFCAKGIAVASLWGPGTLVTVSS |
| 66 | QSLEESGGDLVKPGASLRLTCTASGLSFSSRYWIYWVRQAPGKGLEWIACIDTGSRGFTYYPSWAKGRFTISKTSSTTVTLQMTSLTAADTATYFCARLDTYDDYDLWGPGTLVTVSS |
| 67 | QSVEESGGRLVTPGTPLTLTCTASGFSLYSYFLTWVRQSPGKGLEWIGFMNSGGSTYYASWVNGRFTISKTSATVDLKITGATTEDTATYFCARMFYAGDSGHYFDLWGPGTLVTVSS |
| 68 | QSVEESGGRLVTPGTPLTLTCTVSGIDLSSYAMSWVRQAPGKGLEWIGMIRSSGITWYASWAKGRFTISKTSTTVDLKITSPTTEDTATYFCARDSDYDDYGNSYYGMDPWGPGTLVTVSS |
| 69 | QEQLEESGGDLVKPEGSLTLTCTASGFDFSSNAMCWVRQAPGKGLEWIACIYAGSRGSAYYASWVNGRFSISKTSSTTVTLQMTSLTAADTATYFCAREYVGSQGYFNLWGPGTLV |

Fig. 4 continued

| | |
|---|---|
| | TVSS |
| 70 | QSVEESGGRLVTPGTPLTLTCTVSGFSLSVYAMSWVRQAPGKGLEWIGIITWSADTYYTSWAKGRFSISKTSTTVDLKVASPTTEDTATYFCARFDYLVGGTWAGVLWGPGTLVTVSS |
| 71 | QSVEESGGRLVTPGTPLTLTCTASGFSLNSYAMGWVRQAPGKGLEWIGINGVSGTTYYATWANGRFTISKTSTTVDLKIIRPTTEDTATYFCARGVGDTTDTQLDLWGQGTLVTVSS |
| 72 | QEQLVESGGGLVQPEGSLTLTCTASGFDFSGSYWNCWVRQAPGKGLEWIACIDGEGSGNTYYASWVNGRFTISKTSSTTVTLQMTRLTAADTATYFCARDPSAWGGLDLWGPGTLVTVSS |
| 73 | QSLEESGGDLVKPGASLTLTCKASGFSFSSGYDMCWVRQAPGKGLEWIACIDTGDGSTYYASWVNGRFTISKTSSTTVTLQMTSLTAADTATYFCARYNNGWDYFNLWGPGTLVTVSS |
| 74 | QSVEESGGRLVTPGTPLTLTCTVSGFSLIAYGVNWVRQAPGKGLQWIGSISNSGGTYYASWAKGRFTVSKTSTTVDLRITSPTTEDTATYFCGRGSLWGPGTLVTVSS |
| 75 | QEQLVESGGGLVQPEGSLTLTCTASGFTISNSYYMCWVRQAPGKGLEWIGCIDAGSVGDTSYATWAKGRFTISKTSSTTVTLQMTSLTAADTATYFCARRYGAGSGYFISPNLWGPGTLVTVSS |
| 76 | QEQLVESGGGLVQPEGSLTLTCKASGFDFSSNAMCWVRQAPGKGPEWIACIYNGDGSTYYASWVNGRFTISRSTSLNTVTLQMTSLTAADTATYFCAREYVDSQGYFNLWGPGTLVTVSS |
| 77 | QSLEESGGRLVTPGTPLTLTCTVSGFSLSSYAMGWVRQAPGKGLEWIGIISNSGATAYASWAKGRFTISKTSSTTVDLKMTTPTTEDTATYFCARGRSGGWDAFDPWGPGTLVTVSS |
| 78 | QSLEESGGRLVTPGTPLTLTCTVSGIDLNTNGVSWVRQAPGKGLEWIGYIFTGGNTYYASWAKGRFTISKTSTTVDLKMTSLTTADTATYFCARFDIWGPGTLVTVSL |
| 79 | QEQLEESGGGLVKPGASLTFTCRASGFSFSSGYYMCWVRQAPGKGLEWIACIYVGITGSTYYASWAKGRFTISKTSSTSVTLQMTSLTAADTATYFCARDTGNSNYQFNLWGPGTLVTVSS |
| 80 | QSLEESGGDLVKPGASLTLTCTASGFSFSSGYCLCWVRQAPGKGLEWIACKHGGASGT |

Fig. 4 continued

| | |
|---|---|
| | TYYATWAKGRFTISKTSSTTVTLQVTSLTVADTATYFCARDDVSVGDANYPYTAFDLWGPGTLVTVSS |
| 81 | QSLEESGGDLVKPGASLTLTCTASGSDISSYWMCWVRQAPGKGLEWIACSYAGGSGGTYYASWAKGRFTISKTSSTTVTLQMTSLTAADTATYFCAREAYSSANSYYDLWGPGTLVTVSS |
| 82 | QSLEESGGDLVKPGASLTLTCTASGFSFSSYYYMSWVRQAPGKGLEWIACTDGTGGITYYASWAKGRFTTSKTSPTTVTLQMTSLTAADTATYFCARDPTAAGGVYFDLWGPGTLVTVSS |
| 83 | QEQLEESGGDLVKPEGSLTLTCTASGFDFSYNTICWVRQAPGKGLEWIAYINTGSSGTTYYASWAKGRFTISKTSSTTVTLQLNSLTAADTATYFCAGGSGYSKFRLWGPGTLVTVSS |
| 84 | QSLEESGGDLVKPGASLTLTCTASGFSFSSSYYMCWVRQAPGKGLEWIACIYAGSSGSTYYASWAKGRFTISKTSSTTVALQMTSLTAADTATYFCARDRGDTDISLWGPGTLVTVSS |
| 85 | QSVEESGGRLVAPGTPLTLTCTVSGFSLSNYAMSWVRQAPGKGLEYIGFINIIDSTYYTNWAKGRFTISKTSTTVDLKMTSPTTEDTATYFCARGPYYVNNENVFDPWGPGTLVTVSS |
| 86 | QSLEESGGRLVTPGGSLTLTCTVSGIDLSNYAVGWVRQAPGKGLEYIGVINAGGSAYYATWAKGRFTISRTSTTVDLKITSPTTEDTATYFCARSYAGNRYDFAIWGPGTLVTVSL |
| 87 | QSLEESGGDLVKPGASLTLTCTASGFSVSSSYYMCWVRQAPGKGLEWIACIYADSSGSTYYASWAKGRFTISSTSSTTVTLQMTSLTAADTATYFCARGPYSFDFWGPGTLVTVSS |
| 88 | QSLEESGGDLVKPGASLTLTCTASGFSFSSRYYVCWVRQAPGKGLEWIACIDAGDGSTDYARWAKGRFTISKTSSTTVTLQMTGLTAADTATYFCARGDAYRDDYASDLWGPGTLVTVSS |
| 89 | QSLEESGGRLVTPGESLTLTCTVSGIDLSANAMSWVRQAPGKGLEWIGTIFDTYLTYNANWAKGRFTISRTSTTVELKMTSPTIEDTATYFCARYIGSVGYRRMDIWGPGTLVTVAL |
| 90 | QSVEESGGRLVTPGGSLTLTCTASGFSLNNYHMSWVRQAPGKGLEWIGFIRTDGSAFYATWAKGRFTISKTSATVDLKVTSATTEDTATYFCARMFYAGDSGHYFDLWGPGTLVTVSS |
| 91 | QSVEESGGRLVTPGTPLTLTCTVSGFSLSNYGLTWVRQAPGKGLEWIGYINNNGRTYYASRAKGRFTISKTSTTVDLQMTSPTTEDTATYFCARNGAGGYYYSSLYIWGPGTLVTVSL |
| 92 | QSLEESGGDLVKPGASLTLTCTASGFSFSSSYYMCWVRQAPGKGLEWIACVYAGSSGS |

Fig. 4 continued

| | |
|---|---|
| | TYYASWAKGRFTISKTSSTTVTLQMTSLTAADTATYFCARDRGGTDISLWGPGTLVTVSS |
| 93 | QSVEESGGRLVTPGTPLTLTCKASGFSLSTYAMSWVRQAPGKGLEYIGIIDASVTTYYASWAKGRFTISKTSTTVDLTITSPTTEDTATYFCARSSSTYAYGFDPWGPGTLVTVSS |
| 94 | QEQLKESGGGLVQPGGSLKLSCKASGFDFSNYGVSWVRQAPGKGLEWVGYIDPVFRSAYYASWVNGRFTISSHNAQNTLYLQLNSLTAADTATYFCARKGYFHYFNLWGPGTLVTVSS |
| 95 | QSLEESGGDLVKPGASLTLTCTASGFSFSVSYWICWVRQAPGKGLEWIACIGGNSGNIYYARWAKGRFTISKTSSTTVTLQMTSLTAADTATYFCARDRAGNSYYFNLWGPGTLVTVSS |
| 96 | QSLEESGGDLVKPGASLTLTCTASGFSFSSGYDMCWVRQAPGKGLEWIGCIYSSNGLTWYATWAKGRFTVSKTSSTTVTLQMTSLTAADTASYFCWRVWSLWGPGTLVTVSS |
| 97 | QEQLVEYGGDLVQPEGSLTLTCKASGFDFSSNAMCWVRQAPGKGLEWIGCIVTGSGSTYYASWAKGRITISETSSTTVTLQMTSLTAADTATYFCARGYDGYGYVLVLWGPGTLVTVSS |
| 98 | QSLEESGGDLVKPGASLTLTCTASGFSFSSSYYMCWVRQAPGKGLEWVAGVDGSGGIKWYANWAKGRFTISKTSPTTVTLQMTSLTAADTATYFCARDPTAAGGVYFDLWGPGTLVTVSS |
| 99 | QSLEESGGDLVKPGASLTLTCTASGFSFSSSYWIYWVRQAPGKGLEWIACFHAGSGSTYYASWVNGRFTISKTSSTTVTLQMTSLTAADTATYFCARGSGSIYYTPSYFDLWGPGTLVTVSS |
| 100 | QSVEESGGRLVTPGTPLTLTCTVSGFSLSRYGVSWVRQAPGKGLEWIAWISSSGSAYYATWAKGRFTISKTSTTVDLKITSPTTEDTATYFCGESDIWGPGTLVTVSL |
| 101 | QSLEESGGGLVQPEGSLTLACTASGFSFNNNYYMCWVRQAPGKGLEWVACIYTGSTGSTYYANWAKGRFTISKLSSTTVTLQMTSLTAADTATYFCARDDKVEHGYGLWGPGTLVTVSS |
| 102 | QSLEESGGDLVKPGASLTLTCTASGFSFSSNYYMCWVRQAPGKGLEWIACIYAGSSGSSYYASWAKGRFTISKTSSTTVTLQMTSLTAADTATYFCARSMEAYGYAGYAMPGYYFNLWGPGTLVTVSS |

Fig. 4 continued

| | |
|---|---|
| 103 | QSVEESGGRLVTPGTPLTLTCTVSGFSLSSYAMSWVRQAPGKGLEWIGIIRRSGATWYANWARGRFTISKTSTTVDLKITSPTTEDTATYFCARDSDYDDYGDSYYGMDPWGPGTLVTVSS |
| 104 | QSLEESGGDLVKPGASLTLTCTASGFSFSSSYCMCWVRQAPGKGLEWIGCIYDGSSDSAYYATWAKGRFTISKTSSTTVTLQMTSLTAADTATYFCARDYDTYDYDGYTYAAGFDLWGPGTLVTVST |
| 105 | QSLEESGGRLVTPGTPLTLTCTVSGIDLSSYAMGWVRQAPGKGLQYIGIITYGGSTYYASWAKGRFTISKTSTTVNLKMTSLTTEDTATYFCARGLGGASTTWDIWGPGTLVTVSL |
| 106 | QSLEESGGDLVKPGASLTLTCTASGFSFSSGYDMCWVRQAPGKGLEWIACIAVYSSGSTYYASWAKGRFTISKTSSTTVTLQMPSLTAADTATYFCARDIITDSVWITRLDLWGQGTLVTVSS |
| 107 | QSVEESGGRLVTPGTPLTLTCTASGFSFSDYYMSWVRQAPGKGLEWIGVVSWNGNTYYASWAKGRFTVSKTSTTVDLKIISPTTEDTATYFCARFDYLVGDTYAGVLWGPGTLVTVSS |
| 108 | QSLEESGGRLVTPGTPLTLTCTVSGIDLSSHATSWVRQAPGKGLEWIGFIKSGGSTYYASWAKGRFTISETSATVDLKITSPTTEDTATYFCASMFYAGDSSGNYLHLWGPGTLVTVSS |
| 109 | QSLEESGGDLVKPGASLTLTCTASGFSFSSGYWICWVRQAPGKGLEWIACIDAGSNGSTYYASWARGRFTISKTSSTTVTLQMTSLTAADTATYFCAREGSSAYPSYFNFWGPGTLVTVSS |
| 110 | QSLEESGGRLVTPGGSLTLTCTVSGIDLSSYTMAWVRQAPGKGLEYIGVINTGGSAYYASWAKGRFTISKTSTTVDLKITSPTTEDTATYFCARSYGGNRYDFNIWGPGTLVTVSL |
| 111 | QSVEESGGRLVTPGTPLTLTCTASGFSLSSYHMCWVRQAPGKGLEWIGFIKADGNTYYATWAKGRFTISRSSATVDLKITSATAEDTATYFCARMFYAGHTSGHYFDLWGPGTLVTVSS |
| 112 | QSLEESGGDLVKPEASLTLTCTASGFSFSGDYDMCWVRQAPGKGLEWIACIGAGSSNDTYYASWAKGRFTISKTSSTTVTLQMTSLTAADTATYFCARGFDYTYGDAGYTYSTSHYFNLWGPGTLVTVSS |
| 113 | QSLEESGGGLVQPEGSLTLTCTASGFSFSSSYYMCWVRQAPGKGLEWIACISVGSSGSTYYANWAKGRFTISKTSSTTVTLQMTSLTAADTATYFCAREGADYQGHFNLWGPGTLV |

Fig. 4 continued

| | |
|---|---|
| | TVSS |
| 114 | QSVEESGGRLVTPGTPLTLTCTVSGFSLSSYAMSWVRQAPGKGLEWIGIIRRSGFTYYASWARGRFTISKTSTTVDLKITSPTTEDTATYFCARDSDYDDYGNSYYGMDPWGPGTLVTVSS |
| 115 | QSVEESGGRLVTPGTPLTLTCTVSGFSLSSYTMTWVRQAPGKGLEWIGLISRSGRTYYATWAKGRLTISKTSTTVDLKITSPTTEDTATYFCAREIGSGYDAPYYFNLWGPGTLVTVSS |
| 116 | QSLEESGGGLVQPEGSLTLTCTASGFSFNSKYYMCWVRQAPGKGLEWIACIYTGTTGSTYYASWAKYRFTISKISSTTVTLQMTSLTAADTATYFCARDDRVEHGYGLWGPGTLVTVSS |
| 117 | QEQLEESGGGLVKPEGSLTLTCKASGFTISSYYIYWVRQAPGKGLEWIGCIAIINSITYYANWAKGRFTISKTSSTTVTLQMTSLTAADTATYFCARDLSSSIYDMDLWGPGTLVTVSS |
| 118 | QSLEESGGDLVKPGASLTLTCKASGLDFSSVYDMCWVRQAPGKGLEWIACIYSDGSGSTYYANWAKGRFTISETSSTTVTLQMTNLTAADTATYFCARVLNGWGEYYFNLWGPGTLVTVSS |
| 119 | QSVEESGGRLVTPGTPLTLTCTASGFSLSSYHMSWVRQAPGKGLEYIGFIVGTGDTYYASWAKGRFTISKTSTTVDLKITSPTTEDTATYFCGRGVAAGDIWGPGTLVTVSL |
| 120 | QSLEESGGRLVTPGTPLTLTCTASGFSLSGLVVSWVRQAPGKGLEWIGVIGKSGSTYYASWAKGRFSISKTSSTTVDLKIASPTTEDTATYFCGRNISGSAVWGPGTLVTVSL |
| 121 | QEQLVESGGGLVQPEGSLTLTCKASGFDFNRDAMSWVRQAPGKGLEWIGSIVSGSGSTYYASWAKGRFTISETSSTTVTLQMTSLTAADTATYFCARGGDGYGYVLVLWGPGTLVTVSS |
| 122 | QSLEESGGDLVKPGASLKLSCAASGFTLSSYWICWVRQAPGKGLEWIACIYAGSSGSTYYASWAKGRFTISKTSSTTVTLQMTSLTAADTATYFCARGISYALLWGPGTLVTVSS |
| 123 | QSVEESGGRLVTPGTPLTLTCTVSGIDLSRYAMIWVRQAPGKGLESIGIIDIRGTTYYASWAKGRFTISKTSSTTVDLKMTSLTTEDTATYFCARGGVGHEVNNLWGPGTLVTVSS |
| 124 | QSLEESGGDLVKPGASLTLTCTASGFSFSNNYWICWVRQAPGKGLEWIACIVAGSSGRTYYANWAKGRFTISKTSSTTVTLQMTSLTAADTATYFCARKLSDWDYGYFNLWGPGTLVTVSS |
| 125 | QSLEESGGDLVKPGASLTLTCTASGIDFSTYYYMCCVRQAPGKGLEWIACIHAGSSGST |

Fig. 4 continued

| | |
|---|---|
| | YYASWAKGRFTISKTSSTTVTLQMTSLTAADTATYFCARGYAGYYGYGYPTPSWLDLWGQGTLVTVSS |
| 126 | QSVEESGGRLVTPGTPLTLTCKASGFSLSSYWMSWVRQAPGEGLEWIGTINAASGATWYASWAKGRFTISKTSTTVDLKMTSLTTEDTATYFCARGGTTGSNYYGMDPWGPGTLVTVSS |
| 127 | QSVEESGGRLVTPGTPLTLTCTVSGIDLSRNAASWVRQAPGKGLEWIGIISTGGSTYYATWAKGPFTISKTSTTVDLKMTSLTTEDTATYFCVVGIRFWGPGTLVTVSS |
| 128 | QSVEESGGRLVTPGTPLTLTCTVSGFSLSNYAMTWVRQAPGKGLEWIGIIINTGYTYYASWAKGRFTISKASTTVDLKITSPTTEDTATYFCARVLGAGSSYYTSYDRLDLWGQGTLVTVSS |
| 129 | QSLEESGGRLVTPGTPLTLTCTVSGIDLISNAISWVRQAPGKGLEWIGHSDIRGSAYYASWAKGRFTISRTSSTTVDLKMTSLTTEDTATYFCARIADVNTQLDLWGQGTLVTVSS |
| 130 | QSLEESGGDLVKPGASLTLTCAASGFSFSVGYYMCWVRQAPGKGLEWVACIYAGSNGSTYYASWAKGRFTFSKPSSTTVTLQMTSLTAADTATYFCARGAGYAGYGFNLWGPGTLVTVSS |
| 131 | QEQLVESGGGLVKPEGSLTLTCTASGFSFSSSYWICWVRQAPGKGLEWIACIYADGSGSIYCATWAKGRFTISKTSSTTVTLQMTSLTAADTATYFCSRGNAGSYWDIYYGMDLWGPGTLVTVSS |
| 132 | QSLEESGGDLVKPGASLTLTCTASGFSFSSSYYMCWVRQAPGKGLEWIACIYIGDGNTYYASWAKGRFTISKTSSTTVTLQMTSLTAADTATYFCARGSGGYFVDNLWGPGTLVTVSS |
| 133 | QSVEESGGRLVTPGTPLTLTCTASGFDINNYHMTWVRQAPGKGLEWIGFIKAGGSAGYASWAKGRFTISKTSATVDLRITGATTEDTGTYFCVRMFYAGDSGHYFDLWGPGTLVTVSS |
| 134 | QSVEESGGRLVTPGTPLTLTCTVSGFSLSSYDMTWVRQAPGKGLEWIGVISSSDSTYYASWAKGRFTISKPSSTTVDLKVTSPTTEDTATYFCARDHPAFSTVDLDIWGPGTLVTVSL |
| 135 | QEQLVESGGGLVKSGASLTLTCTASGFSLSSSYCVCWVRQAPGKGLEWIACIYGGSSGGTYYASWAKGRITISKTSSTTVTLQMTSLTAADTATYFCARDAGSSGYYINLWGPGTLVTVSS |

Fig. 4 continued

| | |
|---|---|
| 136 | QSLEESGGDLVKPGASLTLTCTASGFSFSSNAMCWVRQAPGKGPEWIGCIYTSSSGSTYYASWVNGRFTISKTSSTTVTLQMTSLTVADTATYFCARYNNGWDYFNLWGPGTLVTVSS |
| 137 | QEQLVESGGGLVKPGASLTLTCTASGFSFNGNYYMCWVRQAPGKGLEWIACIYADNSGSTYYASWAKGRFTISKTSSTTVTLQMTSLTAADPATYFCVRHKPAGGSSYILWGPGTLVTVSS |
| 138 | QSLEESGGRLVTPGTPLTLTCTVSGIDLSSYHMNWVRQAPGKGLEWIGVIYGSGSTDYASWAKGRFTISKTSTTVDLKITSPTTEDTATYFCARGILVSNLWGPGTLVTVSS |
| 139 | QSLEESGGDLVKPGASLTLTCTASGFTISSSYYMCWVRQAPGKGLEWIACIYSDSSGSTYNANWVKGRFTISKTSSTTVTLRMTSLTAADTATYFCARGTYPFTLWGPGTLVTVSS |
| 140 | QSVEESGGRLVTPGTPLTLTCTVSGFSLSSYPVNWVRQAPGKGLEWIGVIGNRGSTDYASWAKGRFTISKTSTTVDLKITSPTTEDTATYFCARGSGYGTGWDAFDPWGPGTLVTVSS |
| 141 | QSLKESGGGLVTPGTPLTLTCKVSGFSLSSYDMSWVRQAPGKGLEWIGTIYDGGSTYYASWTKGRFTISKASTTVDLKITSPTTEDTATYFCARGSTNMEFWFWGPGTLVSVSS |
| 142 | QSVEESGGRLVTPGTPLTLTCTVSGFSLNNYGMTWVRQAPGKGLEWIGIINIIDNTYYASWAKGRFTISKTSTTVDLKITSPTTEDTATYFCARADYYPDTTGWYLNIWGPGTLVTVSL |
| 143 | QSVEESGGRLVTPGTPLTLTCTVSGFSLSTYWMSWVRQAPGKGLEWIGTISTGGSAYYASWAKSRFTISKTSTTVDLKITSPTTEDTATYFCARDGDSYFKLWGPGTLVTVSS |
| 144 | QSLEESGGRLVTPGTPLTLTCTVSGIDLSSYAMGWVRQAPGKGLEYIGYINRGNTYYANWAKGRFTISKTSTTVDLKITSPTTEDTATYFCARDSYGGDYAFNLWGPGTLVTVSS |
| 145 | QSLEESGGGLVKPGASLTLTCTASGFSFSSSYYMCWVRQAPGKGLEWIACIHAGSSGSAYYASWAKGRFTISKTSSTTVTLQMTSLTAADTATYFCARDGYDDYGDPFNLWGPGTLVTVSS |
| 146 | QSLEESGGDLVKPGASLTLTCTASGFSFSSGQDMCWVRQAPGKGLEWIACIYGGDGNTYYASWAKGRFTIYKTSSTTVTLKMTSPTAADTATYLCARLHYSPYGDAGYPYVSFNLWGPGTLVTVSS |
| 147 | QSVEESGGRLVTPGTPLTLTCTASGFSLSSYNMGWVRQAPGKGLEWIGYIWSGGSAYYASWAKGRFTISRTSTTVTLKMTSLTAADTATYFCARNGASGTFDIWGPGTLVTVSL |

Fig. 4 continued

| | |
|---|---|
| 148 | QEQLVESGGGLVQPEGSLTLTCTASGFSFSSSYYMCWVRQAPGKGLEWIACIYAGSSGSTYYASWAKGRLTISKISSTTVTLQMTSLTAADTATYFCARGGGSGGVDNNLWGPGTLVTVSS |
| | **LC VR** |
| 149 | AQVLTQTPSSVSAAVGGTVTINCQASQSLYNNKNLAWYQQKLGQPPKLLIYDVSTLASGVPSRFKGSGSGTQFTLTISGVQCDDAATYYCQGEFSCSSGDCYAFGGGTEVVVK |
| 150 | AQVLTQTASSVSAVVGGTVTISCQSSQSVYDKKWLGWYQQKPGQPPKLLIYKASTLASGVPSRFKGSGSGTQFTLTISDLECDDAATYYCAGGYSGNIWSFGGGTEVVVK |
| 151 | AQVLTQTPSSVSAAVGGTVTIICQASQSLYNNKNLAWYQQKLGQPPKLLIYDVSTLASGAPSRFKSSGSGKQFTLTISGVQCDDAATYYCQGEFSCSSGDCYAFGGGTEVVVK |
| 152 | AQVLTQTASPVSAAVGDTVTISCQSSESVYNNNLLSWYQQKPGQPPKLLIYTTSSLASGVPSRFKGSGSGTQFTLTISGVQCDDAATVYCQGGYTDATYAFGGGTEVVVK |
| 153 | DIVMTQTPSSVSAAVGGTVTINCQASQSVSNLLAWYQQKPGQPPKLLIYGASNLESGVPSRFRGSGSGTEFTLTISGMKAEDAATYYCQSGYYTFGAGTKVEIK |
| 154 | AQVLTQTPSSVSAAVGGTVTINCQASQSLYNNKNLAWYQQKPGQPPKLLIYDASTLASGVPSRFKGSGSGTQFTLTISGVQCDDAATYYCQGEFSCGSGDCYAFGGGTEVVVK |
| 155 | DPVLTQTPSSASEPVGGTVTIKCQASEDIESYLAWYQQKPGQPPKLLIYDASDLASGVPSRFKGSGSGTQFTLTISGVQCADAATYYCQSYYYGSSYVVAFGGGTEVVVK |
| 156 | AQVLTQTPSSVSAAVGGTVTINCQASQSLYNNKNLGWYQQKLGQPPKLLIYDVSTLASGVPSRFKGSGSGTQFTLTISDLECDDAATYYCQGEFSCSSGDCYAFGGGTEVVVK |
| 157 | DIVMTQTPASVEAAVGGSVTIKCQASQTISSYLAWYQQKPGQPPKLLIYGASTLASGVPSRFSGSGSGTEYTLTISGVQCDDAATYYCLYSYYTSNSADNTFGGGTEVVVK |
| 158 | AAVLTQTPSPVSAAVGGTVSISCQSSQSVYDNNALAWYQQKPGQPPKLLIYETSTLASGVPSRFEGSGSGTQFTLTISDVQCDDAATYYCAGGYNSGSDAAFGGGTEVVVK |
| 159 | AQVLTQTPSPVSAPVGGTVTISCQSSQNVDRNNRLAWYQQKLGQPPKLLIYYASILASGVPSRFKGSGSGTQFTLTINELQCDDAATYYCQGYYSGDINVFGVGTEVVVK |
| 160 | DIVMTQTPASVEAAVGGTVTIKCQASQSIGSNLAWYQQKPGQPPKLLIYKASTLASGVPSRFKGSGSGTEFTLTISDLECADAATYYCQSYYGTSNSYGDAFGGGTEVVVK |
| 161 | DVVMTQTPASVSEPVGGTVTIKCQASEDIESYLAWYQQKPGQPPKLLIYQASKLASGVS |

Fig. 4 continued

| | |
|---|---|
| | SRFSGSGYGTEFTLTLSDLECADAATYYCQCTLYGVNFVPNVFGGGTEVVVK |
| 162 | DVVMTQTPASVSEPVGGTVTIKCQASEDIESYLAWYQQKPGQPPKLLIYSASTLASGVS SRFKGSGSGTEFTLTISDLECADAATYYCQCILYGVNFVPNTFGGGTEVVVK |
| 163 | DVVMTQTPASVSAAVGGTVTIKCQASQNIYDNLAWYQQKPGQRPKLLIYGASNLESG VPSRFKGSGSGTEYTLTISDLECADAATYYCQCSYDGGSYVPNAFGGGTEVVVQ |
| 164 | AAVLTQTPSPVSAAVGGTVSISCQSSPSVYNNNRLSWFQQKPGQPPKLLIYYASTLASG VPSRFKGSGSGTQFTLTISDVQCDDAATYYCAGGYSTISDNAFGGGTEVVVK |
| 165 | DVVMTQTPASVSEPVGGTVTIKCQASQNIGNNLAWYQQKPGQPPKLLIDYASTLASG VPSRFKGSGSGTQFTLAISDLDCADAATYYCQCTFYGSGYVAAFGGGTEVVVK |
| 166 | DVVMTQTPASVSEPVGGTVSINCQASEDIESYLAWYQQKPGQPPKLLIYGASNLASGV SSRFKGSGSGTEYTLTISDLECDDAATYYCQCGIYGVNFVPNVFGGGTEVVVK |
| 167 | AYDMTQTPASVEVGVGGTVTIKCQASQNINSWLSWYQQKPGQPPKLLIYKASTLASG VSSRFKGSGSGTEFTLTISDLECADAATYYCQQGAGWNNLDNAFGGGTEVVVK |
| 168 | AQVLTQTPSSVSAAVGGTVTINCQSSQSVYSNNHLAWYQQKPGQPPNLLIYRASKLAS GVPSRFSGSRSGTQFTLTISGVQCDDAATYYCLGVYDDDADNAFGGGTEVVVK |
| 169 | AVVMTQTASPVSAAVGGTVTINCQSSQIVHNNNNLAWYQLKPGQPPKLLIFQASTLA SGVPSRFKGSGSGTQFTLTISDLECDDAAAYYCAGGYSTNTDTYIFGGGTEVVVR |
| 170 | AQVLTQTPSSVSAAVGGTVTINCQASQSLYNKKNLAWYQQKLGQPPKLLIYDASTLTS GVSSRFKGSGSGTQFTLTISGVQCDDAATYYCQGEFSCSAGDCYAFGGGTELVVK |
| 171 | AQVLTQTASSVSAVVGGTVTISCQSSQSVYDNKWLGWYQQKPGQPPKLLIYSASTLAS GVPSRFKGSGSGTHFTLTISDLECDDATTYYCAGGYSGNIWSFGGGTEVVVK |
| 172 | AQVLTQTPSPVSAAVGGTVTISCQSSQSVYDNKWLGWYQQKPGQPPKLLIYKASTLAS GVPSRFKGSGSGTQFTLTISDLECDDATTYYCAGGYSGNIWSFGGGTEVVVK |
| 173 | AAVLTQTPASVSAAVGGTVTISCQSSKSVFDNNWLSWFQQKPGQPPKLLIYKASTLAS GVPSRFKGSGSGTQFTLTISDVQCDDAATYYCAGIYSSDSDNAFGGGTEVVVK |
| 174 | AQVLTQTPSSVSAVVGGTVTINCQASQSLYNKKNLAWYQQKLGQPPKLLIYDASTLAS GVPSRFKGSGSGTQFTLTISGVQCDDAASYYCQGEFSCSSGDCYAFGGGTELVVK |
| 175 | AYDMTQTPFSVSAAVGGTVTINCQASETIYSYLNWYQQKPGQPPKLLIYSASTLASGVP SRFKGSGSGTQFTLTISGVECADAATYYCQQGYSGRNVENTFGGGTEVVVK |

Fig. 4 continued

| | |
|---|---|
| 176 | AAVLTQTPSPVSAAVGGTVTISCQSSQNIYNKNQLSWFQQKPGQPPKLLIYEASKLASG VPSRFKGSGSGTQFTLTISDVQCDDAATYYCLGGYISSSDTTFGGGTEVVVK |
| 177 | DVVMTQTPASVSTAVGGTVTIKCQASQSIGGSLAWYQQKPGQPPNLLIYSASNLASGV SSRFKGSRSGTEFTLTISDLECADAATYYCQCTYYDDSYDVPFGGGTEVVVK |
| 178 | AAVLTQTPSPVSAAVGGTVTISCQSSQSVNNNKNLAWYQQKLGQPPKLLIYDTSTLAS GVPSRFKGSGSGTQFTLTISDLECDDATTYYCAGGYSSSADTFAFGGGTEVVVR |
| 179 | DIVMTQTPASVSAAVGGTVTIKCQASQNIGSTLAWYQQKPGQPPKRLIYGASTLSSGV PSRFKGSGSGTDFTLTISDLECADAATYYCQSNYGSNSGGYVFPFGGGTEVVVK |
| 180 | DVVMTQTPASVSEPVGGTVTIKCQASEDIETYLAWYQQKPGQPPKLLIYRASTLASGVP SRFKGSGSGTQFTLTISDLECADAATYYCQCTLYGVNFVANAFGGGTEVVVK |
| 181 | AFELTQTPSSVSAAVGGTVTINCQASEDIENYLAWYQQKPGQPPKLLIYSASTLASGVSS RFKGSGSGTEYTLTISDLGCADAATYYCQSYYDGAVTFTFGGGTEVVVK |
| 182 | AQVLTQTASPVSAAVGGTVTIKCQSSQSVDNNWLSWYQQKPGQPPKLLIYTTSKLASG VPSRFKGSGSGTQFTLTISDVQCDDAATYYCLGGYDSMSADCFAFGGGTEVVVK |
| 183 | AQVLTQTPSSVSAAVGGAVTINCQSSQSVYSNNHLAWYQQKPGQPPKLLIYRASKLAS GVPSRFSGSGSGTQFTLTISGVQCDDAATYFCLGVYDDDADNAFGGGTAVVVK |
| 184 | AVVMTQTASPVSAAVGGTVTINCQSSQSVHNNNNLAWYQQKPGQPPKLLIFQASTL ASGVPSRFKGSGSGTQFTLTISDLECDDAAAYYCAGGYSTNTDTFTFGGGTEVVVR |
| 185 | ALVMTQTPASVEAAVGGTVTISCQASEDISSSLAWYQQKPGQPPNLLIYRASNLASGV PSRFKGSGSGTQFTLTISGVQCADAATYYCQAYYYSISDDLYNAFGGGTEVVVK |
| 186 | AVVMTQTASPVSAAVGGTVTISCQASQSVHNNNNLAWYQQKPGQPPKLLIFQASTLA SGVPSRFKGSGSGTEFTLTISDLECDDAAAYYCAGGYSTNTDTFTFGGGTEVVVR |
| 187 | DVVMTQTPASVSAAVGGTVTIKCQASEDIESYLAWYQQKPGQPPKLLIYRASTLASGV PSRFKGSGSGTQFTLTISDLECADAATYYCQCTIYGVNFVPNAFGGGTEVVVK |
| 188 | DVVMTQTPASVSAAVGGTVTIKCQATEDIESFLAWYQQKPGQPPKLLIYRASTLESGVP SRFKGSGSGTEFTLTISDLECADAATYYCQCTVYGVNFVANAFGGGTEVVVR |
| 189 | AIKMTQTPSSVSAAVGGTVTINCRASEDIKSYLAWYQQKPGQPPKLLIYDASDLASGVP SRFKGSGSGTEYTLTISGVQCDDAATYYCQSVWYAGGAAFGGGTEVVVQ |
| 190 | AQVLTQTASPVSAAVGGTVTINCQASQSVYNHKNLAWYQQKPGQPPKLLIYDTSTLAS |

Fig. 4 continued

| | |
|---|---|
| | GVSSRFKGSGSGTQFTLTISGVQCDDAATYYCAGEFSCASADCFAFGGGTEVVVK |
| 191 | DVVMTQTPASVSEPVGGTVTIKCQASQSIGSSLAWYQQKAGQRPKLLIYYVSNLESGVSSRFSGSGSGTEFTLTISGVQCDDAATYYCQSYGYGSGYVFAFGGGTEVVVK |
| 192 | AQVLTQTPSPVSAAVGGTVSISCQSSQSVYGVNELSWYQQKAGQPPKLLIYKAATLASGVPSRFKGSGSGTQFTLTISDVQCDDAATYYCLGNYDCESDDCYAFGGGTEVVVK |
| 193 | DVVMTQTPASVEAPVGGTVTIKCQASQSISNLLAWYQQIPGQSPKLLIYDASDLASGVPSRFKGSGSGTEYTLTISDLECADAATYYCQCTYGSSSSSAYGWAFGGGTEVVVK |
| 194 | AAVLTQTPSPVSAAVGGTVSISCQSSKSVYNNNWLSWFQQKPGQPPKLLIYGASTLASGVPSRFKGSGSGTQFTLTISDVQCDDAATYYCLGSYISSSDNAFGGGTEVVVK |
| 195 | AAVLTQTPSPVSAAVGGTVSISCQSSPSVYNNNRLSWFQQKPGQPPKLLIYYASTLASGVPSRFKGSGSGTQFTLTISDVQCDDAATYYCAGGYSSISDNGFGRGTEVVVK |
| 196 | DVVMTQTLPSVSEPVGGTVTIKCQASQSIGSYLSWYQQKPGQPPKLLIYDASTLASGVPSRFKGGGSGTQFTLTISDLECADAATYYCQGYYYYISNTYGYPFGGGTEVVVK |
| 197 | DVVMTQTPASVSEPVGGTVTIKCQASQNIGNNLAWYQQKPGQPPKLLMYDASDLASRVPSRFSGSGSGTEFTLTISDLECADAATYYCQCTYGYSGYVSAFGGGTEVVVK |
| 198 | ALVMTQTPSPVSAAVGGTVTINCQASEDIYSNLAWFQQKPGQPPKLLIYSASTLASGVSSRFKGSGSGTKFTLTISGLQCDDAATYYCLGVYTYISADNAFGGGTEVVVK |
| 199 | AQVLTQTPSSVSAAVGGTVTINCQASQSLYNNKNLAWYQQKLGQPPKLLIYDVSTLASGVPSRFKGSGSGKQFTLTISGVQCDDAATYYCQGEFSCSSGDCYAFGGGTEVVVK |
| 200 | AAVLTQTPSPVSAAVGGTVSISCQSSKTVYNNNWLAWFQQKPGQPPKLLIYGASTLASGVPSRFKGSGSGTQFTLTISDVQCDDAATYYCLGSYISSSDNGFGGGTEVVVK |
| 201 | AAVLTQTPSPVSAAVGGTVTISCQSSPSVYNNVRLSWFQQKPGQPPKLLIYSASTLASGVPSRFKGSGSGTQFTLTISDVQCDDAATYYCAGGYSDISDNAFGGGTEVVVK |
| 202 | AQVLTQTPSSVSAAVGGTVTISCQSSQSVYSTNLAWYQQKPGQPPKLLIDYASTLASGVPSRFKGSGSGTQFTLTISGVQCDDAAAYYCQGEFNCGSGDCSTFGGGTEVVVK |
| 203 | DVVMTQTPASASAAVGGTVTINCQASENIANHLAWYQQKPGQPPKLLIYSASALASGVPSRFKGSGSGTEFALTISDLECDDAAIYYCQCTFWDINNFGGFGGGTEVVVK |
| 204 | AAVLTQTPSPVSAAVGGTVTIKCQSSQSVYGNNELSWYQQKPGQPPKLLIYDASKLASGVPHRFSGSGSGTQFTLTISGVQCDDAATYYCLGGYDADADNAFGGGTEVVVK |

Fig. 4 continued

| | |
|---|---|
| 205 | AQVLTQTPSSVSAAVGGTVTINCQASQSLYNKKNLAWYQQKLGQPPKLLIYDVSTLAS GVPSRFKGSGSGTQFTLTISDLECGDAAAYFCQGEFSCSSGDCYAFGGGTEVVVK |
| 206 | AQVLTQTASSVSAAVGGSVTISCQSSQSVYGSDALAWFQQRPGQSPKRLIYGASTLAS GISSRFKGSGSGTQFTLTISDLECDDAATYFCAGAYSGNVGTFGGGTEVVVK |
| 207 | AYDMTQTPASVEVAVGGTVTIKCQASQSISSNLAWYQQKSGQPPKLLIYLASTLASGVP SRFKGSGSGTEFTLTISDLECADAATYYCQQTYSGSNVENSFGGGTEVVVK |
| 208 | AIDMTQTPSPVSAAVGDTVTINCQASENIYSFLAWYQQKPGHSPKLLIYSASTLESGVPS RFKGSGSGTQFTLTISDVQCDDAATYYCQQTYIYNNAEDNTFGGGTEVVVK |
| 209 | DVVMTQTPASVEAAVGGTVTIKCQASQSISDYLSWYQQKPGQPPKLLIYRASNLASGV PSRFKASESGTEFTLTISDLECADAATYYCQCTFGATNDDYGNAFGGGTEVVVK |
| 210 | DIVMTQTPASVEAAVGGTVTIKCQASQSISSYLSWYQQKPGQPPKLLIYDASDLASGVS SRFKGSGSGTEFTLTISDLECADAATYYCQCTVGSSGVTGYGNAFGGGTEVVVK |
| 211 | DPVMTQTPASVSEPVGGTVTIKCQASQNINNLLAWYQQKPGQPPKLLIYKASTLASGV SSRFKGSGSGTEFTLTISDLECADAATYYCQNYYGYGLSTNYVVFGGGTEVVVK |
| 212 | AQVLTQTPSSVSAAVGGTVTINCQASQSVYANNYLAWYQQKPGQPPKLLIYKASTLAS GVPSRFSGSGSGTQFTLTINGVQCDDAATYYCQGEFSCSSGDCTAFGGGTEVVVK |
| 213 | DVVMTQTPASVEAAVGGTVTIKCQASESISNYLSWYQQKPGQPPKLLICYDSTLESGVP SRFKGSGSGTDFTLTISDLECADAATYYCQCTAGSINVSYGNAFGGGTEVVVK |
| 214 | AQVLTQTASPVSEPVGGTVTIKCQSSQSVYNNNWLSWFQQKPGQPPKRLIYGASTLAS GVPSRFKGSGSGTHFTLTISDVQCDDAATYYCLGSYDCSSVDCNAFGGGTEVVVK |
| 215 | AAVLTQTPSPVSAAVGGTVTISCQASQSVHKHKNLAWYQQKPGQPPKLLIYEASKLAS GVPPRFSGSGSGTQFTLTMSDLECDDAATYYCAGGYDSTIDTFTFGGGTEVVVK |
| 216 | DVVMTQTPASVEAAVGGTVTIKCQASQSISSYLSWYQQKPGQPPKLLIYRASSLKSGVP SRFKGTGSGTEFTLTISDLECADAATYYCQCTYGSSTSSRSGNAFGGGTEVVVT |
| 217 | DIVMTQTPASVEAAVGGTVTIKCQASQNINNELSWYQQKPGQPPKLLIYKASTLASGV PSRFKGSGSGTQFTLTISDLECADAATYYCQSYYYGISSTYAFYTFGGGTEVVVK |
| 218 | DVVMTQTPASASAAVGGAVTIKCRASEDIESYLAWYQQKPGQPPKLLIYSASSLASGVP SRFKGSGSGTEFTLTISDLECDDAATYYCQCTYWDSSTVGAFGGGTAVVVK |
| 219 | AAVLTQTPSPVSAAVGGTVSISCQSSQSVYNDNDLAWFQQKPGQPPKLLIYGASTLAS |

Fig. 4 continued

| | |
|---|---|
| | GVPSRFKGSGSGTQFTLTISGVQCDDAATYYCSGGYISSSDNAFGGGTEVVVK |
| 220 | DVVMTQTPASVSAAVGGTVTIKCQASESIYSGLAWYQQKPGQPPKLLIYRASTLESGVS SRFKGSGSGTQFTLTISDLECADAATYYCQSTYYGSSGNAFGGGTEVVVK |
| 221 | DIVMTQTPASVSAAVGGTVTINCQASQSISYYLNWYQQKPGQPPKLLIYRASTLASGVP SRFSGSGSGTQFTLTISGVQCDDAATYYCLYGYVTSSNADFAFGGGTEVVVE |
| 222 | AQVLTQTPSSVSAAVGDTVTINCQASQSVYKNNYLAWFQQKPGQPPKRLIYSASTLDS GVSSRFKGSGSGTQFTLTISDVQCDDAATYYCLGTYDCVSADCGAFGGGTEVVVK |
| 223 | AQVLTQTASSVSAAVGGTVTISCQSSQSVYNNNWLGWYQQKPGQPPKLLIYSASTLAS GVPSRFKGSGSGTQFTLTISGVQCYDAATYYCQGTYSNNGWYFAFGGGTEVVVK |
| 224 | DIVMTQTPASVSEPVGGTVTIKCQASEDIYNLLAWYHQKPGQPPKLLIYGASTLASGVP SRFKGSGSGTQFTLTISDLECADAATYYCQSYYYGISSTYAFYTFGGGTEVVVE |
| 225 | AFELTQTPSSVSAAVGGTVTINCQASEDIESYLAWYQQKPGQPPKFLIYGASTLASGVPS RFKGSGSGTEYTLTISDLECADAATYYCQTYYGGINIFTFGGGTEVVVE |
| 226 | AQVLTQTASPVSAAVGSTVTINCQASQSVYSNNYLSWFQQKPGQPPKLLIYDASDLAS GVPSRFKGSGSGTQFTLTISDLECDDAATYYCLGTYDCSSTDCYAFGGGTEVVVK |
| 227 | DVVMTQTPASVSEPVGGTVSLKCQASESIDSYLNWYQQKPGQPPKLLIYGASTLASGV SSRFKGSRSGTEYTLTISDLECADAATYYCQCTVYGVNFVPNAFGGGTEVVVK |
| 228 | ALVMTQTPSSVSAAVGGTVTINCQASQNIYSSLAWYQQKPGQPPKLLIYGASNLESGV PSRFKGSGSGTEFTLTISALECDDAATYYCQGGYYISSTDNAFGGGTEVVVK |
| 229 | AYDMTQTPASVEAVVGGSVTIKCQASQSISYYLAWYQQKPGQRPKLLIYRASTLASGV PSRFKGSGSGTEYTLTISDLECADAATYYCQQGYSSSNVDNAFGGGTEVVVK |
| 230 | AFELTQTPSSVSAAVGGTVTIKCQASQNIYSRLAWYQQKPGQRPKLLIYAASTLASGVP SRFKGNGSGTEFTLTISDLECADAATYYCQGGYYGSSDTVTFGGGTEVVVK |
| 231 | AAVLTQTPSPVSAAVGGTVTISCQSSQSVTDNFLSWFQQKPGQRPKLLIYGASTLASGV PSRFKGSGSGTQFTLTISDVQCDDAATYYCAGGYSGSSDVFAFGGGTEVVVK |
| 232 | AYDMTQTPSSVSAAVGGTVTINCQASEDIESYLAWYQQKPGQPPKLLIYSASTLASGVP SRFKGSGSGTQFTLTISDLECADAATYYCQCTVYGVNYVPNAFGGGTEVVVK |
| 233 | DVVMTQTPASVSAAVGGTVTIKCQASQSIGSSLAWYQQKPGQSPKLLIYSASNLASGV SSRFKGSGSGTEYTLTISDLECADAATYYCQCTYYGGSGDVPFGGGTEVVVK |

Fig. 4 continued

| | |
|---|---|
| 234 | DIVMTQTPASVEAAVGGTVTIKCQASQSISSYLAWYQQKPGQPPKLLIYRTSILESGVPS RFKGSGSGTEFTLTISDLECADAATYYCQCTYGTTNTGHYVGFGGGTEVVVK |
| 235 | DVVMTQTPASVSEPVGGTVTIKCQASQNIGSDLAWYQQKPGQRPKLLIYDASALASG VPSRFSGSGSGTEFTLTISGVQCDDSATYYCQCTYYSGSPHTFGGGTEVVVK |
| 236 | DIVMTQTPASVEAAVGGTVTIKCQASQSISSYLAWYQQKPGQPPKLLIYRASTLASGVP SRFKGSGSGTEFTLTISDLECADAATYYCQSNYGSSSISNYGGGAFGGGTEVVVK |
| 237 | AQVLTQTPASVSAAVRGTVTIKCQASESVVGKNELSWYHQKPGQPPKLLIFGTSTLASG VPSRFSGSGSETQFTLAISDLECGDAATYYCAGGYSGNMYVFGGGTEVVVK |
| 238 | AAVLTQTPSPVSAAVGGTVTISCQASQSVHNNKNLAWYQQKPGQPPKLLIYDVSTVAS GVPSRFKGSGSGTQFTLTISDLECDDAATYYCAGGYGSYTDTFAFGGGTEVVVK |
| 239 | AAVLTQTPSPVSAAVGGTVTIKCQSSQSVYRNNELSWYQQKPGQPPKVLVYDASNLAS GVPDRFSGSGSGTQFTLTISGVQCDDAATYYCLGGYDDDADNTFGGGTEVVVK |
| 240 | DVVMTQTPASVSEPVGGTVTIKCQASEDIESFLAWYQQKPGQPPKLLIYSASTLASGVP SRFKGSGSGTQFTLTIGDLECADAATYFCQCTIYGVNFVPNAFGGGTEVVVK |
| 241 | DVVMTQTPASVSEPVGGTVTIKCQASEDISSRLAWYQQKPGQPPKLLIYRASTLASGVP SRFKGSGSGPEYTLTISDLECADAATYYCQSNYAIISCGAAFGGGTEVVVK |
| 242 | ALVMTQTPSSVSAAVGGTVTINCQASQNIYSNLAWYQQKPGQRPKLLIYGASNLESGV PSRFKGSGSGTEFTLTISDLECDDAATYYCQSAYYSSSAVYAFGGGTEVVVK |
| 243 | AIDMTQTPSSVSAAVGDTVTINCQASENIYSFLAWYQQKPGQRPKLLIYDSSTLASGVP SRFSGSGSGTEFTLTISGIQCDDAATYYCQQTYIYNNAESNAFGGGTEVVVK |
| 244 | AQVLTQTPSPVSAAVGGTVTINCQSSQSVADNNLLAWYQQKPGQPPKLLIYKASTLAS GVPSRFKGSGYGTQFTLTISDLECDDAATYYCVGGYSTSGYAFGGGTEVVVK |
| 245 | AQVLTQTPSPVSAAVGGTVTINCQASQSVYGTNRLAWYQQKPGQPPKLLIYDASTLAS GVPSRFSGSGSGTQFTLTISGVQCDDAATYCCQGEFSCSNGDCIAFGGGTEVVVK |
| 246 | AFELTQTPSSVSAAVGGTVTIKCQASQNIYSKFAWYQQKPGQRPKLLIYSASTLASGVPS RFKGNGSGTEFTLTISDLECADAATYYCQGGYYGSSDTVTFGGGTEVVVK |
| 247 | AYDMTQTPASVEVALGGTVTIKCQASQSIGVSLAWYQQKPGQRPKLLIYSASTLASGVS SRFKGSGSGTEFTLTISGVECADAATYYCQQGYTSSNVDNVFGGGTEVVVK |
| 248 | AQVLTQTASPVSAAVGSTVTINCQASQSVYNNNYLGWFQQKPGQPPKRLIYSASKLES |

Fig. 4 continued

| | |
|---|---|
| | GVPSRFSGSGSGTQFTLTISDVQCEDAATYYCLGSYDCSSADCNVFGGGTEVVVK |
| 249 | DVVMTQTPASVSAAVGGTVTINCQASESIDNWLAWYQQKPGQPPKLLIYSASNLASG VSSRFEGSTSGTQFTLTISDLECADAATYYCQSTFYGVNPVPNAFGGGTEVVVK |
| 250 | AAVLTQTPSPVSAAVGGTVTIKCQSSQSVYSNNNLAWYQQKPGQPPKLLIYDASNLAS GVPDRFSGSGSGTQFTLTISGVQCDDAATYYCLGVYDDDADNAFGGGTEVVVK |
| 251 | DVVMTQTPASVEAAVGGTVTIKCQASQSISSYLSWYQQKPGQPPKLLIYRASSLESGVP SRFKGTGSGTEFTLTISDLECADAATYYCQCTYGSSTSSRSGNAFGGGTEVVVK |
| 252 | DVVMTQTPASVEADVGGTVTIKCQASQSIRSYLAWYQQKPGQPPKVLIYRASTLESGV PSRFKGSGSGTQFTLTISDLECADAATYYCQCTYGSSGSSFLAFGGGTEVVVK |
| 253 | AYDMTQTPASVEVAVGGTVTIKCQASESISVNLAWYQQKSGQPPKLLIYLASTLASGVP SRFKGSGSGTEFTLTISDLECADAATYYCQQTYSGSNVENSFGGGTEVVLK |
| 254 | AAVLTQTPSPVSAAVGGTVSISCQSSESIYKNNYLAWYQQKSGQPPKLLIYRASTLTSGV PSRFKGSGSGTQFTLTISDVQCDDAATYYCAGDYSSSSDNTFGGGTEVVVK |
| 255 | DVVMTQTPASASEPVGGTVTIKCQASQNIYSDFAWYRQKPGQPPKLLIYSASALASGV PSRFKGSGSGTDFTLTISDLECDDAAIYYCQSTYWESNNIGTFGGGTEVVVK |
| 256 | AAVLTQTPSPVSAAVGGTVTISCQASQSVYNHKNLAWYQQKPGQPPKLLIYSASSLAS GVPSRFKGSGSGTQFTLTISDLDCDDAATYYCAGGYSGSADTFAFGGGTEVVVK |
| 257 | AFELTQTPASVEAAVGGTVTIKCQASQSISAYLSWYQQKPGQPPKLLIYDASDLASGVS SRFKGSGSGTEYTLTISGVQCADAATYYCQSYAGISSGVAFGGGTEVVVK |
| 258 | DIVMTQTPASVEAAVGGTVTIKCQASQTITSYLAWYQQKPGQPPKLLIYRASILESGVPS RFKGSGSGTEFTLTISDLECADAATYYCQCTYGTTNTGHYVGFGGGTEVVVK |
| 259 | AQVLTQTPSPVSAAVGGTVTINCQASQSVYNNKNLAWYQQKPGQPPKLLIYDASKLAS GVPLRFSGSGSGTQFTLTISGVQCDDAATYYCAGGYDSSVDTFAFGGGTEVVVK |
| 260 | DTVMTQTPASVEAAVGGTVTIQCQASENIYSLLAWYQQKPGQPPKLLIYRASTLASGV PSRFKGSGSGTEFTLTISDLECADAATYYCQSHYCCSSNYDYIYAFGGGTEVVVK |
| 261 | DPVLTQTPPSASEPAGGTVTIKCQASEDIYSLLAWYQQKPGQPPKLLIYAASTLASGVPS RFKGSGSGTQFTLTISDLECADAATYYCQSYYYSISDSVDYPFGGGTEVVVK |
| 262 | DVVMTQTPASVEAAVGGTVTIKCQASQSISTYLSWYQQKPGQPPKLLIYRATTLESGVP SRFKGTGSGTEFTLTINDLECADAATYYCQCTYGSSASSSYGNAFGGGTEVVVK |

Fig. 4 continued

| | |
|---|---|
| 263 | AQVLTQTPSSVSEPVGGTVTINCQASENIYSSLAWYQQKPGQPPKLLIYDASDLASGVPSRFSGSGLGTEFTLTISGVQCDDAATYYCQTYYPSSVTYAFGGGTEVVVK |
| 264 | AYDMTQTPSSVSAAVGGTVTINCQASESIGSWLAWYQQKPGQPPKLLIYSASSLASGVSSRFGGSTSGTEYTLTISDLECADAATYYCQSTFYGVNPVPTAFGGGTEVVVK |
| 265 | AQVLTQTASPVSAAVGGTVTINCQSSQSVYNNNRLSWFQQKPGQPPKQLIYRSSTLASGVPSRFSGSGSGTQFTLTISDVQCDDAATYYCAGGYSSSSDNAFGGGTEVVVK |
| 266 | AAVLTQTPSPVSAAVGGTVTISCQASQSVYNNNNLAWYQQKPGQPPKLLIYTASSLASGVPSRFKGSGSGTQFTLTISEVQCEDAATYYCQGYYSGYINAFGGGTEVVVK |
| 267 | DIVMTQTPASVEAAVGGTVTIKCQASQSIGSYLSWYQQKPGQPPKLLIYYASDLESGVPSRFKGSGSGTEFTLTISDLECADACTYYCQCTYGSISSSAGNAFGGGTEVVVK |
| 268 | AQVLTQTASPVSAAVGGTVTISCQSSESVYNNNLLSWYKQKPGQPPKLLIYKASTLDSGVPSRFKGSGSGTQFTLTISGVQCDDAATYYCQGGYTDATYAFGGGTEVVVK |
| 269 | AQVLTQTPSPVSATVGGTVTINCQASQSVYNNRLAWYQQKPGQPPKLLIYEASTLTSGVSSRFKGSGSGAQFTLTISGVQCADAATYYCQGEFSCSNGDCIAFGGGTEVVVK |
| 270 | DVVMTQTPASVEAAVGGTVTIKCQASQSISTYSSWYEQKPGQPPKLLIYYASDLESGVPSRFKGSGSGTEFTLTISDLECADAATYYCQCTYGSISSSGNAFGGGTEVVVK |
| 271 | AQVLTQTPSSVSAAVGGTVTISCQSSQSVYASVWLGWYQQKPGQPPKQLIYAASTLASGVPSRFKGSGSGTQFTLTISDLECGDAATYYCAGGYIGDIYAFGGGTEVVVE |
| 272 | DVVMTQTPASVEAAVGGTVTIKCQASQSIYNYLSWYQQKPGQPPKLLIYGASDLASGVPSRFSGSGSGTEFTLTISDLECADAATYYCQCTYGSSRVSSYGDAFGGGTEVVVK |
| 273 | DVVMTQTPVSVSAAVGGTVTINCQASQNIYSYLAWYQQKSGQPPKLLIYDASDLESGVPSRFKGSGSGTEYTLTISDLECADAATYYCQSYYGISAYAFGGGTEVVVK |
| 274 | DIVMTQTPASVSEPVGGTVTIKCQASQSIYSYLAWYQQKPGQRPKLLIYGASTLASGVPSRFKGSGSGTDFALTISDLECADAATYYCQDNYGSSTTYGNSFGGGTEVVVK |
| 275 | DIVMTQTPASVEAAVGGTVTIKCQASESIGSVLAWYQQKPGQSPKLLIGSASTLASGVPSRFKGSGSGTQFTLTISDLECADAATYYCQSYYHSTSGSSYGNTFGGGTEVVVK |
| 276 | ALVMTQTPSSVSAAVGGTVTINCQASQNIYSNLAWYQQKPGQPPKLLIYGASDLESGVPSRFKGSGSGTEYTLTISDLECDDAATYYCQSTYYNISADFYAFGGGTEVVVK |
| 277 | AAVLTQTPSPVSAVVGGTVSISCQSNKNVYDNNALSWYQQKPGQPPKFLIYRASTLAS |

Fig. 4 continued

| | |
|---|---|
| | GVPSRFKGSGSGTQFTLTISDVQCDDAATYYCAGDYISDSDNTFGGGTEVVVK |
| 278 | DIVMTQTPASVSEPVGGTVTIKCQASQSIINYLSWYQQKPGQPPKLLIYRASTLESGVPSRFKGSGSGTEFTLTISDLECADAATYYCQCTYGSSSGSYGGWAFGGGTEVVVK |
| 279 | DIVMTQTPASVSEPVGGTVTIKCQASQSIYSYLSWYQQKPGQPPKLLIYQASILASGVPSQFKGSGSGTDFTLTISDLECADAATYYCQSNYGFSSGSYAFGGGTEVVVK |
| 280 | DVVMTQTPASVEAAVGGTVTIKCQASQSISSWLAWYQQKPGQPPKLLIYRASTLESGVPSRFKGSGSGTEFTLTISDLECADAATYYCQCTYGSLSSTYGWAFGGGTEVVVK |
| 281 | AAVLTQTPSSVSAAVGGTVTINCQSSQSVNNAKNLAWYQQKPGQPPKLLIYDASTLASGVPSRFKGSGSGTQFTLIMSDLECGDAATYFCAGGYDRFIDTFAFGGGTEVVVK |
| 282 | AAVLTQTPSPVSAAVGGTVSISCQSSKSVYDNNWLSWYQQKPGQPPKLLIYQASTLASGVPSRFKGSGSGTQFTLTISDVQCDDAATYYCAGGYITNSDNGFGGGTEVVVK |
| 283 | DVVMTQTPASVSESVGGTVTIKCQASQSIGSSLAWYQQKPGQPPKLLIYYTSTLASGVPSRFSGSGSGTEFTLTTSGVQCDDAATYYCQSYGYGSGYVFAFGGGTEVVVK |
| 284 | AIEMTQTPFSVSAAVGGTVTINCQASENIYRNLAWYQQKPGQPPKLLIYKASTLASGVSSRFKGSGSGTQFTLTIGGVQCDDAATYYCLYSYYIDSNVDFAFGGGTEVVVK |
| 285 | DVVMTQTPASVSEPVGGTVTIKCQASEDIESYLAWYQQKPGQPPKLLIYSASTLASGVPSRFSGSGYGTEFTLTISDLECADAATYYCQCTLYGVNFVPNVFGGGTEVVVK |
| 286 | DVVMTQTPASVSEPVGGTVTIKCQASQSISSWLSWYQQKPGQPPKVLIYDASDLASGVSSRFKGTGAGTEFTLTISDLECADAATYYCQCTVGSSGVTGYGNAFGGGTEVVVK |
| 287 | DVVMTQTPASVSEPVGGTVTIKCQASQSIGSDLAWYQQKPGQPPKLLIYDASSLESGVPSRFKGSGSGTDFTLTISDLECADAATYYCQCTYYGGSPNVFGGGTEVVVK |
| 288 | AIEMTQTPASVEAAVGGTVTIKCQGSQSISSYLSWYQQKPGQPPKLLIYGASTLASGVSSRFKGSGSGTEFTLTISGVECADAATYYCQQGYTTSNVDNTFGGGTEVVVK |
| 289 | AAVLTQTPSPVSAPVGGTVSISCQSSPSVYSVYLSWYQQKPGQPPKLLIYRASTLASGVPSRFKGSGSGTQFTLTISDVQCDDAATYYCAGAYVGSSDNTFGGGTEMVVK |
| 290 | AAVLTQTPSPVSAAVGGTVSISCQSSKSVYNNKWLSWFQQKPGQPPKLLIYGAFTLASGVPSRFRGSGSGTQFTLTISDVQCDDAATYYCAGDYSSNSDDAFGGGTEVVVK |
| 291 | DIVMTQTPASVEAAVGGTVTIKCQASESVGDALAWYQQKPGQPPKLLIYRASTLESGVPSRFKGSGSGTEFTLTISDLECADVATYYCQSYWYTMGNSYGNTFGGGTEVVVK |

Fig. 4 continued

| | |
|---|---|
| 292 | AAVLTQTPSPVSAAVGGTVSISCQSSKTIYNDNWLSWFQQKPGQPPKLLIYGASTLASG VPSRFKGSGSGTQFTLTISDVQCDDAATYYCLGSYINSSDNAFGGGTEVVVK |
| 293 | AIKMTQTPSSVSAAVGGTVTINCRASEDIKSYLAWYQQKPGQPPKLLIYDASDLASGVP SRFKGSGSGTEYTLTISGVQCDDAATYYCQSAYYSSSTDGGAFGGGTEVVVK |
| 294 | ALVMTQTPSSVSAPVGGTVTINCQASQSIYSNLAWYQQKPGQRPKLLIYGASNLESGV PSRFKGSGSGTQFTLTISDLECADAATYCCQGYYYADSDDNIAFGGGTEVVVE |
| 295 | AQVLTQTASPVSAAVGSTVTISCQASQSVYNNNYLAWFQQKPGQPPKLLIYLASTLAS GVPSRFKGSGSGTQFTLTISGVQCGDAATYYCQGYYSTGMFAFGGGTEVVVK |
| 296 | DVVMTQTPSSVSAAVGGTVTINCRASEDIERFLAWYQQKPGQPPKLLIYKASTLASGVP SRFKGSGSGTDFTLTISDLECADAATYYCQCTLYGVNFVPNAFGGGTEVVVK |
| | **HC CDR-H1** |
| 297 | AYAIN |
| 298 | GYDMN |
| 299 | TYAIS |
| 300 | GLVVS |
| 301 | SSYYMC |
| 302 | IYAIS |
| 303 | SSYYMC |
| 304 | MYAIN |
| 305 | SYYYMC |
| 306 | RNAMS |
| 307 | DNYAMC |
| 308 | SGYYMC |
| 309 | GNYYIC |
| 310 | RSYYMC |
| 311 | SMYWMC |
| 312 | SYDMS |
| 313 | SSYWIC |
| 314 | SSYYIC |

Fig. 4 continued

| | |
|---|---|
| 315 | DGYWMC |
| 316 | SYAMS |
| 317 | NYQMT |
| 318 | MYAIN |
| 319 | NYDMN |
| 320 | NYDMN |
| 321 | SNAMI |
| 322 | MYTIN |
| 323 | SNSIS |
| 324 | STYWMS |
| 325 | NYALS |
| 326 | SHATS |
| 327 | TYGVS |
| 328 | SNYYIC |
| 329 | TYAMT |
| 330 | SSYWIC |
| 331 | NYAMS |
| 332 | NYQMT |
| 333 | STYWAC |
| 334 | SYQMT |
| 335 | SSYYMC |
| 336 | SNYYMC |
| 337 | SSYYMC |
| 338 | NWIMS |
| 339 | STYSMC |
| 340 | SGYDMC |
| 341 | STYYTC |
| 342 | SAAMG |
| 343 | SYDMS |

Fig. 4 continued

| | |
|---|---|
| 344 | STYWIC |
| 345 | SSYWIC |
| 346 | SDGIS |
| 347 | SYAIS |
| 348 | SNALG |
| 349 | SYDMS |
| 350 | NYAMG |
| 351 | VYAMS |
| 352 | TYGVS |
| 353 | MYAIN |
| 354 | RYAMS |
| 355 | SYAMG |
| 356 | SSYWIC |
| 357 | NYYMT |
| 358 | SYHMS |
| 359 | TIPMC |
| 360 | DNYAMC |
| 361 | SYHMG |
| 362 | SRYWIY |
| 363 | SYFLT |
| 364 | SYAMS |
| 365 | SNAMC |
| 366 | VYAMS |
| 367 | SYAMG |
| 368 | GSYWNC |
| 369 | SGYDMC |
| 370 | AYGVN |
| 371 | NSYYMC |
| 372 | SNAMC |

Fig. 4 continued

| | |
|---|---|
| 373 | SYAMG |
| 374 | TNGVS |
| 375 | SGYYMC |
| 376 | SGYCLC |
| 377 | SYWMC |
| 378 | SYYYMS |
| 379 | YNTIC |
| 380 | SSYYMC |
| 381 | NYAMS |
| 382 | NYAVG |
| 383 | SSYYMC |
| 384 | SRYYVC |
| 385 | ANAMS |
| 386 | NYHMS |
| 387 | NYGLT |
| 388 | SSYYMC |
| 389 | TYAMS |
| 390 | NYGVS |
| 391 | VSYWIC |
| 392 | SGYDMC |
| 393 | SNAMC |
| 394 | SSYYMC |
| 395 | SSYWIY |
| 396 | RYGVS |
| 397 | NNYYMC |
| 398 | SNYYMC |
| 399 | SYAMS |
| 400 | SSYCMC |
| 401 | SYAMG |

Fig. 4 continued

| | |
|---|---|
| 402 | SGYDMC |
| 403 | DYYMS |
| 404 | SHATS |
| 405 | SGYWIC |
| 406 | SYTMA |
| 407 | SYHMC |
| 408 | GDYDMC |
| 409 | SSYYMC |
| 410 | SYAMS |
| 411 | SYTMT |
| 412 | SKYYMC |
| 413 | SYYIY |
| 414 | SVYDMC |
| 415 | SYHMS |
| 416 | GLVVS |
| 417 | RDAMS |
| 418 | SYWIC |
| 419 | RYAMI |
| 420 | NNYWIC |
| 421 | TYYYMC |
| 422 | SYWMS |
| 423 | RNAAS |
| 424 | NYAMT |
| 425 | SNAIS |
| 426 | VGYYMC |
| 427 | SSYWIC |
| 428 | SSYYMC |
| 429 | NYHMT |
| 430 | SYDMT |

Fig. 4 continued

| | |
|---|---|
| 431 | SSYCVC |
| 432 | SNAMC |
| 433 | GNYYMC |
| 434 | SYHMN |
| 435 | SSYYMC |
| 436 | SYPVN |
| 437 | SYDMS |
| 438 | NYGMT |
| 439 | TYWMS |
| 440 | SYAMG |
| 441 | SSYYMC |
| 442 | SGQDMC |
| 443 | SYNMG |
| 444 | SSYYMC |
| | **HC CDR-H2** |
| 445 | GIANNGPTYYANWAKG |
| 446 | MIYPNSGTNYATWAKG |
| 447 | GISNSGTTYYASWAKG |
| 448 | VIGKSGNTYYASWAKG |
| 449 | CIYAGSSGSTYYASWAKG |
| 450 | GIGNNGIIHYANWAKG |
| 451 | CIYGGSSGKTWYASWAKG |
| 452 | GIANNGPTYYASWAKG |
| 453 | CIYADDATTYYATWAKG |
| 454 | IIRNTGTTWYASWAKG |
| 455 | CIYVGSGSTYYASWAQG |
| 456 | CIYTSSGSTYYASWAKG |
| 457 | CIYAGSSGSTYYASWAKG |
| 458 | CIYAGSSDSTYYASWAKG |

Fig. 4 continued

| | |
|---|---|
| 459 | CIYTGSSGKTHYASWAKG |
| 460 | IIYDSGSTYYANWAKG |
| 461 | CIAAGSGSTYYASWAKG |
| 462 | CIYAGSSGSTYYASWAKG |
| 463 | CIYTGPGGTFYASWAKG |
| 464 | IIHYSGYTAYASWAKG |
| 465 | FIKADGSAYYANWAKG |
| 466 | GIATNGIIHYASWVKG |
| 467 | MIYPNSGTNYASWAKG |
| 468 | MIYPNGGTNYATWAKG |
| 469 | IIYASDSTYYATWAKG |
| 470 | GIATHGIIHYASWVKG |
| 471 | IISSSGSTYYASWAKG |
| 472 | CIVTGRGNTYYANWAKG |
| 473 | FINIIHGAYYASWAKG |
| 474 | FIKTGGSAYYASWAKG |
| 475 | YINTGGSASYATWAKG |
| 476 | CIYTGSTGSTYYASWAKG |
| 477 | IISNSGATAYASWAKG |
| 478 | CIGTSSTISYYASWAKG |
| 479 | IIHYSGYIAYANWAKG |
| 480 | FIKPGGSAYYASWAKG |
| 481 | CIDGGSSGITGYANWAKG |
| 482 | FINTGGSAYYASWAKG |
| 483 | CIYAGSSGSTYYASWAKG |
| 484 | CIYTGSSGSTYYASWAKG |
| 485 | CIHAGSSGAAYYATWAKG |
| 486 | IITTSGNTYYASWAKG |
| 487 | CIYTGSSGGTYYASWAKG |

Fig. 4 continued

| | |
|---|---|
| 488 | CIYTVNDNTWYASWAKG |
| 489 | CIVDGSSGNTYYASWAKG |
| 490 | YISTSGTPYYASWVNG |
| 491 | IIYNSGTTYYANWAKG |
| 492 | CIYTDSSTSTYYASWAKG |
| 493 | CIVGGGGVNTYYANWAKG |
| 494 | FIYPGVGITHYAHSVKG |
| 495 | GVANNGITNYASWARG |
| 496 | YISTGGSAYYATWVNG |
| 497 | IIYDSGSTYYASWAKG |
| 498 | VISSNGGTVYANWAKG |
| 499 | IITFSGNTYYASWAKG |
| 500 | YINIYGRTYYANWAKS |
| 501 | GIANNGPTYYASWAKG |
| 502 | IISSSGNSYYASWAKG |
| 503 | IISSGLTYYASWAKG |
| 504 | CINFGRSGNIYYARWAKG |
| 505 | FIDPYSSPYYASWAKG |
| 506 | VIYGSGSAWYASWAKG |
| 507 | CIYPDYGDTFYATWAKG |
| 508 | CIFGSSGSIAYATWAKG |
| 509 | FITTTGGSYYASWARG |
| 510 | CIDTGSRGFTYYPSWAKG |
| 511 | FMNSGGSTYYASWVNG |
| 512 | MIRSSGITWYASWAKG |
| 513 | CIYAGSRGSAYYASWVNG |
| 514 | IITWSADTYYTSWAKG |
| 515 | INGVSGTTYYATWANG |
| 516 | CIDGEGSGNTYYASWVNG |

Fig. 4 continued

| | |
|---|---|
| 517 | CIDTGDGSTYYASWVNG |
| 518 | SISNSGGTYYASWAKG |
| 519 | CIDAGSVGDTSYATWAKG |
| 520 | CIYNGDGSTYYASWVNG |
| 521 | IISNSGATAYASWAKG |
| 522 | YIFTGGNTYYASWAKG |
| 523 | CIYVGITGSTYYASWAKG |
| 524 | CKHGGASGTTYYATWAKG |
| 525 | CSYAGGSGGTYYASWAKG |
| 526 | CTDGTGGITYYASWAKG |
| 527 | YINTGSSGTTYYASWAKG |
| 528 | CIYAGSSGSTYYASWAKG |
| 529 | FINIIDSTYYTNWAKG |
| 530 | VINAGGSAYYATWAKG |
| 531 | CIYADSSGSTYYASWAKG |
| 532 | CIDAGDGSTDYARWAKG |
| 533 | TIFDTYLTYNANWAKG |
| 534 | FIRTDGSAFYATWAKG |
| 535 | YINNNGRTYYASRAKG |
| 536 | CVYAGSSGSTYYASWAKG |
| 537 | IIDASVTTYYASWAKG |
| 538 | YIDPVFRSAYYASWVNG |
| 539 | CIGGNSGNIYYARWAKG |
| 540 | CIYSSNGLTWYATWAKG |
| 541 | CIVTGSGSTYYASWAKG |
| 542 | GVDGSGGIKWYANWAKG |
| 543 | CFHAGSGSTYYASWVNG |
| 544 | WISSSGSAYYATWAKG |
| 545 | CIYTGSTGSTYYANWAKG |

Fig. 4 continued

| | |
|---|---|
| 546 | CIYAGSSGSSYYASWAKG |
| 547 | IIRRSGATWYANWARG |
| 548 | CIYDGSSDSAYYATWAKG |
| 549 | IITYGGSTYYASWAKG |
| 550 | CIAVYSSGSTYYASWAKG |
| 551 | VVSWNGNTYYASWAKG |
| 552 | FIKSGGSTYYASWAKG |
| 553 | CIDAGSNGSTYYASWARG |
| 554 | VINTGGSAYYASWAKG |
| 555 | FIKADGNTYYATWAKG |
| 556 | CIGAGSSNDTYYASWAKG |
| 557 | CISVGSSGSTYYANWAKG |
| 558 | IIRRSGFTYYASWARG |
| 559 | LISRSGRTYYATWAKG |
| 560 | CIYTGTTGSTYYASWAKY |
| 561 | CIAIINSITYYANWAKG |
| 562 | CIYSDGSGSTYYANWAKG |
| 563 | FIVGTGDTYYASWAKG |
| 564 | VIGKSGSTYYASWAKG |
| 565 | SIVSGSGSTYYASWAKG |
| 566 | CIYAGSSGSTYYASWAKG |
| 567 | IIDIRGTTYYASWAKG |
| 568 | CIVAGSSGRTYYANWAKG |
| 569 | CIHAGSSGSTYYASWAKG |
| 570 | TINAASGATWYASWAKG |
| 571 | IISTGGSTYYATWAKG |
| 572 | IIINTGYTYYASWAKG |
| 573 | HSDIRGSAYYASWAKG |
| 574 | CIYAGSNGSTYYASWAKG |

Fig. 4 continued

| | |
|---|---|
| 575 | CIYADGSGSIYCATWAKG |
| 576 | CIYIGDGNTYYASWAKG |
| 577 | FIKAGGSAGYASWAKG |
| 578 | VISSSDSTYYASWAKG |
| 579 | CIYGGSSGGTYYASWAKG |
| 580 | CIYTSSSGSTYYASWVNG |
| 581 | CIYADNSGSTYYASWAKG |
| 582 | VIYGSGSTDYASWAKG |
| 583 | CIYSDSSGSTYNANWVKG |
| 584 | VIGNRGSTDYASWAKG |
| 585 | TIYDGGSTYYASWTKG |
| 586 | IINIIDNTYYASWAKG |
| 587 | TISTGGSAYYASWAKS |
| 588 | YINRGNTYYANWAKG |
| 589 | CIHAGSSGSAYYASWAKG |
| 590 | CIYGGDGNTYYASWAKG |
| 591 | YIWSGGSAYYASWAKG |
| 592 | CIYAGSSGSTYYASWAKG |
| | **HC CDR-H3** |
| 593 | FPPGTNGGTDYFNI |
| 594 | DSGWGAFDP |
| 595 | FPPGSNSGTDYFNI |
| 596 | NISGSAV |
| 597 | DLGAGYAGYGYASDFNL |
| 598 | FPPGSNSGTDYFNI |
| 599 | DNYDWYFNL |
| 600 | FPPGSNSGTDYFNI |
| 601 | RDADYVGFIWAYYFNL |
| 602 | GNPGWAST |

Fig. 4 continued

| | |
|---|---|
| 603 | GVVIGNAYSMAHFSL |
| 604 | RLNYVTYPAYGYGYFNL |
| 605 | DKPAGGSSYTL |
| 606 | GGGIIYTQNL |
| 607 | AGSVGYGYDTAYFNL |
| 608 | TLNTLPFNI |
| 609 | DLGDDGYAYGL |
| 610 | GTGSSHYTSNL |
| 611 | DLNGADSGSAL |
| 612 | GGDADNFYYNI |
| 613 | DFYAGSSGNVNGDI |
| 614 | FPPGSNGGTAYFNI |
| 615 | DSGWGAFDP |
| 616 | DSGWGAFDP |
| 617 | GYSDIDI |
| 618 | FPPGSNGGTAYFNI |
| 619 | GLGRGEYTSNDAFDP |
| 620 | GSSDEIALDL |
| 621 | GPYYVGSEYVFDP |
| 622 | MFYAGDSGHYLHL |
| 623 | NNL |
| 624 | GGYSYGGAVSL |
| 625 | GRSGGWDALDP |
| 626 | EDYAGGTDYYFRL |
| 627 | GGDADNFYYNI |
| 628 | DFYAGSSGNVNGDI |
| 629 | ELDYFNL |
| 630 | DFYAGSSGNVNGDI |
| 631 | GAGSNGDFNL |

Fig. 4 continued

| | |
|---|---|
| 632 | GAGSYGGAVRL |
| 633 | DGYDDYGDPFNL |
| 634 | ISAGSDSYIIDNI |
| 635 | DAGNSGYYINL |
| 636 | LYKL |
| 637 | PYVGYGYATDL |
| 638 | DSYAGDYAFNL |
| 639 | THNTLPFYI |
| 640 | GSGGSDYFNL |
| 641 | DLGADGYAYHL |
| 642 | DPIYDDYGGRLDL |
| 643 | FPPGSNGGTDYFNI |
| 644 | DSYAGDYAFNL |
| 645 | ARNTLPFNI |
| 646 | GLYSASGWSYCFDI |
| 647 | FDFLVGLTYAGVL |
| 648 | NGASGTYYSSLYI |
| 649 | FPPGSNSGTDYFNI |
| 650 | GSGWDL |
| 651 | GLGAASATWDI |
| 652 | DKAGDSYYFNL |
| 653 | GVAVGDI |
| 654 | GILVSDL |
| 655 | GPIMVVSPSYFNF |
| 656 | SYYSGGYKYVYVFDL |
| 657 | GIAVASL |
| 658 | LDTYDDYDL |
| 659 | MFYAGDSGHYFDL |
| 660 | DSDYDDYGNSYYGMDP |

Fig. 4 continued

| | |
|---|---|
| 661 | EYVGSQGYFNL |
| 662 | FDYLVGGTWAGVL |
| 663 | GVGDTTDTQLDL |
| 664 | DPSAWGGLDL |
| 665 | YNNGWDYFNL |
| 666 | GSL |
| 667 | RYGAGSGYFISPNL |
| 668 | EYVDSQGYFNL |
| 669 | GRSGGWDAFDP |
| 670 | FDI |
| 671 | DTGNSNYQFNL |
| 672 | DDVSVGDANYPYTAFDL |
| 673 | EAYSSANSYYDL |
| 674 | DPTAAGGVYFDL |
| 675 | GSGYSKFRL |
| 676 | DRGDTDISL |
| 677 | GPYYVNNENVFDP |
| 678 | SYAGNRYDFAI |
| 679 | GPYSFDF |
| 680 | GDAYRDDYASDL |
| 681 | YIGSVGYRRMDI |
| 682 | MFYAGDSGHYFDL |
| 683 | NGAGGYYYSSLYI |
| 684 | DRGGTDISL |
| 685 | SSSTYAYGFDP |
| 686 | KGYFHYFNL |
| 687 | DRAGNSYYFNL |
| 688 | VWSL |
| 689 | GYDGYGYVLVL |

Fig. 4 continued

| | |
|---|---|
| 690 | DPTAAGGVYFDL |
| 691 | GSGSIYYTPSYFDL |
| 692 | SDI |
| 693 | DDKVEHGYGL |
| 694 | SMEAYGYAGYAMPGYYFNL |
| 695 | DSDYDDYGDSYYGMDP |
| 696 | DYDTYDYDGYTYAAGFDL |
| 697 | GLGGASTTWDI |
| 698 | DIITDSVWITRLDL |
| 699 | FDYLVGDTYAGVL |
| 700 | MFYAGDSSGNYLHL |
| 701 | EGSSAYPSYFNF |
| 702 | SYGGNRYDFNI |
| 703 | MFYAGHTSGHYFDL |
| 704 | GFDYTYGDAGYTYSTSHYFNL |
| 705 | EGADYQGHFNL |
| 706 | DSDYDDYGNSYYGMDP |
| 707 | EIGSGYDAPYYFNL |
| 708 | DDRVEHGYGL |
| 709 | DLSSSIYDMDL |
| 710 | VLNGWGEYYFNL |
| 711 | GVAAGDI |
| 712 | NISGSAV |
| 713 | GGDGYGYVLVL |
| 714 | GISYALL |
| 715 | GGVGHEVNNL |
| 716 | KLSDWDYGYFNL |
| 717 | GYAGYYGYGYPTPSWLDL |
| 718 | GGTTGSNYYGMDP |

Fig. 4 continued

| | |
|---|---|
| 719 | GIRF |
| 720 | VLGAGSSYYTSYDRLDL |
| 721 | IADVNTQLDL |
| 722 | GAGYAGYGFNL |
| 723 | GNAGSYWDIYYGMDL |
| 724 | GSGGYFVDNL |
| 725 | MFYAGDSGHYFDL |
| 726 | DHPAFSTVDLDI |
| 727 | DAGSSGYYINL |
| 728 | YNNGWDYFNL |
| 729 | HKPAGGSSYIL |
| 730 | GILVSNL |
| 731 | GTYPFTL |
| 732 | GSGYGTGWDAFDP |
| 733 | GSTNMEFWF |
| 734 | ADYYPDTTGWYLNI |
| 735 | DGDSYFKL |
| 736 | DSYGGDYAFNL |
| 737 | DGYDDYGDPFNL |
| 738 | LHYSPYGDAGYPYVSFNL |
| 739 | NGASGTFDI |
| 740 | GGGSGGVDNNL |
| | **LC CDR-L1** |
| 741 | QASQSLYNNKNLA |
| 742 | QSSQSVYDKKWLG |
| 743 | QASQSLYNNKNLA |
| 744 | QSSESVYNNNLLS |
| 745 | QASQSVSNLLA |
| 746 | QASQSLYNNKNLA |

Fig. 4 continued

| | |
|---|---|
| 747 | QASEDIESYLA |
| 748 | QASQSLYNNKNLG |
| 749 | QASQTISSYLA |
| 750 | QSSQSVYDNNALA |
| 751 | QSSQNVDRNNRLA |
| 752 | QASQSIGSNLA |
| 753 | QASEDIESYLA |
| 754 | QASEDIESYLA |
| 755 | QASQNIYDNLA |
| 756 | QSSPSVYNNNRLS |
| 757 | QASQNIGNNLA |
| 758 | QASEDIESYLA |
| 759 | QASQNINSWLS |
| 760 | QSSQSVYSNNHLA |
| 761 | QSSQIVHNNNNLA |
| 762 | QASQSLYNKKNLA |
| 763 | QSSQSVYDNKWLG |
| 764 | QSSQSVYDNKWLG |
| 765 | QSSKSVFDNNWLS |
| 766 | QASQSLYNKKNLA |
| 767 | QASETIYSYLN |
| 768 | QSSQNIYNKNQLS |
| 769 | QASQSIGGSLA |
| 770 | QSSQSVNNNKNLA |
| 771 | QASQNIGSTLA |
| 772 | QASEDIETYLA |
| 773 | QASEDIENYLA |
| 774 | QSSQSVDNNWLS |
| 775 | QSSQSVYSNNHLA |

Fig. 4 continued

| | |
|---|---|
| 776 | QSSQSVHNNNNLA |
| 777 | QASEDISSSLA |
| 778 | QASQSVHNNNNLA |
| 779 | QASEDIESYLA |
| 780 | QATEDIESFLA |
| 781 | RASEDIKSYLA |
| 782 | QASQSVYNHKNLA |
| 783 | QASQSIGSSLA |
| 784 | QSSQSVYGVNELS |
| 785 | QASQSISNLLA |
| 786 | QSSKSVYNNNWLS |
| 787 | QSSPSVYNNNRLS |
| 788 | QASQSIGSYLS |
| 789 | QASQNIGNNLA |
| 790 | QASEDIYSNLA |
| 791 | QASQSLYNNKNLA |
| 792 | QSSKTVYNNNWLA |
| 793 | QSSPSVYNNVRLS |
| 794 | QSSQSVYSTNLA |
| 795 | QASENIANHLA |
| 796 | QSSQSVYGNNELS |
| 797 | QASQSLYNKKNLA |
| 798 | QSSQSVYGSDALA |
| 799 | QASQSISSNLA |
| 800 | QASENIYSFLA |
| 801 | QASQSISDYLS |
| 802 | QASQSISSYLS |
| 803 | QASQNINNLLA |
| 804 | QASQSVYANNYLA |

Fig. 4 continued

| | |
|---|---|
| 805 | QASESISNYLS |
| 806 | QSSQSVYNNNWLS |
| 807 | QASQSVHKHKNLA |
| 808 | QASQSISSYLS |
| 809 | QASQNINNELS |
| 810 | RASEDIESYLA |
| 811 | QSSQSVYNDNDLA |
| 812 | QASESIYSGLA |
| 813 | QASQSISYYLN |
| 814 | QASQSVYKNNYLA |
| 815 | QSSQSVYNNNWLG |
| 816 | QASEDIYNLLA |
| 817 | QASEDIESYLA |
| 818 | QASQSVYSNNYLS |
| 819 | QASESIDSYLN |
| 820 | QASQNIYSSLA |
| 821 | QASQSISYYLA |
| 822 | QASQNIYSRLA |
| 823 | QSSQSVTDNFLS |
| 824 | QASEDIESYLA |
| 825 | QASQSIGSSLA |
| 826 | QASQSISSYLA |
| 827 | QASQNIGSDLA |
| 828 | QASQSISSYLA |
| 829 | QASESVVGKNELS |
| 830 | QASQSVHNNKNLA |
| 831 | QSSQSVYRNNELS |
| 832 | QASEDIESFLA |
| 833 | QASEDISSRLA |

Fig. 4 continued

| | |
|---|---|
| 834 | QASQNIYSNLA |
| 835 | QASENIYSFLA |
| 836 | QSSQSVADNNLLA |
| 837 | QASQSVYGTNRLA |
| 838 | QASQNIYSKFA |
| 839 | QASQSIGVSLA |
| 840 | QASQSVYNNNYLG |
| 841 | QASESIDNWLA |
| 842 | QSSQSVYSNNNLA |
| 843 | QASQSISSYLS |
| 844 | QASQSIRSYLA |
| 845 | QASESISVNLA |
| 846 | QSSESIYKNNYLA |
| 847 | QASQNIYSDFA |
| 848 | QASQSVYNHKNLA |
| 849 | QASQSISAYLS |
| 850 | QASQTITSYLA |
| 851 | QASQSVYNNKNLA |
| 852 | QASENIYSLLA |
| 853 | QASEDIYSLLA |
| 854 | QASQSISTYLS |
| 855 | QASENIYSSLA |
| 856 | QASESIGSWLA |
| 857 | QSSQSVYNNNRLS |
| 858 | QASQSVYNNNNLA |
| 859 | QASQSIGSYLS |
| 860 | QSSESVYNNNLLS |
| 861 | QASQSVYNNRLA |
| 862 | QASQSISTYSS |

Fig. 4 continued

| | |
|---|---|
| 863 | QSSQSVYASVWLG |
| 864 | QASQSIYNYLS |
| 865 | QASQNIYSYLA |
| 866 | QASQSIYSYLA |
| 867 | QASESIGSVLA |
| 868 | QASQNIYSNLA |
| 869 | QSNKNVYDNNALS |
| 870 | QASQSIINYLS |
| 871 | QASQSIYSYLS |
| 872 | QASQSISSWLA |
| 873 | QSSQSVNNAKNLA |
| 874 | QSSKSVYDNNWLS |
| 875 | QASQSIGSSLA |
| 876 | QASENIYRNLA |
| 877 | QASEDIESYLA |
| 878 | QASQSISSWLS |
| 879 | QASQSIGSDLA |
| 880 | QGSQSISSYLS |
| 881 | QSSPSVYSVYLS |
| 882 | QSSKSVYNNKWLS |
| 883 | QASESVGDALA |
| 884 | QSSKTIYNDNWLS |
| 885 | RASEDIKSYLA |
| 886 | QASQSIYSNLA |
| 887 | QASQSVYNNNYLA |
| 888 | RASEDIERFLA |
| | **LC CDR-L2** |
| 889 | DVSTLAS |
| 890 | KASTLAS |

Fig. 4 continued

| | |
|---|---|
| 891 | DVSTLAS |
| 892 | TTSSLAS |
| 893 | GASNLES |
| 894 | DASTLAS |
| 895 | DASDLAS |
| 896 | DVSTLAS |
| 897 | GASTLAS |
| 898 | ETSTLAS |
| 899 | YASILAS |
| 900 | KASTLAS |
| 901 | QASKLAS |
| 902 | SASTLAS |
| 903 | GASNLES |
| 904 | YASTLAS |
| 905 | YASTLAS |
| 906 | GASNLAS |
| 907 | KASTLAS |
| 908 | RASKLAS |
| 909 | QASTLAS |
| 910 | DASTLTS |
| 911 | SASTLAS |
| 912 | KASTLAS |
| 913 | KASTLAS |
| 914 | DASTLAS |
| 915 | SASTLAS |
| 916 | EASKLAS |
| 917 | SASNLAS |
| 918 | DTSTLAS |
| 919 | GASTLSS |

Fig. 4 continued

| | |
|---|---|
| 920 | RASTLAS |
| 921 | SASTLAS |
| 922 | TTSKLAS |
| 923 | RASKLAS |
| 924 | QASTLAS |
| 925 | RASNLAS |
| 926 | QASTLAS |
| 927 | RASTLAS |
| 928 | RASTLES |
| 929 | DASDLAS |
| 930 | DTSTLAS |
| 931 | YVSNLES |
| 932 | KAATLAS |
| 933 | DASDLAS |
| 934 | GASTLAS |
| 935 | YASTLAS |
| 936 | DASTLAS |
| 937 | DASDLAS |
| 938 | SASTLAS |
| 939 | DVSTLAS |
| 940 | GASTLAS |
| 941 | SASTLAS |
| 942 | YASTLAS |
| 943 | SASALAS |
| 944 | DASKLAS |
| 945 | DVSTLAS |
| 946 | GASTLAS |
| 947 | LASTLAS |
| 948 | SASTLES |

Fig. 4 continued

| | |
|---|---|
| 949 | RASNLAS |
| 950 | DASDLAS |
| 951 | KASTLAS |
| 952 | KASTLAS |
| 953 | YDSTLES |
| 954 | GASTLAS |
| 955 | EASKLAS |
| 956 | RASSLKS |
| 957 | KASTLAS |
| 958 | SASSLAS |
| 959 | GASTLAS |
| 960 | RASTLES |
| 961 | RASTLAS |
| 962 | SASTLDS |
| 963 | SASTLAS |
| 964 | GASTLAS |
| 965 | GASTLAS |
| 966 | DASDLAS |
| 967 | GASTLAS |
| 968 | GASNLES |
| 969 | RASTLAS |
| 970 | AASTLAS |
| 971 | GASTLAS |
| 972 | SASTLAS |
| 973 | SASNLAS |
| 974 | RTSILES |
| 975 | DASALAS |
| 976 | RASTLAS |
| 977 | GTSTLAS |

Fig. 4 continued

| | |
|---|---|
| 978 | DVSTVAS |
| 979 | DASNLAS |
| 980 | SASTLAS |
| 981 | RASTLAS |
| 982 | GASNLES |
| 983 | DSSTLAS |
| 984 | KASTLAS |
| 985 | DASTLAS |
| 986 | SASTLAS |
| 987 | SASTLAS |
| 988 | SASKLES |
| 989 | SASNLAS |
| 990 | DASNLAS |
| 991 | RASSLES |
| 992 | RASTLES |
| 993 | LASTLAS |
| 994 | RASTLTS |
| 995 | SASALAS |
| 996 | SASSLAS |
| 997 | DASDLAS |
| 998 | RASILES |
| 999 | DASKLAS |
| 1000 | RASTLAS |
| 1001 | AASTLAS |
| 1002 | RATTLES |
| 1003 | DASDLAS |
| 1004 | SASSLAS |
| 1005 | RSSTLAS |
| 1006 | TASSLAS |

Fig. 4 continued

| | |
|---|---|
| 1007 | YASDLES |
| 1008 | KASTLDS |
| 1009 | EASTLTS |
| 1010 | YASDLES |
| 1011 | AASTLAS |
| 1012 | GASDLAS |
| 1013 | DASDLES |
| 1014 | GASTLAS |
| 1015 | SASTLAS |
| 1016 | GASDLES |
| 1017 | RASTLAS |
| 1018 | RASTLES |
| 1019 | QASILAS |
| 1020 | RASTLES |
| 1021 | DASTLAS |
| 1022 | QASTLAS |
| 1023 | YTSTLAS |
| 1024 | KASTLAS |
| 1025 | SASTLAS |
| 1026 | DASDLAS |
| 1027 | DASSLES |
| 1028 | GASTLAS |
| 1029 | RASTLAS |
| 1030 | GAFTLAS |
| 1031 | RASTLES |
| 1032 | GASTLAS |
| 1033 | DASDLAS |
| 1034 | GASNLES |
| 1035 | LASTLAS |

Fig. 4 continued

| | |
|---|---|
| 1036 | KASTLAS |
| | **LC CDR-L3** |
| 1037 | QGEFSCSSGDCYA |
| 1038 | AGGYSGNIWS |
| 1039 | QGEFSCSSGDCYA |
| 1040 | QGGYTDATYA |
| 1041 | QSGYYT |
| 1042 | QGEFSCGSGDCYA |
| 1043 | QSYYYGSSYVVA |
| 1044 | QGEFSCSSGDCYA |
| 1045 | LYSYYTSNSADNT |
| 1046 | AGGYNSGSDAA |
| 1047 | QGYYSGDINV |
| 1048 | QSYYGTSNSYGDA |
| 1049 | QCTLYGVNFVPNV |
| 1050 | QCILYGVNFVPNT |
| 1051 | QCSYDGGSYVPNA |
| 1052 | AGGYSTISDNA |
| 1053 | QCTFYGSGYVAA |
| 1054 | QCGIYGVNFVPNV |
| 1055 | QQGAGWNNLDNA |
| 1056 | LGVYDDDADNA |
| 1057 | AGGYSTNTDTYI |
| 1058 | QGEFSCSAGDCYA |
| 1059 | AGGYSGNIWS |
| 1060 | AGGYSGNIWS |
| 1061 | AGIYSSDSDNA |
| 1062 | QGEFSCSSGDCYA |
| 1063 | QQGYSGRNVENT |

Fig. 4 continued

| | |
|---|---|
| 1064 | LGGYISSSDTT |
| 1065 | QCTYYDDSYDVP |
| 1066 | AGGYSSSADTFA |
| 1067 | QSNYGSNSGGYVFP |
| 1068 | QCTLYGVNFVANA |
| 1069 | QSYYDGAVTFT |
| 1070 | LGGYDSMSADCFA |
| 1071 | LGVYDDDADNA |
| 1072 | AGGYSTNTDTFT |
| 1073 | QAYYYSISDDLYNA |
| 1074 | AGGYSTNTDTFT |
| 1075 | QCTIYGVNFVPNA |
| 1076 | QCTVYGVNFVANA |
| 1077 | QSVWYAGGAA |
| 1078 | AGEFSCASADCFA |
| 1079 | QSYGYGSGYVFA |
| 1080 | LGNYDCESDDCYA |
| 1081 | QCTYGSSSSSAYGWA |
| 1082 | LGSYISSSDNA |
| 1083 | AGGYSSISDNG |
| 1084 | QGYYYYISNTYGYP |
| 1085 | QCTYGYSGYVSA |
| 1086 | LGVYTYISADNA |
| 1087 | QGEFSCSSGDCYA |
| 1088 | LGSYISSSDNG |
| 1089 | AGGYSDISDNA |
| 1090 | QGEFNCGSGDCST |
| 1091 | QCTFWDINNFGG |
| 1092 | LGGYDADADNA |

Fig. 4 continued

| | |
|---|---|
| 1093 | QGEFSCSSGDCYA |
| 1094 | AGAYSGNVGT |
| 1095 | QQTYSGSNVENS |
| 1096 | QQTYIYNNAEDNT |
| 1097 | QCTFGATNDDYGNA |
| 1098 | QCTVGSSGVTGYGNA |
| 1099 | QNYYGYGLSTNYVV |
| 1100 | QGEFSCSSGDCTA |
| 1101 | QCTAGSINVSYGNA |
| 1102 | LGSYDCSSVDCNA |
| 1103 | AGGYDSTIDTFT |
| 1104 | QCTYGSSTSSRSGNA |
| 1105 | QSYYYGISSTYAFYT |
| 1106 | QCTYWDSSTVGA |
| 1107 | SGGYISSSDNA |
| 1108 | QSTYYGSSGNA |
| 1109 | LYGYVTSSNADFA |
| 1110 | LGTYDCVSADCGA |
| 1111 | QGTYSNNGWYFA |
| 1112 | QSYYYGISSTYAFYT |
| 1113 | QTYYGGINIFT |
| 1114 | LGTYDCSSTDCYA |
| 1115 | QCTVYGVNFVPNA |
| 1116 | QGGYYISSTDNA |
| 1117 | QQGYSSSNVDNA |
| 1118 | QGGYYGSSDTVT |
| 1119 | AGGYSGSSDVFA |
| 1120 | QCTVYGVNYVPNA |
| 1121 | QCTYYGGSGDVP |

Fig. 4 continued

| | |
|---|---|
| 1122 | QCTYGTTNTGHYVG |
| 1123 | QCTYYSGSPHT |
| 1124 | QSNYGSSSISNYGGGA |
| 1125 | AGGYSGNMYV |
| 1126 | AGGYGSYTDTFA |
| 1127 | LGGYDDDADNT |
| 1128 | QCTIYGVNFVPNA |
| 1129 | QSNYAIISCGAA |
| 1130 | QSAYYSSSAVYA |
| 1131 | QQTYIYNNAESNA |
| 1132 | VGGYSTSGYA |
| 1133 | QGEFSCSNGDCIA |
| 1134 | QGGYYGSSDTVT |
| 1135 | QQGYTSSNVDNV |
| 1136 | LGSYDCSSADCNV |
| 1137 | QSTFYGVNPVPNA |
| 1138 | LGVYDDDADNA |
| 1139 | QCTYGSSTSSRSGNA |
| 1140 | QCTYGSSGSSFLA |
| 1141 | QQTYSGSNVENS |
| 1142 | AGDYSSSSDNT |
| 1143 | QSTYWESNNIGT |
| 1144 | AGGYSGSADTFA |
| 1145 | QSYAGISSGVA |
| 1146 | QCTYGTTNTGHYVG |
| 1147 | AGGYDSSVDTFA |
| 1148 | QSHYCCSSNYDYIYA |
| 1149 | QSYYYSISDSVDYP |
| 1150 | QCTYGSSASSSYGNA |

Fig. 4 continued

| | |
|---|---|
| 1151 | QTYYPSSVTYA |
| 1152 | QSTFYGVNPVPTA |
| 1153 | AGGYSSSSDNA |
| 1154 | QGYYSGYINA |
| 1155 | QCTYGSISSSAGNA |
| 1156 | QGGYTDATYA |
| 1157 | QGEFSCSNGDCIA |
| 1158 | QCTYGSISSSSGNA |
| 1159 | AGGYIGDIYA |
| 1160 | QCTYGSSRVSSYGDA |
| 1161 | QSYYGISAYA |
| 1162 | QDNYGSSTTYGNS |
| 1163 | QSYYHSTSGSSYGNT |
| 1164 | QSTYYNISADFYA |
| 1165 | AGDYISDSDNT |
| 1166 | QCTYGSSSGSYGGWA |
| 1167 | QSNYGFSSGSYA |
| 1168 | QCTYGSLSSTYGWA |
| 1169 | AGGYDRFIDTFA |
| 1170 | AGGYITNSDNG |
| 1171 | QSYGYGSGYVFA |
| 1172 | LYSYYIDSNVDFA |
| 1173 | QCTLYGVNFVPNV |
| 1174 | QCTVGSSGVTGYGNA |
| 1175 | QCTYYGGSPNV |
| 1176 | QQGYTTSNVDNT |
| 1177 | AGAYVGSSDNT |
| 1178 | AGDYSSNSDDA |
| 1179 | QSYWYTMGNSYGNT |

Fig. 4 continued

| | |
|---|---|
| 1180 | LGSYINSSDNA |
| 1181 | QSAYYSSSTDGGA |
| 1182 | QGYYYADSDDNIA |
| 1183 | QGYYSTGMFA |
| 1184 | QCTLYGVNFVPNA |
| 1205 | QSTLYGVNFVPNV |
| 1206 | QSTIYGVNFVPNA |

Fig. 4 continued

Fig. 5

| Antibody | EC50 (ng/mL) |
|---|---|
| MAB-17-0127 | 3,1 |
| MAB-17-0119 | 4,5 |
| MAB-17-0200 | 3,8 |
| MAB-17-0193 | 3,4 |
| MAB-17-0201 | 4 |
| MAB-17-0212 | 3,4 |
| MAB-17-0218 | 3,9 |
| MAB-17-0225 | 3,1 |
| MAB-17-0223 | 2,1 |

Fig. 6

| Antibody | EC50 (ng/mL) |
|---|---|
| MAB-17-0127 | 5,1 |
| MAB-17-0119 | 8,3 |
| MAB-17-0200 | 2,7 |
| MAB-17-0193 | 4,3 |
| MAB-17-0201 | 3,9 |
| MAB-17-0212 | 3,5 |
| MAB-17-0218 | 4,8 |
| MAB-17-0225 | 2,6 |
| MAB-17-0223 | 1,7 |

Fig. 7

| HEK-Blue-IL18™ NF-κB signalling inhibition | |
|---|---|
| Antibody | EC50 (µg/mL) (1/2 Max) |
| MAB-17-0127 | 12,2 |
| MAB-17-0119 | > 50 |
| MAB-17-0200 | 17,6 |
| MAB-17-0193 | 43,5 |
| MAB-17-0201 | 3,2 |
| MAB-17-0212 | 18,3 |
| MAB-17-0218 | 14,1 |
| MAB-17-0225 | 5,6 |
| MAB-17-0223 | 7,2 |
| MAB1181 | > 50 |

Fig. 8

| A-549_IL18Rβ_IL1R9 IL-6 release inhibition | |
|---|---|
| Antibody | EC50 (ng/mL) |
| MAB-17-0127 | 1131 |
| MAB-17-0119 | 6350 |
| MAB-17-0200 | 617 |
| MAB-17-0193 | 2023 |
| MAB-17-0201 | 133 |
| MAB-17-0212 | 790 |
| MAB-17-0218 | 1810 |
| MAB-17-0225 | 725 |
| MAB-17-0223 | 710 |
| MAB-17-0545 | 180 |
| MAB-17-0547 | 3890 |
| MAB1181 | 16220 |

Figs. 9A-9B

| A: KG-1 IFN-γ release inhibition at 1,4 µg/ml antibody concentration | | |
|---|---|---|
| Antibody [1,4µg/ml] | IFN-γ (pg/mL) | StDev (pg/ml) |
| MAB-17-0127 | 190 | 112 |
| MAB-17-0119 | 387 | 65 |
| MAB-17-0200 | 50 | 18 |
| MAB-17-0193 | 258 | 139 |
| MAB-17-0201 | 19 | 7 |
| MAB-17-0212 | 394 | 35 |
| MAB-17-0218 | 64 | 11 |
| MAB-17-0225 | 46 | 27 |
| MAB-17-0223 | 48 | 14 |
| MAB1181 | 377 | 159 |
| No mAB | > 1000 | n.d. |

| B: KG-1 IFN-γ release inhibition | |
|---|---|
| Antibody | EC50 (ng/mL) |
| MAB-17-0201 | 41,3 |
| MAB-17-0223 | 425,3 |
| MAB-17-0545 | 68 |
| MAB-17-0547 | 235,8 |

Fig. 10

| Antibody Alias | Heavy chain sequences | | | |
|---|---|---|---|---|
| | HC VR | CDR_H1 | CDR_H2 | CDR_H3 |
| MAB-17-0119 | EVQLEESGGRLVQPGTSLRLSCAVSGFSLNSYDMSWVRQAPGKGLE<br>YVGIIYNSGTTYYANWAKGRFTISKDTSKTTLYLQMNSLRAEDTAT<br>YFCARTHNTLPFYIWGQGTLVTVSS<br>(SEQ ID NO: 1185) | SYDMS<br>(SEQ ID NO: 343) | IIYNSGTTYYANWAKG<br>(SEQ ID NO: 491) | THNTLPFYI<br>(SEQ ID NO: 639) |
| MAB-17-0127 | EVQLVESGGGLVQPGGSLRLSCAASGFSFSSSYYMCWVRQAPGKGL<br>EWVACIYAGSSGSTYYASWAKGRFTISKDISKTTLYLQMNSLRAED<br>TAVYFCARGGGSGGVDNNLWGQGTLVTVSS<br>(SEQ ID NO: 1186) | SSYYMC<br>(SEQ ID NO: 444) | CIYAGSSGSTYYASWAKG<br>(SEQ ID NO: 592) | GGGSGGVDNNL<br>(SEQ ID NO: 740) |
| MAB-17-0193 | EVQLEESGGGLVQPGGSLRLSCAASGFSFNNNYYMCWVRQAPGKGL<br>EWVACIYTGSTGSTYYANWAKGRFTISKDLSKTTLYLQMNSLRAED<br>TATYFCARDDKVEHGYGLWGQGTLVTVSS<br>(SEQ ID NO: 1187) | NNYYMC<br>(SEQ ID NO: 397) | CIYTGSTGSTYYANWAKG<br>(SEQ ID NO: 545) | DDKVEHGYGL<br>(SEQ ID NO: 693) |
| MAB-17-0200 | EVQLEESGGRLVQPGTSLRLSCAASGFSLSSNSISWVRQAPGKGLE<br>WVGIISSSGSTYYASWAKGRFTISKDASKTTLYLQMNSLRAEDTAT<br>YFCAKGLGRGEYTSNDAFDPWGQGTLVTVSS<br>(SEQ ID NO: 1188) | SNSIS<br>(SEQ ID NO: 323) | IISSSGSTYYASWAKG<br>(SEQ ID NO: 471) | GLGRGEYTSNDAFDP<br>(SEQ ID NO: 619) |
| MAB-17-0201 | EVQLEESGGDLVQPGGSLRLSCAASGFSFNGNYYICWVRQAPGKGL<br>EWVACIYAGSSGSTYYASWAKGRFTISRDTSKNTLYLQMNSLRAED<br>TAVYFCVRDKPAGGSSYTLWGQGTLVTVSS<br>(SEQ ID NO: 1189) | GNYYIC<br>(SEQ ID NO: 309) | CIYAGSSGSTYYASWAKG<br>(SEQ ID NO: 457) | DKPAGGSSYTL<br>(SEQ ID NO: 605) |
| MAB-17-0212 | EVQLEESGGDLVQPGGSLRLSCAASGFDFSSNYYMCWVRQAPGKGL<br>EWVACIYTGSSGSTYYASWAKGRFTISKDTSKNTLYLQMNSLRAED<br>TAVYFCARGAGSYGGAVRLWGQGTLVTVSS<br>(SEQ ID NO: 1190) | SNYYMC<br>(SEQ ID NO: 336) | CIYTGSSGSTYYASWAKG<br>(SEQ ID NO: 484) | GAGSYGGAVRL<br>(SEQ ID NO: 632) |
| MAB-17-0218 | EVQLEESGGDLVQPGGSLRLSCAASGFSFSRSYYMCWVRQAPGKGL<br>EWVACIYAGSSDSTYYASWAKGRFTISRDTSKNTLYLQMNSLRAED<br>TAVYFCARGGGIIYTQNLWGQGTLVTVSS<br>(SEQ ID NO: 1191) | RSYYMC<br>(SEQ ID NO: 310) | CIYAGSSDSTYYASWAKG<br>(SEQ ID NO: 458) | GGGIIYTQNL<br>(SEQ ID NO: 606) |

Fig. 10 Continued

| | Heavy chain sequences | | | |
|---|---|---|---|---|
| Antibody Alias | HC VR | CDR_H1 | CDR_H2 | CDR_H3 |
| MAB-17-0223 | EVQLEESGGDLVQPGGSLRLSCAASGFSFSSSYYMCWVRQAPGKGLEWVACIYAGSSGSTYYASWAKGRFTISRDNSKNTLYLQMNSLRAEDTAVYFCARGAGSNGDFNLWGQGTLVTVSS (SEQ ID NO:1192) | SSYYMC (SEQ ID NO: 335) | CIYAGSSGSTYYASWAKG (SEQ ID NO: 483) | GAGSNGDFNL (SEQ ID NO: 631) |
| MAB-17-0225 | EVQLEESGGDLVQPGGSLRLSCAASGFSFSSSYYMCWVRQAPGKGLEWVACVYAGSSGSTYYASWAKGRFTISRDNSKNTLYLQMNSLRAEDTAVYFCARDRGGTDISLWGQGTLVTVSS (SEQ ID NO: 1193) | SSYYMC (SEQ ID NO: 388) | CVYAGSSGSTYYASWAKG (SEQ ID NO: 536) | DRGGTDISL (SEQ ID NO: 684) |
| MAB-17-0545 | Same as MAB-17-0201 (SEQ ID NO: 1189) | (SEQ ID NO: 309) | (SEQ ID NO: 457) | (SEQ ID NO: 605) |
| MAB-17-0547 | Same as MAB-17-0223 (SEQ ID NO: 1192) | (SEQ ID NO: 335) | (SEQ ID NO: 483) | (SEQ ID NO: 631) |

| | Light chain sequences | | | |
|---|---|---|---|---|
| Antibody Alias | LC VR | CDR_H1 | CDR_H2 | CDR_H3 |
| MAB-17-0119 | DIVMTQSPSSLSASVGDRVTITCQSSPSVYNNNRLSWFQQKPGQAPKLLIYYASTLASGVPSRFSGSGSGTDFTLTISSLQPEDFATYYCAGGYSSISDNGFGQGTKVVIK (SEQ ID NO: 1194) | QSSPSVYNNNRLS (SEQ ID NO: 787) | YASTLAS (SEQ ID NO: 935) | AGGYSSISDNG (SEQ ID NO: 1083) |
| MAB-17-0127 | DIQMTQSPSSLSASVGDRVTITCRASEDIERFLAWYQQKPGQAPKLLIYKASTLASGVPSRFSGSGSGTDFTLTISSLQPEDFATYYCQCTLYGVNFVPNAFGGGTKVVIK (SEQ ID NO: 1195) | RASEDIERFLA (SEQ ID NO: 888) | KASTLAS (SEQ ID NO: 1036) | QCTLYGVNFVPNA (SEQ ID NO: 1184) |
| MAB-17-0193 | DIQMTQSPSSLSASVGDRVTITCQASESIDNWLAWYQQKPGQAPKLLIYSASNLASGVPSRFSGSGSGTDFTLTISSLQPEDFATYYCQSTFYGVNPVPNAFGQGTKVVIK (SEQ ID NO: 1196) | QASESIDNWLA (SEQ ID NO: 841) | SASNLAS (SEQ ID NO: 989) | QSTFYGVNPVPNA (SEQ ID NO: 1137) |

Fig. 10 Continued

| | Light chain sequences | | | |
|---|---|---|---|---|
| Antibody Alias | LC VR | CDR_H1 | CDR_H2 | CDR_H3 |
| MAB-17-0200 | DIQMTQSPSSLSASVGDRVTITCQASETIYSYLNWYQQKPGQAPKL<br>LIYSASTLASGVPSRFSGSGSGTDFTLTISSLQPEDFATYYCQQGY<br>SGRNVENTFGQGTKVVIK<br>(SEQ ID NO: 1197) | QASETIYSYLN<br>(SEQ ID NO: 767) | SASTLAS<br>(SEQ ID NO: 915) | QQGYSGRNVENT<br>(SEQ ID NO: 1063) |
| MAB-17-0201 | DIQMTQSPSSLSASVGDRVTITCQASEDIESYLAWYQQKPGQAPKL<br>LIYQASKLASGVPSRFSGSGSGTDFTLTISSLQPEDFATYYCQCTL<br>YGVNFVPNVFGGGTKVVIK<br>(SEQ ID NO: 1198) | QASEDIESYLA<br>(SEQ ID NO: 753) | QASKLAS<br>(SEQ ID NO: 901) | QCTLYGVNFVPNV<br>(SEQ ID NO: 1049) |
| MAB-17-0212 | DIQMTQSPSSLSASVGDRVTITCQATEDIESFLAWYQQKPGQAPKL<br>LIYRASTLESGVPSRFSGSGSGTDFTLTISSLQPEDFATYYCQCTV<br>YGVNFVANAFGGGTKVVIK<br>(SEQ ID NO: 1199) | QATEDIESFLA<br>(SEQ ID NO: 780) | RASTLES<br>(SEQ ID NO: 928) | QCTVYGVNFVANA<br>(SEQ ID NO: 1076) |
| MAB-17-0218 | DIQMTQSPSSLSASVGDRVTITCQASEDIESYLAWYQQKPGQAPKL<br>LIYSASTLASGVPSRFSGSGSGTDFTLTISSLQPEDFATYYCQCIL<br>YGVNFVPNTFGGGTKVVIK<br>(SEQ ID NO: 1200) | QASEDIESYLA<br>(SEQ ID NO: 754) | SASTLAS<br>(SEQ ID NO: 902) | QCILYGVNFVPNT<br>(SEQ ID NO: 1050) |
| MAB-17-0223 | DIQMTQSPSSLSASVGDRVTITCQASEDIESYLAWYQQKPGQAPKL<br>LIYRASTLASGVPSRFSGSGSGTDFTLTISSLQPEDFATYYCQCTI<br>YGVNFVPNAFGGGTKVVIK<br>(SEQ ID NO: 1201) | QASEDIESYLA<br>(SEQ ID NO: 779) | RASTLAS<br>(SEQ ID NO: 927) | QCTIYGVNFVPNA<br>(SEQ ID NO: 1075) |
| MAB-17-0225 | DIQMTQSPSSLSASVGDRVTITCQASEDIESFLAWYQQKPGQAPKL<br>LIYSASTLASGVPSRFSGSGSGTDFTLTISSLQPEDFATYFCQCTI<br>YGVNFVPNAFGGGTKVVIK<br>(SEQ ID NO: 1202) | QASEDIESFLA<br>(SEQ ID NO: 832) | SASTLAS<br>(SEQ ID NO: 980) | QCTIYGVNFVPNA<br>(SEQ ID NO: 1128) |
| MAB-17-0545 | DIQMTQSPSSLSASVGDRVTITCQASEDIESYLAWYQQKPGQAPKL<br>LIYQASKLASGVPSRFSGSGSGTDFTLTISSLQPEDFATYYCQSTL<br>YGVNFVPNVFGGGTKVVIK<br>(SEQ ID NO: 1203) | Same as MAB-17-<br>0201<br>(SEQ ID NO: 753) | Same as MAB-17-<br>0201<br>(SEQ ID NO: 901) | QSTLYGVNFVPNV<br>(SEQ ID NO: 1205) |
| MAB-17-0547 | DIQMTQSPSSLSASVGDRVTITCQASEDIESYLAWYQQKPGQAPKL<br>LIYRASTLASGVPSRFSGSGSGTDFTLTISSLQPEDFATYYCQSTI<br>YGVNFVPNAFGGGTKVVIK<br>(SEQ ID NO: 1204) | Same as MAB-17-<br>0223<br>(SEQ ID NO: 779) | Same as MAB-17-<br>0223<br>(SEQ ID NO: 927) | QSTIYGVNFVPNA<br>(SEQ ID NO: 1206) |

ANTIBODIES SPECIFICALLY BINDING TO HUMAN IL-1R7

FIELD OF INVENTION

The present invention relates to monoclonal antibodies or antigen-binding fragments thereof that specifically bind to human IL-1R7. The invention also relates to uses of said antibodies and to pharmaceutical compositions comprising them.

BACKGROUND

IL-1R7 is a coreceptor for IL-18 signaling, which is also known as IL-18 receptor β-chain. IL-18 is classified as one of the members of the IL-1 cytokine superfamily, which acts as an important regulator of innate and acquired immune responses (Garcia et al., 2003; Dinarello et al., 2013). It plays effector and regulatory roles in a variety of early inflammatory responses and is known to be expressed at the sites of chronic inflammation, in autoimmune diseases, in a variety of cancers, and in the context of numerous infectious diseases (Lebel-Binay et al., 2000; Diakowska et al., 2006; Kinjo et al., 2002; Fabbi et al., 2015).

The IL-18 family of cytokines are synthesized as precursor molecules and cleaved by the enzyme caspase-1 before or during release from the cell. After release from the cell, signaling transduction of IL-18 occurs through receptor-binding. One of its main receptors is IL-1R5, also known as IL-18 receptor α-chain. More specifically, a receptor complex consisting of IL-1R5 and IL-1R7 is known to transduce IL-18 signaling (Debets et al., 2000).

Upon ligand binding, the pro-inflammatory IL-18 signaling cascade continues, leading to activation and transcription of numerous target genes which affect the activation of diverse cell types such as macrophages, dendritic cells, mast cells, B and T cells, fibroblasts and many other cell types.

The IL-1 and IL-18 family of cytokines have many parallels, for example the structure of their receptors and the signal transduction pathways utilized. For example, IL-1R5 serves the same function for the IL-18 pathway as IL-1R3 does for the IL-1 family signaling pathways.

Most IL-1 family members signaling occurs through heterodimeric plasma membrane receptors, and most of them utilize a common signaling chain (IL-1R3) (Riva et al., 2012). Blocking of IL-1R3 leads to problematic results, since IL-1R3 is a receptor for several interleukins and therefore fulfills various functions (pro-inflammatory as well as anti-inflammatory signaling cascades). Similar to IL-1R3, it is extremely difficult to find antibodies that effectively inhibit the signaling pathway by blocking human IL-1R7. This is demonstrated by the fact that no such effective antibodies are disclosed in the literature.

There are many antibodies described that inhibit the effects of IL-18 through direct binding to IL-18 (US 2014/0112915; US 2014/0004128; US 2013/0101595). Nevertheless, previous experience with direct inhibition of IL-18 produced conflicting results. Therefore, other methods for inhibiting the IL-18 signaling pathway were required, for example by blocking its receptor IL-1R5. For this purpose, several antibodies are known (WO 2007/096396).

However, IL-1R5 can act as a receptor not only for IL-18 but also for the anti-inflammatory cytokine IL-37. Binding of IL-18 to IL-1R5 leads to pro-inflammatory actions, while binding of IL-37 to IL-1R5 leads to anti-inflammatory actions (Mologora et. al., 2016). Thus, the blocking of the IL-1R5 receptor can be counterproductive in the treatment of patients with an anti-IL-18 modality as it may interfere with other mechanisms that could be beneficial to such patients. The inhibition of IL-1R7 remains therefore the only selective anti-inflammatory intervention.

Moreover, even though IL-1R5 is a functional component of the IL-18 receptor, its binding affinity for IL-18 is relatively low and in addition, IL-1R7 is required for high affinity binding of IL-18. Until now, the known antibodies that block IL-1R5 and IL-1R7 with the aim of inhibiting IL-18 mediated signaling, do not act with a potency that would allow their use as therapeutic antibodies.

Expression of IL-1R7 was demonstrated in Th1 cells, elucidating the role of IL-1R7 in Th1-mediated pathologies (Debets el al., 2000). Debets et al. developed an anti-IL-1R7 mouse antibody (anti-IL-1R7 mAb: TC30-28E3, anti-IL18 mAb: C18.6), which effectively inhibited IL-18 responses in vitro, demonstrating a critical role of IL-1R7 in IL-18 action. However, the antibody developed by Debets and colleagues is a rat-anti-mouse antibody and was only tested in vitro. The development of a potent antibody with high specificity against human IL-1R7 has proved to be difficult and was not achieved up till now.

Therefore, there is a need for effective antibodies against the human IL-1R7. This need is solved with the antibodies of the present invention.

SUMMARY OF INVENTION

A first aspect of the present invention provides monoclonal antibodies that specifically bind to human IL-1R7, or an antigen-binding fragment thereof or a polypeptide that contains at least a portion of said antibody that is sufficient to confer IL-1R7 binding specificity. The invention also relates to compositions comprising said antibodies and methods of treating an IL-18 mediated disease.

Definitions

The term "rabbit" according to the invention means an animal of the members of the taxonomic order Lagomorpha, which includes the families (hares and rabbits) and Ochotonidae (pikas), preferably of genus *Oryctolagus*.

The term "antibody" encompasses the various forms of antibody structures including, but not being limited to, whole antibodies and antibody fragments as long as it shows the properties according to the invention.

The term "rabbit monoclonal antibody" according to the invention means a monoclonal antibody produced by immunizing a rabbit and isolated from an antibody producing cell of said rabbit as well as such an antibody which is further modified, preferably a humanized antibody, a chimeric antibody, a fragment thereof, or a further genetically engineered and recombinant produced antibody as long as the characteristic properties according to the invention are retained. Preferably the antibody is from a B cell or a rabbit hybridoma cell of said rabbit.

The term "antibody producing cell" according to the invention means a rabbit B cell which produce antibodies, preferably a B cell or rabbit hybridoma cell.

"Native antibodies" are usually heterotetrameric glycoproteins composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH)

followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software.

The "constant domains (constant parts)" are not involved directly in binding of an antibody to an antigen, but exhibit e.g. also effector functions. The heavy chain constant region gene fragment that corresponds to human IgG1 is called γ1 chain. The heavy chain constant region gene fragment that correspond to human IgG3 is called γ3 chain. Human constant γ heavy chains are described in detail by Kabat, E. A. et al., Sequences of Proteins of Immunological Interest, 5th ed., Public Health Service, National Institutes of Health, Bethesda, Md. (1991), and by Brueggemann, M., et al., J. Exp. Med. 166 (1987) 1351-1361; Love, T. W., et al., Methods Enzymol. 178 (1989) 515-527.

Constant domains of IgG1 or IgG3 type are glycosylated at Asn297. "Asn 297" according to the invention means amino acid asparagine located at about position 297 in the Fc region; based on minor sequence variations of antibodies, Asn297 can also be located some amino acids (usually not more than +3 amino acids) upstream or downstream.

The term "antibody effector function(s)" or "effector function" as used herein refers to a function contributed by an Fc effector domain(s) of an IgG (e.g., the Fc region of an immunoglobulin). Such function can be effected by, for example, binding of an Fc effector domain(s) to an Fc receptor on an immune cell with phagocytic or lytic activity or by binding of an Fc effector domain(s) to components of the complement system. Typical effector functions are ADCC, ADCP and CDC.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

"Antibody-dependent cell-mediated cytotoxicity" and "ADCC" refer to a cell mediated reaction in which nonspecific cytotoxic cells that express FcRs (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch, and Kinet, Annu. Rev. Immunol 9 (1991) 457-492. The term "Antibody-dependent cellular phagocytosis" and "ADCP" refer to a process by which antibody-coated cells are internalized, either in whole or in part, by phagocytic immune cells (e.g., macrophages, neutrophils and dendritic cells) that bind to an immunoglobulin Fc region.

"C1q" is a polypeptide that includes a binding site for the Fc region of an immunoglobulin. C1q together with two serine proteases, C1r and C1s, forms the complex C1, the first component of the complement dependent cytotoxicity (CDC) pathway. Human C1q can be purchased commercially from, e.g. Quidel, San Diego, Calif.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions.

Unless otherwise specified herein, numbering of amino acid residues in the Fc region or constant region is according to the EU numbering system, also called the EU index, as described in Kabat, et al., Sequences of Proteins of Immunological Interest, 5th Ed. Public Health Service, National Institutes of Health, Bethesda, Md. (1991).

A "variant Fc region" comprises an amino acid sequence which differs from that of a "native" or "wildtype" sequence Fc region by virtue of at least one "amino acid modification" as herein defined.

The term "Fc-variant" as used herein refers to a polypeptide comprising a modification in the Fc domain. The modification can be an addition, deletion, or substitution. Substitutions can include naturally occurring amino acids and non-naturally occurring amino acids. Variants may comprise non-natural amino acids.

The term "Fc region-containing polypeptide" refers to a polypeptide, such as an antibody or immunoadhesin (see definitions below), which comprises an Fc region.

The terms "Fc receptor" or "FcR" are used to describe a receptor that binds to the Fc region of an antibody. A FcR which binds an IgG antibody (a gamma receptor) includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see review in Daeron, M., Annu. Rev. Immunol. 15 (1997) 203-234). FcRs are reviewed in Ravetch, and Kinet, Annu. Rev. Immunol 9 (1991) 457-492; Capel, et al., Immunomethods 4 (1994) 25-34; and de Haas, et al., J. Lab. Clin. Med. 126 (1995) 330-41. Other FcRs, including those to be identified in the future, are encompassed by the term "FcR" herein. The term also includes the neonatal receptor, FcRn, which is responsible for the transfer of maternal IgGs to the fetus (Guyer, et al., J. Immunol. 117 (1976) 587 and Kim, et al., J. Immunol. 24 (1994) 249).

By "IgG Fc ligand" as used herein is meant a molecule, preferably a polypeptide, from any organism that binds to the Fc region of an IgG antibody to form an Fc/Fc ligand complex. Fc ligands include but are not limited to FcγRs, FcRn, Clq, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis, et al., Immunological Reviews 190 (2002) 123-136, entirely incorporated by reference). Fc ligands may include undiscovered molecules that bind Fc. Particular IgG Fc ligands are FcRn and Fc gamma receptors. By "Fc ligand" as used herein is meant a molecule, preferably a polypeptide, from any organism that binds to the Fc region of an antibody to form an Fc/Fc ligand complex.

By "Fc gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIA, FcγRIB, and FcγRIC; FcγRII (CD32), including isoforms FcγRIIA (including allotypes H131 and R131), FcγRIIB (including FcγRIIB-I and FcγRIIB-2), and FcγRIIc; and FcγRIII (CD 16), including isoforms FcγRIIIA (including allotypes V158 and F158) and FcγRIIIb (including allotypes FcγRIIB-NAI and FcγRIIB-NA2) (Jefferis, et al., Immunol Lett 82(2002) 57-65, entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD 16), and FCYRIII-2 (CD 16-2), as well as any undiscovered mouse FcγRs or FcγR isoforms or allotypes.

By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin.

An "immunoconjugate" means an antibody conjugated to one or more cytotoxic agents, such as a chemotherapeutic agent, a drug, a growth inhibitory agent, a toxin, another antibody or a radioactive isotope.

The terms "monoclonal antibody" or "monoclonal antibody composition" as used herein refer to a preparation of antibody molecules of a single amino acid composition.

The term "humanized antibody" or "humanized version of an antibody" refers to antibodies for which both heavy and light chains are humanized as a result of antibody engineering. A humanized chain is typically a chain in which the V-region amino acid sequence has been changed so that, analyzed as a whole, is closer in homology to a human germline sequence than to the germline sequence of the species of origin. Humanization assessment is based on the resulting amino acid sequence and not on the methodology per se.

The terms "specifically binding, against target, or anti-target antibody", as used herein, refer to binding of the antibody to the respective antigen (target) or antigen-expressing cell, measured by ELISA, wherein said ELISA preferably comprises coating the respective antigen to a solid support, adding said antibody under conditions to allow the formation of an immune complex with the respective antigen or protein, detecting said immune complex by measuring the Optical Density values (OD) using a secondary antibody binding to an antibody according to the invention and using a peroxidase-mediated color development.

The term "antigen" according to the invention refers to the antigen used for immunization or a protein comprising said antigen as part of its protein sequence. For example, for immunization a fragment of the extracellular domain of a protein (e.g. the first 20 amino acids) can be used and for detection/assay and the like the extracellular domain of the protein or the full-length protein can be used.

The term "specifically binding" or "specifically recognized" herein means that an antibody exhibits appreciable affinity for an antigen and, preferably, does not exhibit significant cross-reactivity.

An antibody that "does not exhibit significant cross-reactivity" is one that will not appreciably bind to an undesirable other protein. Specific binding can be determined according to any art-recognized means for determining such binding, e.g. by competitive binding assays such as ELISA.

The "variable region (or domain) of an antibody according to the invention" (variable region of a light chain (VL), variable region of a heavy chain (VH)) as used herein denotes each of the pair of light and heavy chain regions which are involved directly in binding the antibody to the antigen. The variable light and heavy chain regions have the same general structure and each region comprises four framework (FR) regions whose sequences are widely conserved, connected by three complementary determining regions, CDRs.

The term "antigen-binding portion of an antibody" when used herein refer to the amino acid residues of an antibody which are responsible for antigen-binding. The antigen-binding portion of an antibody comprises preferably amino acid residues from the "complementary determining regions" or "CDRs". The CDR sequences are defined according to Kabat et al, Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable region. For example, a heavy chain variable region may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "cancer" as used herein may be, for example, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers. Preferably such cancer is a breast cancer, colon cancer, lung cancer, or pancreatic cancer.

The term "IL-18 related diseases" as used herein includes, but is not limited to, rheumatoid arthritis, osteoarthritis, juvenile chronic arthritis, Lyme arthritis, psoriatic arthritis, reactive arthritis, spondyloarthropathy, lupus (e.g., Systemic Lupus Erythematosus, and Lupus Nephritis), Crohn's disease, ulcerative colitis, inflammatory bowel disease, insulin dependent diabetes mellitus, thyroiditis, asthma, allergic diseases, psoriasis, psoriasis type 1, psoriasis type 2, scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult respiratory distress syndrome, alopecia, alopecia greata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease, arteriosclerosis, atopic allergy, autoimmune bullous disease, pemphigus vulgaris, pemphigus foliaceus, pemphigoid, linear IgA disease, autoimmune haemolytic anemia, Coombs positive haemolytic anemia, acquired pernicious anemia, juvenile pernicious anemia, myalgic encephalitis/Royal Free Disease. chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency, common variable hypogammaglobulinemia, dilated cardiomyopathy, female infertility, ovarian failure, premature ovarian failure, fibrotic lung disease, cryptogenic fibrosing alveolitis, post inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, post-infectious interstitial lung disease, gouty arthritis, autoimmune hepatitis, type-1 autoimmune hepatitis, classical autoimmune or lupoid hepatitis, type-2 autoimmune hepatitis, anti-LKM antibody hepatitis, autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopaenia, autoimmune neutropenia, renal disease NOS, glomerulonephritides, microscopic vasulitis of the kidneys, Lyme disease, discoid lupus erythematosus, male infertility idiopathic or NOS, sperm autoimmunity, all subtypes of multiple sclerosis, sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjogren's syndrome, Takayasu's disease/arteritis, autoimmune thrombocytopenia, idiopathic thrombocytopenia, autoimmune thyroid disease, hyperthyroidism, goitrous autoimmune hypothyroidism or Hashimoto's disease, atrophic autoimmune hypothyroidism, primary myxoedema, phacogenic uveitis, primary vasculitis, vitiligo, acute liver disease, chronic liver diseases, allergy and asthma, mental disorders, depression, schizophrenia, Th2 Type and Th1 Type mediated diseases, Chronic Obstructive Pulmonary Disease (COPD), inflammatory, autoimmune and bone diseases. The term "IL-18 related diseases" further comprises cancer induced modalities such as tumor-induced chronic inflammation.

DETAILED DESCRIPTION OF THE INVENTION

The present invention relates to a monoclonal antibody, or an antigen-binding fragment thereof, capable of binding to human IL-1R7. As outlined above, the development of such antibodies had proven to be very difficult and before the existence of the antibodies of this invention, there were no antibodies available that bind to the human version of IL-1R7. Even less, antibodies existed that bind to human IL-1R7 with a specificity and efficiency sufficient to allow for their use as therapeutic agents. The possibility to develop and obtain such antibodies was not expected, due to the previous difficulties experienced in the generation such antibodies.

Thus, it was very surprising for the inventors to find that the antibodies of the present invention show the beneficial and advantageous characteristics as described and further detailed below.

In one aspect of the invention, an antibody or antigen-binding fragment comprises a VH region selected from the group of VH regions comprising the CDR regions selected from the group consisting of a CDR1H region of SEQ ID NO: 297+n, a CDR2H region of SEQ ID NO: 445+n and a CDR3H region of SEQ ID NO: 593+n, wherein n is a number selected from the group consisting of 0 to 147, and a VL region selected from the group of VL regions comprising CDR regions selected from the group consisting of a CDR1L region of SEQ ID NO: 741+m, a CDR2L region of SEQ ID NO: 889+m and a CDR3L region of SEQ ID NO: 1037+m, wherein m is a number selected from the group consisting of 0 to 147 or of SEQ ID NO: 1205 or 1206, wherein the CDRs of the VH or VL chains may comprise any one or more amino acid mutations that does not diminish their activity according to the invention.

In another aspect of the present invention, an antibody or antigen-binding fragment comprises a VH region selected from the group of VH regions comprising three CDRs that are at least 90% identical to a group of three CDR regions selected from the groups consisting of a CDR1H region of SEQ ID NO: 297+n, a CDR2H region of SEQ ID NO: 445+n and a CDR3H region of SEQ ID NO: 593+n, wherein n is a number selected from the group consisting of 0 to 147, and a VL region selected from the group of VL regions comprising three CDRS that are at least 90% identical to a group of three CDR regions selected from the groups consisting of a CDR1L region of SEQ ID NO: 741+m, a CDR2L region of SEQ ID NO: 889+m and a CDR3L region of SEQ ID NO: 1037+m, wherein m is a number selected from the group consisting of 0 to 147 or of SEQ ID NO: 1205 and 1206.

Preferably, the CDRs have a sequence identity to their respective SEQ ID NOs of at least 91%, preferably 92%, 93%, 94%, 95%, 96%, 97%, 98%, or 99%. Most favorable effects were found for antibodies or antigen-binding fragments that comprise a VH region selected from the group of VH regions comprising a CDR1H region of SEQ ID NO: 297+n, a CDR2H region of SEQ ID NO: 445+n and a CDR3H region of SEQ ID NO: 593+n, wherein n is a number selected from the group consisting of 0 to 147, and a VL region selected from the group of VL regions comprising a CDR1L region of SEQ ID NO: 741+m, a CDR2L region of SEQ ID NO: 889+m and a CDR3L region of SEQ ID NO: 1037+m, wherein m is a number selected from the group consisting of 0 to 147 or of SEQ ID NO: 1205 and 1206.

In another aspect of the invention, the antibody or antigen-binding fragment comprises a heavy chain variable (VH) region is at least 85% identical to a VH region selected from the group consisting of VH regions of SEQ ID NO: 1 to 148 and of SEQ ID NO: 1185-1193.

The antibody according to the invention may also comprise a light chain variable (VL) region that is at least 85% identical to a VL region selected from the group consisting of VL regions of SEQ ID NO: 149 to 296 and of SEQ ID NO: 1194-1204.

It is preferred that the antibody comprises a VH region that is at least 85% identical to a VH region of SEQ ID NO: 1+n and a VL region that is at least 85% identical to a VL region of SEQ ID NO: 149+m, wherein n and m are numbers selected from the group consisting of 0 to 147. Further it is preferred, that the antibody comprises a VH region that is at least 85% identical to a VH region of SEQ ID NO: 1185-1193, and a VL region that is at least 85% identical to a VL region of SEQ ID NO: 1194-1204.

Further preferred, the antibody comprises a VH region that is at least 86% identical, preferably 87%, 88%, 89%, 90%, 91%, 92%, 93% 94%, 95%, 96%, 97%, 98%, or 99% identical to a VH region of SEQ ID NO: 1+n or SEQ ID NO: 1185-1193 and a VL region that is at least 86% identical, preferably 87%, 88%, 89%, 90%, 91%, 92%, 93% 94%, 95%, 96%, 97%, 98%, or 99% identical to a VL region of SEQ ID NO: 149+m or SEQ ID NO: 1194-1204, wherein n and m are numbers selected from the group consisting of 0 to 147.

It is most preferred that such antibody comprises a VH region selected from the group consisting of VH regions of SEQ ID NO: 1+n and SEQ ID NO: 1185-1193 and a VL region selected from the group consisting of VL regions of SEQ ID NO: 149+m and SEQ ID NO: 1194-1204, wherein n and m are number selected from the group consisting of 0 to 147.

In the above embodiments, n and m are preferably the same.

Particularly good effects were achieved when said VH region is selected from the group consisting of VH regions of SEQ ID NO: 1 to 148 and SEQ ID NO: 1185-1193 and that said VL region is selected from the group consisting of VL regions of SEQ ID NO: 149 to 296 and SEQ ID NO: 1194-1204.

Especially preferred are antibodies including one of the following combinations of six CDRs of the heavy and light chain sequences as shown in a single row of the following table representing the SEQ ID NOs:

| CDRH1 | CDRH2 | CDRH3 | CDRL1 | CDRL2 | CDRL3 |
|---|---|---|---|---|---|
| 343 | 491 | 639 | 787 | 935 | 1083 |
| 444 | 592 | 740 | 888 | 1036 | 1184 |
| 397 | 545 | 693 | 841 | 989 | 1137 |
| 323 | 471 | 619 | 767 | 915 | 1063 |
| 309 | 457 | 605 | 753 | 901 | 1049 |
| 336 | 484 | 632 | 780 | 928 | 1076 |
| 310 | 458 | 606 | 754 | 902 | 1050 |
| 335 | 483 | 631 | 779 | 927 | 1075 |
| 388 | 536 | 684 | 832 | 980 | 1128 |
| 309 | 457 | 605 | 753 | 901 | 1205 |
| 335 | 483 | 631 | 779 | 927 | 1206 |

The favorable effects of such antibodies are, for example, the particular high selectivity for binding to human IL-1R7 and their potency in inhibiting IL-18 signaling. This high specificity and selectivity in binding to IL-1R7 (and not to IL-1R5) is shown in FIG. 2 and FIG. 3. The efficiency in IL-18 signaling inhibition can be seen in FIG. 1, as example.

According to the invention, a monoclonal antibody, or an antigen-binding fragment thereof is capable of binding to human IL-1R7 and exhibits an inhibition of IL-18 signaling of at least 30%, in an IL-18 functional assay as described in Example 1.

Preferably, said inhibition of IL-18 signaling is at least 35%, preferably 40%, 50%, 60%, 70%, 80% and most preferred 90%, in an IL-18 functional assay.

In another embodiment according to the invention, a monoclonal antibody, or an antigen-binding fragment thereof is capable of binding to human IL-1R7 and exhibits a binding specificity to cells expressing human IL-1R7 receptor of more than 10.000 RFU (Relative Fluorescence Units) in an huIL-1R7 cell binding assay as described in Example 2.

Preferably, said binding specificity is more than 20.000 RFU, more preferably more than 30.000 RFU, 40.000 RFU, 50.000 RFU, 60.000 RFU, 70.000 RFU, 80.000 RFU, 90.000 RFU, and most preferred more than 100.000 RFU.

These values illustrate the particular high efficiency of the antibodies according to the invention in binding to the IL-1R7 receptor and inhibiting IL-18 signaling. It further highlights their potency for use in the treatment of diseases, wherein IL-18 signaling shall be reduced.

As detailed in the introduction, the IL-18 pathway is highly regulated and previous experience with inhibition through IL-18 directly produced conflicting results: There were pro-inflammatory effects described that are related to IL-18 activity with signaling through IL-1R5 and IL-1R7. There were also strong anti-inflammatory effects described that are related to IL-37 activity with signaling through IL-1R5 and another receptor IL-1R8 (TIR8/SIGIRR. This means that IL-1R5 can act as a receptor not only for IL-18 but also for the anti-inflammatory cytokine IL-37 and that the blocking of the IL-1R5 receptor can constitute a risk for patients with reduced immune response.

The inhibition of IL-1R7 is therefore, the only selective anti-inflammatory intervention without the risk to interfere with other mechanisms that may not be beneficial for patients treated with an anti-IL-18 modality.

It will therefore be particularly appreciated in the field that the antibodies according to the invention show a very strong binding to the IL-1R7 receptor and a very weak binding to the IL-1R5 receptor.

The antibodies according to the invention may exhibit a binding specificity to cells expressing human IL-1R5 receptor of less than 1.000 RFU in an huIL-1R5 cell binding assay as described in Example 2.

Preferably, said binding specificity to cells expressing human IL-1R5 receptor is less than 1.000 RFU, 800 RFU, more preferably less than 700 RFU, 600 RFU, 500 RFU, 400 RFU, 300 RFU, 200 RFU, 100 RFU.

A monoclonal antibody according to the invention can be rabbit antibody. In a preferred embodiment, the antibody of the invention is a rabbit/human chimeric antibody. In a further preferred version, the antibody is a humanized antibody.

The amino acid sequences of several exemplary humanized antibodies are shown in FIG. 10. Most favorable effects were found for the humanized antibodies having a heavy chain variable region (VH) as shown in SEQ ID NO: 1185-1193 and a light chain variable region (VL) as shown in SEQ ID NO: 1194-1204. Especially preferred are the humanized antibodies including one of the following combinations of heavy chain and light chain variable regions: VH of SEQ ID NO: 1185 and VL of SEQ ID NO: 1194; VH of SEQ ID NO: 1186 and VL of SEQ ID NO: 1195; VH of SEQ ID NO: 1187 and VL of SEQ ID NO: 1196; VH of SEQ ID NO: 1188 and VL of SEQ ID NO: 1197; VH of SEQ ID NO: 1189 and VL of SEQ ID NO: 1198; VH of SEQ ID NO: 1190 and VL of SEQ ID NO: 1199; VH of SEQ ID NO: 1191 and VL of SEQ ID NO: 1200; VH of SEQ ID NO: 1192 and VL of SEQ ID NO: 1201; VH of SEQ ID NO: 1193 and VL of SEQ ID NO: 1202; VH of SEQ ID NO: 1189 and VL of SEQ ID NO: 1203, and VH of SEQ ID NO: 1192 and VL of SEQ ID NO: 1204.

According to the preferred therapeutic application of the antibodies according to the invention, the effector functions (such as ADCC, CDC and ADCP) of the antibodies of the invention are reduced or lacking. Therefore, the antibodies of the invention avoid unwanted depletion of immune cells and reduce the risk of adverse events, e.g. opportunistic infections.

In one embodiment, the antibody according to the invention comprises one or more mutations that reduce the interactions with the FcR receptor.

It is preferred that an antibody according to the invention exhibits a reduced affinity to the human Fcγ receptors compared to the wildtype IgG Fcγ. This can lead to a reduced signaling through the human Fcγ receptor compared to the wildtype IgG Fcγ receptor signaling.

In one specific embodiment, the antibody according to the invention comprises at least amino acid substitutions at L234A and L235A of the human IgG1 Fc region. In another embodiment, the antibody may comprise at least amino acid substitutions at S228P and L235E of the human IgG4 Fc region.

Additionally, an antibody according to the invention may be used in the treatment of a IL-18 mediated disease.

Purified preparations of antibodies of the invention may be incorporated into pharmaceutical compositions for use in the treatment of human disease and disorders as such as those outlined below. Typically, such compositions further comprise a pharmaceutically acceptable (i.e., inert) carrier as known and called for by acceptable pharmaceutical practice. Examples of such carries include sterilized carrier such as saline Ringers solution or dextrose solution, buffered with suitable buffers to a pH within the range of 5 to 8. Pharmaceutical compositions for injection or continuous infusion are suitably free of visible particulate matter and may comprise between 0.1 ng to 100 mg of antibody, typically between 5 mg and 35 mg of antibody. In any case, pharmaceutical composition according to the invention comprise a pharmaceutically acceptable carrier and a therapeutically effective amount of the antibody according to the invention. Methods for the preparation of such pharmaceutical compositions are well known o those skilled in the art.

Effective doses and treatment regimen for administering the antibody of the invention are generally determined empirically and are dependent on factors such as the age, weight and health status of the patient and disease to be treated. Such factors are within the purview of the attending physician. In general, they will be between 1 mg and 1000 mg. In one embodiment, the dosing regimen for treating a human patient is administered i.v. or s.c. 1 time per week or 1 time every 4 weeks or 1 times every 3 months. Compositions of the present invention may also be used once or even prophylactically.

Depending on the disease or disorder to be treated the pharmaceutical composition comprising a therapeutic active amount of the antibody of the invention may be used simultaneously, separately or sequentially with an effective amount of another medicament such as other anti-inflammatory or anti-tumor agents.

The disease treated with an antibody or pharmaceutical composition according to the invention may be an immune disease or an autoimmune disease or an inflammatory or an autoinflammatory disease or a cardiovascular disease. The disease may also be an inflammasome-mediated disease.

A disease treated with an antibody or pharmaceutical composition according to the invention can be a disease selected from the group of diseases comprising type 1 or 2 diabetes, inflammatory bowel disease, Crohn's disease (CD); ulcerative colitis (UC), multiple sclerosis, sarcoidosis, Giant Cell arthritis (GCA), age-related macular degeneration (AMD), chronic obstructive pulmonary disease (COPD), adult onset Still's Disease (AOSD), systemic juvenile idiopahteic arthritis (SJIA), severe asthma, Uvenitis, Geographic Atrophy, atherosclerosis and tumor-induced chronic inflammation.

The present invention also comprises a method of treating an IL-18 mediated disease in a patient. Such method comprises the administration of a pharmaceutically effective amount of the antibody or a pharmaceutical composition according to the invention to a patient.

The method may be applied in cases in which the patient has not responded to anti-TNF therapy.

The method may also be used in the treatment of an immune disease or an autoimmune disease or an inflammatory or an autoinflammatory disease or a cardiovascular disease. An inflammasome-mediated disease may also be treated with the method according to the invention.

In another aspect of the invention, the disease that is treated with the present method is one selected from the group of diseases comprising type 1 or 2 diabetes, inflammatory bowel disease, Crohn's disease (CD); ulcerative colitis (UC), multiple sclerosis, sarcoidosis, Giant Cell arthritis (GCA), age-related macular degeneration (AMD), chronic obstructive pulmonary disease (COPD), adult onset Still's Disease (AOSD), systemic juvenile idiopahteic arthritis (SJIA), severe asthma, Uvenitis, Geographic Atrophy, atherosclerosis and tumor-induced chronic inflammation.

EXAMPLES

The following examples are used in conjunction with the figures and tables to illustrate the invention.

Example 1

IL-18 Functional Assay

1. Cultivate HEK-Blue™ cells (InvivoGen; Cat.no.: hkb-hmil18) according to manufacturer's protocol.
2. Seed out 12.5 k HEK-Blue™ cells in 15 μL medium per well into a clear cell-culture treated 384 well plate with flat bottom.
3. Add 5 μL of B-cell supernatant or standard antibody dilution series to each well.
4. Incubate for 1 hour at 37° C./5% CO2.
5. Add 5 μL of a 0.1 mg/ml huIL-18 solution to each well.
6. Incubate overnight at 37° C./5% CO2.
7. Add 20 μL QUANTI-Blue™ (1 pouch dissolved in 50 ml) into a new clear non-binding plate.
8. Add 5 μL of HEK-Blue™ cell supernatant and incubate at 37° C./5% CO2 for 45 min.
9. Determine SEAP levels using a spectrophotometer at 620-655 nm.

Example 2 huIL-1R7 and huIL-1R5 Cell Binding Assay

1. Seed an adequate amount of HEK293 cells transfected with huIL-1R7 or huIL-1R5 (1,000 to 2000 cells/well) in 20 μl medium into a black 384 well plate with clear bottom.
2. Incubate plates for 4 h at 37° C. and 5% $CO_2$
3. Add 5 μl B-cell supernatants or standard antibody dilution series to the cells.
4. Incubate plates overnight at 37° C. and 5% $CO_2$.
5. Wash plate 3× with 25 μL PBS and add 20 μL of an appropriate detection antibody (assay conc. 0.8 μg/ml).
6. Incubate plate 4 hrs at 37° C. and 5% $CO_2$ in the dark.
7. Add 5 μl of a 25 μg/ml Hoechst solution and cover with aluminium foil. While incubating cells for 10 min at RT shortly spin down plates for 10 sec 300×g.
8. Analyze binding of antibodies to cells with a CellIn-sight™ High Content Screening Platform.

Example 3

Biochemical Human-IL1R7 ELISA

Binding of humanized anti-IL1R7-IgG1-LALA monoclonal antibodies to human IL1R7 protein was tested in a biochemical ELISA. Recombinant human-IL1R7-Fc protein (MAB Discovery) was incubated in a 384-well Nunc™ MaxiSorp™ plate at a concentration of 0.5 μg/ml in PBS for one hour at room temperature. After washing three times with wash buffer (PBS, 0.1% Tween), plates were blocked with PBS, 2% BSA, 0.05% Tween for one hour at room temperature. Plates were washed again three times with wash buffer and antibodies at concentrations ranging from 10 μg/ml to 6 pg/ml in PBS, 0.5% BSA, 0.05% Tween were incubated for one hour at room temperature. After 3 washes in wash buffer, wells were incubated with 12.5 μl of a 1:5000 dilution of anti-human peroxidase-linked, species specific $F(ab)_2$ Fragment from goat (AbD Serotec) in ELISA buffer for one hour at room temperature. Wells were washed six times with wash buffer and 15 μl well TMB substrate solution (Invitrogen) were added. After 30 minutes at room temperature 15 μl Stop solution (1M HCl) were added per well and absorbance at 450 and 620 nm wavelength was measured using a Tecan M1000 microplate reader. Fitting curves and EC50 calculation were obtained by using Excel (Microsoft) and XLfit (IDBS). As shown in FIG. 5 EC50 binding values ranged between 2.1 ng/ml to 4.5 ng/ml.

Example 4

Cell Binding to hIL1R7 Expressing Cells

To determine the potency of humanized anti-IL1R7 IgG1-LALA monoclonal antibodies in binding to cell-expressed human IL1R7, HEK-293 cells were transfected with DNA encoding human-IL1R7. 48 h after transfection, 2000 cells were seeded in 20 μl DMEM containing 10% FBS, 1× Pen/Strep in a cell-culture treated, clear bottom 384-well plate. Antibodies were added to final concentrations ranging from 10 μg/ml to 2 pg/ml in 5 μl medium. After 24 h cells were washed three times with 25 μl wash buffer (PBS, 0.05% Tween) before Alexa-Fluor-488-conjugated goat anti-human-IgG (Jackson Laboratories) were added at a concentration of 0.8 μg/ml in 20 μl medium. Four hours later, 5 μl Hoechst dye in medium was added to a final concentration of 5 μg/ml. Fluorescent cell binding signals were measured using a CellInsight automated high content imager (Thermo Fisher Scientific). Fitting curves and EC50 calculation were obtained by using Excel (Microsoft) and XLfit (IDBS). FIG. 6 summarizes the EC50 binding values ranging from 1.7 to 8.3 ng/ml.

Example 5

Neutralization of IL-18 Induced NF-κB Signaling

The ability of humanized, monoclonal a-IL1R7 IgG1-LALA antibodies to interfere with IL-18 induced NF-κB signalling was tested using HEK-Blue-IL18™ reporter cells (InvivoGen). Cells were seeded in 15 μl DMEM, 10% FCS, 1% Pen/Strep at a cell density of 12500 cells/well in a 384-well tissue culture plate. Antibodies were added for final antibody concentrations ranging from 50 to 0.024 μg/ml and incubated for 1 h. Human IL-18 was added at a final concentration of 100 pg/ml and cells were incubated for 24 h. 5 μl of the medium supernatant of each well were transferred to a white, clear bottom 384-well plate containing 20 μl of 2× QUANTI-Blue™ reagent (InvivoGen). After 45 minutes incubation at 37° C. and 5% $CO_2$, optical density at a wavelength of 655 nm was measured reflecting NF-κB dependent activation of phosphatase secretion. Fitting curves and EC50 calculation were obtained by using Excel (Microsoft) and XLfit (IDBS). EC50 values in FIG. 7 indicate the potency of anti-IL1R7 antibodies to induce NF-kB signaling in the HEK-Blue-IL18™ reporter cells.

Example 6

Neutralization of IL-18 Induced IL-6 Cytokine Release

A-549_L18Rb_IL1R9 cells were stimulated with hIL-18 to test the ability of humanized, monoclonal anti-IL1R7

IgG1-LALA antibodies to inhibit IL-18 induced IL-6 cytokine release. Cells were plated in F-12K Nutrient Mixture Kaighn's Modification+10% FCS in 384-well cell culture plates at a density of 12500 cells/well. After 24 h cells were washed 3× with Cell wash buffer (PBS, 0.05% Tween) and 15 µl medium and 10 µl antibodies were added for final antibody concentrations ranging from 33.3 to 0.016 µg/ml. 1 h later, human IL18 was added to a final concentration of 10 ng/ml and cells were incubated for 6 h. IL-6 concentrations in cell culture supernatants were quantified using a human-IL6 DuoSet ELISA kit from R&D Systems. Fitting curves and EC50 calculation were obtained by using Excel (Microsoft) and XLfit (IDBS). FIG. 8 summarizes the EC50 values ranging from 133 to 6350 ng/ml.

Example 7

Neutralization of IL-18 Induced IFN-γ Release

The ability of humanized, monoclonal anti-IL1R7 IgG1-LALA antibodies to inhibit IL-18 induced release of IFN-γ was tested using KG-1 myeloblast cells. KG-1 cells were seeded at a density of 6750 cells/well in 15 µl RPMI 1640 medium containing 20% FBS and 2 mM L-Glutamine in a 384-well cell culture plate. Antibodies were added to a final concentration of 1.4 µg/ml or for dose titration experiments in a range of 5000 to 0.03 ng/ml. After 1 hour of incubation, human IL-18 (final concentration 5 ng/ml) and TNF-α (final concentration 10 ng/ml) were added and cells were incubated for 48 h at 37° C. and 5% $CO_2$. IFN-γ concentrations in the medium supernatant was quantified using a human-IFN-γ ELISA kit from R&D Systems. FIG. 9A summarizes the measured IFN-γ concentrations after treatment of KG-1 cells with 1.4 µg/ml antibody. FIG. 9B shows IFN-γ release EC50 inhibition values determined in dose titration experiments. Fitting curves and EC50 calculation were obtained by using Excel (Microsoft) and XLfit (IDBS).

FIGURE LEGEND

FIG. 1: IL-18 functional assay

Shown are the results of experiments that were performed as detailed in Example 1.

FIG. 2: huIL-1R7 cell binding assay

Results of experiments are shown that were performed in accordance with Example 2.

FIG. 3: huIL-1R5 cell binding assay

Shown are the results of experiments that were carried out as detailed in Example 2.

FIG. 4: Sequences (amino acids in one letter code)

Complete sequences of Variable Regions (VR):

Heavy chain: VH complete: SEQ ID NO: 1-148

Light chain: VL complete: SEQ ID NO: 149-296

Complementary Determining Regions (CDR):

Heavy Chain: CDR-H1: SEQ ID NO: 297-444

CDR-H2: SEQ ID NO: 445-592

CDR-H3: SEQ ID NO: 593-740

Light Chain: CDR-L1: SEQ ID NO: 741-888

CDR-L2: SEQ ID NO: 889-1036

CDR-L3: SEQ ID NO: 1037-1184, 1205, 1206

FIG. 5: Binding of Humanized a-IL1R7 Antibodies to Human IL-1R7 in a Biochemical ELISA Shown are the results of experiments that were carried out as detailed in Example 3. Binding of humanized anti-IL-1R7 IgG1-LALA antibodies to recombinant human IL-1R7 protein was tested in biochemical ELISA. EC50 binding values range from 2.1 ng/ml to 4.5 ng/ml.

FIG. 6: Binding of humanized a-IL1R7 antibodies to HEK-293-hIL1R7 cells

Shown are the results of experiments that were carried out as detailed in Example 4. Binding of humanized anti-IL-1R7 IgG1-LALA antibodies to cell surface expressed human IL1R7 was tested using HEK-293 cells transfected with DNA encoding human-IL1R7. EC50 binding values range from 1.7 to 8.3 ng/ml.

FIG. 7: Neutralization of IL-18 induced NF-kB signaling in a HEK-Blue-IL18™ Reporter Cell Line Shown are the results of experiments that were carried out as detailed in Example 5. HEK-Blue-IL18™ reporter cells, stimulated with 100 pg/ml human IL-18 were treated with increasing concentrations of humanized, monoclonal a-IL1R7 IgG1-LALA antibodies to interfere with IL-18 induced NF-kB signaling. Inhibition EC50 values range between 3.2 and >50 µg/ml.

FIG. 8: Neutralization of IL18-induced IL-6 release by A-549_IL18Rb_IL1R9 Cells Shown are the results of experiments that were carried out as detailed in Example 6. Neutralization of IL-18 induced secretion of IL-6 has been tested using A-549_IL18Rb_IL1R9 cells. Cells were incubated with increasing concentrations of humanized, monoclonal a-IL1R7 IgG1-LALA antibodies or a reference mouse-a-hIL1R7 antibody from R&D Systems (MAB1181) together with 10 ng/ml IL-18 for 6 h. IL-6 release in the culture supernatant was quantified by ELISA.

FIG. 9: Neutralization of IL-18 induced IFN-g release by KG-1 myeloblasts

Shown are the results of experiments that were carried out as detailed in Example 7. KG-1 myeloblasts were treated with humanized, monoclonal a-IL1R7 IgG1-LALA antibodies or a reference mouse-a-hIL1R7 antibody from R&D Systems (MAB1181) to test their ability to block hIL-18 induced IFN-γ release. FIG. 9A shows inhibition of IFN-γ release at an antibody concentration of 1.4 µg/ml. In FIG. 9B the inhibition EC50 values from antibody dose titration (5000 to 0.03 ng/ml) experiments are shown.

FIG. 10: Sequences of humanized antibodies

Complete sequences of variable regions and the respective CDRs

The invention claimed is:

1. A monoclonal antibody, or an antigen-binding fragment thereof, capable of binding to human IL-1R7, wherein the antibody comprises a VH region comprising at least the CDR3H and a VL region comprising at least the CDR3L of the SEQ ID Nos shown in a single row of the following table:

| CDR1H | CDR2H | CDR3H | CDR1L | CDR2L | CDR3L |
|---|---|---|---|---|---|
| 309 | 457 | 605 | 753 | 901 | 1205 |
| 343 | 491 | 639 | 787 | 935 | 1083 |
| 444 | 592 | 740 | 888 | 1036 | 1184 |
| 397 | 545 | 693 | 841 | 989 | 1137 |
| 323 | 471 | 619 | 767 | 915 | 1063 |
| 309 | 457 | 605 | 753 | 901 | 1049 |
| 336 | 484 | 632 | 780 | 928 | 1076 |
| 310 | 458 | 606 | 754 | 902 | 1050 |
| 335 | 483 | 631 | 779 | 927 | 1075 |
| 388 | 536 | 684 | 832 | 980 | 1128 |
| 335 | 483 | 631 | 779 | 927 | 1206. |

2. The antibody or antigen-binding fragment of claim 1, comprising six CDR regions of the SEQ ID Nos shown in a single row of the table shown in claim 1.

3. The antibody or antigen-binding fragment of claim 1, comprising:

a) a VH region comprising a CDR1H region of SEQ ID NO: 309, a CDR2H region of SEQ ID NO: 457 and a CDR3H region of SEQ ID NO: 605 and b) a VL region comprising a CDR1L region of SEQ ID NO: 753, a CDR2L region of SEQ ID NO: 901 and a CDR3L region of SEQ ID NO: 1205.

4. The antibody or antigen-binding fragment of claim 1, wherein the antibody comprises a heavy chain variable (VH) region that is at least 85% identical to a VH region selected from the group consisting of VH regions of SEQ ID NO: 1 to 148 and SEQ ID NO: 1185-1193.

5. The antibody or antigen-binding fragment of claim 1, wherein the antibody comprises a light chain variable (VL) region that is at least 85% identical to a VL region selected from the group consisting of VL regions of SEQ ID NO: 149 to 296 and SEQ ID NO: 1194-1204.

6. The antibody or antigen-binding fragment of claim 1, exhibiting an inhibition of IL-18 signaling of at least 30%, in an IL-18 functional assay.

7. The antibody or antigen-binding fragment of claim 1, exhibiting a binding specificity to cells expressing human IL-1R7 receptor of more than 10.000 RFU in an huIL-1R7 cell binding assay.

8. The antibody or antigen-binding fragment of claim 1, exhibiting a binding specificity to cells expressing human IL-1R5 receptor of less than 1.000 RFU in an huIL-1R5 cell binding assay.

9. The antibody or antigen-binding fragment of claim 1, wherein the antibody is a rabbit, rabbit/human chimeric or humanized antibody.

10. The antibody or antigen-binding fragment of claim 1, exhibiting a reduced affinity to the human Fcγ receptors compared to the wildtype IgG Fcγ.

11. The antibody or antigen-binding fragment of claim 1, wherein signaling through the human Fcγ receptor is reduced compared to the wildtype IgG Fcγ receptor signaling.

12. A pharmaceutical composition comprising a pharmaceutically acceptable carrier and a therapeutically effective amount of the antibody or antigen-binding fragment of claim 1.

13. The antibody or antigen-binding fragment of claim 4, wherein the antibody comprises a heavy chain variable (VH) region that is at least 85% identical to a VH region of SEQ ID NO: 1189.

14. The antibody or antigen-binding fragment of claim 5, wherein the antibody comprises a light chain variable (VL) region that is at least 85% identical to a VL region of SEQ ID NO: 1203.

15. The antibody or antigen-binding fragment of claim 1, wherein the antibody comprises a VH region comprising the CDR3H and at least one of the CDR1H and CDR2H and a VL region comprising the CDR3L and at least one of the CDR1L and CDR2L of the SEQ ID Nos shown in a single row of the table shown in claim 1.

* * * * *

SEQUENCE LISTING

```
<160> NUMBER OF SEQ ID NOS: 1206

<210> SEQ ID NO 1
<211> LENGTH: 119
<212> TYPE: PRT
<213> ORGANISM: Oryctolagus cuniculus
```

<400> SEQUENCE: 1

```
Gln Ser Leu Glu Glu Ser Gly Gly Arg Leu Val Thr Pro Gly Thr Pro
1               5                   10                  15

Leu Thr Leu Thr Cys Thr Ile Ser Gly Ile Asp Leu Ser Ala Tyr Ala
            20                  25                  30

Ile Asn Trp Val Arg Gln Ala Pro Gly Lys Gly Leu Glu Trp Ile Gly
        35                  40                  45

Gly Ile Ala Asn Asn Gly Pro Thr Tyr Tyr Ala Asn Trp Ala Lys Gly
    50                  55                  60

Arg Phe Thr Ile Ser Lys Ile Ser Thr Thr Val Asp Leu Lys Ile Thr
65                  70                  75                  80

Ser Pro Thr Thr Glu Asp Thr Ala Thr Tyr Phe Cys Ala Arg Phe Pro
                85                  90                  95

Pro Gly Thr Asn Gly Gly Thr Asp Tyr Phe Asn Ile Trp Gly Pro Gly
            100                 105                 110

Thr Leu Val Thr Val Ser Leu
        115
```

<210> SEQ ID NO 2
<211> LENGTH: 114
<212> TYPE: PRT
<213> ORGANISM: Oryctolagus cuniculus

<400> SEQUENCE: 2

```
Gln Ser Val Glu Glu Ser Gly Gly Arg Leu Val Thr Pro Gly Thr Pro
1               5                   10                  15

Leu Thr Val Thr Cys Thr Val Ser Gly Phe Ser Leu Ser Gly Tyr Asp
            20                  25                  30

Met Asn Trp Val Arg Gln Ala Pro Gly Lys Gly Leu Glu Trp Ile Gly
        35                  40                  45

Met Ile Tyr Pro Asn Ser Gly Thr Asn Tyr Ala Thr Trp Ala Lys Gly
    50                  55                  60

Arg Phe Thr Ile Ser Lys Thr Pro Thr Thr Val Ala Leu Lys Ile Thr
65                  70                  75                  80

Ser Pro Thr Thr Glu Asp Thr Ala Thr Tyr Phe Cys Ala Arg Asp Ser
                85                  90                  95

Gly Trp Gly Ala Phe Asp Pro Trp Gly Pro Gly Thr Leu Val Thr Ile
            100                 105                 110

Ser Ser
```

<210> SEQ ID NO 3
<211> LENGTH: 119
<212> TYPE: PRT
<213> ORGANISM: Oryctolagus cuniculus

<400> SEQUENCE: 3

```
Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Ala
            20                  25                  30

Ile Ser Trp Val Arg Gln Ala Pro Gly Lys Gly Leu Glu Trp Ile Gly
        35                  40                  45

Gly Ile Ser Asn Ser Gly Thr Thr Tyr Tyr Ala Ser Trp Ala Lys Gly
    50                  55                  60

Arg Phe Thr Ile Ser Lys Ile Ser Thr Thr Val Asp Leu Lys Ile Thr
65                  70                  75                  80
```

```
Ser Pro Thr Thr Glu Asp Thr Ala Thr Tyr Phe Cys Ala Arg Phe Pro
                85                  90                  95

Pro Gly Ser Asn Ser Gly Thr Asp Tyr Phe Asn Ile Trp Gly Pro Gly
            100                 105                 110

Thr Leu Val Thr Val Ser Leu
        115


<210> SEQ ID NO 4
<211> LENGTH: 113
<212> TYPE: PRT
<213> ORGANISM: Oryctolagus cuniculus

<400> SEQUENCE: 4

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Gly Leu Val
            20                  25                  30

Val Ser Trp Val Arg Gln Ala Pro Gly Lys Gly Leu Glu Trp Ile Gly
        35                  40                  45

Val Ile Gly Lys Ser Gly Asn Thr Tyr Tyr Ala Ser Trp Ala Lys Gly
    50                  55                  60

Arg Phe Ser Ile Ser Lys Thr Ser Ser Thr Thr Val Asp Leu Lys Ile
65                  70                  75                  80

Ala Ser Pro Thr Thr Glu Asp Thr Ala Thr Tyr Phe Cys Gly Arg Asn
                85                  90                  95

Ile Ser Gly Ser Ala Val Trp Gly Pro Gly Thr Leu Val Thr Val Ser
            100                 105                 110

Leu


<210> SEQ ID NO 5
<211> LENGTH: 126
<212> TYPE: PRT
<213> ORGANISM: Oryctolagus cuniculus

<400> SEQUENCE: 5

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Ser Tyr
            20                  25                  30

Tyr Met Cys Trp Val Arg Gln Ala Pro Gly Lys Trp Leu Glu Trp Ile
        35                  40                  45

Ala Cys Ile Tyr Ala Gly Ser Ser Gly Ser Thr Tyr Tyr Ala Ser Trp
    50                  55                  60

Ala Lys Gly Arg Phe Thr Val Ser Lys Thr Ser Ser Thr Thr Val Thr
65                  70                  75                  80

Leu Glu Met Thr Ser Leu Thr Ala Ala Asp Thr Ala Thr Tyr Phe Cys
                85                  90                  95

Ala Arg Asp Leu Gly Ala Gly Tyr Ala Gly Tyr Gly Tyr Ala Ser Asp
            100                 105                 110

Phe Asn Leu Trp Gly Pro Gly Thr Leu Val Thr Val Ser Ser
        115                 120                 125


<210> SEQ ID NO 6
<211> LENGTH: 119
<212> TYPE: PRT
<213> ORGANISM: Oryctolagus cuniculus
```

-continued

<400> SEQUENCE: 6

Gln Ser Leu Glu Glu Ser Gly Gly Arg Leu Val Thr Pro Gly Thr Pro
1 5 10 15

Leu Thr Leu Thr Cys Thr Val Ser Gly Phe Ser Leu Ser Ile Tyr Ala
20 25 30

Ile Ser Trp Val Arg Gln Ala Pro Gly Lys Gly Leu Glu Trp Ile Gly
35 40 45

Gly Ile Gly Asn Asn Gly Ile Ile His Tyr Ala Asn Trp Ala Lys Gly
50 55 60

Arg Phe Thr Ser Ser Lys Ile Ser Thr Thr Val Asp Leu Lys Ile Thr
65 70 75 80

Ser Pro Thr Thr Glu Asp Thr Ala Thr Tyr Phe Cys Ala Arg Phe Pro
85 90 95

Pro Gly Ser Asn Ser Gly Thr Asp Tyr Phe Asn Ile Trp Gly Pro Gly
100 105 110

Thr Leu Val Thr Val Ser Leu
115

<210> SEQ ID NO 7
<211> LENGTH: 118
<212> TYPE: PRT
<213> ORGANISM: Oryctolagus cuniculus

<400> SEQUENCE: 7

Gln Ser Leu Glu Glu Ser Gly Gly Asp Leu Val Lys Pro Gly Ala Ser
1 5 10 15

Leu Thr Leu Thr Cys Thr Ala Ser Gly Phe Ser Phe Ser Ser Ser Tyr
20 25 30

Tyr Met Cys Trp Val Arg Gln Ala Pro Gly Lys Gly Leu Glu Trp Ile
35 40 45

Gly Cys Ile Tyr Gly Gly Ser Ser Gly Lys Thr Trp Tyr Ala Ser Trp
50 55 60

Ala Lys Gly Arg Phe Thr Ile Ser Lys Thr Ser Ser Thr Thr Val Thr
65 70 75 80

Leu Gln Met Thr Ser Leu Thr Ala Ala Asp Thr Ala Thr Tyr Phe Cys
85 90 95

Ala Arg Asp Asn Tyr Asp Trp Tyr Phe Asn Leu Trp Gly Pro Gly Thr
100 105 110

Leu Val Thr Val Ser Ser
115

<210> SEQ ID NO 8
<211> LENGTH: 119
<212> TYPE: PRT
<213> ORGANISM: Oryctolagus cuniculus

<400> SEQUENCE: 8

Gln Ser Leu Glu Glu Ser Gly Gly Arg Leu Val Thr Pro Gly Thr Pro
1 5 10 15

Leu Thr Leu Thr Cys Thr Val Ser Gly Phe Ser Leu Ser Met Tyr Ala
20 25 30

Ile Asn Trp Val Arg Gln Ala Pro Gly Lys Gly Leu Glu Trp Ile Gly
35 40 45

Gly Ile Ala Asn Asn Gly Pro Thr Tyr Tyr Ala Ser Trp Ala Lys Gly
50 55 60

Arg Phe Thr Ile Ser Lys Ile Ser Thr Thr Val Asp Leu Arg Ile Thr

-continued

```
65                  70                  75                  80

Ser Pro Thr Thr Glu Asp Thr Ala Thr Tyr Phe Cys Ala Arg Phe Pro
                85                  90                  95

Pro Gly Ser Asn Ser Gly Thr Asp Tyr Phe Asn Ile Trp Gly Pro Gly
            100                 105                 110

Thr Leu Val Thr Val Ser Leu
        115


<210> SEQ ID NO 9
<211> LENGTH: 124
<212> TYPE: PRT
<213> ORGANISM: Oryctolagus cuniculus

<400> SEQUENCE: 9

Gln Ser Leu Glu Glu Ser Gly Gly Asp Leu Val Lys Pro Gly Ala Ser
1               5                   10                  15

Leu Thr Leu Thr Cys Lys Ala Ser Gly Phe Asp Leu Ser Ser Tyr Tyr
            20                  25                  30

Tyr Met Cys Trp Phe Arg Gln Ala Pro Gly Lys Gly Pro Glu Trp Ile
        35                  40                  45

Ala Cys Ile Tyr Ala Asp Asp Ala Thr Thr Tyr Tyr Ala Thr Trp Ala
    50                  55                  60

Lys Gly Arg Phe Thr Val Ser Ile Thr Ser Ser Thr Thr Val Thr Leu
65                  70                  75                  80

Gln Met Pro Ser Leu Thr Ala Ala Asp Thr Ala Thr Tyr Phe Cys Ala
                85                  90                  95

Arg Arg Asp Ala Asp Tyr Val Gly Phe Ile Trp Ala Tyr Tyr Phe Asn
            100                 105                 110

Leu Trp Gly Pro Gly Thr Leu Val Thr Val Ser Ser
        115                 120


<210> SEQ ID NO 10
<211> LENGTH: 113
<212> TYPE: PRT
<213> ORGANISM: Oryctolagus cuniculus

<400> SEQUENCE: 10

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Arg Asn Ala
            20                  25                  30

Met Ser Trp Val Arg Gln Ala Pro Gly Lys Gly Leu Glu Trp Ile Gly
        35                  40                  45

Ile Ile Arg Asn Thr Gly Thr Thr Trp Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Asn
                85                  90                  95

Pro Gly Trp Ala Ser Thr Trp Gly Pro Gly Thr Leu Val Thr Val Ser
            100                 105                 110

Ser


<210> SEQ ID NO 11
<211> LENGTH: 124
<212> TYPE: PRT
<213> ORGANISM: Oryctolagus cuniculus
```

-continued

<400> SEQUENCE: 11

Gln Glu Gln Leu Val Glu Ser Gly Gly Gly Leu Val Gln Pro Gly Ala
1 5 10 15

Ser Leu Thr Leu Thr Cys Lys Thr Ser Gly Phe Ser Phe Ser Asp Asn
20 25 30

Tyr Ala Met Cys Trp Val Arg Gln Ala Pro Gly Lys Gly Leu Glu Trp
35 40 45

Ile Ala Cys Ile Tyr Val Gly Ser Gly Ser Thr Tyr Tyr Ala Ser Trp
50 55 60

Ala Gln Gly Arg Phe Thr Ile Ser Lys Thr Ser Ser Thr Thr Val Thr
65 70 75 80

Leu Gln Met Thr Ser Leu Thr Ala Ala Asp Thr Ala Thr His Phe Cys
85 90 95

Ala Arg Gly Val Val Ile Gly Asn Ala Tyr Ser Met Ala His Phe Ser
100 105 110

Leu Trp Gly Ser Gly Thr Leu Val Thr Val Ser Ser
115 120

<210> SEQ ID NO 12
<211> LENGTH: 125
<212> TYPE: PRT
<213> ORGANISM: Oryctolagus cuniculus

<400> SEQUENCE: 12

Gln Ser Leu Glu Glu Ser Gly Gly Gly Leu Val Lys Pro Gly Ala Ser
1 5 10 15

Leu Thr Leu Thr Cys Thr Ala Ser Gly Phe Ser Phe Ser Ser Gly Tyr
20 25 30

Tyr Met Cys Trp Val Arg Gln Ala Pro Gly Lys Gly Leu Glu Trp Ile
35 40 45

Gly Cys Ile Tyr Thr Ser Ser Gly Ser Thr Tyr Tyr Ala Ser Trp Ala
50 55 60

Lys Gly Arg Phe Thr Ile Ser Lys Thr Ser Ser Thr Thr Val Thr Leu
65 70 75 80

Gln Met Thr Ser Leu Thr Ala Ala Asp Thr Ala Thr Tyr Phe Cys Ala
85 90 95

Arg Arg Leu Asn Tyr Val Thr Tyr Pro Ala Tyr Gly Tyr Gly Tyr Phe
100 105 110

Asn Leu Trp Gly Pro Gly Thr Leu Val Thr Val Ser Ser
115 120 125

<210> SEQ ID NO 13
<211> LENGTH: 121
<212> TYPE: PRT
<213> ORGANISM: Oryctolagus cuniculus

<400> SEQUENCE: 13

Gln Glu Gln Leu Glu Glu Ser Gly Gly Asp Leu Val Lys Pro Gly Ala
1 5 10 15

Ser Leu Thr Leu Thr Cys Thr Ala Ser Gly Phe Ser Phe Asn Gly Asn
20 25 30

Tyr Tyr Ile Cys Trp Val Arg Gln Ala Pro Gly Lys Gly Leu Glu Trp
35 40 45

Ile Ala Cys Ile Tyr Ala Gly Ser Ser Gly Ser Thr Tyr Tyr Ala Ser
50 55 60

```
Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Val Arg Asp Lys Pro Ala Gly Gly Ser Ser Tyr Thr Leu Trp Gly
            100                 105                 110

Pro Gly Thr Leu Val Thr Val Ser Ser
        115                 120


<210> SEQ ID NO 14
<211> LENGTH: 120
<212> TYPE: PRT
<213> ORGANISM: Oryctolagus cuniculus

<400> SEQUENCE: 14

Gln Glu Gln Leu Glu Glu Ser Gly Gly Asp Leu Val Lys Pro Gly Ala
1               5                   10                  15

Ser Leu Thr Leu Thr Cys Thr Ala Ser Gly Phe Ser Phe Ser Arg Ser
            20                  25                  30

Tyr Tyr Met Cys Trp Val Arg Gln Ala Pro Gly Lys Gly Leu Glu Trp
        35                  40                  45

Ile Ala Cys Ile Tyr Ala Gly Ser Ser Asp Ser Thr Tyr Tyr Ala Ser
    50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Gly Gly Gly Ile Ile Tyr Thr Gln Asn Leu Trp Gly Pro
            100                 105                 110

Gly Thr Leu Val Thr Val Ser Ser
        115                 120


<210> SEQ ID NO 15
<211> LENGTH: 124
<212> TYPE: PRT
<213> ORGANISM: Oryctolagus cuniculus

<400> SEQUENCE: 15

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Val Ser Met Tyr
            20                  25                  30

Trp Met Cys Trp Val Arg Gln Ala Pro Gly Lys Gly Leu Glu Trp Ile
        35                  40                  45

Ala Cys Ile Tyr Thr Gly Ser Ser Gly Lys Thr His Tyr Ala Ser Trp
    50                  55                  60

Ala Lys Gly Arg Ser Thr Ile Ser Lys Thr Ser Ser Thr Thr Val Thr
65                  70                  75                  80

Leu Gln Met Thr Ser Leu Thr Ala Ala Asp Thr Ala Leu Tyr Ser Cys
                85                  90                  95

Ala Arg Ala Gly Ser Val Gly Tyr Gly Tyr Asp Thr Ala Tyr Phe Asn
            100                 105                 110

Leu Trp Gly Pro Gly Thr Leu Val Thr Val Ser Ser
        115                 120


<210> SEQ ID NO 16
<211> LENGTH: 114
```

<212> TYPE: PRT
<213> ORGANISM: Oryctolagus cuniculus

<400> SEQUENCE: 16

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Ser Tyr Asp
            20                  25                  30

Met Ser Trp Val Arg Gln Ala Pro Gly Lys Gly Leu Glu Tyr Ile Gly
        35                  40                  45

Ile Ile Tyr Asp Ser Gly Ser Thr Tyr Tyr Ala Asn Trp Ala Lys Gly
    50                  55                  60

Arg Phe Thr Ile Ala Lys Thr Ser Thr Thr Val Asp Leu Lys Ile Thr
65                  70                  75                  80

Ser Pro Thr Thr Glu Asp Thr Ala Thr Tyr Phe Cys Ala Arg Thr Leu
                85                  90                  95

Asn Thr Leu Pro Phe Asn Ile Trp Gly Pro Gly Thr Leu Val Thr Val
            100                 105                 110

Ser Leu
```

<210> SEQ ID NO 17
<211> LENGTH: 120
<212> TYPE: PRT
<213> ORGANISM: Oryctolagus cuniculus

<400> SEQUENCE: 17

```
Gln Glu Gln Leu Glu Glu Ser Gly Gly Gly Leu Val Gln Pro Glu Gly
1               5                   10                  15

Ser Leu Thr Leu Thr Cys Thr Ala Ser Gly Phe Ser Phe Ser Ser Ser
            20                  25                  30

Tyr Trp Ile Cys Trp Val Arg Gln Ala Pro Gly Lys Gly Leu Glu Trp
        35                  40                  45

Ile Ala Cys Ile Ala Ala Gly Ser Gly Ser Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Leu Gly Asp Asp Gly Tyr Ala Tyr Gly Leu Trp Gly Pro
            100                 105                 110

Gly Thr Leu Val Thr Val Ser Ser
        115                 120
```

<210> SEQ ID NO 18
<211> LENGTH: 120
<212> TYPE: PRT
<213> ORGANISM: Oryctolagus cuniculus

<400> SEQUENCE: 18

```
Gln Ser Leu Glu Glu Ser Gly Gly Val Leu Val Lys Pro Gly Ala Ser
1               5                   10                  15

Leu Thr Leu Thr Cys Thr Ala Ser Gly Ile Asp Phe Ser Ser Ser Tyr
            20                  25                  30

Tyr Ile Cys Trp Val Arg Gln Ala Pro Gly Lys Gly Leu Glu Trp Ile
        35                  40                  45

Ala Cys Ile Tyr Ala Gly Ser Ser Gly Ser Thr Tyr Tyr Ala Ser Trp
    50                  55                  60
```

```
Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Gly Thr Gly Ser Ser His Tyr Thr Ser Asn Leu Trp Gly Pro
            100                 105                 110

Gly Thr Leu Val Thr Val Ser Ser
        115                 120


<210> SEQ ID NO 19
<211> LENGTH: 120
<212> TYPE: PRT
<213> ORGANISM: Oryctolagus cuniculus

<400> SEQUENCE: 19

Gln Glu Gln Leu Val Glu Ser Gly Gly Gly Leu Val Gln Pro Glu Gly
1               5                   10                  15

Ser Leu Thr Leu Thr Cys Thr Ala Ser Gly Phe Ser Phe Ser Asp Gly
            20                  25                  30

Tyr Trp Met Cys Trp Val Arg Gln Ala Pro Gly Lys Gly Leu Glu Trp
        35                  40                  45

Ile Gly Cys Ile Tyr Thr Gly Pro Gly Gly Thr Phe Tyr Ala Ser Trp
    50                  55                  60

Ala Lys Gly Arg Phe Thr Ile Ser Lys Thr Ser Ser Thr Thr Val Thr
65                  70                  75                  80

Leu Gln Leu Asn Ser Leu Thr Ala Ala Asp Thr Ala Thr Tyr Phe Cys
                85                  90                  95

Ala Arg Asp Leu Asn Gly Ala Asp Ser Gly Ser Ala Leu Trp Gly Pro
            100                 105                 110

Gly Thr Leu Val Thr Val Ser Ser
        115                 120


<210> SEQ ID NO 20
<211> LENGTH: 116
<212> TYPE: PRT
<213> ORGANISM: Oryctolagus cuniculus

<400> SEQUENCE: 20

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Ala
            20                  25                  30

Met Ser Trp Val Arg Gln Ala Pro Gly Lys Gly Leu Glu Trp Ile Gly
        35                  40                  45

Ile Ile His Tyr Ser Gly Tyr Thr Ala Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Gly
                85                  90                  95

Asp Ala Asp Asn Phe Tyr Tyr Asn Ile Trp Gly Pro Gly Thr Leu Val
            100                 105                 110

Thr Val Ser Leu
        115


<210> SEQ ID NO 21
```

<211> LENGTH: 120
<212> TYPE: PRT
<213> ORGANISM: Oryctolagus cuniculus

<400> SEQUENCE: 21

Gln Glu Gln Leu Lys Glu Ser Gly Gly Gly Leu Val Thr Pro Gly Gly
1 5 10 15

Thr Leu Thr Leu Thr Cys Thr Ala Ser Gly Phe Thr Ile Ser Asn Tyr
20 25 30

Gln Met Thr Trp Val Arg Gln Ala Pro Gly Lys Gly Leu Glu Tyr Ile
35 40 45

Gly Phe Ile Lys Ala Asp Gly Ser Ala Tyr Tyr Ala Asn Trp Ala Lys
50 55 60

Gly Arg Phe Thr Ile Ser Arg Thr Ser Thr Ala Val Thr Leu Ser Leu
65 70 75 80

Thr Thr Pro Thr Thr Gly Asp Thr Ala Thr Tyr Phe Cys Ala Arg Asp
85 90 95

Phe Tyr Ala Gly Ser Ser Gly Asn Val Asn Gly Asp Ile Trp Gly Pro
100 105 110

Gly Thr Leu Val Thr Val Ser Leu
115 120

<210> SEQ ID NO 22
<211> LENGTH: 119
<212> TYPE: PRT
<213> ORGANISM: Oryctolagus cuniculus

<400> SEQUENCE: 22

Gln Ser Leu Glu Glu Ser Gly Gly Arg Leu Val Thr Pro Gly Thr Pro
1 5 10 15

Leu Thr Leu Thr Cys Thr Val Ser Gly Phe Ser Leu Asn Met Tyr Ala
20 25 30

Ile Asn Trp Val Arg Gln Ala Pro Gly Lys Gly Leu Glu Trp Ile Gly
35 40 45

Gly Ile Ala Thr Asn Gly Ile Ile His Tyr Ala Ser Trp Val Lys Gly
50 55 60

Gln Phe Thr Ile Ser Lys Ile Ser Thr Thr Val Asp Leu Lys Ile Thr
65 70 75 80

Ser Pro Thr Thr Glu Asp Thr Ala Thr Tyr Phe Cys Thr Arg Phe Pro
85 90 95

Pro Gly Ser Asn Gly Gly Thr Ala Tyr Phe Asn Ile Trp Gly Pro Gly
100 105 110

Thr Leu Val Thr Val Ser Leu
115

<210> SEQ ID NO 23
<211> LENGTH: 114
<212> TYPE: PRT
<213> ORGANISM: Oryctolagus cuniculus

<400> SEQUENCE: 23

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser Asn Tyr Asp
20 25 30

Met Asn Trp Val Arg Gln Ala Pro Gly Lys Gly Leu Glu Trp Ile Gly
35 40 45

-continued

```
Met Ile Tyr Pro Asn Ser Gly Thr Asn Tyr Ala Ser Trp Ala Lys Gly
    50                  55                  60

Arg Phe Thr Ile Ser Lys Thr Pro Thr Thr Val Ala Leu Lys Ile Thr
65                  70                  75                  80

Ser Pro Thr Thr Glu Asp Thr Ala Thr Tyr Phe Cys Ala Arg Asp Ser
                85                  90                  95

Gly Trp Gly Ala Phe Asp Pro Trp Gly Pro Gly Thr Leu Val Thr Val
            100                 105                 110

Ser Ser


<210> SEQ ID NO 24
<211> LENGTH: 114
<212> TYPE: PRT
<213> ORGANISM: Oryctolagus cuniculus

<400> SEQUENCE: 24

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Asp
            20                  25                  30

Met Asn Trp Val Arg Gln Ala Pro Gly Lys Gly Leu Glu Trp Ile Gly
        35                  40                  45

Met Ile Tyr Pro Asn Gly Gly Thr Asn Tyr Ala Thr Trp Ala Lys Gly
    50                  55                  60

Arg Phe Thr Ile Ser Lys Thr Pro Thr Thr Val Ala Leu Lys Ile Thr
65                  70                  75                  80

Ser Pro Thr Thr Glu Asp Thr Ala Thr Tyr Phe Cys Ala Arg Asp Ser
                85                  90                  95

Gly Trp Gly Ala Phe Asp Pro Trp Gly Pro Gly Thr Leu Val Thr Val
            100                 105                 110

Ser Ser


<210> SEQ ID NO 25
<211> LENGTH: 112
<212> TYPE: PRT
<213> ORGANISM: Oryctolagus cuniculus

<400> SEQUENCE: 25

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Met Ile Trp Val Arg Gln Ala Pro Gly Lys Gly Leu Glu Trp Ile Gly
        35                  40                  45

Ile Ile Tyr Ala Ser Asp Ser Thr Tyr Tyr Ala Thr Trp Ala Lys Gly
    50                  55                  60

Arg Phe Thr Ile Ser Lys Thr Ser Thr Thr Val Asp Leu Arg Met Thr
65                  70                  75                  80

Ser Leu Thr Thr Glu Asp Thr Ala Thr Tyr Phe Cys Ala Arg Gly Tyr
                85                  90                  95

Ser Asp Ile Asp Ile Trp Gly Pro Gly Thr Leu Val Thr Val Ser Leu
            100                 105                 110


<210> SEQ ID NO 26
<211> LENGTH: 119
<212> TYPE: PRT
<213> ORGANISM: Oryctolagus cuniculus
```

<400> SEQUENCE: 26

```
Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Met Tyr Thr
            20                  25                  30

Ile Asn Trp Val Arg Gln Ala Pro Gly Lys Gly Leu Glu Trp Ile Gly
        35                  40                  45

Gly Ile Ala Thr His Gly Ile Ile His Tyr Ala Ser Trp Val Lys Gly
    50                  55                  60

Arg Phe Thr Ile Ser Lys Ile Ser Thr Thr Val Asp Leu Lys Ile Thr
65                  70                  75                  80

Ser Pro Thr Thr Glu Asp Thr Ala Thr Tyr Phe Cys Ala Arg Phe Pro
                85                  90                  95

Pro Gly Ser Asn Gly Gly Thr Ala Tyr Phe Asn Ile Trp Gly Pro Gly
            100                 105                 110

Thr Leu Val Thr Val Ser Leu
        115
```

<210> SEQ ID NO 27
<211> LENGTH: 121
<212> TYPE: PRT
<213> ORGANISM: Oryctolagus cuniculus

<400> SEQUENCE: 27

```
Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Asn Ser
            20                  25                  30

Ile Ser Trp Val Arg Gln Ala Pro Gly Lys Gly Leu Glu Trp Leu Gly
        35                  40                  45

Ile Ile Ser Ser Ser Gly Ser Thr Tyr Tyr Ala Ser Trp Ala Lys Gly
    50                  55                  60

Arg Phe Thr Ile Ser Lys Ala Ser Ser Thr Thr Val Asp Leu Lys Ile
65                  70                  75                  80

Thr Ser Pro Thr Thr Glu Asp Thr Ala Thr Tyr Phe Cys Ala Lys Gly
                85                  90                  95

Leu Gly Arg Gly Glu Tyr Thr Ser Asn Asp Ala Phe Asp Pro Trp Gly
            100                 105                 110

Pro Gly Thr Leu Val Thr Val Ser Ser
        115                 120
```

<210> SEQ ID NO 28
<211> LENGTH: 118
<212> TYPE: PRT
<213> ORGANISM: Oryctolagus cuniculus

<400> SEQUENCE: 28

```
Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Thr Ser Thr Tyr
            20                  25                  30

Trp Met Ser Trp Val Arg Gln Ala Pro Gly Lys Gly Pro Glu Trp Ile
        35                  40                  45

Gly Cys Ile Val Thr Gly Arg Gly Asn Thr Tyr Tyr Ala Asn Trp Ala
    50                  55                  60
```

-continued

```
Lys Gly Arg Phe Thr Ile Ser Lys Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Gly Ser Ser Asp Glu Ile Ala Leu Asp Leu Trp Gly Gln Gly Thr
            100                 105                 110

Leu Val Thr Val Ser Ser
        115


<210> SEQ ID NO 29
<211> LENGTH: 118
<212> TYPE: PRT
<213> ORGANISM: Oryctolagus cuniculus

<400> SEQUENCE: 29

Gln Ser Val Glu Glu Ser Gly Gly Arg Leu Val Ala Pro Gly Thr Pro
1               5                   10                  15

Leu Thr Leu Thr Cys Thr Val Ser Gly Phe Ser Leu Asn Asn Tyr Ala
            20                  25                  30

Leu Ser Trp Val Arg Gln Ala Pro Gly Lys Gly Leu Glu Tyr Ile Gly
        35                  40                  45

Phe Ile Asn Ile Ile His Gly Ala Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Pro
                85                  90                  95

Tyr Tyr Val Gly Ser Glu Tyr Val Phe Asp Pro Trp Gly Pro Gly Thr
            100                 105                 110

Leu Val Thr Val Ser Ser
        115


<210> SEQ ID NO 30
<211> LENGTH: 118
<212> TYPE: PRT
<213> ORGANISM: Oryctolagus cuniculus

<400> SEQUENCE: 30

Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Leu Ser Ser His Ala
            20                  25                  30

Thr Ser Trp Val Arg Gln Ala Pro Gly Lys Gly Leu Glu Trp Ile Gly
        35                  40                  45

Phe Ile Lys Thr Gly Gly Ser Ala Tyr Tyr Ala Ser Trp Ala Lys Gly
    50                  55                  60

Arg Phe Thr Ile Ser Lys Thr Ser Ala Thr Val Asp Leu Lys Ile Thr
65                  70                  75                  80

Ser Pro Thr Thr Glu Asp Thr Ala Thr Tyr Phe Cys Ala Ser Met Phe
                85                  90                  95

Tyr Ala Gly Asp Ser Gly His Tyr Leu His Leu Trp Gly Pro Gly Thr
            100                 105                 110

Leu Val Thr Val Ser Ser
        115


<210> SEQ ID NO 31
<211> LENGTH: 108
```

<212> TYPE: PRT
<213> ORGANISM: Oryctolagus cuniculus

<400> SEQUENCE: 31

Gln Ser Val Glu Glu Ser Gly Gly Gly Leu Val Thr Pro Gly Gly Pro
1               5                   10                  15

Leu Thr Leu Thr Cys Thr Val Ser Gly Phe Ser Leu Ser Thr Tyr Gly
            20                  25                  30

Val Ser Trp Val Arg Gln Ala Pro Gly Lys Gly Leu Glu Trp Ile Gly
        35                  40                  45

Tyr Ile Asn Thr Gly Gly Ser Ala Ser Tyr Ala Thr Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Ala Asn Asn
                85                  90                  95

Leu Trp Gly Pro Gly Thr Leu Val Thr Val Ser Ser
            100                 105

<210> SEQ ID NO 32
<211> LENGTH: 120
<212> TYPE: PRT
<213> ORGANISM: Oryctolagus cuniculus

<400> SEQUENCE: 32

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Asn Tyr
            20                  25                  30

Tyr Ile Cys Trp Val Arg Gln Ala Pro Gly Lys Gly Leu Glu Trp Ile
        35                  40                  45

Ala Cys Ile Tyr Thr Gly Ser Thr Gly Ser Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Arg Ala Thr Tyr Phe Cys
                85                  90                  95

Ala Arg Gly Gly Tyr Ser Tyr Gly Gly Ala Val Ser Leu Trp Gly Pro
            100                 105                 110

Gly Thr Leu Val Thr Val Ser Ser
        115                 120

<210> SEQ ID NO 33
<211> LENGTH: 116
<212> TYPE: PRT
<213> ORGANISM: Oryctolagus cuniculus

<400> SEQUENCE: 33

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Thr Thr Tyr Ala
            20                  25                  30

Met Thr Trp Val Arg Gln Ala Pro Gly Lys Gly Leu Glu Trp Ile Gly
        35                  40                  45

Ile Ile Ser Asn Ser Gly Ala Thr Ala Tyr Ala Ser Trp Ala Lys Gly
    50                  55                  60

Arg Phe Thr Ile Ser Lys Thr Ser Thr Thr Val Asp Leu Lys Ile Thr

```
65                  70                  75                  80

Thr Pro Thr Thr Glu Asp Thr Ala Thr Tyr Phe Cys Ala Arg Gly Arg
                85                  90                  95

Ser Gly Gly Trp Asp Ala Leu Asp Pro Trp Gly Pro Gly Thr Leu Val
            100                 105                 110

Thr Val Ser Ser
        115


<210> SEQ ID NO 34
<211> LENGTH: 122
<212> TYPE: PRT
<213> ORGANISM: Oryctolagus cuniculus

<400> SEQUENCE: 34

Gln Glu Gln Leu Glu Glu Ser Gly Gly Asp Leu Val Lys Pro Glu Gly
1               5                   10                  15

Ser Leu Thr Leu Thr Cys Thr Ala Ser Gly Phe Ser Phe Ser Ser Ser
            20                  25                  30

Tyr Trp Ile Cys Trp Val Arg Gln Ala Pro Gly Lys Gly Leu Glu Trp
        35                  40                  45

Ile Ala Cys Ile Gly Thr Ser Ser Thr Ile Ser Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Arg Met Thr Ser Leu Thr Ala Ala Asp Thr Ala Thr Tyr Phe Cys
                85                  90                  95

Ala Arg Glu Asp Tyr Ala Gly Gly Thr Asp Tyr Tyr Phe Arg Leu Trp
            100                 105                 110

Gly Pro Gly Thr Leu Val Thr Val Ser Ser
        115                 120


<210> SEQ ID NO 35
<211> LENGTH: 116
<212> TYPE: PRT
<213> ORGANISM: Oryctolagus cuniculus

<400> SEQUENCE: 35

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Ala
            20                  25                  30

Met Ser Trp Val Arg Gln Ala Pro Gly Lys Gly Leu Glu Trp Ile Gly
        35                  40                  45

Ile Ile His Tyr Ser Gly Tyr Ile Ala Tyr Ala Asn Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Gly
                85                  90                  95

Asp Ala Asp Asn Phe Tyr Tyr Asn Ile Trp Gly Pro Gly Thr Leu Val
            100                 105                 110

Thr Val Ser Leu
        115


<210> SEQ ID NO 36
<211> LENGTH: 120
<212> TYPE: PRT
```

<213> ORGANISM: Oryctolagus cuniculus

<400> SEQUENCE: 36

Gln Glu Gln Leu Lys Glu Ser Gly Gly Gly Leu Val Thr Pro Gly Gly
1 5 10 15

Thr Leu Thr Leu Thr Cys Thr Ala Ser Gly Phe Thr Ile Ser Asn Tyr
20 25 30

Gln Met Thr Trp Val Arg Gln Ala Pro Gly Lys Gly Leu Glu Tyr Ile
35 40 45

Gly Phe Ile Lys Pro Gly Gly Ser Ala Tyr Tyr Ala Ser Trp Ala Lys
50 55 60

Gly Arg Phe Thr Ile Ser Arg Thr Ser Thr Thr Val Thr Leu Lys Leu
65 70 75 80

Thr Ser Pro Thr Thr Gly Asp Thr Ala Thr Tyr Phe Cys Ala Arg Asp
85 90 95

Phe Tyr Ala Gly Ser Ser Gly Asn Val Asn Gly Asp Ile Trp Gly Pro
100 105 110

Gly Thr Leu Val Thr Val Ser Leu
115 120

<210> SEQ ID NO 37
<211> LENGTH: 116
<212> TYPE: PRT
<213> ORGANISM: Oryctolagus cuniculus

<400> SEQUENCE: 37

Gln Ser Leu Glu Glu Ser Gly Gly Asp Leu Val Lys Pro Gly Ala Ser
1 5 10 15

Leu Thr Leu Thr Cys Thr Ala Ser Gly Phe Ser Phe Ser Ser Thr Tyr
20 25 30

Trp Ala Cys Trp Val Arg Gln Ala Pro Gly Lys Gly Leu Glu Trp Ile
35 40 45

Ala Cys Ile Asp Gly Gly Ser Ser Gly Ile Thr Gly Tyr Ala Asn Trp
50 55 60

Ala Lys Gly Arg Phe Thr Leu Ser Arg Thr Ser Ser Thr Ala Val Thr
65 70 75 80

Leu Gln Met Thr Ser Leu Thr Ala Ala Asp Thr Ala Thr Tyr Phe Cys
85 90 95

Ala Arg Glu Leu Asp Tyr Phe Asn Leu Trp Gly Pro Gly Thr Leu Val
100 105 110

Thr Val Ser Ser
115

<210> SEQ ID NO 38
<211> LENGTH: 120
<212> TYPE: PRT
<213> ORGANISM: Oryctolagus cuniculus

<400> SEQUENCE: 38

Gln Glu Gln Leu Lys Glu Ser Gly Gly Gly Leu Val Thr Pro Gly Gly
1 5 10 15

Thr Leu Thr Leu Thr Cys Thr Ala Ser Gly Phe Thr Ile Ser Ser Tyr
20 25 30

Gln Met Thr Trp Val Arg Gln Ala Pro Gly Lys Gly Leu Glu Tyr Ile
35 40 45

Gly Phe Ile Asn Thr Gly Gly Ser Ala Tyr Tyr Ala Ser Trp Ala Lys
50 55 60

Gly Arg Phe Thr Ile Ser Arg Thr Ser Thr Thr Val Asp Leu Ile Ile
65 70 75 80

Thr Ser Pro Thr Thr Gly Asp Thr Ala Thr Tyr Phe Cys Ala Arg Asp
85 90 95

Phe Tyr Ala Gly Ser Ser Gly Asn Val Asn Gly Asp Ile Trp Gly Pro
100 105 110

Gly Thr Leu Val Thr Val Ser Leu
115 120

<210> SEQ ID NO 39
<211> LENGTH: 119
<212> TYPE: PRT
<213> ORGANISM: Oryctolagus cuniculus

<400> SEQUENCE: 39

Gln Ser Leu Glu Glu Ser Gly Gly Asp Leu Val Lys Pro Gly Ala Ser
1 5 10 15

Leu Thr Leu Thr Cys Thr Ala Ser Gly Phe Ser Phe Ser Ser Ser Tyr
20 25 30

Tyr Met Cys Trp Val Arg Gln Ala Pro Gly Lys Gly Leu Glu Trp Ile
35 40 45

Ala Cys Ile Tyr Ala Gly Ser Ser Gly Ser Thr Tyr Tyr Ala Ser Trp
50 55 60

Ala Lys Gly Arg Phe Thr Ile Ser Lys Thr Ser Ser Thr Thr Val Thr
65 70 75 80

Leu Gln Met Thr Ser Leu Thr Ala Ala Asp Thr Ala Thr Tyr Phe Cys
85 90 95

Ala Arg Gly Ala Gly Ser Asn Gly Asp Phe Asn Leu Trp Gly Pro Gly
100 105 110

Thr Leu Val Thr Val Ser Ser
115

<210> SEQ ID NO 40
<211> LENGTH: 120
<212> TYPE: PRT
<213> ORGANISM: Oryctolagus cuniculus

<400> SEQUENCE: 40

Gln Ser Leu Glu Glu Ser Gly Gly Asp Leu Val Lys Pro Gly Ala Ser
1 5 10 15

Leu Thr Leu Thr Cys Lys Ala Ser Gly Phe Asp Phe Ser Ser Asn Tyr
20 25 30

Tyr Met Cys Trp Val Arg Gln Ala Pro Gly Lys Gly Leu Glu Trp Ile
35 40 45

Ala Cys Ile Tyr Thr Gly Ser Ser Gly Ser Thr Tyr Tyr Ala Ser Trp
50 55 60

Ala Lys Gly Arg Phe Thr Ile Ser Lys Thr Ser Ser Thr Thr Val Thr
65 70 75 80

Leu Gln Met Thr Ser Leu Thr Ala Ala Asp Arg Ala Thr Tyr Phe Cys
85 90 95

Ala Arg Gly Ala Gly Ser Tyr Gly Gly Ala Val Arg Leu Trp Gly Pro
100 105 110

Gly Thr Leu Val Thr Val Ser Ser
115 120

<210> SEQ ID NO 41

<211> LENGTH: 121
<212> TYPE: PRT
<213> ORGANISM: Oryctolagus cuniculus

<400> SEQUENCE: 41

```
Gln Ser Leu Glu Glu Ser Gly Gly Asp Leu Val Lys Pro Glu Gly Ser
1               5                   10                  15

Leu Thr Leu Thr Cys Thr Ala Ser Gly Phe Ser Phe Ser Ser Ser Tyr
            20                  25                  30

Tyr Met Cys Trp Val Arg Gln Ala Pro Gly Lys Gly Leu Glu Trp Ile
        35                  40                  45

Ala Cys Ile His Ala Gly Ser Ser Gly Ala Ala Tyr Tyr Ala Thr Trp
    50                  55                  60

Ala Lys Gly Arg Phe Thr Ile Ser Lys Ala Ser Ser Thr Thr Val Thr
65                  70                  75                  80

Leu His Met Thr Ser Leu Thr Ala Ala Asp Thr Ala Thr Tyr Phe Cys
                85                  90                  95

Val Arg Asp Gly Tyr Asp Asp Tyr Gly Asp Pro Phe Asn Leu Trp Gly
            100                 105                 110

Pro Gly Thr Leu Val Thr Val Ser Ser
        115                 120
```

<210> SEQ ID NO 42
<211> LENGTH: 118
<212> TYPE: PRT
<213> ORGANISM: Oryctolagus cuniculus

<400> SEQUENCE: 42

```
Gln Ser Val Glu Glu Ser Gly Gly His Leu Val Thr Pro Gly Thr Pro
1               5                   10                  15

Leu Thr Leu Thr Cys Thr Val Ser Gly Phe Ser Leu Ser Asn Trp Ile
            20                  25                  30

Met Ser Trp Val Arg Gln Ala Pro Gly Glu Gly Leu Glu Trp Ile Gly
        35                  40                  45

Ile Ile Thr Thr Ser Gly Asn Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Ile Ser
                85                  90                  95

Ala Gly Ser Asp Ser Tyr Ile Ile Asp Asn Ile Trp Gly Pro Gly Thr
            100                 105                 110

Leu Val Thr Val Ser Leu
        115
```

<210> SEQ ID NO 43
<211> LENGTH: 120
<212> TYPE: PRT
<213> ORGANISM: Oryctolagus cuniculus

<400> SEQUENCE: 43

```
Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Leu Ser Ser Thr Tyr
            20                  25                  30

Ser Met Cys Trp Val Arg Gln Ala Pro Gly Lys Gly Leu Glu Trp Val
        35                  40                  45
```

```
Ala Cys Ile Tyr Thr Gly Ser Ser Gly Gly Thr Tyr Tyr Ala Ser Trp
    50                  55                  60

Ala Lys Gly Arg Phe Thr Ile Ser Lys Thr Ser Ser Thr Thr Val Gly
65                  70                  75                  80

Leu Lys Met Thr Ser Leu Thr Ala Ala Asp Thr Ala Thr Tyr Phe Cys
                85                  90                  95

Ala Arg Asp Ala Gly Asn Ser Gly Tyr Tyr Ile Asn Leu Trp Gly Pro
            100                 105                 110

Gly Thr Leu Val Thr Val Ser Ser
        115                 120


<210> SEQ ID NO 44
<211> LENGTH: 112
<212> TYPE: PRT
<213> ORGANISM: Oryctolagus cuniculus

<400> SEQUENCE: 44

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Asp Phe Ser Ser Gly Tyr
            20                  25                  30

Asp Met Cys Trp Val Arg Gln Ala Pro Gly Lys Gly Leu Glu Leu Ile
        35                  40                  45

Ala Cys Ile Tyr Thr Val Asn Asp Asn Thr Trp Tyr Ala Ser Trp Ala
    50                  55                  60

Lys Gly Arg Phe Thr Ile Ser Lys Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Leu Tyr Lys Leu Trp Gly Pro Gly Thr Leu Val Thr Val Ser Ser
            100                 105                 110


<210> SEQ ID NO 45
<211> LENGTH: 120
<212> TYPE: PRT
<213> ORGANISM: Oryctolagus cuniculus

<400> SEQUENCE: 45

Gln Ser Leu Glu Glu Ser Gly Gly Asp Leu Val Lys Pro Gly Ala Ser
1               5                   10                  15

Leu Thr Leu Thr Cys Thr Ala Ser Gly Ile Tyr Phe Ser Ser Thr Tyr
            20                  25                  30

Tyr Thr Cys Trp Val Arg Gln Ala Pro Gly Lys Gly Leu Glu Trp Ile
        35                  40                  45

Ala Cys Ile Val Asp Gly Ser Ser Gly Asn Thr Tyr Tyr Ala Ser Trp
    50                  55                  60

Ala Lys Gly Arg Phe Thr Ile Ser Lys Ser Ser Ser Thr Thr Val Thr
65                  70                  75                  80

Leu Gln Met Thr Ser Leu Thr Val Ala Asp Thr Ala Thr Tyr Phe Cys
                85                  90                  95

Gly Arg Pro Tyr Val Gly Tyr Gly Tyr Ala Thr Asp Leu Trp Gly Pro
            100                 105                 110

Gly Thr Leu Val Thr Val Ser Ser
        115                 120


<210> SEQ ID NO 46
<211> LENGTH: 116
```

<212> TYPE: PRT
<213> ORGANISM: Oryctolagus cuniculus

<400> SEQUENCE: 46

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser Ser Ala Ala
20 25 30

Met Gly Trp Val Arg Gln Ala Pro Gly Lys Gly Leu Glu Tyr Ile Gly
35 40 45

Tyr Ile Ser Thr Ser Gly Thr Pro Tyr Tyr Ala Ser Trp Val Asn Gly
50 55 60

Arg Phe Thr Ile Ser Lys Thr Ser Thr Thr Val Asp Leu Lys Ile Thr
65 70 75 80

Ser Pro Thr Thr Glu Asp Thr Ala Thr Tyr Phe Cys Ala Arg Asp Ser
85 90 95

Tyr Ala Gly Asp Tyr Ala Phe Asn Leu Trp Gly Pro Gly Thr Leu Val
100 105 110

Thr Val Ser Ser
115

<210> SEQ ID NO 47
<211> LENGTH: 114
<212> TYPE: PRT
<213> ORGANISM: Oryctolagus cuniculus

<400> SEQUENCE: 47

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Asn Ser Tyr Asp
20 25 30

Met Ser Trp Val Arg Gln Ala Pro Gly Lys Gly Leu Glu Tyr Ile Gly
35 40 45

Ile Ile Tyr Asn Ser Gly Thr Thr Tyr Tyr Ala Asn Trp Ala Lys Gly
50 55 60

Arg Phe Thr Ile Ala Lys Thr Ser Thr Thr Val Asn Leu Lys Ile Thr
65 70 75 80

Ser Pro Thr Thr Glu Asp Thr Ala Thr Tyr Phe Cys Ala Arg Thr His
85 90 95

Asn Thr Leu Pro Phe Tyr Ile Trp Gly Pro Gly Thr Leu Val Thr Val
100 105 110

Ser Leu

<210> SEQ ID NO 48
<211> LENGTH: 119
<212> TYPE: PRT
<213> ORGANISM: Oryctolagus cuniculus

<400> SEQUENCE: 48

Gln Ser Leu Glu Glu Ser Gly Gly Asp Leu Val Lys Pro Glu Gly Ser
1 5 10 15

Leu Thr Leu Thr Cys Thr Ala Ser Gly Phe Ser Phe Ser Ser Thr Tyr
20 25 30

Trp Ile Cys Trp Val Arg Gln Ala Pro Gly Lys Gly Leu Glu Trp Ile
35 40 45

Ala Cys Ile Tyr Thr Asp Ser Ser Thr Ser Thr Tyr Tyr Ala Ser Trp
50 55 60

```
Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Gly Ser Gly Gly Ser Asp Tyr Phe Asn Leu Trp Gly Pro Gly
            100                 105                 110

Thr Leu Val Thr Val Ser Ser
        115


<210> SEQ ID NO 49
<211> LENGTH: 121
<212> TYPE: PRT
<213> ORGANISM: Oryctolagus cuniculus

<400> SEQUENCE: 49

Gln Glu Glu Leu Val Glu Ser Gly Gly Gly Leu Val Gln Pro Glu Gly
1               5                   10                  15

Ser Leu Thr Leu Thr Cys Thr Ala Ser Gly Phe Ser Phe Ser Ser Ser
            20                  25                  30

Tyr Trp Ile Cys Trp Val Arg Gln Ala Pro Gly Lys Gly Leu Glu Trp
        35                  40                  45

Ile Ala Cys Ile Val Gly Gly Gly Gly Val Asn Thr Tyr Tyr Ala Asn
    50                  55                  60

Trp Ala Lys Gly Arg Phe Thr Ile Ser Lys Thr Ser Ser Thr Thr Val
65                  70                  75                  80

Thr Leu Glu Met Thr Ser Leu Thr Val Ala Asp Thr Ala Thr Tyr Phe
                85                  90                  95

Cys Ala Arg Asp Leu Gly Ala Asp Gly Tyr Ala Tyr His Leu Trp Gly
            100                 105                 110

Pro Gly Thr Leu Val Thr Val Ser Ser
        115                 120


<210> SEQ ID NO 50
<211> LENGTH: 121
<212> TYPE: PRT
<213> ORGANISM: Oryctolagus cuniculus

<400> SEQUENCE: 50

Gln Glu Leu Val Glu Ser Gly Gly Gly Leu Val Gln Ala Gly Glu Ser
1               5                   10                  15

Leu Lys Leu Ser Cys Lys Ala Ser Gly Ile Asp Phe Ser Ser Asp Gly
            20                  25                  30

Ile Ser Trp Val Arg Gln Ala Pro Gly Lys Gly Leu Lys Trp Ile Ala
        35                  40                  45

Phe Ile Tyr Pro Gly Val Gly Ile Thr His Tyr Ala His Ser Val Lys
    50                  55                  60

Gly Arg Leu Thr Ile Ser Ser Asp Asn Ala Gln Asn Thr Val Phe Leu
65                  70                  75                  80

Gln Met Thr Ser Leu Thr Ala Ser Asp Thr Ala Thr Tyr Phe Cys Val
                85                  90                  95

Arg Asp Pro Ile Tyr Asp Asp Tyr Gly Gly Arg Leu Asp Leu Trp Gly
            100                 105                 110

Gln Gly Thr Leu Val Thr Val Ser Ser
        115                 120


<210> SEQ ID NO 51
```

<211> LENGTH: 119
<212> TYPE: PRT
<213> ORGANISM: Oryctolagus cuniculus

<400> SEQUENCE: 51

```
Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Ile Ser Trp Val Arg Gln Ala Pro Gly Lys Gly Leu Glu Trp Ile Gly
        35                  40                  45

Gly Val Ala Asn Asn Gly Ile Thr Asn Tyr Ala Ser Trp Ala Arg Gly
    50                  55                  60

Arg Phe Thr Ile Ser Lys Ile Ser Thr Thr Val Asp Leu Lys Ile Ile
65                  70                  75                  80

Ser Pro Thr Thr Glu Asp Thr Ala Thr Tyr Phe Cys Ala Arg Phe Pro
                85                  90                  95

Pro Gly Ser Asn Gly Gly Thr Asp Tyr Phe Asn Ile Trp Gly Pro Gly
            100                 105                 110

Thr Leu Val Thr Val Ser Leu
        115
```

<210> SEQ ID NO 52
<211> LENGTH: 116
<212> TYPE: PRT
<213> ORGANISM: Oryctolagus cuniculus

<400> SEQUENCE: 52

```
Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asn Ala
            20                  25                  30

Leu Gly Trp Val Arg Gln Ala Pro Gly Lys Gly Leu Glu Tyr Ile Gly
        35                  40                  45

Tyr Ile Ser Thr Gly Gly Ser Ala Tyr Tyr Ala Thr Trp Val Asn Gly
    50                  55                  60

Arg Phe Thr Ile Ser Lys Thr Ser Thr Thr Val Asp Leu Lys Met Thr
65                  70                  75                  80

Ser Leu Thr Ala Ala Asp Thr Ala Thr Tyr Phe Cys Ala Arg Asp Ser
                85                  90                  95

Tyr Ala Gly Asp Tyr Ala Phe Asn Leu Trp Gly Pro Gly Thr Leu Val
            100                 105                 110

Thr Val Ser Ser
        115
```

<210> SEQ ID NO 53
<211> LENGTH: 114
<212> TYPE: PRT
<213> ORGANISM: Oryctolagus cuniculus

<400> SEQUENCE: 53

```
Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Asn Ser Tyr Asp
            20                  25                  30

Met Ser Trp Val Arg Gln Ala Pro Gly Lys Gly Leu Glu Tyr Ile Gly
        35                  40                  45
```

```
Ile Ile Tyr Asp Ser Gly Ser Thr Tyr Tyr Ala Ser Trp Ala Lys Gly
    50                  55                  60

Arg Phe Thr Ile Ala Lys Thr Ser Thr Thr Val Asp Leu Lys Ile Thr
65                  70                  75                  80

Ser Pro Thr Thr Glu Asp Thr Ala Thr Tyr Phe Cys Ala Arg Ala Arg
                85                  90                  95

Asn Thr Leu Pro Phe Asn Ile Trp Gly Pro Gly Thr Leu Val Thr Val
            100                 105                 110

Ser Leu


<210> SEQ ID NO 54
<211> LENGTH: 119
<212> TYPE: PRT
<213> ORGANISM: Oryctolagus cuniculus

<400> SEQUENCE: 54

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Asn Tyr Ala
            20                  25                  30

Met Gly Trp Val Arg Gln Ala Pro Gly Lys Gly Leu Glu Trp Ile Gly
        35                  40                  45

Val Ile Ser Ser Asn Gly Gly Thr Val Tyr Ala Asn Trp Ala Lys Gly
    50                  55                  60

Arg Phe Thr Ile Ser Lys Val Ser Thr Ser Val Pro Leu Lys Ile Thr
65                  70                  75                  80

Ser Pro Thr Thr Glu Asp Thr Ala Thr Tyr Phe Cys Ala Arg Gly Leu
                85                  90                  95

Tyr Ser Ala Ser Gly Trp Ser Tyr Cys Phe Asp Ile Trp Gly Pro Gly
            100                 105                 110

Thr Leu Val Thr Val Ser Leu
        115


<210> SEQ ID NO 55
<211> LENGTH: 118
<212> TYPE: PRT
<213> ORGANISM: Oryctolagus cuniculus

<400> SEQUENCE: 55

Gln Ser Val Glu Glu Ser Gly Gly Arg Leu Val Thr Pro Gly Gly Ser
1               5                   10                  15

Leu Thr Leu Thr Cys Thr Val Ser Gly Ile Asp Leu Ser Val Tyr Ala
            20                  25                  30

Met Ser Trp Val Arg Gln Ala Pro Gly Lys Gly Leu Glu Trp Ile Gly
        35                  40                  45

Ile Ile Thr Phe Ser Gly Asn Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Ala Thr Gly Asp Thr Ala Thr Tyr Phe Cys Ala Arg Phe Asp
                85                  90                  95

Phe Leu Val Gly Leu Thr Tyr Ala Gly Val Leu Trp Gly Pro Gly Thr
            100                 105                 110

Leu Val Thr Val Ser Ser
        115
```

```
<210> SEQ ID NO 56
<211> LENGTH: 118
<212> TYPE: PRT
<213> ORGANISM: Oryctolagus cuniculus

<400> SEQUENCE: 56

Gln Ser Val Glu Glu Ser Gly Gly Arg Leu Val Thr Pro Gly Thr Pro
1               5                   10                  15

Leu Thr Leu Thr Cys Ala Val Ser Gly Phe Ser Leu Ser Thr Tyr Gly
            20                  25                  30

Val Ser Trp Val Arg Gln Ala Pro Gly Lys Gly Leu Glu Trp Ile Gly
        35                  40                  45

Tyr Ile Asn Ile Tyr Gly Arg Thr Tyr Tyr Ala Asn Trp Ala Lys Ser
    50                  55                  60

Arg Phe Thr Ile Ser Lys Thr Ser Thr Thr Val Asp Leu Lys Met Thr
65                  70                  75                  80

Ser Pro Thr Thr Glu Asp Thr Ala Thr Tyr Phe Cys Ala Arg Asn Gly
                85                  90                  95

Ala Ser Gly Thr Tyr Tyr Ser Ser Leu Tyr Ile Trp Gly Pro Gly Thr
            100                 105                 110

Leu Val Thr Val Ser Leu
        115


<210> SEQ ID NO 57
<211> LENGTH: 119
<212> TYPE: PRT
<213> ORGANISM: Oryctolagus cuniculus

<400> SEQUENCE: 57

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Met Tyr Ala
            20                  25                  30

Ile Asn Trp Val Arg Gln Ala Pro Gly Lys Gly Leu Glu Trp Ile Gly
        35                  40                  45

Gly Ile Ala Asn Asn Gly Pro Thr Tyr Tyr Ala Ser Trp Ala Lys Gly
    50                  55                  60

Arg Phe Thr Ile Ser Lys Ile Ser Thr Thr Val Asp Leu Lys Ile Thr
65                  70                  75                  80

Ser Pro Thr Thr Glu Asp Thr Ala Thr Tyr Phe Cys Ala Arg Phe Pro
                85                  90                  95

Pro Gly Ser Asn Ser Gly Thr Asp Tyr Phe Asn Ile Trp Gly Pro Gly
            100                 105                 110

Thr Leu Val Thr Val Ser Leu
        115


<210> SEQ ID NO 58
<211> LENGTH: 111
<212> TYPE: PRT
<213> ORGANISM: Oryctolagus cuniculus

<400> SEQUENCE: 58

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Arg Tyr Ala
            20                  25                  30

Met Ser Trp Val Arg Gln Ala Pro Gly Lys Gly Leu Glu Tyr Ile Gly
        35                  40                  45
```

```
Ile Ile Ser Ser Ser Gly Asn Ser Tyr Tyr Ala Ser Trp Ala Lys Gly
    50                  55                  60

Arg Phe Thr Ile Ser Lys Ala Ser Thr Thr Val Asp Leu Lys Ile Thr
65                  70                  75                  80

Val Pro Thr Thr Glu Asp Thr Ala Thr Tyr Phe Cys Val Gly Gly Ser
                85                  90                  95

Gly Trp Asp Leu Trp Gly Gln Gly Thr Leu Val Thr Val Ser Ser
            100                 105                 110


<210> SEQ ID NO 59
<211> LENGTH: 115
<212> TYPE: PRT
<213> ORGANISM: Oryctolagus cuniculus

<400> SEQUENCE: 59

Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Leu Ser Ser Tyr Ala
            20                  25                  30

Met Gly Trp Val Arg Gln Ala Pro Gly Lys Gly Leu Glu Tyr Ile Gly
        35                  40                  45

Ile Ile Ser Ser Gly Leu Thr Tyr Tyr Ala Ser Trp Ala Lys Gly Arg
    50                  55                  60

Phe Thr Ile Ser Lys Thr Ser Thr Thr Val Asp Leu Lys Met Thr Ser
65                  70                  75                  80

Leu Thr Thr Glu Asp Thr Ala Thr Tyr Phe Cys Ala Arg Gly Leu Gly
                85                  90                  95

Ala Ala Ser Ala Thr Trp Asp Ile Trp Gly Pro Gly Thr Leu Val Thr
            100                 105                 110

Val Ser Leu
        115


<210> SEQ ID NO 60
<211> LENGTH: 120
<212> TYPE: PRT
<213> ORGANISM: Oryctolagus cuniculus

<400> SEQUENCE: 60

Gln Ser Leu Glu Glu Ser Gly Gly Asp Leu Val Lys Pro Gly Ala Ser
1               5                   10                  15

Leu Ala Leu Thr Cys Thr Ala Ser Gly Phe Ser Phe Ser Ser Ser Tyr
            20                  25                  30

Trp Ile Cys Trp Val Arg Gln Ala Pro Gly Lys Gly Leu Glu Trp Ile
        35                  40                  45

Ala Cys Ile Asn Phe Gly Arg Ser Gly Asn Ile Tyr Tyr Ala Arg Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Lys Ala Gly Asp Ser Tyr Tyr Phe Asn Leu Trp Gly Pro
            100                 105                 110

Gly Thr Leu Val Thr Val Ser Ser
        115                 120


<210> SEQ ID NO 61
```

```
<211> LENGTH: 112
<212> TYPE: PRT
<213> ORGANISM: Oryctolagus cuniculus

<400> SEQUENCE: 61

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Asn Asn Tyr Tyr
            20                  25                  30

Met Thr Trp Val Arg Gln Ala Pro Gly Glu Gly Leu Glu Tyr Ile Gly
        35                  40                  45

Phe Ile Asp Pro Tyr Ser Ser Pro Tyr Tyr Ala Ser Trp Ala Lys Gly
    50                  55                  60

Arg Phe Thr Ile Ser Arg Thr Ser Thr Thr Val Asp Leu Lys Ile Ser
65                  70                  75                  80

Ser Pro Thr Ala Glu Asp Thr Ala Thr Tyr Phe Cys Ala Arg Gly Val
                85                  90                  95

Ala Val Gly Asp Ile Trp Gly Pro Gly Thr Leu Val Thr Val Ser Leu
            100                 105                 110


<210> SEQ ID NO 62
<211> LENGTH: 112
<212> TYPE: PRT
<213> ORGANISM: Oryctolagus cuniculus

<400> SEQUENCE: 62

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr His
            20                  25                  30

Met Ser Trp Val Arg Gln Ala Pro Gly Lys Gly Leu Glu Trp Ile Gly
        35                  40                  45

Val Ile Tyr Gly Ser Gly Ser Ala Trp Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Val Arg Gly Ile
                85                  90                  95

Leu Val Ser Asp Leu Trp Gly Pro Gly Thr Leu Val Thr Val Ser Ser
            100                 105                 110


<210> SEQ ID NO 63
<211> LENGTH: 121
<212> TYPE: PRT
<213> ORGANISM: Oryctolagus cuniculus

<400> SEQUENCE: 63

Gln Gln Gln Leu Glu Glu Ser Gly Gly Gly Leu Val Lys Pro Glu Gly
1               5                   10                  15

Ser Leu Thr Leu Thr Cys Lys Ala Ser Gly Phe Asp Phe Ser Thr Ile
            20                  25                  30

Pro Met Cys Trp Val Arg Gln Ala Pro Gly Lys Gly Leu Glu Trp Ile
        35                  40                  45

Ala Cys Ile Tyr Pro Asp Tyr Gly Asp Thr Phe Tyr Ala Thr Trp Ala
    50                  55                  60

Lys Gly Arg Phe Thr Ile Ser Lys Thr Ser Ser Thr Thr Val Thr Leu
65                  70                  75                  80
```

-continued

```
Gln Met Thr Ser Leu Thr Val Ala Asp Thr Ala Thr Tyr Phe Cys Ala
                85                  90                  95

Arg Gly Pro Ile Met Val Val Ser Pro Ser Tyr Phe Asn Phe Trp Gly
            100                 105                 110

Pro Gly Thr Leu Val Thr Val Ser Ser
        115                 120


<210> SEQ ID NO 64
<211> LENGTH: 123
<212> TYPE: PRT
<213> ORGANISM: Oryctolagus cuniculus

<400> SEQUENCE: 64

Gln Ser Leu Glu Glu Ser Gly Gly Asp Leu Val Gln Pro Gly Ala Ser
1               5                   10                  15

Leu Thr Leu Thr Cys Thr Ala Ser Gly Phe Ile Phe Ser Asp Asn Tyr
            20                  25                  30

Ala Met Cys Trp Val Arg Gln Ala Pro Gly Lys Gly Leu Glu Trp Ile
        35                  40                  45

Ala Cys Ile Phe Gly Ser Ser Gly Ser Ile Ala Tyr Ala Thr Trp Ala
    50                  55                  60

Lys Gly Arg Phe Thr Ile Ser Lys Thr Ser Ser Thr Thr Val Thr Leu
65                  70                  75                  80

Gln Met Thr Ser Leu Ala Ala Ala Asp Thr Ala Thr Tyr Phe Cys Ala
                85                  90                  95

Arg Ser Tyr Tyr Ser Gly Gly Tyr Lys Tyr Val Tyr Val Phe Asp Leu
            100                 105                 110

Trp Gly Pro Gly Thr Leu Val Thr Val Ser Ser
        115                 120


<210> SEQ ID NO 65
<211> LENGTH: 113
<212> TYPE: PRT
<213> ORGANISM: Oryctolagus cuniculus

<400> SEQUENCE: 65

Gln Glu Gln Leu Val Glu Ser Gly Gly Gly Leu Phe Gln Pro Gly Gly
1               5                   10                  15

Ser Leu Thr Leu Thr Cys Thr Ala Ser Gly Phe Thr Ile Ser Ser Tyr
            20                  25                  30

His Met Gly Trp Val Arg Gln Ala Pro Gly Glu Gly Leu Glu Tyr Ile
        35                  40                  45

Gly Phe Ile Thr Thr Thr Gly Gly Ser Tyr Tyr Ala Ser Trp Ala Arg
    50                  55                  60

Gly Arg Phe Thr Ile Ser Lys Thr Ser Thr Thr Val Asp Leu Lys Met
65                  70                  75                  80

Thr Ser Leu Thr Ala Ala Asp Thr Ala Thr Tyr Phe Cys Ala Lys Gly
                85                  90                  95

Ile Ala Val Ala Ser Leu Trp Gly Pro Gly Thr Leu Val Thr Val Ser
            100                 105                 110

Ser


<210> SEQ ID NO 66
<211> LENGTH: 118
<212> TYPE: PRT
<213> ORGANISM: Oryctolagus cuniculus

<400> SEQUENCE: 66
```

```
Gln Ser Leu Glu Glu Ser Gly Gly Asp Leu Val Lys Pro Gly Ala Ser
1               5                   10                  15

Leu Arg Leu Thr Cys Thr Ala Ser Gly Leu Ser Phe Ser Ser Arg Tyr
            20                  25                  30

Trp Ile Tyr Trp Val Arg Gln Ala Pro Gly Lys Gly Leu Glu Trp Ile
        35                  40                  45

Ala Cys Ile Asp Thr Gly Ser Arg Gly Phe Thr Tyr Tyr Pro Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Leu Asp Thr Tyr Asp Asp Tyr Asp Leu Trp Gly Pro Gly Thr
            100                 105                 110

Leu Val Thr Val Ser Ser
        115


<210> SEQ ID NO 67
<211> LENGTH: 118
<212> TYPE: PRT
<213> ORGANISM: Oryctolagus cuniculus

<400> SEQUENCE: 67

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Tyr Ser Tyr Phe
            20                  25                  30

Leu Thr Trp Val Arg Gln Ser Pro Gly Lys Gly Leu Glu Trp Ile Gly
        35                  40                  45

Phe Met Asn Ser Gly Gly Ser Thr Tyr Tyr Ala Ser Trp Val Asn Gly
    50                  55                  60

Arg Phe Thr Ile Ser Lys Thr Ser Ala Thr Val Asp Leu Lys Ile Thr
65                  70                  75                  80

Gly Ala Thr Thr Glu Asp Thr Ala Thr Tyr Phe Cys Ala Arg Met Phe
                85                  90                  95

Tyr Ala Gly Asp Ser Gly His Tyr Phe Asp Leu Trp Gly Pro Gly Thr
            100                 105                 110

Leu Val Thr Val Ser Ser
        115


<210> SEQ ID NO 68
<211> LENGTH: 121
<212> TYPE: PRT
<213> ORGANISM: Oryctolagus cuniculus

<400> SEQUENCE: 68

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
            20                  25                  30

Met Ser Trp Val Arg Gln Ala Pro Gly Lys Gly Leu Glu Trp Ile Gly
        35                  40                  45

Met Ile Arg Ser Ser Gly Ile Thr Trp Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80
```

-continued

```
Ser Pro Thr Thr Glu Asp Thr Ala Thr Tyr Phe Cys Ala Arg Asp Ser
                85                  90                  95

Asp Tyr Asp Asp Tyr Gly Asn Ser Tyr Tyr Gly Met Asp Pro Trp Gly
            100                 105                 110

Pro Gly Thr Leu Val Thr Val Ser Ser
        115                 120


<210> SEQ ID NO 69
<211> LENGTH: 120
<212> TYPE: PRT
<213> ORGANISM: Oryctolagus cuniculus

<400> SEQUENCE: 69

Gln Glu Gln Leu Glu Glu Ser Gly Gly Asp Leu Val Lys Pro Glu Gly
1               5                   10                  15

Ser Leu Thr Leu Thr Cys Thr Ala Ser Gly Phe Asp Phe Ser Ser Asn
            20                  25                  30

Ala Met Cys Trp Val Arg Gln Ala Pro Gly Lys Gly Leu Glu Trp Ile
        35                  40                  45

Ala Cys Ile Tyr Ala Gly Ser Arg Gly Ser Ala Tyr Tyr Ala Ser Trp
    50                  55                  60

Val Asn Gly Arg Phe Ser Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Glu Tyr Val Gly Ser Gln Gly Tyr Phe Asn Leu Trp Gly Pro
            100                 105                 110

Gly Thr Leu Val Thr Val Ser Ser
        115                 120


<210> SEQ ID NO 70
<211> LENGTH: 118
<212> TYPE: PRT
<213> ORGANISM: Oryctolagus cuniculus

<400> SEQUENCE: 70

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Val Tyr Ala
            20                  25                  30

Met Ser Trp Val Arg Gln Ala Pro Gly Lys Gly Leu Glu Trp Ile Gly
        35                  40                  45

Ile Ile Thr Trp Ser Ala Asp Thr Tyr Tyr Thr Ser Trp Ala Lys Gly
    50                  55                  60

Arg Phe Ser Ile Ser Lys Thr Ser Thr Thr Val Asp Leu Lys Val Ala
65                  70                  75                  80

Ser Pro Thr Thr Glu Asp Thr Ala Thr Tyr Phe Cys Ala Arg Phe Asp
                85                  90                  95

Tyr Leu Val Gly Gly Thr Trp Ala Gly Val Leu Trp Gly Pro Gly Thr
            100                 105                 110

Leu Val Thr Val Ser Ser
        115


<210> SEQ ID NO 71
<211> LENGTH: 117
<212> TYPE: PRT
<213> ORGANISM: Oryctolagus cuniculus
```

<400> SEQUENCE: 71

```
Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Asn Ser Tyr Ala
            20                  25                  30

Met Gly Trp Val Arg Gln Ala Pro Gly Lys Gly Leu Glu Trp Ile Gly
        35                  40                  45

Ile Asn Gly Val Ser Gly Thr Thr Tyr Tyr Ala Thr Trp Ala Asn Gly
    50                  55                  60

Arg Phe Thr Ile Ser Lys Thr Ser Thr Thr Val Asp Leu Lys Ile Ile
65                  70                  75                  80

Arg Pro Thr Thr Glu Asp Thr Ala Thr Tyr Phe Cys Ala Arg Gly Val
                85                  90                  95

Gly Asp Thr Thr Asp Thr Gln Leu Asp Leu Trp Gly Gln Gly Thr Leu
            100                 105                 110

Val Thr Val Ser Ser
        115
```

<210> SEQ ID NO 72
<211> LENGTH: 120
<212> TYPE: PRT
<213> ORGANISM: Oryctolagus cuniculus

<400> SEQUENCE: 72

```
Gln Glu Gln Leu Val Glu Ser Gly Gly Gly Leu Val Gln Pro Glu Gly
1               5                   10                  15

Ser Leu Thr Leu Thr Cys Thr Ala Ser Gly Phe Asp Phe Ser Gly Ser
            20                  25                  30

Tyr Trp Asn Cys Trp Val Arg Gln Ala Pro Gly Lys Gly Leu Glu Trp
        35                  40                  45

Ile Ala Cys Ile Asp Gly Glu Gly Ser Gly Asn Thr Tyr Tyr Ala Ser
    50                  55                  60

Trp Val Asn Gly Arg Phe Thr Ile Ser Lys Thr Ser Ser Thr Thr Val
65                  70                  75                  80

Thr Leu Gln Met Thr Arg Leu Thr Ala Ala Asp Thr Ala Thr Tyr Phe
                85                  90                  95

Cys Ala Arg Asp Pro Ser Ala Trp Gly Gly Leu Asp Leu Trp Gly Pro
            100                 105                 110

Gly Thr Leu Val Thr Val Ser Ser
        115                 120
```

<210> SEQ ID NO 73
<211> LENGTH: 118
<212> TYPE: PRT
<213> ORGANISM: Oryctolagus cuniculus

<400> SEQUENCE: 73

```
Gln Ser Leu Glu Glu Ser Gly Gly Asp Leu Val Lys Pro Gly Ala Ser
1               5                   10                  15

Leu Thr Leu Thr Cys Lys Ala Ser Gly Phe Ser Phe Ser Ser Gly Tyr
            20                  25                  30

Asp Met Cys Trp Val Arg Gln Ala Pro Gly Lys Gly Leu Glu Trp Ile
        35                  40                  45

Ala Cys Ile Asp Thr Gly Asp Gly Ser Thr Tyr Tyr Ala Ser Trp Val
    50                  55                  60
```

-continued

```
Asn Gly Arg Phe Thr Ile Ser Lys Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Tyr Asn Asn Gly Trp Asp Tyr Phe Asn Leu Trp Gly Pro Gly Thr
            100                 105                 110

Leu Val Thr Val Ser Ser
        115


<210> SEQ ID NO 74
<211> LENGTH: 108
<212> TYPE: PRT
<213> ORGANISM: Oryctolagus cuniculus

<400> SEQUENCE: 74

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ile Ala Tyr Gly
            20                  25                  30

Val Asn Trp Val Arg Gln Ala Pro Gly Lys Gly Leu Gln Trp Ile Gly
        35                  40                  45

Ser Ile Ser Asn Ser Gly Gly Thr Tyr Tyr Ala Ser Trp Ala Lys Gly
    50                  55                  60

Arg Phe Thr Val Ser Lys Thr Ser Thr Thr Val Asp Leu Arg Ile Thr
65                  70                  75                  80

Ser Pro Thr Thr Glu Asp Thr Ala Thr Tyr Phe Cys Gly Arg Gly Ser
                85                  90                  95

Leu Trp Gly Pro Gly Thr Leu Val Thr Val Ser Ser
            100                 105


<210> SEQ ID NO 75
<211> LENGTH: 124
<212> TYPE: PRT
<213> ORGANISM: Oryctolagus cuniculus

<400> SEQUENCE: 75

Gln Glu Gln Leu Val Glu Ser Gly Gly Gly Leu Val Gln Pro Glu Gly
1               5                   10                  15

Ser Leu Thr Leu Thr Cys Thr Ala Ser Gly Phe Thr Ile Ser Asn Ser
            20                  25                  30

Tyr Tyr Met Cys Trp Val Arg Gln Ala Pro Gly Lys Gly Leu Glu Trp
        35                  40                  45

Ile Gly Cys Ile Asp Ala Gly Ser Val Gly Asp Thr Ser Tyr Ala Thr
    50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Arg Tyr Gly Ala Gly Ser Gly Tyr Phe Ile Ser Pro Asn
            100                 105                 110

Leu Trp Gly Pro Gly Thr Leu Val Thr Val Ser Ser
        115                 120


<210> SEQ ID NO 76
<211> LENGTH: 120
<212> TYPE: PRT
<213> ORGANISM: Oryctolagus cuniculus
```

<400> SEQUENCE: 76

Gln Glu Gln Leu Val Glu Ser Gly Gly Gly Leu Val Gln Pro Glu Gly
1 5 10 15

Ser Leu Thr Leu Thr Cys Lys Ala Ser Gly Phe Asp Phe Ser Ser Asn
20 25 30

Ala Met Cys Trp Val Arg Gln Ala Pro Gly Lys Gly Pro Glu Trp Ile
35 40 45

Ala Cys Ile Tyr Asn Gly Asp Gly Ser Thr Tyr Tyr Ala Ser Trp Val
50 55 60

Asn Gly Arg Phe Thr Ile Ser Arg Ser Thr Ser Leu Asn Thr Val Thr
65 70 75 80

Leu Gln Met Thr Ser Leu Thr Ala Ala Asp Thr Ala Thr Tyr Phe Cys
85 90 95

Ala Arg Glu Tyr Val Asp Ser Gln Gly Tyr Phe Asn Leu Trp Gly Pro
100 105 110

Gly Thr Leu Val Thr Val Ser Ser
115 120

<210> SEQ ID NO 77
<211> LENGTH: 117
<212> TYPE: PRT
<213> ORGANISM: Oryctolagus cuniculus

<400> SEQUENCE: 77

Gln Ser Leu Glu Glu Ser Gly Gly Arg Leu Val Thr Pro Gly Thr Pro
1 5 10 15

Leu Thr Leu Thr Cys Thr Val Ser Gly Phe Ser Leu Ser Ser Tyr Ala
20 25 30

Met Gly Trp Val Arg Gln Ala Pro Gly Lys Gly Leu Glu Trp Ile Gly
35 40 45

Ile Ile Ser Asn Ser Gly Ala Thr Ala Tyr Ala Ser Trp Ala Lys Gly
50 55 60

Arg Phe Thr Ile Ser Lys Thr Ser Ser Thr Thr Val Asp Leu Lys Met
65 70 75 80

Thr Thr Pro Thr Thr Glu Asp Thr Ala Thr Tyr Phe Cys Ala Arg Gly
85 90 95

Arg Ser Gly Gly Trp Asp Ala Phe Asp Pro Trp Gly Pro Gly Thr Leu
100 105 110

Val Thr Val Ser Ser
115

<210> SEQ ID NO 78
<211> LENGTH: 108
<212> TYPE: PRT
<213> ORGANISM: Oryctolagus cuniculus

<400> SEQUENCE: 78

Gln Ser Leu Glu Glu Ser Gly Gly Arg Leu Val Thr Pro Gly Thr Pro
1 5 10 15

Leu Thr Leu Thr Cys Thr Val Ser Gly Ile Asp Leu Asn Thr Asn Gly
20 25 30

Val Ser Trp Val Arg Gln Ala Pro Gly Lys Gly Leu Glu Trp Ile Gly
35 40 45

Tyr Ile Phe Thr Gly Gly Asn Thr Tyr Tyr Ala Ser Trp Ala Lys Gly
50 55 60

Arg Phe Thr Ile Ser Lys Thr Ser Thr Thr Val Asp Leu Lys Met Thr

```
65                  70                  75                  80

Ser Leu Thr Thr Ala Asp Thr Ala Thr Tyr Phe Cys Ala Arg Phe Asp
                85                  90                  95

Ile Trp Gly Pro Gly Thr Leu Val Thr Val Ser Leu
            100                 105


<210> SEQ ID NO 79
<211> LENGTH: 121
<212> TYPE: PRT
<213> ORGANISM: Oryctolagus cuniculus

<400> SEQUENCE: 79

Gln Glu Gln Leu Glu Glu Ser Gly Gly Gly Leu Val Lys Pro Gly Ala
1               5                   10                  15

Ser Leu Thr Phe Thr Cys Arg Ala Ser Gly Phe Ser Phe Ser Ser Gly
            20                  25                  30

Tyr Tyr Met Cys Trp Val Arg Gln Ala Pro Gly Lys Gly Leu Glu Trp
        35                  40                  45

Ile Ala Cys Ile Tyr Val Gly Ile Thr Gly Ser Thr Tyr Tyr Ala Ser
    50                  55                  60

Trp Ala Lys Gly Arg Phe Thr Ile Ser Lys Thr Ser Ser Thr Ser Val
65                  70                  75                  80

Thr Leu Gln Met Thr Ser Leu Thr Ala Ala Asp Thr Ala Thr Tyr Phe
                85                  90                  95

Cys Ala Arg Asp Thr Gly Asn Ser Asn Tyr Gln Phe Asn Leu Trp Gly
            100                 105                 110

Pro Gly Thr Leu Val Thr Val Ser Ser
        115                 120


<210> SEQ ID NO 80
<211> LENGTH: 126
<212> TYPE: PRT
<213> ORGANISM: Oryctolagus cuniculus

<400> SEQUENCE: 80

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Gly Tyr
            20                  25                  30

Cys Leu Cys Trp Val Arg Gln Ala Pro Gly Lys Gly Leu Glu Trp Ile
        35                  40                  45

Ala Cys Lys His Gly Gly Ala Ser Gly Thr Thr Tyr Tyr Ala Thr Trp
    50                  55                  60

Ala Lys Gly Arg Phe Thr Ile Ser Lys Thr Ser Ser Thr Thr Val Thr
65                  70                  75                  80

Leu Gln Val Thr Ser Leu Thr Val Ala Asp Thr Ala Thr Tyr Phe Cys
                85                  90                  95

Ala Arg Asp Asp Val Ser Val Gly Asp Ala Asn Tyr Pro Tyr Thr Ala
            100                 105                 110

Phe Asp Leu Trp Gly Pro Gly Thr Leu Val Thr Val Ser Ser
        115                 120                 125


<210> SEQ ID NO 81
<211> LENGTH: 120
<212> TYPE: PRT
<213> ORGANISM: Oryctolagus cuniculus

<400> SEQUENCE: 81
```

```
Gln Ser Leu Glu Glu Ser Gly Gly Asp Leu Val Lys Pro Gly Ala Ser
1               5                   10                  15

Leu Thr Leu Thr Cys Thr Ala Ser Gly Ser Asp Ile Ser Ser Tyr Trp
            20                  25                  30

Met Cys Trp Val Arg Gln Ala Pro Gly Lys Gly Leu Glu Trp Ile Ala
        35                  40                  45

Cys Ser Tyr Ala Gly Gly Ser Gly Gly Thr Tyr Tyr Ala Ser Trp Ala
    50                  55                  60

Lys Gly Arg Phe Thr Ile Ser Lys Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Glu Ala Tyr Ser Ser Ala Asn Ser Tyr Tyr Asp Leu Trp Gly Pro
            100                 105                 110

Gly Thr Leu Val Thr Val Ser Ser
        115                 120


<210> SEQ ID NO 82
<211> LENGTH: 120
<212> TYPE: PRT
<213> ORGANISM: Oryctolagus cuniculus

<400> SEQUENCE: 82

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Tyr Tyr
            20                  25                  30

Tyr Met Ser Trp Val Arg Gln Ala Pro Gly Lys Gly Leu Glu Trp Ile
        35                  40                  45

Ala Cys Thr Asp Gly Thr Gly Gly Ile Thr Tyr Tyr Ala Ser Trp Ala
    50                  55                  60

Lys Gly Arg Phe Thr Thr Ser Lys Thr Ser Pro Thr Thr Val Thr Leu
65                  70                  75                  80

Gln Met Thr Ser Leu Thr Ala Ala Asp Thr Ala Thr Tyr Phe Cys Ala
                85                  90                  95

Arg Asp Pro Thr Ala Ala Gly Gly Val Tyr Phe Asp Leu Trp Gly Pro
            100                 105                 110

Gly Thr Leu Val Thr Val Ser Ser
        115                 120


<210> SEQ ID NO 83
<211> LENGTH: 118
<212> TYPE: PRT
<213> ORGANISM: Oryctolagus cuniculus

<400> SEQUENCE: 83

Gln Glu Gln Leu Glu Glu Ser Gly Gly Asp Leu Val Lys Pro Glu Gly
1               5                   10                  15

Ser Leu Thr Leu Thr Cys Thr Ala Ser Gly Phe Asp Phe Ser Tyr Asn
            20                  25                  30

Thr Ile Cys Trp Val Arg Gln Ala Pro Gly Lys Gly Leu Glu Trp Ile
        35                  40                  45

Ala Tyr Ile Asn Thr Gly Ser Ser Gly Thr Thr Tyr Tyr Ala Ser Trp
    50                  55                  60

Ala Lys Gly Arg Phe Thr Ile Ser Lys Thr Ser Ser Thr Thr Val Thr
65                  70                  75                  80
```

Leu Gln Leu Asn Ser Leu Thr Ala Ala Asp Thr Ala Thr Tyr Phe Cys
85 90 95

Ala Gly Gly Ser Gly Tyr Ser Lys Phe Arg Leu Trp Gly Pro Gly Thr
100 105 110

Leu Val Thr Val Ser Ser
115

<210> SEQ ID NO 84
<211> LENGTH: 118
<212> TYPE: PRT
<213> ORGANISM: Oryctolagus cuniculus

<400> SEQUENCE: 84

Gln Ser Leu Glu Glu Ser Gly Gly Asp Leu Val Lys Pro Gly Ala Ser
1 5 10 15

Leu Thr Leu Thr Cys Thr Ala Ser Gly Phe Ser Phe Ser Ser Ser Tyr
20 25 30

Tyr Met Cys Trp Val Arg Gln Ala Pro Gly Lys Gly Leu Glu Trp Ile
35 40 45

Ala Cys Ile Tyr Ala Gly Ser Ser Gly Ser Thr Tyr Tyr Ala Ser Trp
50 55 60

Ala Lys Gly Arg Phe Thr Ile Ser Lys Thr Ser Ser Thr Thr Val Ala
65 70 75 80

Leu Gln Met Thr Ser Leu Thr Ala Ala Asp Thr Ala Thr Tyr Phe Cys
85 90 95

Ala Arg Asp Arg Gly Asp Thr Asp Ile Ser Leu Trp Gly Pro Gly Thr
100 105 110

Leu Val Thr Val Ser Ser
115

<210> SEQ ID NO 85
<211> LENGTH: 118
<212> TYPE: PRT
<213> ORGANISM: Oryctolagus cuniculus

<400> SEQUENCE: 85

Gln Ser Val Glu Glu Ser Gly Gly Arg Leu Val Ala Pro Gly Thr Pro
1 5 10 15

Leu Thr Leu Thr Cys Thr Val Ser Gly Phe Ser Leu Ser Asn Tyr Ala
20 25 30

Met Ser Trp Val Arg Gln Ala Pro Gly Lys Gly Leu Glu Tyr Ile Gly
35 40 45

Phe Ile Asn Ile Ile Asp Ser Thr Tyr Tyr Thr Asn Trp Ala Lys Gly
50 55 60

Arg Phe Thr Ile Ser Lys Thr Ser Thr Thr Val Asp Leu Lys Met Thr
65 70 75 80

Ser Pro Thr Thr Glu Asp Thr Ala Thr Tyr Phe Cys Ala Arg Gly Pro
85 90 95

Tyr Tyr Val Asn Asn Glu Asn Val Phe Asp Pro Trp Gly Pro Gly Thr
100 105 110

Leu Val Thr Val Ser Ser
115

<210> SEQ ID NO 86
<211> LENGTH: 116
<212> TYPE: PRT
<213> ORGANISM: Oryctolagus cuniculus

<400> SEQUENCE: 86

Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Leu Ser Asn Tyr Ala
            20                  25                  30

Val Gly Trp Val Arg Gln Ala Pro Gly Lys Gly Leu Glu Tyr Ile Gly
        35                  40                  45

Val Ile Asn Ala Gly Gly Ser Ala Tyr Tyr Ala Thr Trp Ala Lys Gly
    50                  55                  60

Arg Phe Thr Ile Ser Arg Thr Ser Thr Thr Val Asp Leu Lys Ile Thr
65                  70                  75                  80

Ser Pro Thr Thr Glu Asp Thr Ala Thr Tyr Phe Cys Ala Arg Ser Tyr
                85                  90                  95

Ala Gly Asn Arg Tyr Asp Phe Ala Ile Trp Gly Pro Gly Thr Leu Val
            100                 105                 110

Thr Val Ser Leu
        115

<210> SEQ ID NO 87
<211> LENGTH: 116
<212> TYPE: PRT
<213> ORGANISM: Oryctolagus cuniculus

<400> SEQUENCE: 87

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Val Ser Ser Ser Tyr
            20                  25                  30

Tyr Met Cys Trp Val Arg Gln Ala Pro Gly Lys Gly Leu Glu Trp Ile
        35                  40                  45

Ala Cys Ile Tyr Ala Asp Ser Ser Gly Ser Thr Tyr Tyr Ala Ser Trp
    50                  55                  60

Ala Lys Gly Arg Phe Thr Ile Ser Ser Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Gly Pro Tyr Ser Phe Asp Phe Trp Gly Pro Gly Thr Leu Val
            100                 105                 110

Thr Val Ser Ser
        115

<210> SEQ ID NO 88
<211> LENGTH: 120
<212> TYPE: PRT
<213> ORGANISM: Oryctolagus cuniculus

<400> SEQUENCE: 88

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Arg Tyr
            20                  25                  30

Tyr Val Cys Trp Val Arg Gln Ala Pro Gly Lys Gly Leu Glu Trp Ile
        35                  40                  45

Ala Cys Ile Asp Ala Gly Asp Gly Ser Thr Asp Tyr Ala Arg Trp Ala
    50                  55                  60

```
Lys Gly Arg Phe Thr Ile Ser Lys Thr Ser Ser Thr Thr Val Thr Leu
65                  70                  75                  80

Gln Met Thr Gly Leu Thr Ala Ala Asp Thr Ala Thr Tyr Phe Cys Ala
                85                  90                  95

Arg Gly Asp Ala Tyr Arg Asp Asp Tyr Ala Ser Asp Leu Trp Gly Pro
            100                 105                 110

Gly Thr Leu Val Thr Val Ser Ser
        115                 120


<210> SEQ ID NO 89
<211> LENGTH: 117
<212> TYPE: PRT
<213> ORGANISM: Oryctolagus cuniculus

<400> SEQUENCE: 89

Gln Ser Leu Glu Glu Ser Gly Gly Arg Leu Val Thr Pro Gly Glu Ser
1               5                   10                  15

Leu Thr Leu Thr Cys Thr Val Ser Gly Ile Asp Leu Ser Ala Asn Ala
            20                  25                  30

Met Ser Trp Val Arg Gln Ala Pro Gly Lys Gly Leu Glu Trp Ile Gly
        35                  40                  45

Thr Ile Phe Asp Thr Tyr Leu Thr Tyr Asn Ala Asn Trp Ala Lys Gly
    50                  55                  60

Arg Phe Thr Ile Ser Arg Thr Ser Thr Thr Val Glu Leu Lys Met Thr
65                  70                  75                  80

Ser Pro Thr Ile Glu Asp Thr Ala Thr Tyr Phe Cys Ala Arg Tyr Ile
                85                  90                  95

Gly Ser Val Gly Tyr Arg Arg Met Asp Ile Trp Gly Pro Gly Thr Leu
            100                 105                 110

Val Thr Val Ala Leu
        115


<210> SEQ ID NO 90
<211> LENGTH: 118
<212> TYPE: PRT
<213> ORGANISM: Oryctolagus cuniculus

<400> SEQUENCE: 90

Gln Ser Val Glu Glu Ser Gly Gly Arg Leu Val Thr Pro Gly Gly Ser
1               5                   10                  15

Leu Thr Leu Thr Cys Thr Ala Ser Gly Phe Ser Leu Asn Asn Tyr His
            20                  25                  30

Met Ser Trp Val Arg Gln Ala Pro Gly Lys Gly Leu Glu Trp Ile Gly
        35                  40                  45

Phe Ile Arg Thr Asp Gly Ser Ala Phe Tyr Ala Thr Trp Ala Lys Gly
    50                  55                  60

Arg Phe Thr Ile Ser Lys Thr Ser Ala Thr Val Asp Leu Lys Val Thr
65                  70                  75                  80

Ser Ala Thr Thr Glu Asp Thr Ala Thr Tyr Phe Cys Ala Arg Met Phe
                85                  90                  95

Tyr Ala Gly Asp Ser Gly His Tyr Phe Asp Leu Trp Gly Pro Gly Thr
            100                 105                 110

Leu Val Thr Val Ser Ser
        115


<210> SEQ ID NO 91
<211> LENGTH: 118
```

<212> TYPE: PRT
<213> ORGANISM: Oryctolagus cuniculus

<400> SEQUENCE: 91

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Gly
            20                  25                  30

Leu Thr Trp Val Arg Gln Ala Pro Gly Lys Gly Leu Glu Trp Ile Gly
        35                  40                  45

Tyr Ile Asn Asn Asn Gly Arg Thr Tyr Tyr Ala Ser Arg Ala Lys Gly
    50                  55                  60

Arg Phe Thr Ile Ser Lys Thr Ser Thr Thr Val Asp Leu Gln Met Thr
65                  70                  75                  80

Ser Pro Thr Thr Glu Asp Thr Ala Thr Tyr Phe Cys Ala Arg Asn Gly
                85                  90                  95

Ala Gly Gly Tyr Tyr Tyr Ser Ser Leu Tyr Ile Trp Gly Pro Gly Thr
            100                 105                 110

Leu Val Thr Val Ser Leu
        115

<210> SEQ ID NO 92
<211> LENGTH: 118
<212> TYPE: PRT
<213> ORGANISM: Oryctolagus cuniculus

<400> SEQUENCE: 92

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Ser Tyr
            20                  25                  30

Tyr Met Cys Trp Val Arg Gln Ala Pro Gly Lys Gly Leu Glu Trp Ile
        35                  40                  45

Ala Cys Val Tyr Ala Gly Ser Ser Gly Ser Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Arg Gly Gly Thr Asp Ile Ser Leu Trp Gly Pro Gly Thr
            100                 105                 110

Leu Val Thr Val Ser Ser
        115

<210> SEQ ID NO 93
<211> LENGTH: 116
<212> TYPE: PRT
<213> ORGANISM: Oryctolagus cuniculus

<400> SEQUENCE: 93

Gln Ser Val Glu Glu Ser Gly Gly Arg Leu Val Thr Pro Gly Thr Pro
1               5                   10                  15

Leu Thr Leu Thr Cys Lys Ala Ser Gly Phe Ser Leu Ser Thr Tyr Ala
            20                  25                  30

Met Ser Trp Val Arg Gln Ala Pro Gly Lys Gly Leu Glu Tyr Ile Gly
        35                  40                  45

Ile Ile Asp Ala Ser Val Thr Thr Tyr Tyr Ala Ser Trp Ala Lys Gly

```
    50                  55                  60

Arg Phe Thr Ile Ser Lys Thr Ser Thr Thr Val Asp Leu Thr Ile Thr
65                  70                  75                  80

Ser Pro Thr Thr Glu Asp Thr Ala Thr Tyr Phe Cys Ala Arg Ser Ser
                85                  90                  95

Ser Thr Tyr Ala Tyr Gly Phe Asp Pro Trp Gly Pro Gly Thr Leu Val
            100                 105                 110

Thr Val Ser Ser
        115


<210> SEQ ID NO 94
<211> LENGTH: 118
<212> TYPE: PRT
<213> ORGANISM: Oryctolagus cuniculus

<400> SEQUENCE: 94

Gln Glu Gln Leu Lys Glu Ser Gly Gly Gly Leu Val Gln Pro Gly Gly
1               5                   10                  15

Ser Leu Lys Leu Ser Cys Lys Ala Ser Gly Phe Asp Phe Ser Asn Tyr
            20                  25                  30

Gly Val Ser Trp Val Arg Gln Ala Pro Gly Lys Gly Leu Glu Trp Val
        35                  40                  45

Gly Tyr Ile Asp Pro Val Phe Arg Ser Ala Tyr Tyr Ala Ser Trp Val
    50                  55                  60

Asn Gly Arg Phe Thr Ile Ser Ser His Asn Ala Gln Asn Thr Leu Tyr
65                  70                  75                  80

Leu Gln Leu Asn Ser Leu Thr Ala Ala Asp Thr Ala Thr Tyr Phe Cys
                85                  90                  95

Ala Arg Lys Gly Tyr Phe His Tyr Phe Asn Leu Trp Gly Pro Gly Thr
            100                 105                 110

Leu Val Thr Val Ser Ser
        115


<210> SEQ ID NO 95
<211> LENGTH: 119
<212> TYPE: PRT
<213> ORGANISM: Oryctolagus cuniculus

<400> SEQUENCE: 95

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Val Ser Tyr
            20                  25                  30

Trp Ile Cys Trp Val Arg Gln Ala Pro Gly Lys Gly Leu Glu Trp Ile
        35                  40                  45

Ala Cys Ile Gly Gly Asn Ser Gly Asn Ile Tyr Tyr Ala Arg Trp Ala
    50                  55                  60

Lys Gly Arg Phe Thr Ile Ser Lys Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Asp Arg Ala Gly Asn Ser Tyr Tyr Phe Asn Leu Trp Gly Pro Gly
            100                 105                 110

Thr Leu Val Thr Val Ser Ser
        115
```

<210> SEQ ID NO 96
<211> LENGTH: 112
<212> TYPE: PRT
<213> ORGANISM: Oryctolagus cuniculus

<400> SEQUENCE: 96

```
Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Gly Tyr
            20                  25                  30

Asp Met Cys Trp Val Arg Gln Ala Pro Gly Lys Gly Leu Glu Trp Ile
        35                  40                  45

Gly Cys Ile Tyr Ser Ser Asn Gly Leu Thr Trp Tyr Ala Thr Trp Ala
    50                  55                  60

Lys Gly Arg Phe Thr Val Ser Lys Thr Ser Ser Thr Thr Val Thr Leu
65                  70                  75                  80

Gln Met Thr Ser Leu Thr Ala Ala Asp Thr Ala Ser Tyr Phe Cys Trp
                85                  90                  95

Arg Val Trp Ser Leu Trp Gly Pro Gly Thr Leu Val Thr Val Ser Ser
            100                 105                 110
```

<210> SEQ ID NO 97
<211> LENGTH: 119
<212> TYPE: PRT
<213> ORGANISM: Oryctolagus cuniculus

<400> SEQUENCE: 97

```
Gln Glu Gln Leu Val Glu Tyr Gly Gly Asp Leu Val Gln Pro Glu Gly
1               5                   10                  15

Ser Leu Thr Leu Thr Cys Lys Ala Ser Gly Phe Asp Phe Ser Ser Asn
            20                  25                  30

Ala Met Cys Trp Val Arg Gln Ala Pro Gly Lys Gly Leu Glu Trp Ile
        35                  40                  45

Gly Cys Ile Val Thr Gly Ser Gly Ser Thr Tyr Tyr Ala Ser Trp Ala
    50                  55                  60

Lys Gly Arg Ile Thr Ile Ser Glu Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Gly Tyr Asp Gly Tyr Gly Tyr Val Leu Val Leu Trp Gly Pro Gly
            100                 105                 110

Thr Leu Val Thr Val Ser Ser
        115
```

<210> SEQ ID NO 98
<211> LENGTH: 120
<212> TYPE: PRT
<213> ORGANISM: Oryctolagus cuniculus

<400> SEQUENCE: 98

```
Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Ser Tyr
            20                  25                  30

Tyr Met Cys Trp Val Arg Gln Ala Pro Gly Lys Gly Leu Glu Trp Val
        35                  40                  45

Ala Gly Val Asp Gly Ser Gly Gly Ile Lys Trp Tyr Ala Asn Trp Ala
    50                  55                  60
```

Lys Gly Arg Phe Thr Ile Ser Lys Thr Ser Pro Thr Thr Val Thr Leu
65 70 75 80

Gln Met Thr Ser Leu Thr Ala Ala Asp Thr Ala Thr Tyr Phe Cys Ala
85 90 95

Arg Asp Pro Thr Ala Ala Gly Gly Val Tyr Phe Asp Leu Trp Gly Pro
100 105 110

Gly Thr Leu Val Thr Val Ser Ser
115 120

<210> SEQ ID NO 99
<211> LENGTH: 122
<212> TYPE: PRT
<213> ORGANISM: Oryctolagus cuniculus

<400> SEQUENCE: 99

Gln Ser Leu Glu Glu Ser Gly Gly Asp Leu Val Lys Pro Gly Ala Ser
1 5 10 15

Leu Thr Leu Thr Cys Thr Ala Ser Gly Phe Ser Phe Ser Ser Ser Tyr
20 25 30

Trp Ile Tyr Trp Val Arg Gln Ala Pro Gly Lys Gly Leu Glu Trp Ile
35 40 45

Ala Cys Phe His Ala Gly Ser Gly Ser Thr Tyr Tyr Ala Ser Trp Val
50 55 60

Asn Gly Arg Phe Thr Ile Ser Lys Thr Ser Ser Thr Thr Val Thr Leu
65 70 75 80

Gln Met Thr Ser Leu Thr Ala Ala Asp Thr Ala Thr Tyr Phe Cys Ala
85 90 95

Arg Gly Ser Gly Ser Ile Tyr Tyr Thr Pro Ser Tyr Phe Asp Leu Trp
100 105 110

Gly Pro Gly Thr Leu Val Thr Val Ser Ser
115 120

<210> SEQ ID NO 100
<211> LENGTH: 108
<212> TYPE: PRT
<213> ORGANISM: Oryctolagus cuniculus

<400> SEQUENCE: 100

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser Arg Tyr Gly
20 25 30

Val Ser Trp Val Arg Gln Ala Pro Gly Lys Gly Leu Glu Trp Ile Ala
35 40 45

Trp Ile Ser Ser Ser Gly Ser Ala Tyr Tyr Ala Thr Trp Ala Lys Gly
50 55 60

Arg Phe Thr Ile Ser Lys Thr Ser Thr Thr Val Asp Leu Lys Ile Thr
65 70 75 80

Ser Pro Thr Thr Glu Asp Thr Ala Thr Tyr Phe Cys Gly Glu Ser Asp
85 90 95

Ile Trp Gly Pro Gly Thr Leu Val Thr Val Ser Leu
100 105

<210> SEQ ID NO 101
<211> LENGTH: 119
<212> TYPE: PRT
<213> ORGANISM: Oryctolagus cuniculus -continued

<400> SEQUENCE: 101

```
Gln Ser Leu Glu Glu Ser Gly Gly Gly Leu Val Gln Pro Glu Gly Ser
1               5                   10                  15

Leu Thr Leu Ala Cys Thr Ala Ser Gly Phe Ser Phe Asn Asn Asn Tyr
            20                  25                  30

Tyr Met Cys Trp Val Arg Gln Ala Pro Gly Lys Gly Leu Glu Trp Val
        35                  40                  45

Ala Cys Ile Tyr Thr Gly Ser Thr Gly Ser Thr Tyr Tyr Ala Asn Trp
    50                  55                  60

Ala Lys Gly Arg Phe Thr Ile Ser Lys Leu Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Asp Lys Val Glu His Gly Tyr Gly Leu Trp Gly Pro Gly
            100                 105                 110

Thr Leu Val Thr Val Ser Ser
        115
```

<210> SEQ ID NO 102
<211> LENGTH: 128
<212> TYPE: PRT
<213> ORGANISM: Oryctolagus cuniculus

<400> SEQUENCE: 102

```
Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Asn Tyr
            20                  25                  30

Tyr Met Cys Trp Val Arg Gln Ala Pro Gly Lys Gly Leu Glu Trp Ile
        35                  40                  45

Ala Cys Ile Tyr Ala Gly Ser Ser Gly Ser Ser Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Ser Met Glu Ala Tyr Gly Tyr Ala Gly Tyr Ala Met Pro Gly
            100                 105                 110

Tyr Tyr Phe Asn Leu Trp Gly Pro Gly Thr Leu Val Thr Val Ser Ser
        115                 120                 125
```

<210> SEQ ID NO 103
<211> LENGTH: 121
<212> TYPE: PRT
<213> ORGANISM: Oryctolagus cuniculus

<400> SEQUENCE: 103

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Lys Gly Leu Glu Trp Ile Gly
        35                  40                  45

Ile Ile Arg Arg Ser Gly Ala Thr Trp Tyr Ala Asn Trp Ala Arg Gly
    50                  55                  60
```

-continued

Arg Phe Thr Ile Ser Lys Thr Ser Thr Thr Val Asp Leu Lys Ile Thr
65 70 75 80

Ser Pro Thr Thr Glu Asp Thr Ala Thr Tyr Phe Cys Ala Arg Asp Ser
85 90 95

Asp Tyr Asp Asp Tyr Gly Asp Ser Tyr Tyr Gly Met Asp Pro Trp Gly
100 105 110

Pro Gly Thr Leu Val Thr Val Ser Ser
115 120

<210> SEQ ID NO 104
<211> LENGTH: 127
<212> TYPE: PRT
<213> ORGANISM: Oryctolagus cuniculus

<400> SEQUENCE: 104

Gln Ser Leu Glu Glu Ser Gly Gly Asp Leu Val Lys Pro Gly Ala Ser
1 5 10 15

Leu Thr Leu Thr Cys Thr Ala Ser Gly Phe Ser Phe Ser Ser Ser Tyr
20 25 30

Cys Met Cys Trp Val Arg Gln Ala Pro Gly Lys Gly Leu Glu Trp Ile
35 40 45

Gly Cys Ile Tyr Asp Gly Ser Ser Asp Ser Ala Tyr Tyr Ala Thr Trp
50 55 60

Ala Lys Gly Arg Phe Thr Ile Ser Lys Thr Ser Ser Thr Thr Val Thr
65 70 75 80

Leu Gln Met Thr Ser Leu Thr Ala Ala Asp Thr Ala Thr Tyr Phe Cys
85 90 95

Ala Arg Asp Tyr Asp Thr Tyr Asp Tyr Asp Gly Tyr Thr Tyr Ala Ala
100 105 110

Gly Phe Asp Leu Trp Gly Pro Gly Thr Leu Val Thr Val Ser Thr
115 120 125

<210> SEQ ID NO 105
<211> LENGTH: 116
<212> TYPE: PRT
<213> ORGANISM: Oryctolagus cuniculus

<400> SEQUENCE: 105

Gln Ser Leu Glu Glu Ser Gly Gly Arg Leu Val Thr Pro Gly Thr Pro
1 5 10 15

Leu Thr Leu Thr Cys Thr Val Ser Gly Ile Asp Leu Ser Ser Tyr Ala
20 25 30

Met Gly Trp Val Arg Gln Ala Pro Gly Lys Gly Leu Gln Tyr Ile Gly
35 40 45

Ile Ile Thr Tyr Gly Gly Ser Thr Tyr Tyr Ala Ser Trp Ala Lys Gly
50 55 60

Arg Phe Thr Ile Ser Lys Thr Ser Thr Thr Val Asn Leu Lys Met Thr
65 70 75 80

Ser Leu Thr Thr Glu Asp Thr Ala Thr Tyr Phe Cys Ala Arg Gly Leu
85 90 95

Gly Gly Ala Ser Thr Thr Trp Asp Ile Trp Gly Pro Gly Thr Leu Val
100 105 110

Thr Val Ser Leu
115

<210> SEQ ID NO 106
<211> LENGTH: 123

<212> TYPE: PRT
<213> ORGANISM: Oryctolagus cuniculus

<400> SEQUENCE: 106

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Gly Tyr
            20                  25                  30

Asp Met Cys Trp Val Arg Gln Ala Pro Gly Lys Gly Leu Glu Trp Ile
        35                  40                  45

Ala Cys Ile Ala Val Tyr Ser Ser Gly Ser Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Pro Ser Leu Thr Ala Ala Asp Thr Ala Thr Tyr Phe Cys
                85                  90                  95

Ala Arg Asp Ile Ile Thr Asp Ser Val Trp Ile Thr Arg Leu Asp Leu
            100                 105                 110

Trp Gly Gln Gly Thr Leu Val Thr Val Ser Ser
        115                 120

<210> SEQ ID NO 107
<211> LENGTH: 118
<212> TYPE: PRT
<213> ORGANISM: Oryctolagus cuniculus

<400> SEQUENCE: 107

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Phe Ser Asp Tyr Tyr
            20                  25                  30

Met Ser Trp Val Arg Gln Ala Pro Gly Lys Gly Leu Glu Trp Ile Gly
        35                  40                  45

Val Val Ser Trp Asn Gly Asn Thr Tyr Tyr Ala Ser Trp Ala Lys Gly
    50                  55                  60

Arg Phe Thr Val Ser Lys Thr Ser Thr Thr Val Asp Leu Lys Ile Ile
65                  70                  75                  80

Ser Pro Thr Thr Glu Asp Thr Ala Thr Tyr Phe Cys Ala Arg Phe Asp
                85                  90                  95

Tyr Leu Val Gly Asp Thr Tyr Ala Gly Val Leu Trp Gly Pro Gly Thr
            100                 105                 110

Leu Val Thr Val Ser Ser
        115

<210> SEQ ID NO 108
<211> LENGTH: 119
<212> TYPE: PRT
<213> ORGANISM: Oryctolagus cuniculus

<400> SEQUENCE: 108

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser His Ala
            20                  25                  30

Thr Ser Trp Val Arg Gln Ala Pro Gly Lys Gly Leu Glu Trp Ile Gly
        35                  40                  45

Phe Ile Lys Ser Gly Gly Ser Thr Tyr Tyr Ala Ser Trp Ala Lys Gly

```
 50                  55                  60

Arg Phe Thr Ile Ser Glu Thr Ser Ala Thr Val Asp Leu Lys Ile Thr
65                  70                  75                  80

Ser Pro Thr Thr Glu Asp Thr Ala Thr Tyr Phe Cys Ala Ser Met Phe
                85                  90                  95

Tyr Ala Gly Asp Ser Ser Gly Asn Tyr Leu His Leu Trp Gly Pro Gly
            100                 105                 110

Thr Leu Val Thr Val Ser Ser
        115


<210> SEQ ID NO 109
<211> LENGTH: 121
<212> TYPE: PRT
<213> ORGANISM: Oryctolagus cuniculus

<400> SEQUENCE: 109

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Gly Tyr
            20                  25                  30

Trp Ile Cys Trp Val Arg Gln Ala Pro Gly Lys Gly Leu Glu Trp Ile
        35                  40                  45

Ala Cys Ile Asp Ala Gly Ser Asn Gly Ser Thr Tyr Tyr Ala Ser Trp
    50                  55                  60

Ala Arg Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Glu Gly Ser Ser Ala Tyr Pro Ser Tyr Phe Asn Phe Trp Gly
            100                 105                 110

Pro Gly Thr Leu Val Thr Val Ser Ser
        115                 120


<210> SEQ ID NO 110
<211> LENGTH: 116
<212> TYPE: PRT
<213> ORGANISM: Oryctolagus cuniculus

<400> SEQUENCE: 110

Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Leu Ser Ser Tyr Thr
            20                  25                  30

Met Ala Trp Val Arg Gln Ala Pro Gly Lys Gly Leu Glu Tyr Ile Gly
        35                  40                  45

Val Ile Asn Thr Gly Gly Ser Ala Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Ser Tyr
                85                  90                  95

Gly Gly Asn Arg Tyr Asp Phe Asn Ile Trp Gly Pro Gly Thr Leu Val
            100                 105                 110

Thr Val Ser Leu
        115
```

-continued

<210> SEQ ID NO 111
<211> LENGTH: 119
<212> TYPE: PRT
<213> ORGANISM: Oryctolagus cuniculus

<400> SEQUENCE: 111

```
Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr His
            20                  25                  30

Met Cys Trp Val Arg Gln Ala Pro Gly Lys Gly Leu Glu Trp Ile Gly
        35                  40                  45

Phe Ile Lys Ala Asp Gly Asn Thr Tyr Tyr Ala Thr Trp Ala Lys Gly
    50                  55                  60

Arg Phe Thr Ile Ser Arg Ser Ser Ala Thr Val Asp Leu Lys Ile Thr
65                  70                  75                  80

Ser Ala Thr Ala Glu Asp Thr Ala Thr Tyr Phe Cys Ala Arg Met Phe
                85                  90                  95

Tyr Ala Gly His Thr Ser Gly His Tyr Phe Asp Leu Trp Gly Pro Gly
            100                 105                 110

Thr Leu Val Thr Val Ser Ser
        115
```

<210> SEQ ID NO 112
<211> LENGTH: 130
<212> TYPE: PRT
<213> ORGANISM: Oryctolagus cuniculus

<400> SEQUENCE: 112

```
Gln Ser Leu Glu Glu Ser Gly Gly Asp Leu Val Lys Pro Glu Ala Ser
1               5                   10                  15

Leu Thr Leu Thr Cys Thr Ala Ser Gly Phe Ser Phe Ser Gly Asp Tyr
            20                  25                  30

Asp Met Cys Trp Val Arg Gln Ala Pro Gly Lys Gly Leu Glu Trp Ile
        35                  40                  45

Ala Cys Ile Gly Ala Gly Ser Ser Asn Asp Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Gly Phe Asp Tyr Thr Tyr Gly Asp Ala Gly Tyr Thr Tyr Ser
            100                 105                 110

Thr Ser His Tyr Phe Asn Leu Trp Gly Pro Gly Thr Leu Val Thr Val
        115                 120                 125

Ser Ser
    130
```

<210> SEQ ID NO 113
<211> LENGTH: 120
<212> TYPE: PRT
<213> ORGANISM: Oryctolagus cuniculus

<400> SEQUENCE: 113

```
Gln Ser Leu Glu Glu Ser Gly Gly Gly Leu Val Gln Pro Glu Gly Ser
1               5                   10                  15

Leu Thr Leu Thr Cys Thr Ala Ser Gly Phe Ser Phe Ser Ser Ser Tyr
            20                  25                  30
```

```
Tyr Met Cys Trp Val Arg Gln Ala Pro Gly Lys Gly Leu Glu Trp Ile
        35                  40                  45

Ala Cys Ile Ser Val Gly Ser Ser Gly Ser Thr Tyr Tyr Ala Asn Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Glu Gly Ala Asp Tyr Gln Gly His Phe Asn Leu Trp Gly Pro
            100                 105                 110

Gly Thr Leu Val Thr Val Ser Ser
        115                 120


<210> SEQ ID NO 114
<211> LENGTH: 121
<212> TYPE: PRT
<213> ORGANISM: Oryctolagus cuniculus

<400> SEQUENCE: 114

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Lys Gly Leu Glu Trp Ile Gly
        35                  40                  45

Ile Ile Arg Arg Ser Gly Phe Thr Tyr Tyr Ala Ser Trp Ala Arg Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Asp Ser
                85                  90                  95

Asp Tyr Asp Asp Tyr Gly Asn Ser Tyr Tyr Gly Met Asp Pro Trp Gly
            100                 105                 110

Pro Gly Thr Leu Val Thr Val Ser Ser
        115                 120


<210> SEQ ID NO 115
<211> LENGTH: 119
<212> TYPE: PRT
<213> ORGANISM: Oryctolagus cuniculus

<400> SEQUENCE: 115

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Thr
            20                  25                  30

Met Thr Trp Val Arg Gln Ala Pro Gly Lys Gly Leu Glu Trp Ile Gly
        35                  40                  45

Leu Ile Ser Arg Ser Gly Arg Thr Tyr Tyr Ala Thr Trp Ala Lys Gly
    50                  55                  60

Arg Leu Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Glu Ile
                85                  90                  95

Gly Ser Gly Tyr Asp Ala Pro Tyr Tyr Phe Asn Leu Trp Gly Pro Gly
            100                 105                 110
```

```
Thr Leu Val Thr Val Ser Ser
        115


<210> SEQ ID NO 116
<211> LENGTH: 119
<212> TYPE: PRT
<213> ORGANISM: Oryctolagus cuniculus

<400> SEQUENCE: 116

Gln Ser Leu Glu Glu Ser Gly Gly Gly Leu Val Gln Pro Glu Gly Ser
1               5                   10                  15

Leu Thr Leu Thr Cys Thr Ala Ser Gly Phe Ser Phe Asn Ser Lys Tyr
            20                  25                  30

Tyr Met Cys Trp Val Arg Gln Ala Pro Gly Lys Gly Leu Glu Trp Ile
        35                  40                  45

Ala Cys Ile Tyr Thr Gly Thr Thr Gly Ser Thr Tyr Tyr Ala Ser Trp
    50                  55                  60

Ala Lys Tyr Arg Phe Thr Ile Ser Lys Ile Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Asp Arg Val Glu His Gly Tyr Gly Leu Trp Gly Pro Gly
            100                 105                 110

Thr Leu Val Thr Val Ser Ser
        115


<210> SEQ ID NO 117
<211> LENGTH: 119
<212> TYPE: PRT
<213> ORGANISM: Oryctolagus cuniculus

<400> SEQUENCE: 117

Gln Glu Gln Leu Glu Glu Ser Gly Gly Gly Leu Val Lys Pro Glu Gly
1               5                   10                  15

Ser Leu Thr Leu Thr Cys Lys Ala Ser Gly Phe Thr Ile Ser Ser Tyr
            20                  25                  30

Tyr Ile Tyr Trp Val Arg Gln Ala Pro Gly Lys Gly Leu Glu Trp Ile
        35                  40                  45

Gly Cys Ile Ala Ile Ile Asn Ser Ile Thr Tyr Tyr Ala Asn Trp Ala
    50                  55                  60

Lys Gly Arg Phe Thr Ile Ser Lys Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Asp Leu Ser Ser Ser Ile Tyr Asp Met Asp Leu Trp Gly Pro Gly
            100                 105                 110

Thr Leu Val Thr Val Ser Ser
        115


<210> SEQ ID NO 118
<211> LENGTH: 121
<212> TYPE: PRT
<213> ORGANISM: Oryctolagus cuniculus

<400> SEQUENCE: 118

Gln Ser Leu Glu Glu Ser Gly Gly Asp Leu Val Lys Pro Gly Ala Ser
1               5                   10                  15
```

```
Leu Thr Leu Thr Cys Lys Ala Ser Gly Leu Asp Phe Ser Ser Val Tyr
            20                  25                  30

Asp Met Cys Trp Val Arg Gln Ala Pro Gly Lys Gly Leu Glu Trp Ile
        35                  40                  45

Ala Cys Ile Tyr Ser Asp Gly Ser Gly Ser Thr Tyr Tyr Ala Asn Trp
    50                  55                  60

Ala Lys Gly Arg Phe Thr Ile Ser Glu Thr Ser Ser Thr Thr Val Thr
65                  70                  75                  80

Leu Gln Met Thr Asn Leu Thr Ala Ala Asp Thr Ala Thr Tyr Phe Cys
                85                  90                  95

Ala Arg Val Leu Asn Gly Trp Gly Glu Tyr Tyr Phe Asn Leu Trp Gly
            100                 105                 110

Pro Gly Thr Leu Val Thr Val Ser Ser
        115                 120


<210> SEQ ID NO 119
<211> LENGTH: 112
<212> TYPE: PRT
<213> ORGANISM: Oryctolagus cuniculus

<400> SEQUENCE: 119

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr His
            20                  25                  30

Met Ser Trp Val Arg Gln Ala Pro Gly Lys Gly Leu Glu Tyr Ile Gly
        35                  40                  45

Phe Ile Val Gly Thr Gly Asp Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Gly Arg Gly Val
                85                  90                  95

Ala Ala Gly Asp Ile Trp Gly Pro Gly Thr Leu Val Thr Val Ser Leu
            100                 105                 110


<210> SEQ ID NO 120
<211> LENGTH: 113
<212> TYPE: PRT
<213> ORGANISM: Oryctolagus cuniculus

<400> SEQUENCE: 120

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Gly Leu Val
            20                  25                  30

Val Ser Trp Val Arg Gln Ala Pro Gly Lys Gly Leu Glu Trp Ile Gly
        35                  40                  45

Val Ile Gly Lys Ser Gly Ser Thr Tyr Tyr Ala Ser Trp Ala Lys Gly
    50                  55                  60

Arg Phe Ser Ile Ser Lys Thr Ser Ser Thr Thr Val Asp Leu Lys Ile
65                  70                  75                  80

Ala Ser Pro Thr Thr Glu Asp Thr Ala Thr Tyr Phe Cys Gly Arg Asn
                85                  90                  95

Ile Ser Gly Ser Ala Val Trp Gly Pro Gly Thr Leu Val Thr Val Ser
            100                 105                 110
```

Leu

<210> SEQ ID NO 121
<211> LENGTH: 119
<212> TYPE: PRT
<213> ORGANISM: Oryctolagus cuniculus

<400> SEQUENCE: 121

Gln Glu Gln Leu Val Glu Ser Gly Gly Gly Leu Val Gln Pro Glu Gly
1 5 10 15

Ser Leu Thr Leu Thr Cys Lys Ala Ser Gly Phe Asp Phe Asn Arg Asp
20 25 30

Ala Met Ser Trp Val Arg Gln Ala Pro Gly Lys Gly Leu Glu Trp Ile
35 40 45

Gly Ser Ile Val Ser Gly Ser Gly Ser Thr Tyr Tyr Ala Ser Trp Ala
50 55 60

Lys Gly Arg Phe Thr Ile Ser Glu Thr Ser Ser Thr Thr Val Thr Leu
65 70 75 80

Gln Met Thr Ser Leu Thr Ala Ala Asp Thr Ala Thr Tyr Phe Cys Ala
85 90 95

Arg Gly Gly Asp Gly Tyr Gly Tyr Val Leu Val Leu Trp Gly Pro Gly
100 105 110

Thr Leu Val Thr Val Ser Ser
115

<210> SEQ ID NO 122
<211> LENGTH: 115
<212> TYPE: PRT
<213> ORGANISM: Oryctolagus cuniculus

<400> SEQUENCE: 122

Gln Ser Leu Glu Glu Ser Gly Gly Asp Leu Val Lys Pro Gly Ala Ser
1 5 10 15

Leu Lys Leu Ser Cys Ala Ala Ser Gly Phe Thr Leu Ser Ser Tyr Trp
20 25 30

Ile Cys Trp Val Arg Gln Ala Pro Gly Lys Gly Leu Glu Trp Ile Ala
35 40 45

Cys Ile Tyr Ala Gly Ser Ser Gly Ser Thr Tyr Tyr Ala Ser Trp Ala
50 55 60

Lys Gly Arg Phe Thr Ile Ser Lys Thr Ser Ser Thr Thr Val Thr Leu
65 70 75 80

Gln Met Thr Ser Leu Thr Ala Ala Asp Thr Ala Thr Tyr Phe Cys Ala
85 90 95

Arg Gly Ile Ser Tyr Ala Leu Leu Trp Gly Pro Gly Thr Leu Val Thr
100 105 110

Val Ser Ser
115

<210> SEQ ID NO 123
<211> LENGTH: 116
<212> TYPE: PRT
<213> ORGANISM: Oryctolagus cuniculus

<400> SEQUENCE: 123

Gln Ser Val Glu Glu Ser Gly Gly Arg Leu Val Thr Pro Gly Thr Pro
1 5 10 15

Leu Thr Leu Thr Cys Thr Val Ser Gly Ile Asp Leu Ser Arg Tyr Ala
20 25 30

```
Met Ile Trp Val Arg Gln Ala Pro Gly Lys Gly Leu Glu Ser Ile Gly
        35                  40                  45

Ile Ile Asp Ile Arg Gly Thr Thr Tyr Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Thr Tyr Phe Cys Ala Arg Gly
                85                  90                  95

Gly Val Gly His Glu Val Asn Asn Leu Trp Gly Pro Gly Thr Leu Val
            100                 105                 110

Thr Val Ser Ser
        115


<210> SEQ ID NO 124
<211> LENGTH: 121
<212> TYPE: PRT
<213> ORGANISM: Oryctolagus cuniculus

<400> SEQUENCE: 124

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Asn Asn Tyr
            20                  25                  30

Trp Ile Cys Trp Val Arg Gln Ala Pro Gly Lys Gly Leu Glu Trp Ile
        35                  40                  45

Ala Cys Ile Val Ala Gly Ser Ser Gly Arg Thr Tyr Tyr Ala Asn Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Lys Leu Ser Asp Trp Asp Tyr Gly Tyr Phe Asn Leu Trp Gly
            100                 105                 110

Pro Gly Thr Leu Val Thr Val Ser Ser
        115                 120


<210> SEQ ID NO 125
<211> LENGTH: 127
<212> TYPE: PRT
<213> ORGANISM: Oryctolagus cuniculus

<400> SEQUENCE: 125

Gln Ser Leu Glu Glu Ser Gly Gly Asp Leu Val Lys Pro Gly Ala Ser
1               5                   10                  15

Leu Thr Leu Thr Cys Thr Ala Ser Gly Ile Asp Phe Ser Thr Tyr Tyr
            20                  25                  30

Tyr Met Cys Cys Val Arg Gln Ala Pro Gly Lys Gly Leu Glu Trp Ile
        35                  40                  45

Ala Cys Ile His Ala Gly Ser Ser Gly Ser Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Gly Tyr Ala Gly Tyr Tyr Gly Tyr Gly Tyr Pro Thr Pro Ser
            100                 105                 110
```

```
Trp Leu Asp Leu Trp Gly Gln Gly Thr Leu Val Thr Val Ser Ser
        115                 120                 125


<210> SEQ ID NO 126
<211> LENGTH: 119
<212> TYPE: PRT
<213> ORGANISM: Oryctolagus cuniculus

<400> SEQUENCE: 126

Gln Ser Val Glu Glu Ser Gly Gly Arg Leu Val Thr Pro Gly Thr Pro
1               5                   10                  15

Leu Thr Leu Thr Cys Lys Ala Ser Gly Phe Ser Leu Ser Ser Tyr Trp
            20                  25                  30

Met Ser Trp Val Arg Gln Ala Pro Gly Glu Gly Leu Glu Trp Ile Gly
        35                  40                  45

Thr Ile Asn Ala Ala Ser Gly Ala Thr Trp Tyr Ala Ser Trp Ala Lys
    50                  55                  60

Gly Arg Phe Thr Ile Ser Lys Thr Ser Thr Thr Val Asp Leu Lys Met
65                  70                  75                  80

Thr Ser Leu Thr Thr Glu Asp Thr Ala Thr Tyr Phe Cys Ala Arg Gly
                85                  90                  95

Gly Thr Thr Gly Ser Asn Tyr Tyr Gly Met Asp Pro Trp Gly Pro Gly
            100                 105                 110

Thr Leu Val Thr Val Ser Ser
        115


<210> SEQ ID NO 127
<211> LENGTH: 109
<212> TYPE: PRT
<213> ORGANISM: Oryctolagus cuniculus

<400> SEQUENCE: 127

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Arg Asn Ala
            20                  25                  30

Ala Ser Trp Val Arg Gln Ala Pro Gly Lys Gly Leu Glu Trp Ile Gly
        35                  40                  45

Ile Ile Ser Thr Gly Gly Ser Thr Tyr Tyr Ala Thr Trp Ala Lys Gly
    50                  55                  60

Pro Phe Thr Ile Ser Lys Thr Ser Thr Thr Val Asp Leu Lys Met Thr
65                  70                  75                  80

Ser Leu Thr Thr Glu Asp Thr Ala Thr Tyr Phe Cys Val Val Gly Ile
                85                  90                  95

Arg Phe Trp Gly Pro Gly Thr Leu Val Thr Val Ser Ser
            100                 105


<210> SEQ ID NO 128
<211> LENGTH: 122
<212> TYPE: PRT
<213> ORGANISM: Oryctolagus cuniculus

<400> SEQUENCE: 128

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Ala
            20                  25                  30
```

```
Met Thr Trp Val Arg Gln Ala Pro Gly Lys Gly Leu Glu Trp Ile Gly
        35                  40                  45

Ile Ile Ile Asn Thr Gly Tyr Thr Tyr Tyr Ala Ser Trp Ala Lys Gly
    50                  55                  60

Arg Phe Thr Ile Ser Lys Ala Ser Thr Thr Val Asp Leu Lys Ile Thr
65                  70                  75                  80

Ser Pro Thr Thr Glu Asp Thr Ala Thr Tyr Phe Cys Ala Arg Val Leu
                85                  90                  95

Gly Ala Gly Ser Ser Tyr Tyr Thr Ser Tyr Asp Arg Leu Asp Leu Trp
            100                 105                 110

Gly Gln Gly Thr Leu Val Thr Val Ser Ser
        115                 120


<210> SEQ ID NO 129
<211> LENGTH: 116
<212> TYPE: PRT
<213> ORGANISM: Oryctolagus cuniculus

<400> SEQUENCE: 129

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ile Ser Asn Ala
            20                  25                  30

Ile Ser Trp Val Arg Gln Ala Pro Gly Lys Gly Leu Glu Trp Ile Gly
        35                  40                  45

His Ser Asp Ile Arg Gly Ser Ala Tyr Tyr Ala Ser Trp Ala Lys Gly
    50                  55                  60

Arg Phe Thr Ile Ser Arg Thr Ser Ser Thr Thr Val Asp Leu Lys Met
65                  70                  75                  80

Thr Ser Leu Thr Thr Glu Asp Thr Ala Thr Tyr Phe Cys Ala Arg Ile
                85                  90                  95

Ala Asp Val Asn Thr Gln Leu Asp Leu Trp Gly Gln Gly Thr Leu Val
            100                 105                 110

Thr Val Ser Ser
        115


<210> SEQ ID NO 130
<211> LENGTH: 120
<212> TYPE: PRT
<213> ORGANISM: Oryctolagus cuniculus

<400> SEQUENCE: 130

Gln Ser Leu Glu Glu Ser Gly Gly Asp Leu Val Lys Pro Gly Ala Ser
1               5                   10                  15

Leu Thr Leu Thr Cys Ala Ala Ser Gly Phe Ser Phe Ser Val Gly Tyr
            20                  25                  30

Tyr Met Cys Trp Val Arg Gln Ala Pro Gly Lys Gly Leu Glu Trp Val
        35                  40                  45

Ala Cys Ile Tyr Ala Gly Ser Asn Gly Ser Thr Tyr Tyr Ala Ser Trp
    50                  55                  60

Ala Lys Gly Arg Phe Thr Phe Ser Lys Pro Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Gly Ala Gly Tyr Ala Gly Tyr Gly Phe Asn Leu Trp Gly Pro
            100                 105                 110
```

```
Gly Thr Leu Val Thr Val Ser Ser
        115                 120


<210> SEQ ID NO 131
<211> LENGTH: 125
<212> TYPE: PRT
<213> ORGANISM: Oryctolagus cuniculus

<400> SEQUENCE: 131

Gln Glu Gln Leu Val Glu Ser Gly Gly Gly Leu Val Lys Pro Glu Gly
1               5                   10                  15

Ser Leu Thr Leu Thr Cys Thr Ala Ser Gly Phe Ser Phe Ser Ser Ser
            20                  25                  30

Tyr Trp Ile Cys Trp Val Arg Gln Ala Pro Gly Lys Gly Leu Glu Trp
        35                  40                  45

Ile Ala Cys Ile Tyr Ala Asp Gly Ser Gly Ser Ile Tyr Cys Ala Thr
    50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ser Arg Gly Asn Ala Gly Ser Tyr Trp Asp Ile Tyr Tyr Gly Met
            100                 105                 110

Asp Leu Trp Gly Pro Gly Thr Leu Val Thr Val Ser Ser
        115                 120                 125


<210> SEQ ID NO 132
<211> LENGTH: 118
<212> TYPE: PRT
<213> ORGANISM: Oryctolagus cuniculus

<400> SEQUENCE: 132

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Ser Tyr
            20                  25                  30

Tyr Met Cys Trp Val Arg Gln Ala Pro Gly Lys Gly Leu Glu Trp Ile
        35                  40                  45

Ala Cys Ile Tyr Ile Gly Asp Gly Asn Thr Tyr Tyr Ala Ser Trp Ala
    50                  55                  60

Lys Gly Arg Phe Thr Ile Ser Lys Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Gly Ser Gly Gly Tyr Phe Val Asp Asn Leu Trp Gly Pro Gly Thr
            100                 105                 110

Leu Val Thr Val Ser Ser
        115


<210> SEQ ID NO 133
<211> LENGTH: 118
<212> TYPE: PRT
<213> ORGANISM: Oryctolagus cuniculus

<400> SEQUENCE: 133

Gln Ser Val Glu Glu Ser Gly Gly Arg Leu Val Thr Pro Gly Thr Pro
1               5                   10                  15

Leu Thr Leu Thr Cys Thr Ala Ser Gly Phe Asp Ile Asn Asn Tyr His
```

```
            20                  25                  30

Met Thr Trp Val Arg Gln Ala Pro Gly Lys Gly Leu Glu Trp Ile Gly
        35                  40                  45

Phe Ile Lys Ala Gly Gly Ser Ala Gly Tyr Ala Ser Trp Ala Lys Gly
    50                  55                  60

Arg Phe Thr Ile Ser Lys Thr Ser Ala Thr Val Asp Leu Arg Ile Thr
65                  70                  75                  80

Gly Ala Thr Thr Glu Asp Thr Gly Thr Tyr Phe Cys Val Arg Met Phe
                85                  90                  95

Tyr Ala Gly Asp Ser Gly His Tyr Phe Asp Leu Trp Gly Pro Gly Thr
            100                 105                 110

Leu Val Thr Val Ser Ser
        115
```

<210> SEQ ID NO 134
<211> LENGTH: 118
<212> TYPE: PRT
<213> ORGANISM: Oryctolagus cuniculus

<400> SEQUENCE: 134

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Asp
            20                  25                  30

Met Thr Trp Val Arg Gln Ala Pro Gly Lys Gly Leu Glu Trp Ile Gly
        35                  40                  45

Val Ile Ser Ser Ser Asp Ser Thr Tyr Tyr Ala Ser Trp Ala Lys Gly
    50                  55                  60

Arg Phe Thr Ile Ser Lys Pro Ser Ser Thr Thr Val Asp Leu Lys Val
65                  70                  75                  80

Thr Ser Pro Thr Thr Glu Asp Thr Ala Thr Tyr Phe Cys Ala Arg Asp
                85                  90                  95

His Pro Ala Phe Ser Thr Val Asp Leu Asp Ile Trp Gly Pro Gly Thr
            100                 105                 110

Leu Val Thr Val Ser Leu
        115
```

<210> SEQ ID NO 135
<211> LENGTH: 121
<212> TYPE: PRT
<213> ORGANISM: Oryctolagus cuniculus

<400> SEQUENCE: 135

```
Gln Glu Gln Leu Val Glu Ser Gly Gly Gly Leu Val Lys Ser Gly Ala
1               5                   10                  15

Ser Leu Thr Leu Thr Cys Thr Ala Ser Gly Phe Ser Leu Ser Ser Ser
            20                  25                  30

Tyr Cys Val Cys Trp Val Arg Gln Ala Pro Gly Lys Gly Leu Glu Trp
        35                  40                  45

Ile Ala Cys Ile Tyr Gly Gly Ser Ser Gly Gly Thr Tyr Tyr Ala Ser
    50                  55                  60

Trp Ala Lys Gly Arg Ile Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Asp Ala Gly Ser Ser Gly Tyr Tyr Ile Asn Leu Trp Gly
```

```
            100                 105                 110

Pro Gly Thr Leu Val Thr Val Ser Ser
        115                 120


<210> SEQ ID NO 136
<211> LENGTH: 118
<212> TYPE: PRT
<213> ORGANISM: Oryctolagus cuniculus

<400> SEQUENCE: 136

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Asn Ala
            20                  25                  30

Met Cys Trp Val Arg Gln Ala Pro Gly Lys Gly Pro Glu Trp Ile Gly
        35                  40                  45

Cys Ile Tyr Thr Ser Ser Ser Gly Ser Thr Tyr Tyr Ala Ser Trp Val
    50                  55                  60

Asn Gly Arg Phe Thr Ile Ser Lys Thr Ser Ser Thr Thr Val Thr Leu
65                  70                  75                  80

Gln Met Thr Ser Leu Thr Val Ala Asp Thr Ala Thr Tyr Phe Cys Ala
                85                  90                  95

Arg Tyr Asn Asn Gly Trp Asp Tyr Phe Asn Leu Trp Gly Pro Gly Thr
            100                 105                 110

Leu Val Thr Val Ser Ser
        115


<210> SEQ ID NO 137
<211> LENGTH: 121
<212> TYPE: PRT
<213> ORGANISM: Oryctolagus cuniculus

<400> SEQUENCE: 137

Gln Glu Gln Leu Val Glu Ser Gly Gly Gly Leu Val Lys Pro Gly Ala
1               5                   10                  15

Ser Leu Thr Leu Thr Cys Thr Ala Ser Gly Phe Ser Phe Asn Gly Asn
            20                  25                  30

Tyr Tyr Met Cys Trp Val Arg Gln Ala Pro Gly Lys Gly Leu Glu Trp
        35                  40                  45

Ile Ala Cys Ile Tyr Ala Asp Asn Ser Gly Ser Thr Tyr Tyr Ala Ser
    50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asp Pro Ala Thr Tyr Phe
                85                  90                  95

Cys Val Arg His Lys Pro Ala Gly Gly Ser Ser Tyr Ile Leu Trp Gly
            100                 105                 110

Pro Gly Thr Leu Val Thr Val Ser Ser
        115                 120


<210> SEQ ID NO 138
<211> LENGTH: 112
<212> TYPE: PRT
<213> ORGANISM: Oryctolagus cuniculus

<400> SEQUENCE: 138

Gln Ser Leu Glu Glu Ser Gly Gly Arg Leu Val Thr Pro Gly Thr Pro
1               5                   10                  15
```

Leu Thr Leu Thr Cys Thr Val Ser Gly Ile Asp Leu Ser Ser Tyr His
20 25 30

Met Asn Trp Val Arg Gln Ala Pro Gly Lys Gly Leu Glu Trp Ile Gly
35 40 45

Val Ile Tyr Gly Ser Gly Ser Thr Asp Tyr Ala Ser Trp Ala Lys Gly
50 55 60

Arg Phe Thr Ile Ser Lys Thr Ser Thr Thr Val Asp Leu Lys Ile Thr
65 70 75 80

Ser Pro Thr Thr Glu Asp Thr Ala Thr Tyr Phe Cys Ala Arg Gly Ile
85 90 95

Leu Val Ser Asn Leu Trp Gly Pro Gly Thr Leu Val Thr Val Ser Ser
100 105 110

<210> SEQ ID NO 139
<211> LENGTH: 116
<212> TYPE: PRT
<213> ORGANISM: Oryctolagus cuniculus

<400> SEQUENCE: 139

Gln Ser Leu Glu Glu Ser Gly Gly Asp Leu Val Lys Pro Gly Ala Ser
1 5 10 15

Leu Thr Leu Thr Cys Thr Ala Ser Gly Phe Thr Ile Ser Ser Ser Tyr
20 25 30

Tyr Met Cys Trp Val Arg Gln Ala Pro Gly Lys Gly Leu Glu Trp Ile
35 40 45

Ala Cys Ile Tyr Ser Asp Ser Ser Gly Ser Thr Tyr Asn Ala Asn Trp
50 55 60

Val Lys Gly Arg Phe Thr Ile Ser Lys Thr Ser Ser Thr Thr Val Thr
65 70 75 80

Leu Arg Met Thr Ser Leu Thr Ala Ala Asp Thr Ala Thr Tyr Phe Cys
85 90 95

Ala Arg Gly Thr Tyr Pro Phe Thr Leu Trp Gly Pro Gly Thr Leu Val
100 105 110

Thr Val Ser Ser
115

<210> SEQ ID NO 140
<211> LENGTH: 118
<212> TYPE: PRT
<213> ORGANISM: Oryctolagus cuniculus

<400> SEQUENCE: 140

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser Ser Tyr Pro
20 25 30

Val Asn Trp Val Arg Gln Ala Pro Gly Lys Gly Leu Glu Trp Ile Gly
35 40 45

Val Ile Gly Asn Arg Gly Ser Thr Asp Tyr Ala Ser Trp Ala Lys Gly
50 55 60

Arg Phe Thr Ile Ser Lys Thr Ser Thr Thr Val Asp Leu Lys Ile Thr
65 70 75 80

Ser Pro Thr Thr Glu Asp Thr Ala Thr Tyr Phe Cys Ala Arg Gly Ser
85 90 95

Gly Tyr Gly Thr Gly Trp Asp Ala Phe Asp Pro Trp Gly Pro Gly Thr
100 105 110

```
Leu Val Thr Val Ser Ser
        115


<210> SEQ ID NO 141
<211> LENGTH: 114
<212> TYPE: PRT
<213> ORGANISM: Oryctolagus cuniculus

<400> SEQUENCE: 141

Gln Ser Leu Lys Glu Ser Gly Gly Gly Leu Val Thr Pro Gly Thr Pro
1               5                   10                  15

Leu Thr Leu Thr Cys Lys Val Ser Gly Phe Ser Leu Ser Ser Tyr Asp
            20                  25                  30

Met Ser Trp Val Arg Gln Ala Pro Gly Lys Gly Leu Glu Trp Ile Gly
        35                  40                  45

Thr Ile Tyr Asp Gly Gly Ser Thr Tyr Tyr Ala Ser Trp Thr Lys Gly
    50                  55                  60

Arg Phe Thr Ile Ser Lys Ala Ser Thr Thr Val Asp Leu Lys Ile Thr
65                  70                  75                  80

Ser Pro Thr Thr Glu Asp Thr Ala Thr Tyr Phe Cys Ala Arg Gly Ser
                85                  90                  95

Thr Asn Met Glu Phe Trp Phe Trp Gly Pro Gly Thr Leu Val Ser Val
            100                 105                 110

Ser Ser


<210> SEQ ID NO 142
<211> LENGTH: 119
<212> TYPE: PRT
<213> ORGANISM: Oryctolagus cuniculus

<400> SEQUENCE: 142

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Gly
            20                  25                  30

Met Thr Trp Val Arg Gln Ala Pro Gly Lys Gly Leu Glu Trp Ile Gly
        35                  40                  45

Ile Ile Asn Ile Ile Asp Asn Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Ala Asp
                85                  90                  95

Tyr Tyr Pro Asp Thr Thr Gly Trp Tyr Leu Asn Ile Trp Gly Pro Gly
            100                 105                 110

Thr Leu Val Thr Val Ser Leu
        115


<210> SEQ ID NO 143
<211> LENGTH: 113
<212> TYPE: PRT
<213> ORGANISM: Oryctolagus cuniculus

<400> SEQUENCE: 143

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Trp
```

```
            20                  25                  30

Met Ser Trp Val Arg Gln Ala Pro Gly Lys Gly Leu Glu Trp Ile Gly
        35                  40                  45

Thr Ile Ser Thr Gly Gly Ser Ala Tyr Tyr Ala Ser Trp Ala Lys Ser
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Asp Gly
                85                  90                  95

Asp Ser Tyr Phe Lys Leu Trp Gly Pro Gly Thr Leu Val Thr Val Ser
            100                 105                 110

Ser


<210> SEQ ID NO 144
<211> LENGTH: 115
<212> TYPE: PRT
<213> ORGANISM: Oryctolagus cuniculus

<400> SEQUENCE: 144

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
            20                  25                  30

Met Gly Trp Val Arg Gln Ala Pro Gly Lys Gly Leu Glu Tyr Ile Gly
        35                  40                  45

Tyr Ile Asn Arg Gly Asn Thr Tyr Tyr Ala Asn Trp Ala Lys Gly Arg
    50                  55                  60

Phe Thr Ile Ser Lys Thr Ser Thr Thr Val Asp Leu Lys Ile Thr Ser
65                  70                  75                  80

Pro Thr Thr Glu Asp Thr Ala Thr Tyr Phe Cys Ala Arg Asp Ser Tyr
                85                  90                  95

Gly Gly Asp Tyr Ala Phe Asn Leu Trp Gly Pro Gly Thr Leu Val Thr
            100                 105                 110

Val Ser Ser
        115


<210> SEQ ID NO 145
<211> LENGTH: 121
<212> TYPE: PRT
<213> ORGANISM: Oryctolagus cuniculus

<400> SEQUENCE: 145

Gln Ser Leu Glu Glu Ser Gly Gly Gly Leu Val Lys Pro Gly Ala Ser
1               5                   10                  15

Leu Thr Leu Thr Cys Thr Ala Ser Gly Phe Ser Phe Ser Ser Ser Tyr
            20                  25                  30

Tyr Met Cys Trp Val Arg Gln Ala Pro Gly Lys Gly Leu Glu Trp Ile
        35                  40                  45

Ala Cys Ile His Ala Gly Ser Ser Gly Ser Ala Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Gly Tyr Asp Asp Tyr Gly Asp Pro Phe Asn Leu Trp Gly
            100                 105                 110
```

```
Pro Gly Thr Leu Val Thr Val Ser Ser
        115                 120


<210> SEQ ID NO 146
<211> LENGTH: 126
<212> TYPE: PRT
<213> ORGANISM: Oryctolagus cuniculus

<400> SEQUENCE: 146

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Gly Gln
            20                  25                  30

Asp Met Cys Trp Val Arg Gln Ala Pro Gly Lys Gly Leu Glu Trp Ile
        35                  40                  45

Ala Cys Ile Tyr Gly Gly Asp Gly Asn Thr Tyr Tyr Ala Ser Trp Ala
    50                  55                  60

Lys Gly Arg Phe Thr Ile Tyr Lys Thr Ser Ser Thr Thr Val Thr Leu
65                  70                  75                  80

Lys Met Thr Ser Pro Thr Ala Ala Asp Thr Ala Thr Tyr Leu Cys Ala
                85                  90                  95

Arg Leu His Tyr Ser Pro Tyr Gly Asp Ala Gly Tyr Pro Tyr Val Ser
            100                 105                 110

Phe Asn Leu Trp Gly Pro Gly Thr Leu Val Thr Val Ser Ser
        115                 120                 125


<210> SEQ ID NO 147
<211> LENGTH: 114
<212> TYPE: PRT
<213> ORGANISM: Oryctolagus cuniculus

<400> SEQUENCE: 147

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Asn
            20                  25                  30

Met Gly Trp Val Arg Gln Ala Pro Gly Lys Gly Leu Glu Trp Ile Gly
        35                  40                  45

Tyr Ile Trp Ser Gly Gly Ser Ala Tyr Tyr Ala Ser Trp Ala Lys Gly
    50                  55                  60

Arg Phe Thr Ile Ser Arg Thr Ser Thr Thr Val Thr Leu Lys Met Thr
65                  70                  75                  80

Ser Leu Thr Ala Ala Asp Thr Ala Thr Tyr Phe Cys Ala Arg Asn Gly
                85                  90                  95

Ala Ser Gly Thr Phe Asp Ile Trp Gly Pro Gly Thr Leu Val Thr Val
            100                 105                 110

Ser Leu


<210> SEQ ID NO 148
<211> LENGTH: 121
<212> TYPE: PRT
<213> ORGANISM: Oryctolagus cuniculus

<400> SEQUENCE: 148

Gln Glu Gln Leu Val Glu Ser Gly Gly Gly Leu Val Gln Pro Glu Gly
1               5                   10                  15

Ser Leu Thr Leu Thr Cys Thr Ala Ser Gly Phe Ser Phe Ser Ser Ser
```

```
            20                  25                  30

Tyr Tyr Met Cys Trp Val Arg Gln Ala Pro Gly Lys Gly Leu Glu Trp
        35                  40                  45

Ile Ala Cys Ile Tyr Ala Gly Ser Ser Gly Ser Thr Tyr Tyr Ala Ser
    50                  55                  60

Trp Ala Lys Gly Arg Leu Thr Ile Ser Lys Ile Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Gly Gly Gly Ser Gly Gly Val Asp Asn Asn Leu Trp Gly
            100                 105                 110

Pro Gly Thr Leu Val Thr Val Ser Ser
        115                 120


<210> SEQ ID NO 149
<211> LENGTH: 113
<212> TYPE: PRT
<213> ORGANISM: Oryctolagus cuniculus

<400> SEQUENCE: 149

Ala Gln Val Leu Thr Gln Thr Pro Ser Ser Val Ser Ala Ala Val Gly
1               5                   10                  15

Gly Thr Val Thr Ile Asn Cys Gln Ala Ser Gln Ser Leu Tyr Asn Asn
            20                  25                  30

Lys Asn Leu Ala Trp Tyr Gln Gln Lys Leu Gly Gln Pro Pro Lys Leu
        35                  40                  45

Leu Ile Tyr Asp Val Ser Thr Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Glu Phe Ser Cys
                85                  90                  95

Ser Ser Gly Asp Cys Tyr Ala Phe Gly Gly Gly Thr Glu Val Val Val
            100                 105                 110

Lys


<210> SEQ ID NO 150
<211> LENGTH: 110
<212> TYPE: PRT
<213> ORGANISM: Oryctolagus cuniculus

<400> SEQUENCE: 150

Ala Gln Val Leu Thr Gln Thr Ala Ser Ser Val Ser Ala Val Val Gly
1               5                   10                  15

Gly Thr Val Thr Ile Ser Cys Gln Ser Ser Gln Ser Val Tyr Asp Lys
            20                  25                  30

Lys Trp Leu Gly Trp Tyr Gln Gln Lys Pro Gly Gln Pro Pro Lys Leu
        35                  40                  45

Leu Ile Tyr Lys Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Gly Tyr Ser Gly
                85                  90                  95

Asn Ile Trp Ser Phe Gly Gly Gly Thr Glu Val Val Val Lys
            100                 105                 110
```

<210> SEQ ID NO 151
<211> LENGTH: 113
<212> TYPE: PRT
<213> ORGANISM: Oryctolagus cuniculus

<400> SEQUENCE: 151

Ala Gln Val Leu Thr Gln Thr Pro Ser Ser Val Ser Ala Ala Val Gly
1               5                   10                  15

Gly Thr Val Thr Ile Ile Cys Gln Ala Ser Gln Ser Leu Tyr Asn Asn
            20                  25                  30

Lys Asn Leu Ala Trp Tyr Gln Gln Lys Leu Gly Gln Pro Pro Lys Leu
        35                  40                  45

Leu Ile Tyr Asp Val Ser Thr Leu Ala Ser Gly Ala Pro Ser Arg Phe
    50                  55                  60

Lys Ser Ser Gly Ser Gly Lys Gln Phe Thr Leu Thr Ile Ser Gly Val
65                  70                  75                  80

Gln Cys Asp Asp Ala Ala Thr Tyr Tyr Cys Gln Gly Glu Phe Ser Cys
                85                  90                  95

Ser Ser Gly Asp Cys Tyr Ala Phe Gly Gly Gly Thr Glu Val Val Val
            100                 105                 110

Lys

<210> SEQ ID NO 152
<211> LENGTH: 110
<212> TYPE: PRT
<213> ORGANISM: Oryctolagus cuniculus

<400> SEQUENCE: 152

Ala Gln Val Leu Thr Gln Thr Ala Ser Pro Val Ser Ala Ala Val Gly
1               5                   10                  15

Asp Thr Val Thr Ile Ser Cys Gln Ser Ser Glu Ser Val Tyr Asn Asn
            20                  25                  30

Asn Leu Leu Ser Trp Tyr Gln Gln Lys Pro Gly Gln Pro Pro Lys Leu
        35                  40                  45

Leu Ile Tyr Thr Thr Ser Ser Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Val Tyr Cys Gln Gly Gly Tyr Thr Asp
                85                  90                  95

Ala Thr Tyr Ala Phe Gly Gly Gly Thr Glu Val Val Val Lys
            100                 105                 110

<210> SEQ ID NO 153
<211> LENGTH: 104
<212> TYPE: PRT
<213> ORGANISM: Oryctolagus cuniculus

<400> SEQUENCE: 153

Asp Ile Val Met Thr Gln Thr Pro Ser Ser Val Ser Ala Ala Val Gly
1               5                   10                  15

Gly Thr Val Thr Ile Asn Cys Gln Ala Ser Gln Ser Val Ser Asn Leu
            20                  25                  30

Leu Ala Trp Tyr Gln Gln Lys Pro Gly Gln Pro Pro Lys Leu Leu Ile
        35                  40                  45

Tyr Gly Ala Ser Asn Leu Glu Ser Gly Val Pro Ser Arg Phe Arg Gly

```
    50                  55                  60

Ser Gly Ser Gly Thr Glu Phe Thr Leu Thr Ile Ser Gly Met Lys Ala
65                  70                  75                  80

Glu Asp Ala Ala Thr Tyr Tyr Cys Gln Ser Gly Tyr Tyr Thr Phe Gly
                85                  90                  95

Ala Gly Thr Lys Val Glu Ile Lys
            100


<210> SEQ ID NO 154
<211> LENGTH: 113
<212> TYPE: PRT
<213> ORGANISM: Oryctolagus cuniculus

<400> SEQUENCE: 154

Ala Gln Val Leu Thr Gln Thr Pro Ser Ser Val Ser Ala Ala Val Gly
1               5                   10                  15

Gly Thr Val Thr Ile Asn Cys Gln Ala Ser Gln Ser Leu Tyr Asn Asn
            20                  25                  30

Lys Asn Leu Ala Trp Tyr Gln Gln Lys Pro Gly Gln Pro Pro Lys Leu
        35                  40                  45

Leu Ile Tyr Asp Ala Ser Thr Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Glu Phe Ser Cys
                85                  90                  95

Gly Ser Gly Asp Cys Tyr Ala Phe Gly Gly Gly Thr Glu Val Val Val
            100                 105                 110

Lys


<210> SEQ ID NO 155
<211> LENGTH: 110
<212> TYPE: PRT
<213> ORGANISM: Oryctolagus cuniculus

<400> SEQUENCE: 155

Asp Pro Val Leu Thr Gln Thr Pro Ser Ser Ala Ser Glu Pro Val Gly
1               5                   10                  15

Gly Thr Val Thr Ile Lys Cys Gln Ala Ser Glu Asp Ile Glu Ser Tyr
            20                  25                  30

Leu Ala Trp Tyr Gln Gln Lys Pro Gly Gln Pro Pro Lys Leu Leu Ile
        35                  40                  45

Tyr Asp Ala Ser Asp Leu Ala Ser Gly Val Pro Ser Arg Phe Lys Gly
    50                  55                  60

Ser Gly Ser Gly Thr Gln Phe Thr Leu Thr Ile Ser Gly Val Gln Cys
65                  70                  75                  80

Ala Asp Ala Ala Thr Tyr Tyr Cys Gln Ser Tyr Tyr Tyr Gly Ser Ser
                85                  90                  95

Tyr Val Val Ala Phe Gly Gly Gly Thr Glu Val Val Val Lys
            100                 105                 110


<210> SEQ ID NO 156
<211> LENGTH: 113
<212> TYPE: PRT
<213> ORGANISM: Oryctolagus cuniculus

<400> SEQUENCE: 156
```

-continued

```
Ala Gln Val Leu Thr Gln Thr Pro Ser Ser Val Ser Ala Ala Val Gly
1               5                   10                  15

Gly Thr Val Thr Ile Asn Cys Gln Ala Ser Gln Ser Leu Tyr Asn Asn
            20                  25                  30

Lys Asn Leu Gly Trp Tyr Gln Gln Lys Leu Gly Gln Pro Pro Lys Leu
        35                  40                  45

Leu Ile Tyr Asp Val Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Gln Gly Glu Phe Ser Cys
                85                  90                  95

Ser Ser Gly Asp Cys Tyr Ala Phe Gly Gly Gly Thr Glu Val Val Val
            100                 105                 110

Lys


<210> SEQ ID NO 157
<211> LENGTH: 111
<212> TYPE: PRT
<213> ORGANISM: Oryctolagus cuniculus

<400> SEQUENCE: 157

Asp Ile Val Met Thr Gln Thr Pro Ala Ser Val Glu Ala Ala Val Gly
1               5                   10                  15

Gly Ser Val Thr Ile Lys Cys Gln Ala Ser Gln Thr Ile Ser Ser Tyr
            20                  25                  30

Leu Ala Trp Tyr Gln Gln Lys Pro Gly Gln Pro Pro Lys Leu Leu Ile
        35                  40                  45

Tyr Gly Ala Ser Thr Leu Ala Ser Gly Val Pro Ser Arg Phe Ser Gly
    50                  55                  60

Ser Gly Ser Gly Thr Glu Tyr Thr Leu Thr Ile Ser Gly Val Gln Cys
65                  70                  75                  80

Asp Asp Ala Ala Thr Tyr Tyr Cys Leu Tyr Ser Tyr Tyr Thr Ser Asn
                85                  90                  95

Ser Ala Asp Asn Thr Phe Gly Gly Gly Thr Glu Val Val Val Lys
            100                 105                 110


<210> SEQ ID NO 158
<211> LENGTH: 111
<212> TYPE: PRT
<213> ORGANISM: Oryctolagus cuniculus

<400> SEQUENCE: 158

Ala Ala Val Leu Thr Gln Thr Pro Ser Pro Val Ser Ala Ala Val Gly
1               5                   10                  15

Gly Thr Val Ser Ile Ser Cys Gln Ser Ser Gln Ser Val Tyr Asp Asn
            20                  25                  30

Asn Ala Leu Ala Trp Tyr Gln Gln Lys Pro Gly Gln Pro Pro Lys Leu
        35                  40                  45

Leu Ile Tyr Glu Thr Ser Thr Leu Ala Ser Gly Val Pro Ser Arg Phe
    50                  55                  60

Glu Gly Ser Gly Ser Gly Thr Gln Phe Thr Leu Thr Ile Ser Asp Val
65                  70                  75                  80

Gln Cys Asp Asp Ala Ala Thr Tyr Tyr Cys Ala Gly Gly Tyr Asn Ser
                85                  90                  95

Gly Ser Asp Ala Ala Phe Gly Gly Gly Thr Glu Val Val Val Lys
```

100 105 110

<210> SEQ ID NO 159
<211> LENGTH: 110
<212> TYPE: PRT
<213> ORGANISM: Oryctolagus cuniculus

<400> SEQUENCE: 159

Ala Gln Val Leu Thr Gln Thr Pro Ser Pro Val Ser Ala Pro Val Gly
1 5 10 15

Gly Thr Val Thr Ile Ser Cys Gln Ser Ser Gln Asn Val Asp Arg Asn
20 25 30

Asn Arg Leu Ala Trp Tyr Gln Gln Lys Leu Gly Gln Pro Pro Lys Leu
35 40 45

Leu Ile Tyr Tyr Ala Ser Ile Leu Ala Ser Gly Val Pro Ser Arg Phe
50 55 60

Lys Gly Ser Gly Ser Gly Thr Gln Phe Thr Leu Thr Ile Asn Glu Leu
65 70 75 80

Gln Cys Asp Asp Ala Ala Thr Tyr Tyr Cys Gln Gly Tyr Tyr Ser Gly
85 90 95

Asp Ile Asn Val Phe Gly Val Gly Thr Glu Val Val Val Lys
100 105 110

<210> SEQ ID NO 160
<211> LENGTH: 111
<212> TYPE: PRT
<213> ORGANISM: Oryctolagus cuniculus

<400> SEQUENCE: 160

Asp Ile Val Met Thr Gln Thr Pro Ala Ser Val Glu Ala Ala Val Gly
1 5 10 15

Gly Thr Val Thr Ile Lys Cys Gln Ala Ser Gln Ser Ile Gly Ser Asn
20 25 30

Leu Ala Trp Tyr Gln Gln Lys Pro Gly Gln Pro Pro Lys Leu Leu Ile
35 40 45

Tyr Lys Ala Ser Thr Leu Ala Ser Gly Val Pro Ser Arg Phe Lys Gly
50 55 60

Ser Gly Ser Gly Thr Glu Phe Thr Leu Thr Ile Ser Asp Leu Glu Cys
65 70 75 80

Ala Asp Ala Ala Thr Tyr Tyr Cys Gln Ser Tyr Tyr Gly Thr Ser Asn
85 90 95

Ser Tyr Gly Asp Ala Phe Gly Gly Gly Thr Glu Val Val Val Lys
100 105 110

<210> SEQ ID NO 161
<211> LENGTH: 111
<212> TYPE: PRT
<213> ORGANISM: Oryctolagus cuniculus

<400> SEQUENCE: 161

Asp Val Val Met Thr Gln Thr Pro Ala Ser Val Ser Glu Pro Val Gly
1 5 10 15

Gly Thr Val Thr Ile Lys Cys Gln Ala Ser Glu Asp Ile Glu Ser Tyr
20 25 30

Leu Ala Trp Tyr Gln Gln Lys Pro Gly Gln Pro Pro Lys Leu Leu Ile
35 40 45

Tyr Gln Ala Ser Lys Leu Ala Ser Gly Val Ser Ser Arg Phe Ser Gly
50 55 60

```
Ser Gly Tyr Gly Thr Glu Phe Thr Leu Thr Leu Ser Asp Leu Glu Cys
65                  70                  75                  80

Ala Asp Ala Ala Thr Tyr Tyr Cys Gln Cys Thr Leu Tyr Gly Val Asn
                85                  90                  95

Phe Val Pro Asn Val Phe Gly Gly Gly Thr Glu Val Val Val Lys
            100                 105                 110


<210> SEQ ID NO 162
<211> LENGTH: 111
<212> TYPE: PRT
<213> ORGANISM: Oryctolagus cuniculus

<400> SEQUENCE: 162

Asp Val Val Met Thr Gln Thr Pro Ala Ser Val Ser Glu Pro Val Gly
1               5                   10                  15

Gly Thr Val Thr Ile Lys Cys Gln Ala Ser Glu Asp Ile Glu Ser Tyr
            20                  25                  30

Leu Ala Trp Tyr Gln Gln Lys Pro Gly Gln Pro Pro Lys Leu Leu Ile
        35                  40                  45

Tyr Ser Ala Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Ile Leu Tyr Gly Val Asn
                85                  90                  95

Phe Val Pro Asn Thr Phe Gly Gly Gly Thr Glu Val Val Val Lys
            100                 105                 110


<210> SEQ ID NO 163
<211> LENGTH: 111
<212> TYPE: PRT
<213> ORGANISM: Oryctolagus cuniculus

<400> SEQUENCE: 163

Asp Val Val Met Thr Gln Thr Pro Ala Ser Val Ser Ala Ala Val Gly
1               5                   10                  15

Gly Thr Val Thr Ile Lys Cys Gln Ala Ser Gln Asn Ile Tyr Asp Asn
            20                  25                  30

Leu Ala Trp Tyr Gln Gln Lys Pro Gly Gln Arg Pro Lys Leu Leu Ile
        35                  40                  45

Tyr Gly Ala Ser Asn Leu Glu Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Cys Ser Tyr Asp Gly Gly Ser
                85                  90                  95

Tyr Val Pro Asn Ala Phe Gly Gly Gly Thr Glu Val Val Val Gln
            100                 105                 110


<210> SEQ ID NO 164
<211> LENGTH: 111
<212> TYPE: PRT
<213> ORGANISM: Oryctolagus cuniculus

<400> SEQUENCE: 164

Ala Ala Val Leu Thr Gln Thr Pro Ser Pro Val Ser Ala Ala Val Gly
1               5                   10                  15
```

```
Gly Thr Val Ser Ile Ser Cys Gln Ser Ser Pro Ser Val Tyr Asn Asn
            20                  25                  30

Asn Arg Leu Ser Trp Phe Gln Gln Lys Pro Gly Gln Pro Pro Lys Leu
        35                  40                  45

Leu Ile Tyr Tyr Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Ala Gly Gly Tyr Ser Thr
                85                  90                  95

Ile Ser Asp Asn Ala Phe Gly Gly Gly Thr Glu Val Val Val Lys
            100                 105                 110


<210> SEQ ID NO 165
<211> LENGTH: 110
<212> TYPE: PRT
<213> ORGANISM: Oryctolagus cuniculus

<400> SEQUENCE: 165

Asp Val Val Met Thr Gln Thr Pro Ala Ser Val Ser Glu Pro Val Gly
1               5                   10                  15

Gly Thr Val Thr Ile Lys Cys Gln Ala Ser Gln Asn Ile Gly Asn Asn
            20                  25                  30

Leu Ala Trp Tyr Gln Gln Lys Pro Gly Gln Pro Pro Lys Leu Leu Ile
        35                  40                  45

Asp Tyr Ala Ser Thr Leu Ala Ser Gly Val Pro Ser Arg Phe Lys Gly
    50                  55                  60

Ser Gly Ser Gly Thr Gln Phe Thr Leu Ala Ile Ser Asp Leu Asp Cys
65                  70                  75                  80

Ala Asp Ala Ala Thr Tyr Tyr Cys Gln Cys Thr Phe Tyr Gly Ser Gly
                85                  90                  95

Tyr Val Ala Ala Phe Gly Gly Gly Thr Glu Val Val Val Lys
            100                 105                 110


<210> SEQ ID NO 166
<211> LENGTH: 111
<212> TYPE: PRT
<213> ORGANISM: Oryctolagus cuniculus

<400> SEQUENCE: 166

Asp Val Val Met Thr Gln Thr Pro Ala Ser Val Ser Glu Pro Val Gly
1               5                   10                  15

Gly Thr Val Ser Ile Asn Cys Gln Ala Ser Glu Asp Ile Glu Ser Tyr
            20                  25                  30

Leu Ala Trp Tyr Gln Gln Lys Pro Gly Gln Pro Pro Lys Leu Leu Ile
        35                  40                  45

Tyr Gly Ala Ser Asn Leu Ala Ser Gly Val Ser Ser Arg Phe Lys Gly
    50                  55                  60

Ser Gly Ser Gly Thr Glu Tyr Thr Leu Thr Ile Ser Asp Leu Glu Cys
65                  70                  75                  80

Asp Asp Ala Ala Thr Tyr Tyr Cys Gln Cys Gly Ile Tyr Gly Val Asn
                85                  90                  95

Phe Val Pro Asn Val Phe Gly Gly Gly Thr Glu Val Val Val Lys
            100                 105                 110


<210> SEQ ID NO 167
<211> LENGTH: 110
```

<212> TYPE: PRT
<213> ORGANISM: Oryctolagus cuniculus

<400> SEQUENCE: 167

```
Ala Tyr Asp Met Thr Gln Thr Pro Ala Ser Val Glu Val Gly Val Gly
1               5                   10                  15

Gly Thr Val Thr Ile Lys Cys Gln Ala Ser Gln Asn Ile Asn Ser Trp
            20                  25                  30

Leu Ser Trp Tyr Gln Gln Lys Pro Gly Gln Pro Pro Lys Leu Leu Ile
        35                  40                  45

Tyr Lys Ala Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gln Gly Ala Gly Trp Asn Asn
                85                  90                  95

Leu Asp Asn Ala Phe Gly Gly Gly Thr Glu Val Val Val Lys
            100                 105                 110
```

<210> SEQ ID NO 168
<211> LENGTH: 111
<212> TYPE: PRT
<213> ORGANISM: Oryctolagus cuniculus

<400> SEQUENCE: 168

```
Ala Gln Val Leu Thr Gln Thr Pro Ser Ser Val Ser Ala Ala Val Gly
1               5                   10                  15

Gly Thr Val Thr Ile Asn Cys Gln Ser Ser Gln Ser Val Tyr Ser Asn
            20                  25                  30

Asn His Leu Ala Trp Tyr Gln Gln Lys Pro Gly Gln Pro Pro Asn Leu
        35                  40                  45

Leu Ile Tyr Arg Ala Ser Lys Leu Ala Ser Gly Val Pro Ser Arg Phe
    50                  55                  60

Ser Gly Ser Arg Ser Gly Thr Gln Phe Thr Leu Thr Ile Ser Gly Val
65                  70                  75                  80

Gln Cys Asp Asp Ala Ala Thr Tyr Tyr Cys Leu Gly Val Tyr Asp Asp
                85                  90                  95

Asp Ala Asp Asn Ala Phe Gly Gly Gly Thr Glu Val Val Val Lys
            100                 105                 110
```

<210> SEQ ID NO 169
<211> LENGTH: 112
<212> TYPE: PRT
<213> ORGANISM: Oryctolagus cuniculus

<400> SEQUENCE: 169

```
Ala Val Val Met Thr Gln Thr Ala Ser Pro Val Ser Ala Ala Val Gly
1               5                   10                  15

Gly Thr Val Thr Ile Asn Cys Gln Ser Ser Gln Ile Val His Asn Asn
            20                  25                  30

Asn Asn Leu Ala Trp Tyr Gln Leu Lys Pro Gly Gln Pro Pro Lys Leu
        35                  40                  45

Leu Ile Phe Gln Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Ala Tyr Tyr Cys Ala Gly Gly Tyr Ser Thr
```

```
                85                  90                  95

Asn Thr Asp Thr Tyr Ile Phe Gly Gly Gly Thr Glu Val Val Val Arg
            100                 105                 110


<210> SEQ ID NO 170
<211> LENGTH: 113
<212> TYPE: PRT
<213> ORGANISM: Oryctolagus cuniculus

<400> SEQUENCE: 170

Ala Gln Val Leu Thr Gln Thr Pro Ser Ser Val Ser Ala Ala Val Gly
1               5                   10                  15

Gly Thr Val Thr Ile Asn Cys Gln Ala Ser Gln Ser Leu Tyr Asn Lys
            20                  25                  30

Lys Asn Leu Ala Trp Tyr Gln Gln Lys Leu Gly Gln Pro Pro Lys Leu
        35                  40                  45

Leu Ile Tyr Asp Ala Ser Thr Leu Thr Ser Gly Val Ser Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Glu Phe Ser Cys
                85                  90                  95

Ser Ala Gly Asp Cys Tyr Ala Phe Gly Gly Gly Thr Glu Leu Val Val
            100                 105                 110

Lys


<210> SEQ ID NO 171
<211> LENGTH: 110
<212> TYPE: PRT
<213> ORGANISM: Oryctolagus cuniculus

<400> SEQUENCE: 171

Ala Gln Val Leu Thr Gln Thr Ala Ser Ser Val Ser Ala Val Val Gly
1               5                   10                  15

Gly Thr Val Thr Ile Ser Cys Gln Ser Ser Gln Ser Val Tyr Asp Asn
            20                  25                  30

Lys Trp Leu Gly Trp Tyr Gln Gln Lys Pro Gly Gln Pro Pro Lys Leu
        35                  40                  45

Leu Ile Tyr Ser Ala Ser Thr Leu Ala Ser Gly Val Pro Ser Arg Phe
    50                  55                  60

Lys Gly Ser Gly Ser Gly Thr His Phe Thr Leu Thr Ile Ser Asp Leu
65                  70                  75                  80

Glu Cys Asp Asp Ala Thr Thr Tyr Tyr Cys Ala Gly Gly Tyr Ser Gly
                85                  90                  95

Asn Ile Trp Ser Phe Gly Gly Gly Thr Glu Val Val Val Lys
            100                 105                 110


<210> SEQ ID NO 172
<211> LENGTH: 110
<212> TYPE: PRT
<213> ORGANISM: Oryctolagus cuniculus

<400> SEQUENCE: 172

Ala Gln Val Leu Thr Gln Thr Pro Ser Pro Val Ser Ala Ala Val Gly
1               5                   10                  15

Gly Thr Val Thr Ile Ser Cys Gln Ser Ser Gln Ser Val Tyr Asp Asn
            20                  25                  30
```

```
Lys Trp Leu Gly Trp Tyr Gln Gln Lys Pro Gly Gln Pro Pro Lys Leu
        35                  40                  45

Leu Ile Tyr Lys Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Thr Thr Tyr Tyr Cys Ala Gly Gly Tyr Ser Gly
                85                  90                  95

Asn Ile Trp Ser Phe Gly Gly Gly Thr Glu Val Val Val Lys
            100                 105                 110


<210> SEQ ID NO 173
<211> LENGTH: 111
<212> TYPE: PRT
<213> ORGANISM: Oryctolagus cuniculus

<400> SEQUENCE: 173

Ala Ala Val Leu Thr Gln Thr Pro Ala Ser Val Ser Ala Ala Val Gly
1               5                   10                  15

Gly Thr Val Thr Ile Ser Cys Gln Ser Ser Lys Ser Val Phe Asp Asn
            20                  25                  30

Asn Trp Leu Ser Trp Phe Gln Gln Lys Pro Gly Gln Pro Pro Lys Leu
        35                  40                  45

Leu Ile Tyr Lys Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Ala Gly Ile Tyr Ser Ser
                85                  90                  95

Asp Ser Asp Asn Ala Phe Gly Gly Gly Thr Glu Val Val Val Lys
            100                 105                 110


<210> SEQ ID NO 174
<211> LENGTH: 113
<212> TYPE: PRT
<213> ORGANISM: Oryctolagus cuniculus

<400> SEQUENCE: 174

Ala Gln Val Leu Thr Gln Thr Pro Ser Ser Val Ser Ala Val Val Gly
1               5                   10                  15

Gly Thr Val Thr Ile Asn Cys Gln Ala Ser Gln Ser Leu Tyr Asn Lys
            20                  25                  30

Lys Asn Leu Ala Trp Tyr Gln Gln Lys Leu Gly Gln Pro Pro Lys Leu
        35                  40                  45

Leu Ile Tyr Asp Ala Ser Thr Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Ser Tyr Tyr Cys Gln Gly Glu Phe Ser Cys
                85                  90                  95

Ser Ser Gly Asp Cys Tyr Ala Phe Gly Gly Gly Thr Glu Leu Val Val
            100                 105                 110

Lys


<210> SEQ ID NO 175
<211> LENGTH: 110
<212> TYPE: PRT
```

<213> ORGANISM: Oryctolagus cuniculus

<400> SEQUENCE: 175

```
Ala Tyr Asp Met Thr Gln Thr Pro Phe Ser Val Ser Ala Ala Val Gly
1               5                   10                  15

Gly Thr Val Thr Ile Asn Cys Gln Ala Ser Glu Thr Ile Tyr Ser Tyr
            20                  25                  30

Leu Asn Trp Tyr Gln Gln Lys Pro Gly Gln Pro Pro Lys Leu Leu Ile
        35                  40                  45

Tyr Ser Ala Ser Thr Leu Ala Ser Gly Val Pro Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Gly Tyr Ser Gly Arg Asn
                85                  90                  95

Val Glu Asn Thr Phe Gly Gly Gly Thr Glu Val Val Val Lys
            100                 105                 110
```

<210> SEQ ID NO 176
<211> LENGTH: 111
<212> TYPE: PRT
<213> ORGANISM: Oryctolagus cuniculus

<400> SEQUENCE: 176

```
Ala Ala Val Leu Thr Gln Thr Pro Ser Pro Val Ser Ala Ala Val Gly
1               5                   10                  15

Gly Thr Val Thr Ile Ser Cys Gln Ser Ser Gln Asn Ile Tyr Asn Lys
            20                  25                  30

Asn Gln Leu Ser Trp Phe Gln Gln Lys Pro Gly Gln Pro Pro Lys Leu
        35                  40                  45

Leu Ile Tyr Glu Ala Ser Lys Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Leu Gly Gly Tyr Ile Ser
                85                  90                  95

Ser Ser Asp Thr Thr Phe Gly Gly Gly Thr Glu Val Val Val Lys
            100                 105                 110
```

<210> SEQ ID NO 177
<211> LENGTH: 110
<212> TYPE: PRT
<213> ORGANISM: Oryctolagus cuniculus

<400> SEQUENCE: 177

```
Asp Val Val Met Thr Gln Thr Pro Ala Ser Val Ser Thr Ala Val Gly
1               5                   10                  15

Gly Thr Val Thr Ile Lys Cys Gln Ala Ser Gln Ser Ile Gly Gly Ser
            20                  25                  30

Leu Ala Trp Tyr Gln Gln Lys Pro Gly Gln Pro Pro Asn Leu Leu Ile
        35                  40                  45

Tyr Ser Ala Ser Asn Leu Ala Ser Gly Val Ser Ser Arg Phe Lys Gly
    50                  55                  60

Ser Arg Ser Gly Thr Glu Phe Thr Leu Thr Ile Ser Asp Leu Glu Cys
65                  70                  75                  80

Ala Asp Ala Ala Thr Tyr Tyr Cys Gln Cys Thr Tyr Tyr Asp Asp Ser
                85                  90                  95
```

Tyr Asp Val Pro Phe Gly Gly Gly Thr Glu Val Val Val Lys
100 105 110

<210> SEQ ID NO 178
<211> LENGTH: 112
<212> TYPE: PRT
<213> ORGANISM: Oryctolagus cuniculus

<400> SEQUENCE: 178

Ala Ala Val Leu Thr Gln Thr Pro Ser Pro Val Ser Ala Ala Val Gly
1 5 10 15

Gly Thr Val Thr Ile Ser Cys Gln Ser Ser Gln Ser Val Asn Asn Asn
20 25 30

Lys Asn Leu Ala Trp Tyr Gln Gln Lys Leu Gly Gln Pro Pro Lys Leu
35 40 45

Leu Ile Tyr Asp Thr Ser Thr Leu Ala Ser Gly Val Pro Ser Arg Phe
50 55 60

Lys Gly Ser Gly Ser Gly Thr Gln Phe Thr Leu Thr Ile Ser Asp Leu
65 70 75 80

Glu Cys Asp Asp Ala Thr Thr Tyr Tyr Cys Ala Gly Gly Tyr Ser Ser
85 90 95

Ser Ala Asp Thr Phe Ala Phe Gly Gly Gly Thr Glu Val Val Val Arg
100 105 110

<210> SEQ ID NO 179
<211> LENGTH: 112
<212> TYPE: PRT
<213> ORGANISM: Oryctolagus cuniculus

<400> SEQUENCE: 179

Asp Ile Val Met Thr Gln Thr Pro Ala Ser Val Ser Ala Ala Val Gly
1 5 10 15

Gly Thr Val Thr Ile Lys Cys Gln Ala Ser Gln Asn Ile Gly Ser Thr
20 25 30

Leu Ala Trp Tyr Gln Gln Lys Pro Gly Gln Pro Pro Lys Arg Leu Ile
35 40 45

Tyr Gly Ala Ser Thr Leu Ser Ser Gly Val Pro Ser Arg Phe Lys Gly
50 55 60

Ser Gly Ser Gly Thr Asp Phe Thr Leu Thr Ile Ser Asp Leu Glu Cys
65 70 75 80

Ala Asp Ala Ala Thr Tyr Tyr Cys Gln Ser Asn Tyr Gly Ser Asn Ser
85 90 95

Gly Gly Tyr Val Phe Pro Phe Gly Gly Gly Thr Glu Val Val Val Lys
100 105 110

<210> SEQ ID NO 180
<211> LENGTH: 111
<212> TYPE: PRT
<213> ORGANISM: Oryctolagus cuniculus

<400> SEQUENCE: 180

Asp Val Val Met Thr Gln Thr Pro Ala Ser Val Ser Glu Pro Val Gly
1 5 10 15

Gly Thr Val Thr Ile Lys Cys Gln Ala Ser Glu Asp Ile Glu Thr Tyr
20 25 30

Leu Ala Trp Tyr Gln Gln Lys Pro Gly Gln Pro Pro Lys Leu Leu Ile
35 40 45

```
Tyr Arg Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Cys Thr Leu Tyr Gly Val Asn
                85                  90                  95

Phe Val Ala Asn Ala Phe Gly Gly Gly Thr Glu Val Val Val Lys
            100                 105                 110


<210> SEQ ID NO 181
<211> LENGTH: 109
<212> TYPE: PRT
<213> ORGANISM: Oryctolagus cuniculus

<400> SEQUENCE: 181

Ala Phe Glu Leu Thr Gln Thr Pro Ser Ser Val Ser Ala Ala Val Gly
1               5                   10                  15

Gly Thr Val Thr Ile Asn Cys Gln Ala Ser Glu Asp Ile Glu Asn Tyr
            20                  25                  30

Leu Ala Trp Tyr Gln Gln Lys Pro Gly Gln Pro Pro Lys Leu Leu Ile
        35                  40                  45

Tyr Ser Ala Ser Thr Leu Ala Ser Gly Val Ser Ser Arg Phe Lys Gly
    50                  55                  60

Ser Gly Ser Gly Thr Glu Tyr Thr Leu Thr Ile Ser Asp Leu Gly Cys
65                  70                  75                  80

Ala Asp Ala Ala Thr Tyr Tyr Cys Gln Ser Tyr Tyr Asp Gly Ala Val
                85                  90                  95

Thr Phe Thr Phe Gly Gly Gly Thr Glu Val Val Val Lys
            100                 105


<210> SEQ ID NO 182
<211> LENGTH: 112
<212> TYPE: PRT
<213> ORGANISM: Oryctolagus cuniculus

<400> SEQUENCE: 182

Ala Gln Val Leu Thr Gln Thr Ala Ser Pro Val Ser Ala Ala Val Gly
1               5                   10                  15

Gly Thr Val Thr Ile Lys Cys Gln Ser Ser Gln Ser Val Asp Asn Asn
            20                  25                  30

Trp Leu Ser Trp Tyr Gln Gln Lys Pro Gly Gln Pro Pro Lys Leu Leu
        35                  40                  45

Ile Tyr Thr Thr Ser Lys Leu Ala Ser Gly Val Pro Ser Arg Phe Lys
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Gly Tyr Asp Ser Met
                85                  90                  95

Ser Ala Asp Cys Phe Ala Phe Gly Gly Gly Thr Glu Val Val Val Lys
            100                 105                 110


<210> SEQ ID NO 183
<211> LENGTH: 111
<212> TYPE: PRT
<213> ORGANISM: Oryctolagus cuniculus

<400> SEQUENCE: 183

Ala Gln Val Leu Thr Gln Thr Pro Ser Ser Val Ser Ala Ala Val Gly
```

```
1               5                   10                  15

Gly Ala Val Thr Ile Asn Cys Gln Ser Ser Gln Ser Val Tyr Ser Asn
            20                  25                  30

Asn His Leu Ala Trp Tyr Gln Gln Lys Pro Gly Gln Pro Pro Lys Leu
        35                  40                  45

Leu Ile Tyr Arg Ala Ser Lys Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Phe Cys Leu Gly Val Tyr Asp Asp
                85                  90                  95

Asp Ala Asp Asn Ala Phe Gly Gly Gly Thr Ala Val Val Val Lys
            100                 105                 110


<210> SEQ ID NO 184
<211> LENGTH: 112
<212> TYPE: PRT
<213> ORGANISM: Oryctolagus cuniculus

<400> SEQUENCE: 184

Ala Val Val Met Thr Gln Thr Ala Ser Pro Val Ser Ala Ala Val Gly
1               5                   10                  15

Gly Thr Val Thr Ile Asn Cys Gln Ser Ser Gln Ser Val His Asn Asn
            20                  25                  30

Asn Asn Leu Ala Trp Tyr Gln Gln Lys Pro Gly Gln Pro Pro Lys Leu
        35                  40                  45

Leu Ile Phe Gln Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Ala Tyr Tyr Cys Ala Gly Gly Tyr Ser Thr
                85                  90                  95

Asn Thr Asp Thr Phe Thr Phe Gly Gly Gly Thr Glu Val Val Val Arg
            100                 105                 110


<210> SEQ ID NO 185
<211> LENGTH: 112
<212> TYPE: PRT
<213> ORGANISM: Oryctolagus cuniculus

<400> SEQUENCE: 185

Ala Leu Val Met Thr Gln Thr Pro Ala Ser Val Glu Ala Ala Val Gly
1               5                   10                  15

Gly Thr Val Thr Ile Ser Cys Gln Ala Ser Glu Asp Ile Ser Ser Ser
            20                  25                  30

Leu Ala Trp Tyr Gln Gln Lys Pro Gly Gln Pro Pro Asn Leu Leu Ile
        35                  40                  45

Tyr Arg Ala Ser Asn Leu Ala Ser Gly Val Pro Ser Arg Phe Lys Gly
    50                  55                  60

Ser Gly Ser Gly Thr Gln Phe Thr Leu Thr Ile Ser Gly Val Gln Cys
65                  70                  75                  80

Ala Asp Ala Ala Thr Tyr Tyr Cys Gln Ala Tyr Tyr Tyr Ser Ile Ser
                85                  90                  95

Asp Asp Leu Tyr Asn Ala Phe Gly Gly Gly Thr Glu Val Val Val Lys
            100                 105                 110
```

<210> SEQ ID NO 186
<211> LENGTH: 112
<212> TYPE: PRT
<213> ORGANISM: Oryctolagus cuniculus

<400> SEQUENCE: 186

```
Ala Val Val Met Thr Gln Thr Ala Ser Pro Val Ser Ala Ala Val Gly
1               5                   10                  15

Gly Thr Val Thr Ile Ser Cys Gln Ala Ser Gln Ser Val His Asn Asn
            20                  25                  30

Asn Asn Leu Ala Trp Tyr Gln Gln Lys Pro Gly Gln Pro Pro Lys Leu
        35                  40                  45

Leu Ile Phe Gln Ala Ser Thr Leu Ala Ser Gly Val Pro Ser Arg Phe
    50                  55                  60

Lys Gly Ser Gly Ser Gly Thr Glu Phe Thr Leu Thr Ile Ser Asp Leu
65                  70                  75                  80

Glu Cys Asp Asp Ala Ala Ala Tyr Tyr Cys Ala Gly Gly Tyr Ser Thr
                85                  90                  95

Asn Thr Asp Thr Phe Thr Phe Gly Gly Gly Thr Glu Val Val Val Arg
            100                 105                 110
```

<210> SEQ ID NO 187
<211> LENGTH: 111
<212> TYPE: PRT
<213> ORGANISM: Oryctolagus cuniculus

<400> SEQUENCE: 187

```
Asp Val Val Met Thr Gln Thr Pro Ala Ser Val Ser Ala Ala Val Gly
1               5                   10                  15

Gly Thr Val Thr Ile Lys Cys Gln Ala Ser Glu Asp Ile Glu Ser Tyr
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Cys Thr Ile Tyr Gly Val Asn
                85                  90                  95

Phe Val Pro Asn Ala Phe Gly Gly Gly Thr Glu Val Val Val Lys
            100                 105                 110
```

<210> SEQ ID NO 188
<211> LENGTH: 111
<212> TYPE: PRT
<213> ORGANISM: Oryctolagus cuniculus

<400> SEQUENCE: 188

```
Asp Val Val Met Thr Gln Thr Pro Ala Ser Val Ser Ala Ala Val Gly
1               5                   10                  15

Gly Thr Val Thr Ile Lys Cys Gln Ala Thr Glu Asp Ile Glu Ser Phe
            20                  25                  30

Leu Ala Trp Tyr Gln Gln Lys Pro Gly Gln Pro Pro Lys Leu Leu Ile
        35                  40                  45

Tyr Arg Ala Ser Thr Leu Glu Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80
```

```
Ala Asp Ala Ala Thr Tyr Tyr Cys Gln Cys Thr Val Tyr Gly Val Asn
                85                  90                  95

Phe Val Ala Asn Ala Phe Gly Gly Gly Thr Glu Val Val Val Arg
            100                 105                 110


<210> SEQ ID NO 189
<211> LENGTH: 108
<212> TYPE: PRT
<213> ORGANISM: Oryctolagus cuniculus

<400> SEQUENCE: 189

Ala Ile Lys Met Thr Gln Thr Pro Ser Ser Val Ser Ala Ala Val Gly
1               5                   10                  15

Gly Thr Val Thr Ile Asn Cys Arg Ala Ser Glu Asp Ile Lys Ser Tyr
            20                  25                  30

Leu Ala Trp Tyr Gln Gln Lys Pro Gly Gln Pro Pro Lys Leu Leu Ile
        35                  40                  45

Tyr Asp Ala Ser Asp Leu Ala Ser Gly Val Pro Ser Arg Phe Lys Gly
    50                  55                  60

Ser Gly Ser Gly Thr Glu Tyr Thr Leu Thr Ile Ser Gly Val Gln Cys
65                  70                  75                  80

Asp Asp Ala Ala Thr Tyr Tyr Cys Gln Ser Val Trp Tyr Ala Gly Gly
                85                  90                  95

Ala Ala Phe Gly Gly Gly Thr Glu Val Val Val Gln
            100                 105


<210> SEQ ID NO 190
<211> LENGTH: 113
<212> TYPE: PRT
<213> ORGANISM: Oryctolagus cuniculus

<400> SEQUENCE: 190

Ala Gln Val Leu Thr Gln Thr Ala Ser Pro Val Ser Ala Ala Val Gly
1               5                   10                  15

Gly Thr Val Thr Ile Asn Cys Gln Ala Ser Gln Ser Val Tyr Asn His
            20                  25                  30

Lys Asn Leu Ala Trp Tyr Gln Gln Lys Pro Gly Gln Pro Pro Lys Leu
        35                  40                  45

Leu Ile Tyr Asp Thr Ser Thr Leu Ala Ser Gly Val Ser Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Ala Gly Glu Phe Ser Cys
                85                  90                  95

Ala Ser Ala Asp Cys Phe Ala Phe Gly Gly Gly Thr Glu Val Val Val
            100                 105                 110

Lys


<210> SEQ ID NO 191
<211> LENGTH: 110
<212> TYPE: PRT
<213> ORGANISM: Oryctolagus cuniculus

<400> SEQUENCE: 191

Asp Val Val Met Thr Gln Thr Pro Ala Ser Val Ser Glu Pro Val Gly
1               5                   10                  15

Gly Thr Val Thr Ile Lys Cys Gln Ala Ser Gln Ser Ile Gly Ser Ser
```

-continued

```
            20                  25                  30

Leu Ala Trp Tyr Gln Gln Lys Ala Gly Gln Arg Pro Lys Leu Leu Ile
        35                  40                  45

Tyr Tyr Val Ser Asn Leu Glu Ser Gly Val Ser Ser Arg Phe Ser Gly
    50                  55                  60

Ser Gly Ser Gly Thr Glu Phe Thr Leu Thr Ile Ser Gly Val Gln Cys
65                  70                  75                  80

Asp Asp Ala Ala Thr Tyr Tyr Cys Gln Ser Tyr Gly Tyr Gly Ser Gly
                85                  90                  95

Tyr Val Phe Ala Phe Gly Gly Gly Thr Glu Val Val Val Lys
            100                 105                 110


<210> SEQ ID NO 192
<211> LENGTH: 113
<212> TYPE: PRT
<213> ORGANISM: Oryctolagus cuniculus

<400> SEQUENCE: 192

Ala Gln Val Leu Thr Gln Thr Pro Ser Pro Val Ser Ala Ala Val Gly
1               5                   10                  15

Gly Thr Val Ser Ile Ser Cys Gln Ser Ser Gln Ser Val Tyr Gly Val
            20                  25                  30

Asn Glu Leu Ser Trp Tyr Gln Gln Lys Ala Gly Gln Pro Pro Lys Leu
        35                  40                  45

Leu Ile Tyr Lys Ala Ala Thr Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Leu Gly Asn Tyr Asp Cys
                85                  90                  95

Glu Ser Asp Asp Cys Tyr Ala Phe Gly Gly Gly Thr Glu Val Val Val
            100                 105                 110

Lys


<210> SEQ ID NO 193
<211> LENGTH: 113
<212> TYPE: PRT
<213> ORGANISM: Oryctolagus cuniculus

<400> SEQUENCE: 193

Asp Val Val Met Thr Gln Thr Pro Ala Ser Val Glu Ala Pro Val Gly
1               5                   10                  15

Gly Thr Val Thr Ile Lys Cys Gln Ala Ser Gln Ser Ile Ser Asn Leu
            20                  25                  30

Leu Ala Trp Tyr Gln Gln Ile Pro Gly Gln Ser Pro Lys Leu Leu Ile
        35                  40                  45

Tyr Asp Ala Ser Asp Leu Ala Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Cys Thr Tyr Gly Ser Ser Ser
                85                  90                  95

Ser Ser Ala Tyr Gly Trp Ala Phe Gly Gly Gly Thr Glu Val Val Val
            100                 105                 110

Lys
```

<210> SEQ ID NO 194
<211> LENGTH: 111
<212> TYPE: PRT
<213> ORGANISM: Oryctolagus cuniculus

<400> SEQUENCE: 194

```
Ala Ala Val Leu Thr Gln Thr Pro Ser Pro Val Ser Ala Ala Val Gly
1               5                   10                  15

Gly Thr Val Ser Ile Ser Cys Gln Ser Ser Lys Ser Val Tyr Asn Asn
            20                  25                  30

Asn Trp Leu Ser Trp Phe Gln Gln Lys Pro Gly Gln Pro Pro Lys Leu
        35                  40                  45

Leu Ile Tyr Gly Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Leu Gly Ser Tyr Ile Ser
                85                  90                  95

Ser Ser Asp Asn Ala Phe Gly Gly Gly Thr Glu Val Val Val Lys
            100                 105                 110
```

<210> SEQ ID NO 195
<211> LENGTH: 111
<212> TYPE: PRT
<213> ORGANISM: Oryctolagus cuniculus

<400> SEQUENCE: 195

```
Ala Ala Val Leu Thr Gln Thr Pro Ser Pro Val Ser Ala Ala Val Gly
1               5                   10                  15

Gly Thr Val Ser Ile Ser Cys Gln Ser Ser Pro Ser Val Tyr Asn Asn
            20                  25                  30

Asn Arg Leu Ser Trp Phe Gln Gln Lys Pro Gly Gln Pro Pro Lys Leu
        35                  40                  45

Leu Ile Tyr Tyr Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Ala Gly Gly Tyr Ser Ser
                85                  90                  95

Ile Ser Asp Asn Gly Phe Gly Arg Gly Thr Glu Val Val Val Lys
            100                 105                 110
```

<210> SEQ ID NO 196
<211> LENGTH: 112
<212> TYPE: PRT
<213> ORGANISM: Oryctolagus cuniculus

<400> SEQUENCE: 196

```
Asp Val Val Met Thr Gln Thr Leu Pro Ser Val Ser Glu Pro Val Gly
1               5                   10                  15

Gly Thr Val Thr Ile Lys Cys Gln Ala Ser Gln Ser Ile Gly Ser Tyr
            20                  25                  30

Leu Ser Trp Tyr Gln Gln Lys Pro Gly Gln Pro Pro Lys Leu Leu Ile
        35                  40                  45

Tyr Asp Ala Ser Thr Leu Ala Ser Gly Val Pro Ser Arg Phe Lys Gly
    50                  55                  60

Gly Gly Ser Gly Thr Gln Phe Thr Leu Thr Ile Ser Asp Leu Glu Cys
```

```
65                  70                  75                  80

Ala Asp Ala Ala Thr Tyr Tyr Cys Gln Gly Tyr Tyr Tyr Tyr Ile Ser
                85                  90                  95

Asn Thr Tyr Gly Tyr Pro Phe Gly Gly Gly Thr Glu Val Val Val Lys
            100                 105                 110


<210> SEQ ID NO 197
<211> LENGTH: 110
<212> TYPE: PRT
<213> ORGANISM: Oryctolagus cuniculus

<400> SEQUENCE: 197

Asp Val Val Met Thr Gln Thr Pro Ala Ser Val Ser Glu Pro Val Gly
1               5                   10                  15

Gly Thr Val Thr Ile Lys Cys Gln Ala Ser Gln Asn Ile Gly Asn Asn
            20                  25                  30

Leu Ala Trp Tyr Gln Gln Lys Pro Gly Gln Pro Pro Lys Leu Leu Met
        35                  40                  45

Tyr Asp Ala Ser Asp Leu Ala Ser Arg Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Thr Tyr Gly Tyr Ser Gly
                85                  90                  95

Tyr Val Ser Ala Phe Gly Gly Gly Thr Glu Val Val Val Lys
            100                 105                 110


<210> SEQ ID NO 198
<211> LENGTH: 110
<212> TYPE: PRT
<213> ORGANISM: Oryctolagus cuniculus

<400> SEQUENCE: 198

Ala Leu Val Met Thr Gln Thr Pro Ser Pro Val Ser Ala Ala Val Gly
1               5                   10                  15

Gly Thr Val Thr Ile Asn Cys Gln Ala Ser Glu Asp Ile Tyr Ser Asn
            20                  25                  30

Leu Ala Trp Phe Gln Gln Lys Pro Gly Gln Pro Pro Lys Leu Leu Ile
        35                  40                  45

Tyr Ser Ala Ser Thr Leu Ala Ser Gly Val Ser Ser Arg Phe Lys Gly
    50                  55                  60

Ser Gly Ser Gly Thr Lys Phe Thr Leu Thr Ile Ser Gly Leu Gln Cys
65                  70                  75                  80

Asp Asp Ala Ala Thr Tyr Tyr Cys Leu Gly Val Tyr Thr Tyr Ile Ser
                85                  90                  95

Ala Asp Asn Ala Phe Gly Gly Gly Thr Glu Val Val Val Lys
            100                 105                 110


<210> SEQ ID NO 199
<211> LENGTH: 113
<212> TYPE: PRT
<213> ORGANISM: Oryctolagus cuniculus

<400> SEQUENCE: 199

Ala Gln Val Leu Thr Gln Thr Pro Ser Ser Val Ser Ala Ala Val Gly
1               5                   10                  15

Gly Thr Val Thr Ile Asn Cys Gln Ala Ser Gln Ser Leu Tyr Asn Asn
            20                  25                  30
```

```
Lys Asn Leu Ala Trp Tyr Gln Gln Lys Leu Gly Gln Pro Pro Lys Leu
        35                  40                  45

Leu Ile Tyr Asp Val Ser Thr Leu Ala Ser Gly Val Pro Ser Arg Phe
    50                  55                  60

Lys Gly Ser Gly Ser Gly Lys Gln Phe Thr Leu Thr Ile Ser Gly Val
65                  70                  75                  80

Gln Cys Asp Asp Ala Ala Thr Tyr Tyr Cys Gln Gly Glu Phe Ser Cys
                85                  90                  95

Ser Ser Gly Asp Cys Tyr Ala Phe Gly Gly Gly Thr Glu Val Val Val
            100                 105                 110

Lys


<210> SEQ ID NO 200
<211> LENGTH: 111
<212> TYPE: PRT
<213> ORGANISM: Oryctolagus cuniculus

<400> SEQUENCE: 200

Ala Ala Val Leu Thr Gln Thr Pro Ser Pro Val Ser Ala Ala Val Gly
1               5                   10                  15

Gly Thr Val Ser Ile Ser Cys Gln Ser Ser Lys Thr Val Tyr Asn Asn
            20                  25                  30

Asn Trp Leu Ala Trp Phe Gln Gln Lys Pro Gly Gln Pro Pro Lys Leu
        35                  40                  45

Leu Ile Tyr Gly Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Leu Gly Ser Tyr Ile Ser
                85                  90                  95

Ser Ser Asp Asn Gly Phe Gly Gly Gly Thr Glu Val Val Val Lys
            100                 105                 110


<210> SEQ ID NO 201
<211> LENGTH: 111
<212> TYPE: PRT
<213> ORGANISM: Oryctolagus cuniculus

<400> SEQUENCE: 201

Ala Ala Val Leu Thr Gln Thr Pro Ser Pro Val Ser Ala Ala Val Gly
1               5                   10                  15

Gly Thr Val Thr Ile Ser Cys Gln Ser Ser Pro Ser Val Tyr Asn Asn
            20                  25                  30

Val Arg Leu Ser Trp Phe Gln Gln Lys Pro Gly Gln Pro Pro Lys Leu
        35                  40                  45

Leu Ile Tyr Ser Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Ala Gly Gly Tyr Ser Asp
                85                  90                  95

Ile Ser Asp Asn Ala Phe Gly Gly Gly Thr Glu Val Val Val Lys
            100                 105                 110


<210> SEQ ID NO 202
<211> LENGTH: 112
```

<212> TYPE: PRT
<213> ORGANISM: Oryctolagus cuniculus

<400> SEQUENCE: 202

Ala Gln Val Leu Thr Gln Thr Pro Ser Ser Val Ser Ala Ala Val Gly
1               5                   10                  15

Gly Thr Val Thr Ile Ser Cys Gln Ser Ser Gln Ser Val Tyr Ser Thr
            20                  25                  30

Asn Leu Ala Trp Tyr Gln Gln Lys Pro Gly Gln Pro Pro Lys Leu Leu
        35                  40                  45

Ile Asp Tyr Ala Ser Thr Leu Ala Ser Gly Val Pro Ser Arg Phe Lys
    50                  55                  60

Gly Ser Gly Ser Gly Thr Gln Phe Thr Leu Thr Ile Ser Gly Val Gln
65                  70                  75                  80

Cys Asp Asp Ala Ala Ala Tyr Tyr Cys Gln Gly Glu Phe Asn Cys Gly
                85                  90                  95

Ser Gly Asp Cys Ser Thr Phe Gly Gly Gly Thr Glu Val Val Val Lys
            100                 105                 110

<210> SEQ ID NO 203
<211> LENGTH: 110
<212> TYPE: PRT
<213> ORGANISM: Oryctolagus cuniculus

<400> SEQUENCE: 203

Asp Val Val Met Thr Gln Thr Pro Ala Ser Ala Ser Ala Ala Val Gly
1               5                   10                  15

Gly Thr Val Thr Ile Asn Cys Gln Ala Ser Glu Asn Ile Ala Asn His
            20                  25                  30

Leu Ala Trp Tyr Gln Gln Lys Pro Gly Gln Pro Pro Lys Leu Leu Ile
        35                  40                  45

Tyr Ser Ala Ser Ala Leu Ala Ser Gly Val Pro Ser Arg Phe Lys Gly
    50                  55                  60

Ser Gly Ser Gly Thr Glu Phe Ala Leu Thr Ile Ser Asp Leu Glu Cys
65                  70                  75                  80

Asp Asp Ala Ala Ile Tyr Tyr Cys Gln Cys Thr Phe Trp Asp Ile Asn
                85                  90                  95

Asn Phe Gly Gly Phe Gly Gly Gly Thr Glu Val Val Val Lys
            100                 105                 110

<210> SEQ ID NO 204
<211> LENGTH: 111
<212> TYPE: PRT
<213> ORGANISM: Oryctolagus cuniculus

<400> SEQUENCE: 204

Ala Ala Val Leu Thr Gln Thr Pro Ser Pro Val Ser Ala Ala Val Gly
1               5                   10                  15

Gly Thr Val Thr Ile Lys Cys Gln Ser Ser Gln Ser Val Tyr Gly Asn
            20                  25                  30

Asn Glu Leu Ser Trp Tyr Gln Gln Lys Pro Gly Gln Pro Pro Lys Leu
        35                  40                  45

Leu Ile Tyr Asp Ala Ser Lys Leu Ala Ser Gly Val Pro His Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Gly Tyr Asp Ala

```
                85                  90                  95

Asp Ala Asp Asn Ala Phe Gly Gly Gly Thr Glu Val Val Val Lys
            100                 105                 110


<210> SEQ ID NO 205
<211> LENGTH: 113
<212> TYPE: PRT
<213> ORGANISM: Oryctolagus cuniculus

<400> SEQUENCE: 205

Ala Gln Val Leu Thr Gln Thr Pro Ser Ser Val Ser Ala Ala Val Gly
1               5                   10                  15

Gly Thr Val Thr Ile Asn Cys Gln Ala Ser Gln Ser Leu Tyr Asn Lys
            20                  25                  30

Lys Asn Leu Ala Trp Tyr Gln Gln Lys Leu Gly Gln Pro Pro Lys Leu
        35                  40                  45

Leu Ile Tyr Asp Val Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Gly Asp Ala Ala Ala Tyr Phe Cys Gln Gly Glu Phe Ser Cys
                85                  90                  95

Ser Ser Gly Asp Cys Tyr Ala Phe Gly Gly Gly Thr Glu Val Val Val
            100                 105                 110

Lys


<210> SEQ ID NO 206
<211> LENGTH: 110
<212> TYPE: PRT
<213> ORGANISM: Oryctolagus cuniculus

<400> SEQUENCE: 206

Ala Gln Val Leu Thr Gln Thr Ala Ser Ser Val Ser Ala Ala Val Gly
1               5                   10                  15

Gly Ser Val Thr Ile Ser Cys Gln Ser Ser Gln Ser Val Tyr Gly Ser
            20                  25                  30

Asp Ala Leu Ala Trp Phe Gln Gln Arg Pro Gly Gln Ser Pro Lys Arg
        35                  40                  45

Leu Ile Tyr Gly Ala Ser Thr Leu Ala Ser Gly Ile Ser Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Phe Cys Ala Gly Ala Tyr Ser Gly
                85                  90                  95

Asn Val Gly Thr Phe Gly Gly Gly Thr Glu Val Val Val Lys
            100                 105                 110


<210> SEQ ID NO 207
<211> LENGTH: 110
<212> TYPE: PRT
<213> ORGANISM: Oryctolagus cuniculus

<400> SEQUENCE: 207

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Asn
            20                  25                  30
```

```
Leu Ala Trp Tyr Gln Gln Lys Ser Gly Gln Pro Pro Lys Leu Leu Ile
        35                  40                  45

Tyr Leu Ala Ser Thr Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gln Thr Tyr Ser Gly Ser Asn
                85                  90                  95

Val Glu Asn Ser Phe Gly Gly Gly Thr Glu Val Val Val Lys
            100                 105                 110
```

<210> SEQ ID NO 208
<211> LENGTH: 111
<212> TYPE: PRT
<213> ORGANISM: Oryctolagus cuniculus

<400> SEQUENCE: 208

```
Ala Ile Asp Met Thr Gln Thr Pro Ser Pro Val Ser Ala Ala Val Gly
1               5                   10                  15

Asp Thr Val Thr Ile Asn Cys Gln Ala Ser Glu Asn Ile Tyr Ser Phe
            20                  25                  30

Leu Ala Trp Tyr Gln Gln Lys Pro Gly His Ser Pro Lys Leu Leu Ile
        35                  40                  45

Tyr Ser Ala Ser Thr Leu Glu Ser Gly Val Pro Ser Arg Phe Lys Gly
    50                  55                  60

Ser Gly Ser Gly Thr Gln Phe Thr Leu Thr Ile Ser Asp Val Gln Cys
65                  70                  75                  80

Asp Asp Ala Ala Thr Tyr Tyr Cys Gln Gln Thr Tyr Ile Tyr Asn Asn
                85                  90                  95

Ala Glu Asp Asn Thr Phe Gly Gly Gly Thr Glu Val Val Val Lys
            100                 105                 110
```

<210> SEQ ID NO 209
<211> LENGTH: 112
<212> TYPE: PRT
<213> ORGANISM: Oryctolagus cuniculus

<400> SEQUENCE: 209

```
Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Ser Asp Tyr
            20                  25                  30

Leu Ser Trp Tyr Gln Gln Lys Pro Gly Gln Pro Pro Lys Leu Leu Ile
        35                  40                  45

Tyr Arg Ala Ser Asn Leu Ala Ser Gly Val Pro Ser Arg Phe Lys Ala
    50                  55                  60

Ser Glu Ser Gly Thr Glu Phe Thr Leu Thr Ile Ser Asp Leu Glu Cys
65                  70                  75                  80

Ala Asp Ala Ala Thr Tyr Tyr Cys Gln Cys Thr Phe Gly Ala Thr Asn
                85                  90                  95

Asp Asp Tyr Gly Asn Ala Phe Gly Gly Gly Thr Glu Val Val Val Lys
            100                 105                 110
```

<210> SEQ ID NO 210
<211> LENGTH: 113
<212> TYPE: PRT
<213> ORGANISM: Oryctolagus cuniculus

<400> SEQUENCE: 210

Asp Ile Val Met Thr Gln Thr Pro Ala Ser Val Glu Ala Ala Val Gly
1 5 10 15

Gly Thr Val Thr Ile Lys Cys Gln Ala Ser Gln Ser Ile Ser Ser Tyr
20 25 30

Leu Ser Trp Tyr Gln Gln Lys Pro Gly Gln Pro Pro Lys Leu Leu Ile
35 40 45

Tyr Asp Ala Ser Asp Leu Ala Ser Gly Val Ser Ser Arg Phe Lys Gly
50 55 60

Ser Gly Ser Gly Thr Glu Phe Thr Leu Thr Ile Ser Asp Leu Glu Cys
65 70 75 80

Ala Asp Ala Ala Thr Tyr Tyr Cys Gln Cys Thr Val Gly Ser Ser Gly
85 90 95

Val Thr Gly Tyr Gly Asn Ala Phe Gly Gly Gly Thr Glu Val Val Val
100 105 110

Lys

<210> SEQ ID NO 211
<211> LENGTH: 112
<212> TYPE: PRT
<213> ORGANISM: Oryctolagus cuniculus

<400> SEQUENCE: 211

Asp Pro Val Met Thr Gln Thr Pro Ala Ser Val Ser Glu Pro Val Gly
1 5 10 15

Gly Thr Val Thr Ile Lys Cys Gln Ala Ser Gln Asn Ile Asn Asn Leu
20 25 30

Leu Ala Trp Tyr Gln Gln Lys Pro Gly Gln Pro Pro Lys Leu Leu Ile
35 40 45

Tyr Lys Ala Ser Thr Leu Ala Ser Gly Val Ser Ser Arg Phe Lys Gly
50 55 60

Ser Gly Ser Gly Thr Glu Phe Thr Leu Thr Ile Ser Asp Leu Glu Cys
65 70 75 80

Ala Asp Ala Ala Thr Tyr Tyr Cys Gln Asn Tyr Tyr Gly Tyr Gly Leu
85 90 95

Ser Thr Asn Tyr Val Val Phe Gly Gly Gly Thr Glu Val Val Val Lys
100 105 110

<210> SEQ ID NO 212
<211> LENGTH: 113
<212> TYPE: PRT
<213> ORGANISM: Oryctolagus cuniculus

<400> SEQUENCE: 212

Ala Gln Val Leu Thr Gln Thr Pro Ser Ser Val Ser Ala Ala Val Gly
1 5 10 15

Gly Thr Val Thr Ile Asn Cys Gln Ala Ser Gln Ser Val Tyr Ala Asn
20 25 30

Asn Tyr Leu Ala Trp Tyr Gln Gln Lys Pro Gly Gln Pro Pro Lys Leu
35 40 45

Leu Ile Tyr Lys Ala Ser Thr Leu Ala Ser Gly Val Pro Ser Arg Phe
50 55 60

Ser Gly Ser Gly Ser Gly Thr Gln Phe Thr Leu Thr Ile Asn Gly Val
65 70 75 80

Gln Cys Asp Asp Ala Ala Thr Tyr Tyr Cys Gln Gly Glu Phe Ser Cys
85 90 95

```
Ser Ser Gly Asp Cys Thr Ala Phe Gly Gly Gly Thr Glu Val Val Val
            100                 105                 110

Lys


<210> SEQ ID NO 213
<211> LENGTH: 112
<212> TYPE: PRT
<213> ORGANISM: Oryctolagus cuniculus

<400> SEQUENCE: 213

Asp Val Val Met Thr Gln Thr Pro Ala Ser Val Glu Ala Ala Val Gly
1               5                   10                  15

Gly Thr Val Thr Ile Lys Cys Gln Ala Ser Glu Ser Ile Ser Asn Tyr
            20                  25                  30

Leu Ser Trp Tyr Gln Gln Lys Pro Gly Gln Pro Pro Lys Leu Leu Ile
        35                  40                  45

Cys Tyr Asp Ser Thr Leu Glu Ser Gly Val Pro Ser Arg Phe Lys Gly
    50                  55                  60

Ser Gly Ser Gly Thr Asp Phe Thr Leu Thr Ile Ser Asp Leu Glu Cys
65                  70                  75                  80

Ala Asp Ala Ala Thr Tyr Tyr Cys Gln Cys Thr Ala Gly Ser Ile Asn
                85                  90                  95

Val Ser Tyr Gly Asn Ala Phe Gly Gly Gly Thr Glu Val Val Val Lys
            100                 105                 110


<210> SEQ ID NO 214
<211> LENGTH: 113
<212> TYPE: PRT
<213> ORGANISM: Oryctolagus cuniculus

<400> SEQUENCE: 214

Ala Gln Val Leu Thr Gln Thr Ala Ser Pro Val Ser Glu Pro Val Gly
1               5                   10                  15

Gly Thr Val Thr Ile Lys Cys Gln Ser Ser Gln Ser Val Tyr Asn Asn
            20                  25                  30

Asn Trp Leu Ser Trp Phe Gln Gln Lys Pro Gly Gln Pro Pro Lys Arg
        35                  40                  45

Leu Ile Tyr Gly Ala Ser Thr Leu Ala Ser Gly Val Pro Ser Arg Phe
    50                  55                  60

Lys Gly Ser Gly Ser Gly Thr His Phe Thr Leu Thr Ile Ser Asp Val
65                  70                  75                  80

Gln Cys Asp Asp Ala Ala Thr Tyr Tyr Cys Leu Gly Ser Tyr Asp Cys
                85                  90                  95

Ser Ser Val Asp Cys Asn Ala Phe Gly Gly Gly Thr Glu Val Val Val
            100                 105                 110

Lys


<210> SEQ ID NO 215
<211> LENGTH: 112
<212> TYPE: PRT
<213> ORGANISM: Oryctolagus cuniculus

<400> SEQUENCE: 215

Ala Ala Val Leu Thr Gln Thr Pro Ser Pro Val Ser Ala Ala Val Gly
1               5                   10                  15

Gly Thr Val Thr Ile Ser Cys Gln Ala Ser Gln Ser Val His Lys His
            20                  25                  30
```

Lys Asn Leu Ala Trp Tyr Gln Gln Lys Pro Gly Gln Pro Pro Lys Leu
35 40 45

Leu Ile Tyr Glu Ala Ser Lys Leu Ala Ser Gly Val Pro Pro Arg Phe
50 55 60

Ser Gly Ser Gly Ser Gly Thr Gln Phe Thr Leu Thr Met Ser Asp Leu
65 70 75 80

Glu Cys Asp Asp Ala Ala Thr Tyr Tyr Cys Ala Gly Gly Tyr Asp Ser
85 90 95

Thr Ile Asp Thr Phe Thr Phe Gly Gly Gly Thr Glu Val Val Val Lys
100 105 110

<210> SEQ ID NO 216
<211> LENGTH: 113
<212> TYPE: PRT
<213> ORGANISM: Oryctolagus cuniculus

<400> SEQUENCE: 216

Asp Val Val Met Thr Gln Thr Pro Ala Ser Val Glu Ala Ala Val Gly
1 5 10 15

Gly Thr Val Thr Ile Lys Cys Gln Ala Ser Gln Ser Ile Ser Ser Tyr
20 25 30

Leu Ser Trp Tyr Gln Gln Lys Pro Gly Gln Pro Pro Lys Leu Leu Ile
35 40 45

Tyr Arg Ala Ser Ser Leu Lys Ser Gly Val Pro Ser Arg Phe Lys Gly
50 55 60

Thr Gly Ser Gly Thr Glu Phe Thr Leu Thr Ile Ser Asp Leu Glu Cys
65 70 75 80

Ala Asp Ala Ala Thr Tyr Tyr Cys Gln Cys Thr Tyr Gly Ser Ser Thr
85 90 95

Ser Ser Arg Ser Gly Asn Ala Phe Gly Gly Gly Thr Glu Val Val Val
100 105 110

Thr

<210> SEQ ID NO 217
<211> LENGTH: 113
<212> TYPE: PRT
<213> ORGANISM: Oryctolagus cuniculus

<400> SEQUENCE: 217

Asp Ile Val Met Thr Gln Thr Pro Ala Ser Val Glu Ala Ala Val Gly
1 5 10 15

Gly Thr Val Thr Ile Lys Cys Gln Ala Ser Gln Asn Ile Asn Asn Glu
20 25 30

Leu Ser Trp Tyr Gln Gln Lys Pro Gly Gln Pro Pro Lys Leu Leu Ile
35 40 45

Tyr Lys Ala Ser Thr Leu Ala Ser Gly Val Pro Ser Arg Phe Lys Gly
50 55 60

Ser Gly Ser Gly Thr Gln Phe Thr Leu Thr Ile Ser Asp Leu Glu Cys
65 70 75 80

Ala Asp Ala Ala Thr Tyr Tyr Cys Gln Ser Tyr Tyr Tyr Gly Ile Ser
85 90 95

Ser Thr Tyr Ala Phe Tyr Thr Phe Gly Gly Gly Thr Glu Val Val Val
100 105 110

Lys

-continued

<210> SEQ ID NO 218
<211> LENGTH: 110
<212> TYPE: PRT
<213> ORGANISM: Oryctolagus cuniculus

<400> SEQUENCE: 218

```
Asp Val Val Met Thr Gln Thr Pro Ala Ser Ala Ser Ala Ala Val Gly
1               5                   10                  15

Gly Ala Val Thr Ile Lys Cys Arg Ala Ser Glu Asp Ile Glu Ser Tyr
            20                  25                  30

Leu Ala Trp Tyr Gln Gln Lys Pro Gly Gln Pro Pro Lys Leu Leu Ile
        35                  40                  45

Tyr Ser Ala Ser Ser Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Asp Asp Ala Ala Thr Tyr Tyr Cys Gln Cys Thr Tyr Trp Asp Ser Ser
                85                  90                  95

Thr Val Gly Ala Phe Gly Gly Gly Thr Ala Val Val Val Lys
            100                 105                 110
```

<210> SEQ ID NO 219
<211> LENGTH: 111
<212> TYPE: PRT
<213> ORGANISM: Oryctolagus cuniculus

<400> SEQUENCE: 219

```
Ala Ala Val Leu Thr Gln Thr Pro Ser Pro Val Ser Ala Ala Val Gly
1               5                   10                  15

Gly Thr Val Ser Ile Ser Cys Gln Ser Ser Gln Ser Val Tyr Asn Asp
            20                  25                  30

Asn Asp Leu Ala Trp Phe Gln Gln Lys Pro Gly Gln Pro Pro Lys Leu
        35                  40                  45

Leu Ile Tyr Gly Ala Ser Thr Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Ser Gly Gly Tyr Ile Ser
                85                  90                  95

Ser Ser Asp Asn Ala Phe Gly Gly Gly Thr Glu Val Val Val Lys
            100                 105                 110
```

<210> SEQ ID NO 220
<211> LENGTH: 109
<212> TYPE: PRT
<213> ORGANISM: Oryctolagus cuniculus

<400> SEQUENCE: 220

```
Asp Val Val Met Thr Gln Thr Pro Ala Ser Val Ser Ala Ala Val Gly
1               5                   10                  15

Gly Thr Val Thr Ile Lys Cys Gln Ala Ser Glu Ser Ile Tyr Ser Gly
            20                  25                  30

Leu Ala Trp Tyr Gln Gln Lys Pro Gly Gln Pro Pro Lys Leu Leu Ile
        35                  40                  45

Tyr Arg Ala Ser Thr Leu Glu Ser Gly Val Ser Ser Arg Phe Lys Gly
    50                  55                  60

Ser Gly Ser Gly Thr Gln Phe Thr Leu Thr Ile Ser Asp Leu Glu Cys
65                  70                  75                  80
```

```
Ala Asp Ala Ala Thr Tyr Tyr Cys Gln Ser Thr Tyr Tyr Gly Ser Ser
                85                  90                  95

Gly Asn Ala Phe Gly Gly Gly Thr Glu Val Val Val Lys
            100                 105


<210> SEQ ID NO 221
<211> LENGTH: 111
<212> TYPE: PRT
<213> ORGANISM: Oryctolagus cuniculus

<400> SEQUENCE: 221

Asp Ile Val Met Thr Gln Thr Pro Ala Ser Val Ser Ala Ala Val Gly
1               5                   10                  15

Gly Thr Val Thr Ile Asn Cys Gln Ala Ser Gln Ser Ile Ser Tyr Tyr
            20                  25                  30

Leu Asn Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Gln Phe Thr Leu Thr Ile Ser Gly Val Gln Cys
65                  70                  75                  80

Asp Asp Ala Ala Thr Tyr Tyr Cys Leu Tyr Gly Tyr Val Thr Ser Ser
                85                  90                  95

Asn Ala Asp Phe Ala Phe Gly Gly Gly Thr Glu Val Val Val Glu
            100                 105                 110


<210> SEQ ID NO 222
<211> LENGTH: 113
<212> TYPE: PRT
<213> ORGANISM: Oryctolagus cuniculus

<400> SEQUENCE: 222

Ala Gln Val Leu Thr Gln Thr Pro Ser Ser Val Ser Ala Ala Val Gly
1               5                   10                  15

Asp Thr Val Thr Ile Asn Cys Gln Ala Ser Gln Ser Val Tyr Lys Asn
            20                  25                  30

Asn Tyr Leu Ala Trp Phe Gln Gln Lys Pro Gly Gln Pro Pro Lys Arg
        35                  40                  45

Leu Ile Tyr Ser Ala Ser Thr Leu Asp Ser Gly Val Ser Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Leu Gly Thr Tyr Asp Cys
                85                  90                  95

Val Ser Ala Asp Cys Gly Ala Phe Gly Gly Gly Thr Glu Val Val Val
            100                 105                 110

Lys


<210> SEQ ID NO 223
<211> LENGTH: 112
<212> TYPE: PRT
<213> ORGANISM: Oryctolagus cuniculus

<400> SEQUENCE: 223

Ala Gln Val Leu Thr Gln Thr Ala Ser Ser Val Ser Ala Ala Val Gly
1               5                   10                  15

Gly Thr Val Thr Ile Ser Cys Gln Ser Ser Gln Ser Val Tyr Asn Asn
```

```
            20                  25                  30

Asn Trp Leu Gly Trp Tyr Gln Gln Lys Pro Gly Gln Pro Pro Lys Leu
        35                  40                  45

Leu Ile Tyr Ser Ala Ser Thr Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Tyr Asp Ala Ala Thr Tyr Tyr Cys Gln Gly Thr Tyr Ser Asn
                85                  90                  95

Asn Gly Trp Tyr Phe Ala Phe Gly Gly Gly Thr Glu Val Val Val Lys
            100                 105                 110


<210> SEQ ID NO 224
<211> LENGTH: 113
<212> TYPE: PRT
<213> ORGANISM: Oryctolagus cuniculus

<400> SEQUENCE: 224

Asp Ile Val Met Thr Gln Thr Pro Ala Ser Val Ser Glu Pro Val Gly
1               5                   10                  15

Gly Thr Val Thr Ile Lys Cys Gln Ala Ser Glu Asp Ile Tyr Asn Leu
            20                  25                  30

Leu Ala Trp Tyr His Gln Lys Pro Gly Gln Pro Pro Lys Leu Leu Ile
        35                  40                  45

Tyr Gly Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Ser Tyr Tyr Tyr Gly Ile Ser
                85                  90                  95

Ser Thr Tyr Ala Phe Tyr Thr Phe Gly Gly Gly Thr Glu Val Val Val
            100                 105                 110

Glu


<210> SEQ ID NO 225
<211> LENGTH: 109
<212> TYPE: PRT
<213> ORGANISM: Oryctolagus cuniculus

<400> SEQUENCE: 225

Ala Phe Glu Leu Thr Gln Thr Pro Ser Ser Val Ser Ala Ala Val Gly
1               5                   10                  15

Gly Thr Val Thr Ile Asn Cys Gln Ala Ser Glu Asp Ile Glu Ser Tyr
            20                  25                  30

Leu Ala Trp Tyr Gln Gln Lys Pro Gly Gln Pro Pro Lys Phe Leu Ile
        35                  40                  45

Tyr Gly Ala Ser Thr Leu Ala Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Thr Tyr Tyr Gly Gly Ile Asn
                85                  90                  95

Ile Phe Thr Phe Gly Gly Gly Thr Glu Val Val Val Glu
            100                 105


<210> SEQ ID NO 226
```

<211> LENGTH: 113
<212> TYPE: PRT
<213> ORGANISM: Oryctolagus cuniculus

<400> SEQUENCE: 226

Ala Gln Val Leu Thr Gln Thr Ala Ser Pro Val Ser Ala Ala Val Gly
1 5 10 15

Ser Thr Val Thr Ile Asn Cys Gln Ala Ser Gln Ser Val Tyr Ser Asn
20 25 30

Asn Tyr Leu Ser Trp Phe Gln Gln Lys Pro Gly Gln Pro Pro Lys Leu
35 40 45

Leu Ile Tyr Asp Ala Ser Asp Leu Ala Ser Gly Val Pro Ser Arg Phe
50 55 60

Lys Gly Ser Gly Ser Gly Thr Gln Phe Thr Leu Thr Ile Ser Asp Leu
65 70 75 80

Glu Cys Asp Asp Ala Ala Thr Tyr Tyr Cys Leu Gly Thr Tyr Asp Cys
85 90 95

Ser Ser Thr Asp Cys Tyr Ala Phe Gly Gly Gly Thr Glu Val Val Val
100 105 110

Lys

<210> SEQ ID NO 227
<211> LENGTH: 111
<212> TYPE: PRT
<213> ORGANISM: Oryctolagus cuniculus

<400> SEQUENCE: 227

Asp Val Val Met Thr Gln Thr Pro Ala Ser Val Ser Glu Pro Val Gly
1 5 10 15

Gly Thr Val Ser Leu Lys Cys Gln Ala Ser Glu Ser Ile Asp Ser Tyr
20 25 30

Leu Asn Trp Tyr Gln Gln Lys Pro Gly Gln Pro Pro Lys Leu Leu Ile
35 40 45

Tyr Gly Ala Ser Thr Leu Ala Ser Gly Val Ser Ser Arg Phe Lys Gly
50 55 60

Ser Arg Ser Gly Thr Glu Tyr Thr Leu Thr Ile Ser Asp Leu Glu Cys
65 70 75 80

Ala Asp Ala Ala Thr Tyr Tyr Cys Gln Cys Thr Val Tyr Gly Val Asn
85 90 95

Phe Val Pro Asn Ala Phe Gly Gly Gly Thr Glu Val Val Val Lys
100 105 110

<210> SEQ ID NO 228
<211> LENGTH: 110
<212> TYPE: PRT
<213> ORGANISM: Oryctolagus cuniculus

<400> SEQUENCE: 228

Ala Leu Val Met Thr Gln Thr Pro Ser Ser Val Ser Ala Ala Val Gly
1 5 10 15

Gly Thr Val Thr Ile Asn Cys Gln Ala Ser Gln Asn Ile Tyr Ser Ser
20 25 30

Leu Ala Trp Tyr Gln Gln Lys Pro Gly Gln Pro Pro Lys Leu Leu Ile
35 40 45

Tyr Gly Ala Ser Asn Leu Glu Ser Gly Val Pro Ser Arg Phe Lys Gly
50 55 60

Ser Gly Ser Gly Thr Glu Phe Thr Leu Thr Ile Ser Ala Leu Glu Cys

```
65                  70                  75                  80

Asp Asp Ala Ala Thr Tyr Tyr Cys Gln Gly Gly Tyr Tyr Ile Ser Ser
                85                  90                  95

Thr Asp Asn Ala Phe Gly Gly Gly Thr Glu Val Val Val Lys
            100                 105                 110


<210> SEQ ID NO 229
<211> LENGTH: 110
<212> TYPE: PRT
<213> ORGANISM: Oryctolagus cuniculus

<400> SEQUENCE: 229

Ala Tyr Asp Met Thr Gln Thr Pro Ala Ser Val Glu Ala Val Val Gly
1               5                   10                  15

Gly Ser Val Thr Ile Lys Cys Gln Ala Ser Gln Ser Ile Ser Tyr Tyr
            20                  25                  30

Leu Ala Trp Tyr Gln Gln Lys Pro Gly Gln Arg Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Gln Gly Tyr Ser Ser Ser Asn
                85                  90                  95

Val Asp Asn Ala Phe Gly Gly Gly Thr Glu Val Val Val Lys
            100                 105                 110


<210> SEQ ID NO 230
<211> LENGTH: 110
<212> TYPE: PRT
<213> ORGANISM: Oryctolagus cuniculus

<400> SEQUENCE: 230

Ala Phe Glu Leu Thr Gln Thr Pro Ser Ser Val Ser Ala Ala Val Gly
1               5                   10                  15

Gly Thr Val Thr Ile Lys Cys Gln Ala Ser Gln Asn Ile Tyr Ser Arg
            20                  25                  30

Leu Ala Trp Tyr Gln Gln Lys Pro Gly Gln Arg Pro Lys Leu Leu Ile
        35                  40                  45

Tyr Ala Ala Ser Thr Leu Ala Ser Gly Val Pro Ser Arg Phe Lys Gly
    50                  55                  60

Asn Gly Ser Gly Thr Glu Phe Thr Leu Thr Ile Ser Asp Leu Glu Cys
65                  70                  75                  80

Ala Asp Ala Ala Thr Tyr Tyr Cys Gln Gly Gly Tyr Tyr Gly Ser Ser
                85                  90                  95

Asp Thr Val Thr Phe Gly Gly Gly Thr Glu Val Val Val Lys
            100                 105                 110


<210> SEQ ID NO 231
<211> LENGTH: 111
<212> TYPE: PRT
<213> ORGANISM: Oryctolagus cuniculus

<400> SEQUENCE: 231

Ala Ala Val Leu Thr Gln Thr Pro Ser Pro Val Ser Ala Ala Val Gly
1               5                   10                  15

Gly Thr Val Thr Ile Ser Cys Gln Ser Ser Gln Ser Val Thr Asp Asn
            20                  25                  30
```

```
Phe Leu Ser Trp Phe Gln Gln Lys Pro Gly Gln Arg Pro Lys Leu Leu
        35                  40                  45

Ile Tyr Gly Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Ala Gly Gly Tyr Ser Gly Ser
                85                  90                  95

Ser Asp Val Phe Ala Phe Gly Gly Gly Thr Glu Val Val Val Lys
            100                 105                 110
```

<210> SEQ ID NO 232
<211> LENGTH: 111
<212> TYPE: PRT
<213> ORGANISM: Oryctolagus cuniculus

<400> SEQUENCE: 232

```
Ala Tyr Asp Met Thr Gln Thr Pro Ser Ser Val Ser Ala Ala Val Gly
1               5                   10                  15

Gly Thr Val Thr Ile Asn Cys Gln Ala Ser Glu Asp Ile Glu Ser Tyr
            20                  25                  30

Leu Ala Trp Tyr Gln Gln Lys Pro Gly Gln Pro Pro Lys Leu Leu Ile
        35                  40                  45

Tyr Ser Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Cys Thr Val Tyr Gly Val Asn
                85                  90                  95

Tyr Val Pro Asn Ala Phe Gly Gly Gly Thr Glu Val Val Val Lys
            100                 105                 110
```

<210> SEQ ID NO 233
<211> LENGTH: 110
<212> TYPE: PRT
<213> ORGANISM: Oryctolagus cuniculus

<400> SEQUENCE: 233

```
Asp Val Val Met Thr Gln Thr Pro Ala Ser Val Ser Ala Ala Val Gly
1               5                   10                  15

Gly Thr Val Thr Ile Lys Cys Gln Ala Ser Gln Ser Ile Gly Ser Ser
            20                  25                  30

Leu Ala Trp Tyr Gln Gln Lys Pro Gly Gln Ser Pro Lys Leu Leu Ile
        35                  40                  45

Tyr Ser Ala Ser Asn Leu Ala Ser Gly Val Ser Ser Arg Phe Lys Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Cys Thr Tyr Tyr Gly Gly Ser
                85                  90                  95

Gly Asp Val Pro Phe Gly Gly Gly Thr Glu Val Val Val Lys
            100                 105                 110
```

<210> SEQ ID NO 234
<211> LENGTH: 112
<212> TYPE: PRT
<213> ORGANISM: Oryctolagus cuniculus

<400> SEQUENCE: 234

Asp Ile Val Met Thr Gln Thr Pro Ala Ser Val Glu Ala Ala Val Gly
1 5 10 15

Gly Thr Val Thr Ile Lys Cys Gln Ala Ser Gln Ser Ile Ser Ser Tyr
20 25 30

Leu Ala Trp Tyr Gln Gln Lys Pro Gly Gln Pro Pro Lys Leu Leu Ile
35 40 45

Tyr Arg Thr Ser Ile Leu Glu Ser Gly Val Pro Ser Arg Phe Lys Gly
50 55 60

Ser Gly Ser Gly Thr Glu Phe Thr Leu Thr Ile Ser Asp Leu Glu Cys
65 70 75 80

Ala Asp Ala Ala Thr Tyr Tyr Cys Gln Cys Thr Tyr Gly Thr Thr Asn
85 90 95

Thr Gly His Tyr Val Gly Phe Gly Gly Gly Thr Glu Val Val Val Lys
100 105 110

<210> SEQ ID NO 235
<211> LENGTH: 109
<212> TYPE: PRT
<213> ORGANISM: Oryctolagus cuniculus

<400> SEQUENCE: 235

Asp Val Val Met Thr Gln Thr Pro Ala Ser Val Ser Glu Pro Val Gly
1 5 10 15

Gly Thr Val Thr Ile Lys Cys Gln Ala Ser Gln Asn Ile Gly Ser Asp
20 25 30

Leu Ala Trp Tyr Gln Gln Lys Pro Gly Gln Arg Pro Lys Leu Leu Ile
35 40 45

Tyr Asp Ala Ser Ala Leu Ala Ser Gly Val Pro Ser Arg Phe Ser Gly
50 55 60

Ser Gly Ser Gly Thr Glu Phe Thr Leu Thr Ile Ser Gly Val Gln Cys
65 70 75 80

Asp Asp Ser Ala Thr Tyr Tyr Cys Gln Cys Thr Tyr Tyr Ser Gly Ser
85 90 95

Pro His Thr Phe Gly Gly Gly Thr Glu Val Val Val Lys
100 105

<210> SEQ ID NO 236
<211> LENGTH: 114
<212> TYPE: PRT
<213> ORGANISM: Oryctolagus cuniculus

<400> SEQUENCE: 236

Asp Ile Val Met Thr Gln Thr Pro Ala Ser Val Glu Ala Ala Val Gly
1 5 10 15

Gly Thr Val Thr Ile Lys Cys Gln Ala Ser Gln Ser Ile Ser Ser Tyr
20 25 30

Leu Ala Trp Tyr Gln Gln Lys Pro Gly Gln Pro Pro Lys Leu Leu Ile
35 40 45

Tyr Arg Ala Ser Thr Leu Ala Ser Gly Val Pro Ser Arg Phe Lys Gly
50 55 60

Ser Gly Ser Gly Thr Glu Phe Thr Leu Thr Ile Ser Asp Leu Glu Cys
65 70 75 80

Ala Asp Ala Ala Thr Tyr Tyr Cys Gln Ser Asn Tyr Gly Ser Ser Ser
85 90 95

```
Ile Ser Asn Tyr Gly Gly Gly Ala Phe Gly Gly Gly Thr Glu Val Val
            100                 105                 110

Val Lys


<210> SEQ ID NO 237
<211> LENGTH: 110
<212> TYPE: PRT
<213> ORGANISM: Oryctolagus cuniculus

<400> SEQUENCE: 237

Ala Gln Val Leu Thr Gln Thr Pro Ala Ser Val Ser Ala Ala Val Arg
1               5                   10                  15

Gly Thr Val Thr Ile Lys Cys Gln Ala Ser Glu Ser Val Val Gly Lys
            20                  25                  30

Asn Glu Leu Ser Trp Tyr His Gln Lys Pro Gly Gln Pro Pro Lys Leu
        35                  40                  45

Leu Ile Phe Gly Thr Ser Thr Leu Ala Ser Gly Val Pro Ser Arg Phe
    50                  55                  60

Ser Gly Ser Gly Ser Glu Thr Gln Phe Thr Leu Ala Ile Ser Asp Leu
65                  70                  75                  80

Glu Cys Gly Asp Ala Ala Thr Tyr Tyr Cys Ala Gly Gly Tyr Ser Gly
                85                  90                  95

Asn Met Tyr Val Phe Gly Gly Gly Thr Glu Val Val Val Lys
            100                 105                 110


<210> SEQ ID NO 238
<211> LENGTH: 112
<212> TYPE: PRT
<213> ORGANISM: Oryctolagus cuniculus

<400> SEQUENCE: 238

Ala Ala Val Leu Thr Gln Thr Pro Ser Pro Val Ser Ala Ala Val Gly
1               5                   10                  15

Gly Thr Val Thr Ile Ser Cys Gln Ala Ser Gln Ser Val His Asn Asn
            20                  25                  30

Lys Asn Leu Ala Trp Tyr Gln Gln Lys Pro Gly Gln Pro Pro Lys Leu
        35                  40                  45

Leu Ile Tyr Asp Val Ser Thr Val Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Gly Tyr Gly Ser
                85                  90                  95

Tyr Thr Asp Thr Phe Ala Phe Gly Gly Gly Thr Glu Val Val Val Lys
            100                 105                 110


<210> SEQ ID NO 239
<211> LENGTH: 111
<212> TYPE: PRT
<213> ORGANISM: Oryctolagus cuniculus

<400> SEQUENCE: 239

Ala Ala Val Leu Thr Gln Thr Pro Ser Pro Val Ser Ala Ala Val Gly
1               5                   10                  15

Gly Thr Val Thr Ile Lys Cys Gln Ser Ser Gln Ser Val Tyr Arg Asn
            20                  25                  30

Asn Glu Leu Ser Trp Tyr Gln Gln Lys Pro Gly Gln Pro Pro Lys Val
        35                  40                  45
```

```
Leu Val Tyr Asp Ala Ser Asn Leu Ala Ser Gly Val Pro Asp Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Gly Tyr Asp Asp
                85                  90                  95

Asp Ala Asp Asn Thr Phe Gly Gly Gly Thr Glu Val Val Val Lys
            100                 105                 110


<210> SEQ ID NO 240
<211> LENGTH: 111
<212> TYPE: PRT
<213> ORGANISM: Oryctolagus cuniculus

<400> SEQUENCE: 240

Asp Val Val Met Thr Gln Thr Pro Ala Ser Val Ser Glu Pro Val Gly
1               5                   10                  15

Gly Thr Val Thr Ile Lys Cys Gln Ala Ser Glu Asp Ile Glu Ser Phe
            20                  25                  30

Leu Ala Trp Tyr Gln Gln Lys Pro Gly Gln Pro Pro Lys Leu Leu Ile
        35                  40                  45

Tyr Ser Ala Ser Thr Leu Ala Ser Gly Val Pro Ser Arg Phe Lys Gly
    50                  55                  60

Ser Gly Ser Gly Thr Gln Phe Thr Leu Thr Ile Gly Asp Leu Glu Cys
65                  70                  75                  80

Ala Asp Ala Ala Thr Tyr Phe Cys Gln Cys Thr Ile Tyr Gly Val Asn
                85                  90                  95

Phe Val Pro Asn Ala Phe Gly Gly Gly Thr Glu Val Val Val Lys
            100                 105                 110


<210> SEQ ID NO 241
<211> LENGTH: 110
<212> TYPE: PRT
<213> ORGANISM: Oryctolagus cuniculus

<400> SEQUENCE: 241

Asp Val Val Met Thr Gln Thr Pro Ala Ser Val Ser Glu Pro Val Gly
1               5                   10                  15

Gly Thr Val Thr Ile Lys Cys Gln Ala Ser Glu Asp Ile Ser Ser Arg
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Pro Glu Tyr Thr Leu Thr Ile Ser Asp Leu Glu Cys
65                  70                  75                  80

Ala Asp Ala Ala Thr Tyr Tyr Cys Gln Ser Asn Tyr Ala Ile Ile Ser
                85                  90                  95

Cys Gly Ala Ala Phe Gly Gly Gly Thr Glu Val Val Val Lys
            100                 105                 110


<210> SEQ ID NO 242
<211> LENGTH: 110
<212> TYPE: PRT
<213> ORGANISM: Oryctolagus cuniculus

<400> SEQUENCE: 242
```

```
Ala Leu Val Met Thr Gln Thr Pro Ser Ser Val Ser Ala Ala Val Gly
1               5                   10                  15

Gly Thr Val Thr Ile Asn Cys Gln Ala Ser Gln Asn Ile Tyr Ser Asn
            20                  25                  30

Leu Ala Trp Tyr Gln Gln Lys Pro Gly Gln Arg Pro Lys Leu Leu Ile
        35                  40                  45

Tyr Gly Ala Ser Asn Leu Glu Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Asp Asp Ala Ala Thr Tyr Tyr Cys Gln Ser Ala Tyr Tyr Ser Ser Ser
                85                  90                  95

Ala Val Tyr Ala Phe Gly Gly Gly Thr Glu Val Val Val Lys
            100                 105                 110


<210> SEQ ID NO 243
<211> LENGTH: 111
<212> TYPE: PRT
<213> ORGANISM: Oryctolagus cuniculus

<400> SEQUENCE: 243

Ala Ile Asp Met Thr Gln Thr Pro Ser Ser Val Ser Ala Ala Val Gly
1               5                   10                  15

Asp Thr Val Thr Ile Asn Cys Gln Ala Ser Glu Asn Ile Tyr Ser Phe
            20                  25                  30

Leu Ala Trp Tyr Gln Gln Lys Pro Gly Gln Arg Pro Lys Leu Leu Ile
        35                  40                  45

Tyr Asp Ser Ser Thr Leu Ala Ser Gly Val Pro Ser Arg Phe Ser Gly
    50                  55                  60

Ser Gly Ser Gly Thr Glu Phe Thr Leu Thr Ile Ser Gly Ile Gln Cys
65                  70                  75                  80

Asp Asp Ala Ala Thr Tyr Tyr Cys Gln Gln Thr Tyr Ile Tyr Asn Asn
                85                  90                  95

Ala Glu Ser Asn Ala Phe Gly Gly Gly Thr Glu Val Val Val Lys
            100                 105                 110


<210> SEQ ID NO 244
<211> LENGTH: 110
<212> TYPE: PRT
<213> ORGANISM: Oryctolagus cuniculus

<400> SEQUENCE: 244

Ala Gln Val Leu Thr Gln Thr Pro Ser Pro Val Ser Ala Ala Val Gly
1               5                   10                  15

Gly Thr Val Thr Ile Asn Cys Gln Ser Ser Gln Ser Val Ala Asp Asn
            20                  25                  30

Asn Leu Leu Ala Trp Tyr Gln Gln Lys Pro Gly Gln Pro Pro Lys Leu
        35                  40                  45

Leu Ile Tyr Lys Ala Ser Thr Leu Ala Ser Gly Val Pro Ser Arg Phe
    50                  55                  60

Lys Gly Ser Gly Tyr Gly Thr Gln Phe Thr Leu Thr Ile Ser Asp Leu
65                  70                  75                  80

Glu Cys Asp Asp Ala Ala Thr Tyr Tyr Cys Val Gly Gly Tyr Ser Thr
                85                  90                  95

Ser Gly Tyr Ala Phe Gly Gly Gly Thr Glu Val Val Val Lys
            100                 105                 110
```

<210> SEQ ID NO 245
<211> LENGTH: 113
<212> TYPE: PRT
<213> ORGANISM: Oryctolagus cuniculus

<400> SEQUENCE: 245

Ala Gln Val Leu Thr Gln Thr Pro Ser Pro Val Ser Ala Ala Val Gly
1 5 10 15

Gly Thr Val Thr Ile Asn Cys Gln Ala Ser Gln Ser Val Tyr Gly Thr
20 25 30

Asn Arg Leu Ala Trp Tyr Gln Gln Lys Pro Gly Gln Pro Pro Lys Leu
35 40 45

Leu Ile Tyr Asp Ala Ser Thr Leu Ala Ser Gly Val Pro Ser Arg Phe
50 55 60

Ser Gly Ser Gly Ser Gly Thr Gln Phe Thr Leu Thr Ile Ser Gly Val
65 70 75 80

Gln Cys Asp Asp Ala Ala Thr Tyr Cys Cys Gln Gly Glu Phe Ser Cys
85 90 95

Ser Asn Gly Asp Cys Ile Ala Phe Gly Gly Gly Thr Glu Val Val Val
100 105 110

Lys

<210> SEQ ID NO 246
<211> LENGTH: 110
<212> TYPE: PRT
<213> ORGANISM: Oryctolagus cuniculus

<400> SEQUENCE: 246

Ala Phe Glu Leu Thr Gln Thr Pro Ser Ser Val Ser Ala Ala Val Gly
1 5 10 15

Gly Thr Val Thr Ile Lys Cys Gln Ala Ser Gln Asn Ile Tyr Ser Lys
20 25 30

Phe Ala Trp Tyr Gln Gln Lys Pro Gly Gln Arg Pro Lys Leu Leu Ile
35 40 45

Tyr Ser Ala Ser Thr Leu Ala Ser Gly Val Pro Ser Arg Phe Lys Gly
50 55 60

Asn Gly Ser Gly Thr Glu Phe Thr Leu Thr Ile Ser Asp Leu Glu Cys
65 70 75 80

Ala Asp Ala Ala Thr Tyr Tyr Cys Gln Gly Gly Tyr Tyr Gly Ser Ser
85 90 95

Asp Thr Val Thr Phe Gly Gly Gly Thr Glu Val Val Val Lys
100 105 110

<210> SEQ ID NO 247
<211> LENGTH: 110
<212> TYPE: PRT
<213> ORGANISM: Oryctolagus cuniculus

<400> SEQUENCE: 247

Ala Tyr Asp Met Thr Gln Thr Pro Ala Ser Val Glu Val Ala Leu Gly
1 5 10 15

Gly Thr Val Thr Ile Lys Cys Gln Ala Ser Gln Ser Ile Gly Val Ser
20 25 30

Leu Ala Trp Tyr Gln Gln Lys Pro Gly Gln Arg Pro Lys Leu Leu Ile
35 40 45

Tyr Ser Ala Ser Thr Leu Ala Ser Gly Val Ser Ser Arg Phe Lys Gly
50 55 60

Ser Gly Ser Gly Thr Glu Phe Thr Leu Thr Ile Ser Gly Val Glu Cys
65 70 75 80

Ala Asp Ala Ala Thr Tyr Tyr Cys Gln Gln Gly Tyr Thr Ser Ser Asn
85 90 95

Val Asp Asn Val Phe Gly Gly Gly Thr Glu Val Val Val Lys
100 105 110

<210> SEQ ID NO 248
<211> LENGTH: 113
<212> TYPE: PRT
<213> ORGANISM: Oryctolagus cuniculus

<400> SEQUENCE: 248

Ala Gln Val Leu Thr Gln Thr Ala Ser Pro Val Ser Ala Ala Val Gly
1 5 10 15

Ser Thr Val Thr Ile Asn Cys Gln Ala Ser Gln Ser Val Tyr Asn Asn
20 25 30

Asn Tyr Leu Gly Trp Phe Gln Gln Lys Pro Gly Gln Pro Pro Lys Arg
35 40 45

Leu Ile Tyr Ser Ala Ser Lys Leu Glu Ser Gly Val Pro Ser Arg Phe
50 55 60

Ser Gly Ser Gly Ser Gly Thr Gln Phe Thr Leu Thr Ile Ser Asp Val
65 70 75 80

Gln Cys Glu Asp Ala Ala Thr Tyr Tyr Cys Leu Gly Ser Tyr Asp Cys
85 90 95

Ser Ser Ala Asp Cys Asn Val Phe Gly Gly Gly Thr Glu Val Val Val
100 105 110

Lys

<210> SEQ ID NO 249
<211> LENGTH: 111
<212> TYPE: PRT
<213> ORGANISM: Oryctolagus cuniculus

<400> SEQUENCE: 249

Asp Val Val Met Thr Gln Thr Pro Ala Ser Val Ser Ala Ala Val Gly
1 5 10 15

Gly Thr Val Thr Ile Asn Cys Gln Ala Ser Glu Ser Ile Asp Asn Trp
20 25 30

Leu Ala Trp Tyr Gln Gln Lys Pro Gly Gln Pro Pro Lys Leu Leu Ile
35 40 45

Tyr Ser Ala Ser Asn Leu Ala Ser Gly Val Ser Ser Arg Phe Glu Gly
50 55 60

Ser Thr Ser Gly Thr Gln Phe Thr Leu Thr Ile Ser Asp Leu Glu Cys
65 70 75 80

Ala Asp Ala Ala Thr Tyr Tyr Cys Gln Ser Thr Phe Tyr Gly Val Asn
85 90 95

Pro Val Pro Asn Ala Phe Gly Gly Gly Thr Glu Val Val Val Lys
100 105 110

<210> SEQ ID NO 250
<211> LENGTH: 111
<212> TYPE: PRT
<213> ORGANISM: Oryctolagus cuniculus

<400> SEQUENCE: 250

Ala Ala Val Leu Thr Gln Thr Pro Ser Pro Val Ser Ala Ala Val Gly

```
1               5                   10                  15

Gly Thr Val Thr Ile Lys Cys Gln Ser Ser Gln Ser Val Tyr Ser Asn
            20                  25                  30

Asn Asn Leu Ala Trp Tyr Gln Gln Lys Pro Gly Gln Pro Pro Lys Leu
        35                  40                  45

Leu Ile Tyr Asp Ala Ser Asn Leu Ala Ser Gly Val Pro Asp Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Val Tyr Asp Asp
                85                  90                  95

Asp Ala Asp Asn Ala Phe Gly Gly Gly Thr Glu Val Val Val Lys
            100                 105                 110


<210> SEQ ID NO 251
<211> LENGTH: 113
<212> TYPE: PRT
<213> ORGANISM: Oryctolagus cuniculus

<400> SEQUENCE: 251

Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Ser Ser Tyr
            20                  25                  30

Leu Ser Trp Tyr Gln Gln Lys Pro Gly Gln Pro Pro Lys Leu Leu Ile
        35                  40                  45

Tyr Arg Ala Ser Ser Leu Glu Ser Gly Val Pro Ser Arg Phe Lys Gly
    50                  55                  60

Thr Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Thr Tyr Gly Ser Ser Thr
                85                  90                  95

Ser Ser Arg Ser Gly Asn Ala Phe Gly Gly Gly Thr Glu Val Val Val
            100                 105                 110

Lys


<210> SEQ ID NO 252
<211> LENGTH: 111
<212> TYPE: PRT
<213> ORGANISM: Oryctolagus cuniculus

<400> SEQUENCE: 252

Asp Val Val Met Thr Gln Thr Pro Ala Ser Val Glu Ala Asp Val Gly
1               5                   10                  15

Gly Thr Val Thr Ile Lys Cys Gln Ala Ser Gln Ser Ile Arg Ser Tyr
            20                  25                  30

Leu Ala Trp Tyr Gln Gln Lys Pro Gly Gln Pro Pro Lys Val Leu Ile
        35                  40                  45

Tyr Arg Ala Ser Thr Leu Glu Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Cys Thr Tyr Gly Ser Ser Gly
                85                  90                  95

Ser Ser Phe Leu Ala Phe Gly Gly Gly Thr Glu Val Val Val Lys
            100                 105                 110
```

<210> SEQ ID NO 253
<211> LENGTH: 110
<212> TYPE: PRT
<213> ORGANISM: Oryctolagus cuniculus

<400> SEQUENCE: 253

```
Ala Tyr Asp Met Thr Gln Thr Pro Ala Ser Val Glu Val Ala Val Gly
1               5                   10                  15

Gly Thr Val Thr Ile Lys Cys Gln Ala Ser Glu Ser Ile Ser Val Asn
            20                  25                  30

Leu Ala Trp Tyr Gln Gln Lys Ser Gly Gln Pro Pro Lys Leu Leu Ile
        35                  40                  45

Tyr Leu Ala Ser Thr Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gln Thr Tyr Ser Gly Ser Asn
                85                  90                  95

Val Glu Asn Ser Phe Gly Gly Gly Thr Glu Val Val Leu Lys
            100                 105                 110
```

<210> SEQ ID NO 254
<211> LENGTH: 111
<212> TYPE: PRT
<213> ORGANISM: Oryctolagus cuniculus

<400> SEQUENCE: 254

```
Ala Ala Val Leu Thr Gln Thr Pro Ser Pro Val Ser Ala Ala Val Gly
1               5                   10                  15

Gly Thr Val Ser Ile Ser Cys Gln Ser Ser Glu Ser Ile Tyr Lys Asn
            20                  25                  30

Asn Tyr Leu Ala Trp Tyr Gln Gln Lys Ser Gly Gln Pro Pro Lys Leu
        35                  40                  45

Leu Ile Tyr Arg Ala Ser Thr Leu Thr Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Ala Gly Asp Tyr Ser Ser
                85                  90                  95

Ser Ser Asp Asn Thr Phe Gly Gly Gly Thr Glu Val Val Val Lys
            100                 105                 110
```

<210> SEQ ID NO 255
<211> LENGTH: 110
<212> TYPE: PRT
<213> ORGANISM: Oryctolagus cuniculus

<400> SEQUENCE: 255

```
Asp Val Val Met Thr Gln Thr Pro Ala Ser Ala Ser Glu Pro Val Gly
1               5                   10                  15

Gly Thr Val Thr Ile Lys Cys Gln Ala Ser Gln Asn Ile Tyr Ser Asp
            20                  25                  30

Phe Ala Trp Tyr Arg Gln Lys Pro Gly Gln Pro Pro Lys Leu Leu Ile
        35                  40                  45

Tyr Ser Ala Ser Ala Leu Ala Ser Gly Val Pro Ser Arg Phe Lys Gly
    50                  55                  60
```

```
Ser Gly Ser Gly Thr Asp Phe Thr Leu Thr Ile Ser Asp Leu Glu Cys
65                  70                  75                  80

Asp Asp Ala Ala Ile Tyr Tyr Cys Gln Ser Thr Tyr Trp Glu Ser Asn
                85                  90                  95

Asn Ile Gly Thr Phe Gly Gly Gly Thr Glu Val Val Val Lys
            100                 105                 110


<210> SEQ ID NO 256
<211> LENGTH: 112
<212> TYPE: PRT
<213> ORGANISM: Oryctolagus cuniculus

<400> SEQUENCE: 256

Ala Ala Val Leu Thr Gln Thr Pro Ser Pro Val Ser Ala Ala Val Gly
1               5                   10                  15

Gly Thr Val Thr Ile Ser Cys Gln Ala Ser Gln Ser Val Tyr Asn His
            20                  25                  30

Lys Asn Leu Ala Trp Tyr Gln Gln Lys Pro Gly Gln Pro Pro Lys Leu
        35                  40                  45

Leu Ile Tyr Ser Ala Ser Ser Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Asp Cys Asp Asp Ala Ala Thr Tyr Tyr Cys Ala Gly Gly Tyr Ser Gly
                85                  90                  95

Ser Ala Asp Thr Phe Ala Phe Gly Gly Gly Thr Glu Val Val Val Lys
            100                 105                 110


<210> SEQ ID NO 257
<211> LENGTH: 109
<212> TYPE: PRT
<213> ORGANISM: Oryctolagus cuniculus

<400> SEQUENCE: 257

Ala Phe Glu Leu Thr Gln Thr Pro Ala Ser Val Glu Ala Ala Val Gly
1               5                   10                  15

Gly Thr Val Thr Ile Lys Cys Gln Ala Ser Gln Ser Ile Ser Ala Tyr
            20                  25                  30

Leu Ser Trp Tyr Gln Gln Lys Pro Gly Gln Pro Pro Lys Leu Leu Ile
        35                  40                  45

Tyr Asp Ala Ser Asp Leu Ala Ser Gly Val Ser Ser Arg Phe Lys Gly
    50                  55                  60

Ser Gly Ser Gly Thr Glu Tyr Thr Leu Thr Ile Ser Gly Val Gln Cys
65                  70                  75                  80

Ala Asp Ala Ala Thr Tyr Tyr Cys Gln Ser Tyr Ala Gly Ile Ser Ser
                85                  90                  95

Gly Val Ala Phe Gly Gly Gly Thr Glu Val Val Val Lys
            100                 105


<210> SEQ ID NO 258
<211> LENGTH: 112
<212> TYPE: PRT
<213> ORGANISM: Oryctolagus cuniculus

<400> SEQUENCE: 258

Asp Ile Val Met Thr Gln Thr Pro Ala Ser Val Glu Ala Ala Val Gly
1               5                   10                  15

Gly Thr Val Thr Ile Lys Cys Gln Ala Ser Gln Thr Ile Thr Ser Tyr
```

```
            20                  25                  30

Leu Ala Trp Tyr Gln Gln Lys Pro Gly Gln Pro Pro Lys Leu Leu Ile
        35                  40                  45

Tyr Arg Ala Ser Ile Leu Glu Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Thr Tyr Gly Thr Thr Asn
                85                  90                  95

Thr Gly His Tyr Val Gly Phe Gly Gly Gly Thr Glu Val Val Val Lys
            100                 105                 110


<210> SEQ ID NO 259
<211> LENGTH: 112
<212> TYPE: PRT
<213> ORGANISM: Oryctolagus cuniculus

<400> SEQUENCE: 259

Ala Gln Val Leu Thr Gln Thr Pro Ser Pro Val Ser Ala Ala Val Gly
1               5                   10                  15

Gly Thr Val Thr Ile Asn Cys Gln Ala Ser Gln Ser Val Tyr Asn Asn
            20                  25                  30

Lys Asn Leu Ala Trp Tyr Gln Gln Lys Pro Gly Gln Pro Pro Lys Leu
        35                  40                  45

Leu Ile Tyr Asp Ala Ser Lys Leu Ala Ser Gly Val Pro Leu Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Ala Gly Gly Tyr Asp Ser
                85                  90                  95

Ser Val Asp Thr Phe Ala Phe Gly Gly Gly Thr Glu Val Val Val Lys
            100                 105                 110


<210> SEQ ID NO 260
<211> LENGTH: 113
<212> TYPE: PRT
<213> ORGANISM: Oryctolagus cuniculus

<400> SEQUENCE: 260

Asp Thr Val Met Thr Gln Thr Pro Ala Ser Val Glu Ala Ala Val Gly
1               5                   10                  15

Gly Thr Val Thr Ile Gln Cys Gln Ala Ser Glu Asn Ile Tyr Ser Leu
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser His Tyr Cys Cys Ser Ser
                85                  90                  95

Asn Tyr Asp Tyr Ile Tyr Ala Phe Gly Gly Gly Thr Glu Val Val Val
            100                 105                 110

Lys


<210> SEQ ID NO 261
```

<211> LENGTH: 112
<212> TYPE: PRT
<213> ORGANISM: Oryctolagus cuniculus

<400> SEQUENCE: 261

Asp Pro Val Leu Thr Gln Thr Pro Pro Ser Ala Ser Glu Pro Ala Gly
1               5                   10                  15

Gly Thr Val Thr Ile Lys Cys Gln Ala Ser Glu Asp Ile Tyr Ser Leu
            20                  25                  30

Leu Ala Trp Tyr Gln Gln Lys Pro Gly Gln Pro Pro Lys Leu Leu Ile
        35                  40                  45

Tyr Ala Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Ser Tyr Tyr Tyr Ser Ile Ser
                85                  90                  95

Asp Ser Val Asp Tyr Pro Phe Gly Gly Gly Thr Glu Val Val Val Lys
            100                 105                 110

<210> SEQ ID NO 262
<211> LENGTH: 113
<212> TYPE: PRT
<213> ORGANISM: Oryctolagus cuniculus

<400> SEQUENCE: 262

Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Ser Thr Tyr
            20                  25                  30

Leu Ser Trp Tyr Gln Gln Lys Pro Gly Gln Pro Pro Lys Leu Leu Ile
        35                  40                  45

Tyr Arg Ala Thr Thr Leu Glu Ser Gly Val Pro Ser Arg Phe Lys Gly
    50                  55                  60

Thr Gly Ser Gly Thr Glu Phe Thr Leu Thr Ile Asn Asp Leu Glu Cys
65                  70                  75                  80

Ala Asp Ala Ala Thr Tyr Tyr Cys Gln Cys Thr Tyr Gly Ser Ser Ala
                85                  90                  95

Ser Ser Ser Tyr Gly Asn Ala Phe Gly Gly Gly Thr Glu Val Val Val
            100                 105                 110

Lys

<210> SEQ ID NO 263
<211> LENGTH: 109
<212> TYPE: PRT
<213> ORGANISM: Oryctolagus cuniculus

<400> SEQUENCE: 263

Ala Gln Val Leu Thr Gln Thr Pro Ser Ser Val Ser Glu Pro Val Gly
1               5                   10                  15

Gly Thr Val Thr Ile Asn Cys Gln Ala Ser Glu Asn Ile Tyr Ser Ser
            20                  25                  30

Leu Ala Trp Tyr Gln Gln Lys Pro Gly Gln Pro Pro Lys Leu Leu Ile
        35                  40                  45

Tyr Asp Ala Ser Asp Leu Ala Ser Gly Val Pro Ser Arg Phe Ser Gly
    50                  55                  60

Ser Gly Leu Gly Thr Glu Phe Thr Leu Thr Ile Ser Gly Val Gln Cys

```
65                  70                  75                  80

Asp Asp Ala Ala Thr Tyr Tyr Cys Gln Thr Tyr Tyr Pro Ser Ser Val
                85                  90                  95

Thr Tyr Ala Phe Gly Gly Gly Thr Glu Val Val Val Lys
            100                 105


<210> SEQ ID NO 264
<211> LENGTH: 111
<212> TYPE: PRT
<213> ORGANISM: Oryctolagus cuniculus

<400> SEQUENCE: 264

Ala Tyr Asp Met Thr Gln Thr Pro Ser Ser Val Ser Ala Ala Val Gly
1               5                   10                  15

Gly Thr Val Thr Ile Asn Cys Gln Ala Ser Glu Ser Ile Gly Ser Trp
            20                  25                  30

Leu Ala Trp Tyr Gln Gln Lys Pro Gly Gln Pro Pro Lys Leu Leu Ile
        35                  40                  45

Tyr Ser Ala Ser Ser Leu Ala Ser Gly Val Ser Ser Arg Phe Gly Gly
    50                  55                  60

Ser Thr Ser Gly Thr Glu Tyr Thr Leu Thr Ile Ser Asp Leu Glu Cys
65                  70                  75                  80

Ala Asp Ala Ala Thr Tyr Tyr Cys Gln Ser Thr Phe Tyr Gly Val Asn
                85                  90                  95

Pro Val Pro Thr Ala Phe Gly Gly Gly Thr Glu Val Val Val Lys
            100                 105                 110


<210> SEQ ID NO 265
<211> LENGTH: 111
<212> TYPE: PRT
<213> ORGANISM: Oryctolagus cuniculus

<400> SEQUENCE: 265

Ala Gln Val Leu Thr Gln Thr Ala Ser Pro Val Ser Ala Ala Val Gly
1               5                   10                  15

Gly Thr Val Thr Ile Asn Cys Gln Ser Ser Gln Ser Val Tyr Asn Asn
            20                  25                  30

Asn Arg Leu Ser Trp Phe Gln Gln Lys Pro Gly Gln Pro Pro Lys Gln
        35                  40                  45

Leu Ile Tyr Arg Ser Ser Thr Leu Ala Ser Gly Val Pro Ser Arg Phe
    50                  55                  60

Ser Gly Ser Gly Ser Gly Thr Gln Phe Thr Leu Thr Ile Ser Asp Val
65                  70                  75                  80

Gln Cys Asp Asp Ala Ala Thr Tyr Tyr Cys Ala Gly Gly Tyr Ser Ser
                85                  90                  95

Ser Ser Asp Asn Ala Phe Gly Gly Gly Thr Glu Val Val Val Lys
            100                 105                 110


<210> SEQ ID NO 266
<211> LENGTH: 110
<212> TYPE: PRT
<213> ORGANISM: Oryctolagus cuniculus

<400> SEQUENCE: 266

Ala Ala Val Leu Thr Gln Thr Pro Ser Pro Val Ser Ala Ala Val Gly
1               5                   10                  15

Gly Thr Val Thr Ile Ser Cys Gln Ala Ser Gln Ser Val Tyr Asn Asn
            20                  25                  30
```

```
Asn Asn Leu Ala Trp Tyr Gln Gln Lys Pro Gly Gln Pro Pro Lys Leu
        35                  40                  45

Leu Ile Tyr Thr Ala Ser Ser Leu Ala Ser Gly Val Pro Ser Arg Phe
    50                  55                  60

Lys Gly Ser Gly Ser Gly Thr Gln Phe Thr Leu Thr Ile Ser Glu Val
65                  70                  75                  80

Gln Cys Glu Asp Ala Ala Thr Tyr Tyr Cys Gln Gly Tyr Tyr Ser Gly
                85                  90                  95

Tyr Ile Asn Ala Phe Gly Gly Gly Thr Glu Val Val Val Lys
            100                 105                 110
```

<210> SEQ ID NO 267
<211> LENGTH: 112
<212> TYPE: PRT
<213> ORGANISM: Oryctolagus cuniculus

<400> SEQUENCE: 267

```
Asp Ile Val Met Thr Gln Thr Pro Ala Ser Val Glu Ala Ala Val Gly
1               5                   10                  15

Gly Thr Val Thr Ile Lys Cys Gln Ala Ser Gln Ser Ile Gly Ser Tyr
            20                  25                  30

Leu Ser Trp Tyr Gln Gln Lys Pro Gly Gln Pro Pro Lys Leu Leu Ile
        35                  40                  45

Tyr Tyr Ala Ser Asp Leu Glu Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Cys Thr Tyr Tyr Cys Gln Cys Thr Tyr Gly Ser Ile Ser
                85                  90                  95

Ser Ser Ala Gly Asn Ala Phe Gly Gly Gly Thr Glu Val Val Val Lys
            100                 105                 110
```

<210> SEQ ID NO 268
<211> LENGTH: 110
<212> TYPE: PRT
<213> ORGANISM: Oryctolagus cuniculus

<400> SEQUENCE: 268

```
Ala Gln Val Leu Thr Gln Thr Ala Ser Pro Val Ser Ala Ala Val Gly
1               5                   10                  15

Gly Thr Val Thr Ile Ser Cys Gln Ser Ser Glu Ser Val Tyr Asn Asn
            20                  25                  30

Asn Leu Leu Ser Trp Tyr Lys Gln Lys Pro Gly Gln Pro Pro Lys Leu
        35                  40                  45

Leu Ile Tyr Lys Ala Ser Thr Leu Asp Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Gly Tyr Thr Asp
                85                  90                  95

Ala Thr Tyr Ala Phe Gly Gly Gly Thr Glu Val Val Val Lys
            100                 105                 110
```

<210> SEQ ID NO 269
<211> LENGTH: 112
<212> TYPE: PRT
<213> ORGANISM: Oryctolagus cuniculus

<400> SEQUENCE: 269

```
Ala Gln Val Leu Thr Gln Thr Pro Ser Pro Val Ser Ala Thr Val Gly
1               5                   10                  15

Gly Thr Val Thr Ile Asn Cys Gln Ala Ser Gln Ser Val Tyr Asn Asn
            20                  25                  30

Arg Leu Ala Trp Tyr Gln Gln Lys Pro Gly Gln Pro Pro Lys Leu Leu
        35                  40                  45

Ile Tyr Glu Ala Ser Thr Leu Thr Ser Gly Val Ser Ser Arg Phe Lys
    50                  55                  60

Gly Ser Gly Ser Gly Ala Gln Phe Thr Leu Thr Ile Ser Gly Val Gln
65                  70                  75                  80

Cys Ala Asp Ala Ala Thr Tyr Tyr Cys Gln Gly Glu Phe Ser Cys Ser
                85                  90                  95

Asn Gly Asp Cys Ile Ala Phe Gly Gly Gly Thr Glu Val Val Val Lys
            100                 105                 110
```

<210> SEQ ID NO 270
<211> LENGTH: 112
<212> TYPE: PRT
<213> ORGANISM: Oryctolagus cuniculus

<400> SEQUENCE: 270

```
Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Ser Thr Tyr
            20                  25                  30

Ser Ser Trp Tyr Glu Gln Lys Pro Gly Gln Pro Pro Lys Leu Leu Ile
        35                  40                  45

Tyr Tyr Ala Ser Asp Leu Glu Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Thr Tyr Gly Ser Ile Ser
                85                  90                  95

Ser Ser Ser Gly Asn Ala Phe Gly Gly Gly Thr Glu Val Val Val Lys
            100                 105                 110
```

<210> SEQ ID NO 271
<211> LENGTH: 110
<212> TYPE: PRT
<213> ORGANISM: Oryctolagus cuniculus

<400> SEQUENCE: 271

```
Ala Gln Val Leu Thr Gln Thr Pro Ser Ser Val Ser Ala Ala Val Gly
1               5                   10                  15

Gly Thr Val Thr Ile Ser Cys Gln Ser Ser Gln Ser Val Tyr Ala Ser
            20                  25                  30

Val Trp Leu Gly Trp Tyr Gln Gln Lys Pro Gly Gln Pro Pro Lys Gln
        35                  40                  45

Leu Ile Tyr Ala Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Gly Asp Ala Ala Thr Tyr Tyr Cys Ala Gly Gly Tyr Ile Gly
                85                  90                  95
```

Asp Ile Tyr Ala Phe Gly Gly Gly Thr Glu Val Val Val Glu
100 105 110

<210> SEQ ID NO 272
<211> LENGTH: 113
<212> TYPE: PRT
<213> ORGANISM: Oryctolagus cuniculus

<400> SEQUENCE: 272

Asp Val Val Met Thr Gln Thr Pro Ala Ser Val Glu Ala Ala Val Gly
1 5 10 15

Gly Thr Val Thr Ile Lys Cys Gln Ala Ser Gln Ser Ile Tyr Asn Tyr
20 25 30

Leu Ser Trp Tyr Gln Gln Lys Pro Gly Gln Pro Pro Lys Leu Leu Ile
35 40 45

Tyr Gly Ala Ser Asp Leu Ala Ser Gly Val Pro Ser Arg Phe Ser Gly
50 55 60

Ser Gly Ser Gly Thr Glu Phe Thr Leu Thr Ile Ser Asp Leu Glu Cys
65 70 75 80

Ala Asp Ala Ala Thr Tyr Tyr Cys Gln Cys Thr Tyr Gly Ser Ser Arg
85 90 95

Val Ser Ser Tyr Gly Asp Ala Phe Gly Gly Gly Thr Glu Val Val Val
100 105 110

Lys

<210> SEQ ID NO 273
<211> LENGTH: 108
<212> TYPE: PRT
<213> ORGANISM: Oryctolagus cuniculus

<400> SEQUENCE: 273

Asp Val Val Met Thr Gln Thr Pro Val Ser Val Ser Ala Ala Val Gly
1 5 10 15

Gly Thr Val Thr Ile Asn Cys Gln Ala Ser Gln Asn Ile Tyr Ser Tyr
20 25 30

Leu Ala Trp Tyr Gln Gln Lys Ser Gly Gln Pro Pro Lys Leu Leu Ile
35 40 45

Tyr Asp Ala Ser Asp Leu Glu Ser Gly Val Pro Ser Arg Phe Lys Gly
50 55 60

Ser Gly Ser Gly Thr Glu Tyr Thr Leu Thr Ile Ser Asp Leu Glu Cys
65 70 75 80

Ala Asp Ala Ala Thr Tyr Tyr Cys Gln Ser Tyr Tyr Gly Ile Ser Ala
85 90 95

Tyr Ala Phe Gly Gly Gly Thr Glu Val Val Val Lys
100 105

<210> SEQ ID NO 274
<211> LENGTH: 111
<212> TYPE: PRT
<213> ORGANISM: Oryctolagus cuniculus

<400> SEQUENCE: 274

Asp Ile Val Met Thr Gln Thr Pro Ala Ser Val Ser Glu Pro Val Gly
1 5 10 15

Gly Thr Val Thr Ile Lys Cys Gln Ala Ser Gln Ser Ile Tyr Ser Tyr
20 25 30

Leu Ala Trp Tyr Gln Gln Lys Pro Gly Gln Arg Pro Lys Leu Leu Ile
35 40 45

```
Tyr Gly Ala Ser Thr Leu Ala Ser Gly Val Pro Ser Arg Phe Lys Gly
    50                  55                  60

Ser Gly Ser Gly Thr Asp Phe Ala Leu Thr Ile Ser Asp Leu Glu Cys
65                  70                  75                  80

Ala Asp Ala Ala Thr Tyr Tyr Cys Gln Asp Asn Tyr Gly Ser Ser Thr
                85                  90                  95

Thr Tyr Gly Asn Ser Phe Gly Gly Gly Thr Glu Val Val Val Lys
            100                 105                 110


<210> SEQ ID NO 275
<211> LENGTH: 113
<212> TYPE: PRT
<213> ORGANISM: Oryctolagus cuniculus

<400> SEQUENCE: 275

Asp Ile Val Met Thr Gln Thr Pro Ala Ser Val Glu Ala Ala Val Gly
1               5                   10                  15

Gly Thr Val Thr Ile Lys Cys Gln Ala Ser Glu Ser Ile Gly Ser Val
            20                  25                  30

Leu Ala Trp Tyr Gln Gln Lys Pro Gly Gln Ser Pro Lys Leu Leu Ile
        35                  40                  45

Gly Ser Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Ser Tyr Tyr His Ser Thr Ser
                85                  90                  95

Gly Ser Ser Tyr Gly Asn Thr Phe Gly Gly Gly Thr Glu Val Val Val
            100                 105                 110

Lys


<210> SEQ ID NO 276
<211> LENGTH: 111
<212> TYPE: PRT
<213> ORGANISM: Oryctolagus cuniculus

<400> SEQUENCE: 276

Ala Leu Val Met Thr Gln Thr Pro Ser Ser Val Ser Ala Ala Val Gly
1               5                   10                  15

Gly Thr Val Thr Ile Asn Cys Gln Ala Ser Gln Asn Ile Tyr Ser Asn
            20                  25                  30

Leu Ala Trp Tyr Gln Gln Lys Pro Gly Gln Pro Pro Lys Leu Leu Ile
        35                  40                  45

Tyr Gly Ala Ser Asp Leu Glu Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Asp Asp Ala Ala Thr Tyr Tyr Cys Gln Ser Thr Tyr Tyr Asn Ile Ser
                85                  90                  95

Ala Asp Phe Tyr Ala Phe Gly Gly Gly Thr Glu Val Val Val Lys
            100                 105                 110


<210> SEQ ID NO 277
<211> LENGTH: 111
<212> TYPE: PRT
<213> ORGANISM: Oryctolagus cuniculus
```

<400> SEQUENCE: 277

Ala Ala Val Leu Thr Gln Thr Pro Ser Pro Val Ser Ala Val Val Gly
1 5 10 15

Gly Thr Val Ser Ile Ser Cys Gln Ser Asn Lys Asn Val Tyr Asp Asn
20 25 30

Asn Ala Leu Ser Trp Tyr Gln Gln Lys Pro Gly Gln Pro Pro Lys Phe
35 40 45

Leu Ile Tyr Arg Ala Ser Thr Leu Ala Ser Gly Val Pro Ser Arg Phe
50 55 60

Lys Gly Ser Gly Ser Gly Thr Gln Phe Thr Leu Thr Ile Ser Asp Val
65 70 75 80

Gln Cys Asp Asp Ala Ala Thr Tyr Tyr Cys Ala Gly Asp Tyr Ile Ser
85 90 95

Asp Ser Asp Asn Thr Phe Gly Gly Gly Thr Glu Val Val Val Lys
100 105 110

<210> SEQ ID NO 278
<211> LENGTH: 113
<212> TYPE: PRT
<213> ORGANISM: Oryctolagus cuniculus

<400> SEQUENCE: 278

Asp Ile Val Met Thr Gln Thr Pro Ala Ser Val Ser Glu Pro Val Gly
1 5 10 15

Gly Thr Val Thr Ile Lys Cys Gln Ala Ser Gln Ser Ile Ile Asn Tyr
20 25 30

Leu Ser Trp Tyr Gln Gln Lys Pro Gly Gln Pro Pro Lys Leu Leu Ile
35 40 45

Tyr Arg Ala Ser Thr Leu Glu Ser Gly Val Pro Ser Arg Phe Lys Gly
50 55 60

Ser Gly Ser Gly Thr Glu Phe Thr Leu Thr Ile Ser Asp Leu Glu Cys
65 70 75 80

Ala Asp Ala Ala Thr Tyr Tyr Cys Gln Cys Thr Tyr Gly Ser Ser Ser
85 90 95

Gly Ser Tyr Gly Gly Trp Ala Phe Gly Gly Gly Thr Glu Val Val Val
100 105 110

Lys

<210> SEQ ID NO 279
<211> LENGTH: 110
<212> TYPE: PRT
<213> ORGANISM: Oryctolagus cuniculus

<400> SEQUENCE: 279

Asp Ile Val Met Thr Gln Thr Pro Ala Ser Val Ser Glu Pro Val Gly
1 5 10 15

Gly Thr Val Thr Ile Lys Cys Gln Ala Ser Gln Ser Ile Tyr Ser Tyr
20 25 30

Leu Ser Trp Tyr Gln Gln Lys Pro Gly Gln Pro Pro Lys Leu Leu Ile
35 40 45

Tyr Gln Ala Ser Ile Leu Ala Ser Gly Val Pro Ser Gln Phe Lys Gly
50 55 60

Ser Gly Ser Gly Thr Asp Phe Thr Leu Thr Ile Ser Asp Leu Glu Cys
65 70 75 80

Ala Asp Ala Ala Thr Tyr Tyr Cys Gln Ser Asn Tyr Gly Phe Ser Ser
85 90 95

Gly Ser Tyr Ala Phe Gly Gly Gly Thr Glu Val Val Val Lys
100 105 110

<210> SEQ ID NO 280
<211> LENGTH: 112
<212> TYPE: PRT
<213> ORGANISM: Oryctolagus cuniculus

<400> SEQUENCE: 280

Asp Val Val Met Thr Gln Thr Pro Ala Ser Val Glu Ala Ala Val Gly
1 5 10 15

Gly Thr Val Thr Ile Lys Cys Gln Ala Ser Gln Ser Ile Ser Ser Trp
20 25 30

Leu Ala Trp Tyr Gln Gln Lys Pro Gly Gln Pro Pro Lys Leu Leu Ile
35 40 45

Tyr Arg Ala Ser Thr Leu Glu Ser Gly Val Pro Ser Arg Phe Lys Gly
50 55 60

Ser Gly Ser Gly Thr Glu Phe Thr Leu Thr Ile Ser Asp Leu Glu Cys
65 70 75 80

Ala Asp Ala Ala Thr Tyr Tyr Cys Gln Cys Thr Tyr Gly Ser Leu Ser
85 90 95

Ser Thr Tyr Gly Trp Ala Phe Gly Gly Gly Thr Glu Val Val Val Lys
100 105 110

<210> SEQ ID NO 281
<211> LENGTH: 112
<212> TYPE: PRT
<213> ORGANISM: Oryctolagus cuniculus

<400> SEQUENCE: 281

Ala Ala Val Leu Thr Gln Thr Pro Ser Ser Val Ser Ala Ala Val Gly
1 5 10 15

Gly Thr Val Thr Ile Asn Cys Gln Ser Ser Gln Ser Val Asn Asn Ala
20 25 30

Lys Asn Leu Ala Trp Tyr Gln Gln Lys Pro Gly Gln Pro Pro Lys Leu
35 40 45

Leu Ile Tyr Asp Ala Ser Thr Leu Ala Ser Gly Val Pro Ser Arg Phe
50 55 60

Lys Gly Ser Gly Ser Gly Thr Gln Phe Thr Leu Ile Met Ser Asp Leu
65 70 75 80

Glu Cys Gly Asp Ala Ala Thr Tyr Phe Cys Ala Gly Gly Tyr Asp Arg
85 90 95

Phe Ile Asp Thr Phe Ala Phe Gly Gly Gly Thr Glu Val Val Val Lys
100 105 110

<210> SEQ ID NO 282
<211> LENGTH: 111
<212> TYPE: PRT
<213> ORGANISM: Oryctolagus cuniculus

<400> SEQUENCE: 282

Ala Ala Val Leu Thr Gln Thr Pro Ser Pro Val Ser Ala Ala Val Gly
1 5 10 15

Gly Thr Val Ser Ile Ser Cys Gln Ser Ser Lys Ser Val Tyr Asp Asn
20 25 30

Asn Trp Leu Ser Trp Tyr Gln Gln Lys Pro Gly Gln Pro Pro Lys Leu
35 40 45

```
Leu Ile Tyr Gln Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Ala Gly Gly Tyr Ile Thr
                85                  90                  95

Asn Ser Asp Asn Gly Phe Gly Gly Gly Thr Glu Val Val Val Lys
            100                 105                 110


<210> SEQ ID NO 283
<211> LENGTH: 110
<212> TYPE: PRT
<213> ORGANISM: Oryctolagus cuniculus

<400> SEQUENCE: 283

Asp Val Val Met Thr Gln Thr Pro Ala Ser Val Ser Glu Ser Val Gly
1               5                   10                  15

Gly Thr Val Thr Ile Lys Cys Gln Ala Ser Gln Ser Ile Gly Ser Ser
            20                  25                  30

Leu Ala Trp Tyr Gln Gln Lys Pro Gly Gln Pro Pro Lys Leu Leu Ile
        35                  40                  45

Tyr Tyr Thr Ser Thr Leu Ala Ser Gly Val Pro Ser Arg Phe Ser Gly
    50                  55                  60

Ser Gly Ser Gly Thr Glu Phe Thr Leu Thr Thr Ser Gly Val Gln Cys
65                  70                  75                  80

Asp Asp Ala Ala Thr Tyr Tyr Cys Gln Ser Tyr Gly Tyr Gly Ser Gly
                85                  90                  95

Tyr Val Phe Ala Phe Gly Gly Gly Thr Glu Val Val Val Lys
            100                 105                 110


<210> SEQ ID NO 284
<211> LENGTH: 111
<212> TYPE: PRT
<213> ORGANISM: Oryctolagus cuniculus

<400> SEQUENCE: 284

Ala Ile Glu Met Thr Gln Thr Pro Phe Ser Val Ser Ala Ala Val Gly
1               5                   10                  15

Gly Thr Val Thr Ile Asn Cys Gln Ala Ser Glu Asn Ile Tyr Arg Asn
            20                  25                  30

Leu Ala Trp Tyr Gln Gln Lys Pro Gly Gln Pro Pro Lys Leu Leu Ile
        35                  40                  45

Tyr Lys Ala Ser Thr Leu Ala Ser Gly Val Ser Ser Arg Phe Lys Gly
    50                  55                  60

Ser Gly Ser Gly Thr Gln Phe Thr Leu Thr Ile Gly Gly Val Gln Cys
65                  70                  75                  80

Asp Asp Ala Ala Thr Tyr Tyr Cys Leu Tyr Ser Tyr Tyr Ile Asp Ser
                85                  90                  95

Asn Val Asp Phe Ala Phe Gly Gly Gly Thr Glu Val Val Val Lys
            100                 105                 110


<210> SEQ ID NO 285
<211> LENGTH: 111
<212> TYPE: PRT
<213> ORGANISM: Oryctolagus cuniculus

<400> SEQUENCE: 285

Asp Val Val Met Thr Gln Thr Pro Ala Ser Val Ser Glu Pro Val Gly
```

```
1               5                   10                  15

Gly Thr Val Thr Ile Lys Cys Gln Ala Ser Glu Asp Ile Glu Ser Tyr
            20                  25                  30

Leu Ala Trp Tyr Gln Gln Lys Pro Gly Gln Pro Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Tyr Gly Thr Glu Phe Thr Leu Thr Ile Ser Asp Leu Glu Cys
65                  70                  75                  80

Ala Asp Ala Ala Thr Tyr Tyr Cys Gln Cys Thr Leu Tyr Gly Val Asn
                85                  90                  95

Phe Val Pro Asn Val Phe Gly Gly Gly Thr Glu Val Val Val Lys
            100                 105                 110


<210> SEQ ID NO 286
<211> LENGTH: 113
<212> TYPE: PRT
<213> ORGANISM: Oryctolagus cuniculus

<400> SEQUENCE: 286

Asp Val Val Met Thr Gln Thr Pro Ala Ser Val Ser Glu Pro Val Gly
1               5                   10                  15

Gly Thr Val Thr Ile Lys Cys Gln Ala Ser Gln Ser Ile Ser Ser Trp
            20                  25                  30

Leu Ser Trp Tyr Gln Gln Lys Pro Gly Gln Pro Pro Lys Val Leu Ile
        35                  40                  45

Tyr Asp Ala Ser Asp Leu Ala Ser Gly Val Ser Ser Arg Phe Lys Gly
    50                  55                  60

Thr Gly Ala Gly Thr Glu Phe Thr Leu Thr Ile Ser Asp Leu Glu Cys
65                  70                  75                  80

Ala Asp Ala Ala Thr Tyr Tyr Cys Gln Cys Thr Val Gly Ser Ser Gly
                85                  90                  95

Val Thr Gly Tyr Gly Asn Ala Phe Gly Gly Gly Thr Glu Val Val Val
            100                 105                 110

Lys


<210> SEQ ID NO 287
<211> LENGTH: 109
<212> TYPE: PRT
<213> ORGANISM: Oryctolagus cuniculus

<400> SEQUENCE: 287

Asp Val Val Met Thr Gln Thr Pro Ala Ser Val Ser Glu Pro Val Gly
1               5                   10                  15

Gly Thr Val Thr Ile Lys Cys Gln Ala Ser Gln Ser Ile Gly Ser Asp
            20                  25                  30

Leu Ala Trp Tyr Gln Gln Lys Pro Gly Gln Pro Pro Lys Leu Leu Ile
        35                  40                  45

Tyr Asp Ala Ser Ser Leu Glu Ser Gly Val Pro Ser Arg Phe Lys Gly
    50                  55                  60

Ser Gly Ser Gly Thr Asp Phe Thr Leu Thr Ile Ser Asp Leu Glu Cys
65                  70                  75                  80

Ala Asp Ala Ala Thr Tyr Tyr Cys Gln Cys Thr Tyr Tyr Gly Gly Ser
                85                  90                  95

Pro Asn Val Phe Gly Gly Gly Thr Glu Val Val Val Lys
            100                 105
```

```
<210> SEQ ID NO 288
<211> LENGTH: 110
<212> TYPE: PRT
<213> ORGANISM: Oryctolagus cuniculus

<400> SEQUENCE: 288

Ala Ile Glu Met Thr Gln Thr Pro Ala Ser Val Glu Ala Ala Val Gly
1               5                   10                  15

Gly Thr Val Thr Ile Lys Cys Gln Gly Ser Gln Ser Ile Ser Ser Tyr
            20                  25                  30

Leu Ser Trp Tyr Gln Gln Lys Pro Gly Gln Pro Pro Lys Leu Leu Ile
        35                  40                  45

Tyr Gly Ala Ser Thr Leu Ala Ser Gly Val Ser Ser Arg Phe Lys Gly
    50                  55                  60

Ser Gly Ser Gly Thr Glu Phe Thr Leu Thr Ile Ser Gly Val Glu Cys
65                  70                  75                  80

Ala Asp Ala Ala Thr Tyr Tyr Cys Gln Gln Gly Tyr Thr Thr Ser Asn
                85                  90                  95

Val Asp Asn Thr Phe Gly Gly Gly Thr Glu Val Val Val Lys
            100                 105                 110


<210> SEQ ID NO 289
<211> LENGTH: 110
<212> TYPE: PRT
<213> ORGANISM: Oryctolagus cuniculus

<400> SEQUENCE: 289

Ala Ala Val Leu Thr Gln Thr Pro Ser Pro Val Ser Ala Pro Val Gly
1               5                   10                  15

Gly Thr Val Ser Ile Ser Cys Gln Ser Ser Pro Ser Val Tyr Ser Val
            20                  25                  30

Tyr Leu Ser Trp Tyr Gln Gln Lys Pro Gly Gln Pro Pro Lys Leu Leu
        35                  40                  45

Ile Tyr Arg Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Ala Gly Ala Tyr Val Gly Ser
                85                  90                  95

Ser Asp Asn Thr Phe Gly Gly Gly Thr Glu Met Val Val Lys
            100                 105                 110


<210> SEQ ID NO 290
<211> LENGTH: 111
<212> TYPE: PRT
<213> ORGANISM: Oryctolagus cuniculus

<400> SEQUENCE: 290

Ala Ala Val Leu Thr Gln Thr Pro Ser Pro Val Ser Ala Ala Val Gly
1               5                   10                  15

Gly Thr Val Ser Ile Ser Cys Gln Ser Ser Lys Ser Val Tyr Asn Asn
            20                  25                  30

Lys Trp Leu Ser Trp Phe Gln Gln Lys Pro Gly Gln Pro Pro Lys Leu
        35                  40                  45

Leu Ile Tyr Gly Ala Phe Thr Leu Ala Ser Gly Val Pro Ser Arg Phe
    50                  55                  60
```

-continued

```
Arg Gly Ser Gly Ser Gly Thr Gln Phe Thr Leu Thr Ile Ser Asp Val
65                  70                  75                  80

Gln Cys Asp Asp Ala Ala Thr Tyr Tyr Cys Ala Gly Asp Tyr Ser Ser
                85                  90                  95

Asn Ser Asp Asp Ala Phe Gly Gly Gly Thr Glu Val Val Val Lys
            100                 105                 110


<210> SEQ ID NO 291
<211> LENGTH: 112
<212> TYPE: PRT
<213> ORGANISM: Oryctolagus cuniculus

<400> SEQUENCE: 291

Asp Ile Val Met Thr Gln Thr Pro Ala Ser Val Glu Ala Ala Val Gly
1               5                   10                  15

Gly Thr Val Thr Ile Lys Cys Gln Ala Ser Glu Ser Val Gly Asp Ala
            20                  25                  30

Leu Ala Trp Tyr Gln Gln Lys Pro Gly Gln Pro Pro Lys Leu Leu Ile
        35                  40                  45

Tyr Arg Ala Ser Thr Leu Glu Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Val Ala Thr Tyr Tyr Cys Gln Ser Tyr Trp Tyr Thr Met Gly
                85                  90                  95

Asn Ser Tyr Gly Asn Thr Phe Gly Gly Gly Thr Glu Val Val Val Lys
            100                 105                 110


<210> SEQ ID NO 292
<211> LENGTH: 111
<212> TYPE: PRT
<213> ORGANISM: Oryctolagus cuniculus

<400> SEQUENCE: 292

Ala Ala Val Leu Thr Gln Thr Pro Ser Pro Val Ser Ala Ala Val Gly
1               5                   10                  15

Gly Thr Val Ser Ile Ser Cys Gln Ser Ser Lys Thr Ile Tyr Asn Asp
            20                  25                  30

Asn Trp Leu Ser Trp Phe Gln Gln Lys Pro Gly Gln Pro Pro Lys Leu
        35                  40                  45

Leu Ile Tyr Gly Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Leu Gly Ser Tyr Ile Asn
                85                  90                  95

Ser Ser Asp Asn Ala Phe Gly Gly Gly Thr Glu Val Val Val Lys
            100                 105                 110


<210> SEQ ID NO 293
<211> LENGTH: 111
<212> TYPE: PRT
<213> ORGANISM: Oryctolagus cuniculus

<400> SEQUENCE: 293

Ala Ile Lys Met Thr Gln Thr Pro Ser Ser Val Ser Ala Ala Val Gly
1               5                   10                  15

Gly Thr Val Thr Ile Asn Cys Arg Ala Ser Glu Asp Ile Lys Ser Tyr
```

```
            20                  25                  30

Leu Ala Trp Tyr Gln Gln Lys Pro Gly Gln Pro Pro Lys Leu Leu Ile
        35                  40                  45

Tyr Asp Ala Ser Asp Leu Ala Ser Gly Val Pro Ser Arg Phe Lys Gly
    50                  55                  60

Ser Gly Ser Gly Thr Glu Tyr Thr Leu Thr Ile Ser Gly Val Gln Cys
65                  70                  75                  80

Asp Asp Ala Ala Thr Tyr Tyr Cys Gln Ser Ala Tyr Tyr Ser Ser Ser
                85                  90                  95

Thr Asp Gly Gly Ala Phe Gly Gly Gly Thr Glu Val Val Val Lys
            100                 105                 110


<210> SEQ ID NO 294
<211> LENGTH: 111
<212> TYPE: PRT
<213> ORGANISM: Oryctolagus cuniculus

<400> SEQUENCE: 294

Ala Leu Val Met Thr Gln Thr Pro Ser Ser Val Ser Ala Pro Val Gly
1               5                   10                  15

Gly Thr Val Thr Ile Asn Cys Gln Ala Ser Gln Ser Ile Tyr Ser Asn
            20                  25                  30

Leu Ala Trp Tyr Gln Gln Lys Pro Gly Gln Arg Pro Lys Leu Leu Ile
        35                  40                  45

Tyr Gly Ala Ser Asn Leu Glu Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Cys Cys Gln Gly Tyr Tyr Tyr Ala Asp Ser
                85                  90                  95

Asp Asp Asn Ile Ala Phe Gly Gly Gly Thr Glu Val Val Val Glu
            100                 105                 110


<210> SEQ ID NO 295
<211> LENGTH: 110
<212> TYPE: PRT
<213> ORGANISM: Oryctolagus cuniculus

<400> SEQUENCE: 295

Ala Gln Val Leu Thr Gln Thr Ala Ser Pro Val Ser Ala Ala Val Gly
1               5                   10                  15

Ser Thr Val Thr Ile Ser Cys Gln Ala Ser Gln Ser Val Tyr Asn Asn
            20                  25                  30

Asn Tyr Leu Ala Trp Phe Gln Gln Lys Pro Gly Gln Pro Pro Lys Leu
        35                  40                  45

Leu Ile Tyr Leu Ala Ser Thr Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Gly Asp Ala Ala Thr Tyr Tyr Cys Gln Gly Tyr Tyr Ser Thr
                85                  90                  95

Gly Met Phe Ala Phe Gly Gly Gly Thr Glu Val Val Val Lys
            100                 105                 110


<210> SEQ ID NO 296
<211> LENGTH: 111
<212> TYPE: PRT
```

<213> ORGANISM: Oryctolagus cuniculus

<400> SEQUENCE: 296

Asp Val Val Met Thr Gln Thr Pro Ser Ser Val Ser Ala Ala Val Gly
1               5                   10                  15

Gly Thr Val Thr Ile Asn Cys Arg Ala Ser Glu Asp Ile Glu Arg Phe
            20                  25                  30

Leu Ala Trp Tyr Gln Gln Lys Pro Gly Gln Pro Pro Lys Leu Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Asp Phe Thr Leu Thr Ile Ser Asp Leu Glu Cys
65                  70                  75                  80

Ala Asp Ala Ala Thr Tyr Tyr Cys Gln Cys Thr Leu Tyr Gly Val Asn
                85                  90                  95

Phe Val Pro Asn Ala Phe Gly Gly Gly Thr Glu Val Val Val Lys
            100                 105                 110

<210> SEQ ID NO 297
<211> LENGTH: 5
<212> TYPE: PRT
<213> ORGANISM: Oryctolagus cuniculus

<400> SEQUENCE: 297

Ala Tyr Ala Ile Asn
1               5

<210> SEQ ID NO 298
<211> LENGTH: 5
<212> TYPE: PRT
<213> ORGANISM: Oryctolagus cuniculus

<400> SEQUENCE: 298

Gly Tyr Asp Met Asn
1               5

<210> SEQ ID NO 299
<211> LENGTH: 5
<212> TYPE: PRT
<213> ORGANISM: Oryctolagus cuniculus

<400> SEQUENCE: 299

Thr Tyr Ala Ile Ser
1               5

<210> SEQ ID NO 300
<211> LENGTH: 5
<212> TYPE: PRT
<213> ORGANISM: Oryctolagus cuniculus

<400> SEQUENCE: 300

Gly Leu Val Val Ser
1               5

<210> SEQ ID NO 301
<211> LENGTH: 6
<212> TYPE: PRT
<213> ORGANISM: Oryctolagus cuniculus

<400> SEQUENCE: 301

Ser Ser Tyr Tyr Met Cys
1               5

<210> SEQ ID NO 302
<211> LENGTH: 5
<212> TYPE: PRT
<213> ORGANISM: Oryctolagus cuniculus

<400> SEQUENCE: 302

Ile Tyr Ala Ile Ser
1               5

<210> SEQ ID NO 303
<211> LENGTH: 6
<212> TYPE: PRT
<213> ORGANISM: Oryctolagus cuniculus

<400> SEQUENCE: 303

Ser Ser Tyr Tyr Met Cys
1               5

<210> SEQ ID NO 304
<211> LENGTH: 5
<212> TYPE: PRT
<213> ORGANISM: Oryctolagus cuniculus

<400> SEQUENCE: 304

Met Tyr Ala Ile Asn
1               5

<210> SEQ ID NO 305
<211> LENGTH: 6
<212> TYPE: PRT
<213> ORGANISM: Oryctolagus cuniculus

<400> SEQUENCE: 305

Ser Tyr Tyr Tyr Met Cys
1               5

<210> SEQ ID NO 306
<211> LENGTH: 5
<212> TYPE: PRT
<213> ORGANISM: Oryctolagus cuniculus

<400> SEQUENCE: 306

Arg Asn Ala Met Ser
1               5

<210> SEQ ID NO 307
<211> LENGTH: 6
<212> TYPE: PRT
<213> ORGANISM: Oryctolagus cuniculus

<400> SEQUENCE: 307

Asp Asn Tyr Ala Met Cys
1               5

<210> SEQ ID NO 308
<211> LENGTH: 6
<212> TYPE: PRT
<213> ORGANISM: Oryctolagus cuniculus

<400> SEQUENCE: 308

Ser Gly Tyr Tyr Met Cys
1               5

<210> SEQ ID NO 309
<211> LENGTH: 6
<212> TYPE: PRT
<213> ORGANISM: Oryctolagus cuniculus

<400> SEQUENCE: 309

Gly Asn Tyr Tyr Ile Cys
1               5

<210> SEQ ID NO 310
<211> LENGTH: 6
<212> TYPE: PRT
<213> ORGANISM: Oryctolagus cuniculus

<400> SEQUENCE: 310

Arg Ser Tyr Tyr Met Cys
1               5

<210> SEQ ID NO 311
<211> LENGTH: 6
<212> TYPE: PRT
<213> ORGANISM: Oryctolagus cuniculus

<400> SEQUENCE: 311

Ser Met Tyr Trp Met Cys
1               5

<210> SEQ ID NO 312
<211> LENGTH: 5
<212> TYPE: PRT
<213> ORGANISM: Oryctolagus cuniculus

<400> SEQUENCE: 312

Ser Tyr Asp Met Ser
1               5

<210> SEQ ID NO 313
<211> LENGTH: 6
<212> TYPE: PRT
<213> ORGANISM: Oryctolagus cuniculus

<400> SEQUENCE: 313

Ser Ser Tyr Trp Ile Cys
1               5

<210> SEQ ID NO 314
<211> LENGTH: 6
<212> TYPE: PRT
<213> ORGANISM: Oryctolagus cuniculus

<400> SEQUENCE: 314

Ser Ser Tyr Tyr Ile Cys
1               5

<210> SEQ ID NO 315
<211> LENGTH: 6
<212> TYPE: PRT
<213> ORGANISM: Oryctolagus cuniculus

<400> SEQUENCE: 315

Asp Gly Tyr Trp Met Cys
1               5

<210> SEQ ID NO 316
<211> LENGTH: 5

<212> TYPE: PRT
<213> ORGANISM: Oryctolagus cuniculus

<400> SEQUENCE: 316

Ser Tyr Ala Met Ser
1 5

<210> SEQ ID NO 317
<211> LENGTH: 5
<212> TYPE: PRT
<213> ORGANISM: Oryctolagus cuniculus

<400> SEQUENCE: 317

Asn Tyr Gln Met Thr
1 5

<210> SEQ ID NO 318
<211> LENGTH: 5
<212> TYPE: PRT
<213> ORGANISM: Oryctolagus cuniculus

<400> SEQUENCE: 318

Met Tyr Ala Ile Asn
1 5

<210> SEQ ID NO 319
<211> LENGTH: 5
<212> TYPE: PRT
<213> ORGANISM: Oryctolagus cuniculus

<400> SEQUENCE: 319

Asn Tyr Asp Met Asn
1 5

<210> SEQ ID NO 320
<211> LENGTH: 5
<212> TYPE: PRT
<213> ORGANISM: Oryctolagus cuniculus

<400> SEQUENCE: 320

Asn Tyr Asp Met Asn
1 5

<210> SEQ ID NO 321
<211> LENGTH: 5
<212> TYPE: PRT
<213> ORGANISM: Oryctolagus cuniculus

<400> SEQUENCE: 321

Ser Asn Ala Met Ile
1 5

<210> SEQ ID NO 322
<211> LENGTH: 5
<212> TYPE: PRT
<213> ORGANISM: Oryctolagus cuniculus

<400> SEQUENCE: 322

Met Tyr Thr Ile Asn
1 5

<210> SEQ ID NO 323
<211> LENGTH: 5
<212> TYPE: PRT
<213> ORGANISM: Oryctolagus cuniculus

<400> SEQUENCE: 323

Ser Asn Ser Ile Ser
1 5

<210> SEQ ID NO 324
<211> LENGTH: 6
<212> TYPE: PRT
<213> ORGANISM: Oryctolagus cuniculus

<400> SEQUENCE: 324

Ser Thr Tyr Trp Met Ser
1 5

<210> SEQ ID NO 325
<211> LENGTH: 5
<212> TYPE: PRT
<213> ORGANISM: Oryctolagus cuniculus

<400> SEQUENCE: 325

Asn Tyr Ala Leu Ser
1 5

<210> SEQ ID NO 326
<211> LENGTH: 5
<212> TYPE: PRT
<213> ORGANISM: Oryctolagus cuniculus

<400> SEQUENCE: 326

Ser His Ala Thr Ser
1 5

<210> SEQ ID NO 327
<211> LENGTH: 5
<212> TYPE: PRT
<213> ORGANISM: Oryctolagus cuniculus

<400> SEQUENCE: 327

Thr Tyr Gly Val Ser
1 5

<210> SEQ ID NO 328
<211> LENGTH: 6
<212> TYPE: PRT
<213> ORGANISM: Oryctolagus cuniculus

<400> SEQUENCE: 328

Ser Asn Tyr Tyr Ile Cys
1 5

<210> SEQ ID NO 329
<211> LENGTH: 5
<212> TYPE: PRT
<213> ORGANISM: Oryctolagus cuniculus

<400> SEQUENCE: 329

Thr Tyr Ala Met Thr
1 5

<210> SEQ ID NO 330
<211> LENGTH: 6
<212> TYPE: PRT
<213> ORGANISM: Oryctolagus cuniculus

<400> SEQUENCE: 330

Ser Ser Tyr Trp Ile Cys
1 5

<210> SEQ ID NO 331
<211> LENGTH: 5
<212> TYPE: PRT
<213> ORGANISM: Oryctolagus cuniculus

<400> SEQUENCE: 331

Asn Tyr Ala Met Ser
1 5

<210> SEQ ID NO 332
<211> LENGTH: 5
<212> TYPE: PRT
<213> ORGANISM: Oryctolagus cuniculus

<400> SEQUENCE: 332

Asn Tyr Gln Met Thr
1 5

<210> SEQ ID NO 333
<211> LENGTH: 6
<212> TYPE: PRT
<213> ORGANISM: Oryctolagus cuniculus

<400> SEQUENCE: 333

Ser Thr Tyr Trp Ala Cys
1 5

<210> SEQ ID NO 334
<211> LENGTH: 5
<212> TYPE: PRT
<213> ORGANISM: Oryctolagus cuniculus

<400> SEQUENCE: 334

Ser Tyr Gln Met Thr
1 5

<210> SEQ ID NO 335
<211> LENGTH: 6
<212> TYPE: PRT
<213> ORGANISM: Oryctolagus cuniculus

<400> SEQUENCE: 335

Ser Ser Tyr Tyr Met Cys
1 5

<210> SEQ ID NO 336
<211> LENGTH: 6
<212> TYPE: PRT
<213> ORGANISM: Oryctolagus cuniculus

<400> SEQUENCE: 336

Ser Asn Tyr Tyr Met Cys
1 5

<210> SEQ ID NO 337
<211> LENGTH: 6
<212> TYPE: PRT
<213> ORGANISM: Oryctolagus cuniculus

<400> SEQUENCE: 337

Ser Ser Tyr Tyr Met Cys 1 5

<210> SEQ ID NO 338
<211> LENGTH: 5
<212> TYPE: PRT
<213> ORGANISM: Oryctolagus cuniculus

<400> SEQUENCE: 338

Asn Trp Ile Met Ser
1 5

<210> SEQ ID NO 339
<211> LENGTH: 6
<212> TYPE: PRT
<213> ORGANISM: Oryctolagus cuniculus

<400> SEQUENCE: 339

Ser Thr Tyr Ser Met Cys
1 5

<210> SEQ ID NO 340
<211> LENGTH: 6
<212> TYPE: PRT
<213> ORGANISM: Oryctolagus cuniculus

<400> SEQUENCE: 340

Ser Gly Tyr Asp Met Cys
1 5

<210> SEQ ID NO 341
<211> LENGTH: 6
<212> TYPE: PRT
<213> ORGANISM: Oryctolagus cuniculus

<400> SEQUENCE: 341

Ser Thr Tyr Tyr Thr Cys
1 5

<210> SEQ ID NO 342
<211> LENGTH: 5
<212> TYPE: PRT
<213> ORGANISM: Oryctolagus cuniculus

<400> SEQUENCE: 342

Ser Ala Ala Met Gly
1 5

<210> SEQ ID NO 343
<211> LENGTH: 5
<212> TYPE: PRT
<213> ORGANISM: Oryctolagus cuniculus

<400> SEQUENCE: 343

Ser Tyr Asp Met Ser
1 5

<210> SEQ ID NO 344
<211> LENGTH: 6
<212> TYPE: PRT
<213> ORGANISM: Oryctolagus cuniculus

<400> SEQUENCE: 344

Ser Thr Tyr Trp Ile Cys
1 5

<210> SEQ ID NO 345
<211> LENGTH: 6
<212> TYPE: PRT
<213> ORGANISM: Oryctolagus cuniculus

<400> SEQUENCE: 345

Ser Ser Tyr Trp Ile Cys
1               5

<210> SEQ ID NO 346
<211> LENGTH: 5
<212> TYPE: PRT
<213> ORGANISM: Oryctolagus cuniculus

<400> SEQUENCE: 346

Ser Asp Gly Ile Ser
1               5

<210> SEQ ID NO 347
<211> LENGTH: 5
<212> TYPE: PRT
<213> ORGANISM: Oryctolagus cuniculus

<400> SEQUENCE: 347

Ser Tyr Ala Ile Ser
1               5

<210> SEQ ID NO 348
<211> LENGTH: 5
<212> TYPE: PRT
<213> ORGANISM: Oryctolagus cuniculus

<400> SEQUENCE: 348

Ser Asn Ala Leu Gly
1               5

<210> SEQ ID NO 349
<211> LENGTH: 5
<212> TYPE: PRT
<213> ORGANISM: Oryctolagus cuniculus

<400> SEQUENCE: 349

Ser Tyr Asp Met Ser
1               5

<210> SEQ ID NO 350
<211> LENGTH: 5
<212> TYPE: PRT
<213> ORGANISM: Oryctolagus cuniculus

<400> SEQUENCE: 350

Asn Tyr Ala Met Gly
1               5

<210> SEQ ID NO 351
<211> LENGTH: 5
<212> TYPE: PRT
<213> ORGANISM: Oryctolagus cuniculus

<400> SEQUENCE: 351

Val Tyr Ala Met Ser
1               5

<210> SEQ ID NO 352

<211> LENGTH: 5
<212> TYPE: PRT
<213> ORGANISM: Oryctolagus cuniculus

<400> SEQUENCE: 352

Thr Tyr Gly Val Ser
1 5

<210> SEQ ID NO 353
<211> LENGTH: 5
<212> TYPE: PRT
<213> ORGANISM: Oryctolagus cuniculus

<400> SEQUENCE: 353

Met Tyr Ala Ile Asn
1 5

<210> SEQ ID NO 354
<211> LENGTH: 5
<212> TYPE: PRT
<213> ORGANISM: Oryctolagus cuniculus

<400> SEQUENCE: 354

Arg Tyr Ala Met Ser
1 5

<210> SEQ ID NO 355
<211> LENGTH: 5
<212> TYPE: PRT
<213> ORGANISM: Oryctolagus cuniculus

<400> SEQUENCE: 355

Ser Tyr Ala Met Gly
1 5

<210> SEQ ID NO 356
<211> LENGTH: 6
<212> TYPE: PRT
<213> ORGANISM: Oryctolagus cuniculus

<400> SEQUENCE: 356

Ser Ser Tyr Trp Ile Cys
1 5

<210> SEQ ID NO 357
<211> LENGTH: 5
<212> TYPE: PRT
<213> ORGANISM: Oryctolagus cuniculus

<400> SEQUENCE: 357

Asn Tyr Tyr Met Thr
1 5

<210> SEQ ID NO 358
<211> LENGTH: 5
<212> TYPE: PRT
<213> ORGANISM: Oryctolagus cuniculus

<400> SEQUENCE: 358

Ser Tyr His Met Ser
1 5

<210> SEQ ID NO 359
<211> LENGTH: 5
<212> TYPE: PRT

<213> ORGANISM: Oryctolagus cuniculus

<400> SEQUENCE: 359

Thr Ile Pro Met Cys
1 5

<210> SEQ ID NO 360
<211> LENGTH: 6
<212> TYPE: PRT
<213> ORGANISM: Oryctolagus cuniculus

<400> SEQUENCE: 360

Asp Asn Tyr Ala Met Cys
1 5

<210> SEQ ID NO 361
<211> LENGTH: 5
<212> TYPE: PRT
<213> ORGANISM: Oryctolagus cuniculus

<400> SEQUENCE: 361

Ser Tyr His Met Gly
1 5

<210> SEQ ID NO 362
<211> LENGTH: 6
<212> TYPE: PRT
<213> ORGANISM: Oryctolagus cuniculus

<400> SEQUENCE: 362

Ser Arg Tyr Trp Ile Tyr
1 5

<210> SEQ ID NO 363
<211> LENGTH: 5
<212> TYPE: PRT
<213> ORGANISM: Oryctolagus cuniculus

<400> SEQUENCE: 363

Ser Tyr Phe Leu Thr
1 5

<210> SEQ ID NO 364
<211> LENGTH: 5
<212> TYPE: PRT
<213> ORGANISM: Oryctolagus cuniculus

<400> SEQUENCE: 364

Ser Tyr Ala Met Ser
1 5

<210> SEQ ID NO 365
<211> LENGTH: 5
<212> TYPE: PRT
<213> ORGANISM: Oryctolagus cuniculus

<400> SEQUENCE: 365

Ser Asn Ala Met Cys
1 5

<210> SEQ ID NO 366
<211> LENGTH: 5
<212> TYPE: PRT
<213> ORGANISM: Oryctolagus cuniculus

<400> SEQUENCE: 366

Val Tyr Ala Met Ser
1 5

<210> SEQ ID NO 367
<211> LENGTH: 5
<212> TYPE: PRT
<213> ORGANISM: Oryctolagus cuniculus

<400> SEQUENCE: 367

Ser Tyr Ala Met Gly
1 5

<210> SEQ ID NO 368
<211> LENGTH: 6
<212> TYPE: PRT
<213> ORGANISM: Oryctolagus cuniculus

<400> SEQUENCE: 368

Gly Ser Tyr Trp Asn Cys
1 5

<210> SEQ ID NO 369
<211> LENGTH: 6
<212> TYPE: PRT
<213> ORGANISM: Oryctolagus cuniculus

<400> SEQUENCE: 369

Ser Gly Tyr Asp Met Cys
1 5

<210> SEQ ID NO 370
<211> LENGTH: 5
<212> TYPE: PRT
<213> ORGANISM: Oryctolagus cuniculus

<400> SEQUENCE: 370

Ala Tyr Gly Val Asn
1 5

<210> SEQ ID NO 371
<211> LENGTH: 6
<212> TYPE: PRT
<213> ORGANISM: Oryctolagus cuniculus

<400> SEQUENCE: 371

Asn Ser Tyr Tyr Met Cys
1 5

<210> SEQ ID NO 372
<211> LENGTH: 5
<212> TYPE: PRT
<213> ORGANISM: Oryctolagus cuniculus

<400> SEQUENCE: 372

Ser Asn Ala Met Cys
1 5

<210> SEQ ID NO 373
<211> LENGTH: 5
<212> TYPE: PRT
<213> ORGANISM: Oryctolagus cuniculus

<400> SEQUENCE: 373

Ser Tyr Ala Met Gly
1 5

<210> SEQ ID NO 374
<211> LENGTH: 5
<212> TYPE: PRT
<213> ORGANISM: Oryctolagus cuniculus

<400> SEQUENCE: 374

Thr Asn Gly Val Ser
1 5

<210> SEQ ID NO 375
<211> LENGTH: 6
<212> TYPE: PRT
<213> ORGANISM: Oryctolagus cuniculus

<400> SEQUENCE: 375

Ser Gly Tyr Tyr Met Cys
1 5

<210> SEQ ID NO 376
<211> LENGTH: 6
<212> TYPE: PRT
<213> ORGANISM: Oryctolagus cuniculus

<400> SEQUENCE: 376

Ser Gly Tyr Cys Leu Cys
1 5

<210> SEQ ID NO 377
<211> LENGTH: 5
<212> TYPE: PRT
<213> ORGANISM: Oryctolagus cuniculus

<400> SEQUENCE: 377

Ser Tyr Trp Met Cys
1 5

<210> SEQ ID NO 378
<211> LENGTH: 6
<212> TYPE: PRT
<213> ORGANISM: Oryctolagus cuniculus

<400> SEQUENCE: 378

Ser Tyr Tyr Tyr Met Ser
1 5

<210> SEQ ID NO 379
<211> LENGTH: 5
<212> TYPE: PRT
<213> ORGANISM: Oryctolagus cuniculus

<400> SEQUENCE: 379

Tyr Asn Thr Ile Cys
1 5

<210> SEQ ID NO 380
<211> LENGTH: 6
<212> TYPE: PRT
<213> ORGANISM: Oryctolagus cuniculus

<400> SEQUENCE: 380

Ser Ser Tyr Tyr Met Cys
1 5

<210> SEQ ID NO 381
<211> LENGTH: 5
<212> TYPE: PRT
<213> ORGANISM: Oryctolagus cuniculus

<400> SEQUENCE: 381

Asn Tyr Ala Met Ser
1               5

<210> SEQ ID NO 382
<211> LENGTH: 5
<212> TYPE: PRT
<213> ORGANISM: Oryctolagus cuniculus

<400> SEQUENCE: 382

Asn Tyr Ala Val Gly
1               5

<210> SEQ ID NO 383
<211> LENGTH: 6
<212> TYPE: PRT
<213> ORGANISM: Oryctolagus cuniculus

<400> SEQUENCE: 383

Ser Ser Tyr Tyr Met Cys
1               5

<210> SEQ ID NO 384
<211> LENGTH: 6
<212> TYPE: PRT
<213> ORGANISM: Oryctolagus cuniculus

<400> SEQUENCE: 384

Ser Arg Tyr Tyr Val Cys
1               5

<210> SEQ ID NO 385
<211> LENGTH: 5
<212> TYPE: PRT
<213> ORGANISM: Oryctolagus cuniculus

<400> SEQUENCE: 385

Ala Asn Ala Met Ser
1               5

<210> SEQ ID NO 386
<211> LENGTH: 5
<212> TYPE: PRT
<213> ORGANISM: Oryctolagus cuniculus

<400> SEQUENCE: 386

Asn Tyr His Met Ser
1               5

<210> SEQ ID NO 387
<211> LENGTH: 5
<212> TYPE: PRT
<213> ORGANISM: Oryctolagus cuniculus

<400> SEQUENCE: 387

Asn Tyr Gly Leu Thr
1               5

<210> SEQ ID NO 388
<211> LENGTH: 6
<212> TYPE: PRT
<213> ORGANISM: Oryctolagus cuniculus

<400> SEQUENCE: 388

Ser Ser Tyr Tyr Met Cys
1               5

<210> SEQ ID NO 389
<211> LENGTH: 5
<212> TYPE: PRT
<213> ORGANISM: Oryctolagus cuniculus

<400> SEQUENCE: 389

Thr Tyr Ala Met Ser
1               5

<210> SEQ ID NO 390
<211> LENGTH: 5
<212> TYPE: PRT
<213> ORGANISM: Oryctolagus cuniculus

<400> SEQUENCE: 390

Asn Tyr Gly Val Ser
1               5

<210> SEQ ID NO 391
<211> LENGTH: 6
<212> TYPE: PRT
<213> ORGANISM: Oryctolagus cuniculus

<400> SEQUENCE: 391

Val Ser Tyr Trp Ile Cys
1               5

<210> SEQ ID NO 392
<211> LENGTH: 6
<212> TYPE: PRT
<213> ORGANISM: Oryctolagus cuniculus

<400> SEQUENCE: 392

Ser Gly Tyr Asp Met Cys
1               5

<210> SEQ ID NO 393
<211> LENGTH: 5
<212> TYPE: PRT
<213> ORGANISM: Oryctolagus cuniculus

<400> SEQUENCE: 393

Ser Asn Ala Met Cys
1               5

<210> SEQ ID NO 394
<211> LENGTH: 6
<212> TYPE: PRT
<213> ORGANISM: Oryctolagus cuniculus

<400> SEQUENCE: 394

Ser Ser Tyr Tyr Met Cys
1               5

<210> SEQ ID NO 395
<211> LENGTH: 6

<212> TYPE: PRT
<213> ORGANISM: Oryctolagus cuniculus

<400> SEQUENCE: 395

Ser Ser Tyr Trp Ile Tyr
1 5

<210> SEQ ID NO 396
<211> LENGTH: 5
<212> TYPE: PRT
<213> ORGANISM: Oryctolagus cuniculus

<400> SEQUENCE: 396

Arg Tyr Gly Val Ser
1 5

<210> SEQ ID NO 397
<211> LENGTH: 6
<212> TYPE: PRT
<213> ORGANISM: Oryctolagus cuniculus

<400> SEQUENCE: 397

Asn Asn Tyr Tyr Met Cys
1 5

<210> SEQ ID NO 398
<211> LENGTH: 6
<212> TYPE: PRT
<213> ORGANISM: Oryctolagus cuniculus

<400> SEQUENCE: 398

Ser Asn Tyr Tyr Met Cys
1 5

<210> SEQ ID NO 399
<211> LENGTH: 5
<212> TYPE: PRT
<213> ORGANISM: Oryctolagus cuniculus

<400> SEQUENCE: 399

Ser Tyr Ala Met Ser
1 5

<210> SEQ ID NO 400
<211> LENGTH: 6
<212> TYPE: PRT
<213> ORGANISM: Oryctolagus cuniculus

<400> SEQUENCE: 400

Ser Ser Tyr Cys Met Cys
1 5

<210> SEQ ID NO 401
<211> LENGTH: 5
<212> TYPE: PRT
<213> ORGANISM: Oryctolagus cuniculus

<400> SEQUENCE: 401

Ser Tyr Ala Met Gly
1 5

<210> SEQ ID NO 402
<211> LENGTH: 6
<212> TYPE: PRT
<213> ORGANISM: Oryctolagus cuniculus

<400> SEQUENCE: 402

Ser Gly Tyr Asp Met Cys
1 5

<210> SEQ ID NO 403
<211> LENGTH: 5
<212> TYPE: PRT
<213> ORGANISM: Oryctolagus cuniculus

<400> SEQUENCE: 403

Asp Tyr Tyr Met Ser
1 5

<210> SEQ ID NO 404
<211> LENGTH: 5
<212> TYPE: PRT
<213> ORGANISM: Oryctolagus cuniculus

<400> SEQUENCE: 404

Ser His Ala Thr Ser
1 5

<210> SEQ ID NO 405
<211> LENGTH: 6
<212> TYPE: PRT
<213> ORGANISM: Oryctolagus cuniculus

<400> SEQUENCE: 405

Ser Gly Tyr Trp Ile Cys
1 5

<210> SEQ ID NO 406
<211> LENGTH: 5
<212> TYPE: PRT
<213> ORGANISM: Oryctolagus cuniculus

<400> SEQUENCE: 406

Ser Tyr Thr Met Ala
1 5

<210> SEQ ID NO 407
<211> LENGTH: 5
<212> TYPE: PRT
<213> ORGANISM: Oryctolagus cuniculus

<400> SEQUENCE: 407

Ser Tyr His Met Cys
1 5

<210> SEQ ID NO 408
<211> LENGTH: 6
<212> TYPE: PRT
<213> ORGANISM: Oryctolagus cuniculus

<400> SEQUENCE: 408

Gly Asp Tyr Asp Met Cys
1 5

<210> SEQ ID NO 409
<211> LENGTH: 6
<212> TYPE: PRT
<213> ORGANISM: Oryctolagus cuniculus

<400> SEQUENCE: 409

Ser Ser Tyr Tyr Met Cys
1 5

<210> SEQ ID NO 410
<211> LENGTH: 5
<212> TYPE: PRT
<213> ORGANISM: Oryctolagus cuniculus

<400> SEQUENCE: 410

Ser Tyr Ala Met Ser
1 5

<210> SEQ ID NO 411
<211> LENGTH: 5
<212> TYPE: PRT
<213> ORGANISM: Oryctolagus cuniculus

<400> SEQUENCE: 411

Ser Tyr Thr Met Thr
1 5

<210> SEQ ID NO 412
<211> LENGTH: 6
<212> TYPE: PRT
<213> ORGANISM: Oryctolagus cuniculus

<400> SEQUENCE: 412

Ser Lys Tyr Tyr Met Cys
1 5

<210> SEQ ID NO 413
<211> LENGTH: 5
<212> TYPE: PRT
<213> ORGANISM: Oryctolagus cuniculus

<400> SEQUENCE: 413

Ser Tyr Tyr Ile Tyr
1 5

<210> SEQ ID NO 414
<211> LENGTH: 6
<212> TYPE: PRT
<213> ORGANISM: Oryctolagus cuniculus

<400> SEQUENCE: 414

Ser Val Tyr Asp Met Cys
1 5

<210> SEQ ID NO 415
<211> LENGTH: 5
<212> TYPE: PRT
<213> ORGANISM: Oryctolagus cuniculus

<400> SEQUENCE: 415

Ser Tyr His Met Ser
1 5

<210> SEQ ID NO 416
<211> LENGTH: 5
<212> TYPE: PRT
<213> ORGANISM: Oryctolagus cuniculus

<400> SEQUENCE: 416

Gly Leu Val Val Ser 1 5

<210> SEQ ID NO 417
<211> LENGTH: 5
<212> TYPE: PRT
<213> ORGANISM: Oryctolagus cuniculus

<400> SEQUENCE: 417

Arg Asp Ala Met Ser
1 5

<210> SEQ ID NO 418
<211> LENGTH: 5
<212> TYPE: PRT
<213> ORGANISM: Oryctolagus cuniculus

<400> SEQUENCE: 418

Ser Tyr Trp Ile Cys
1 5

<210> SEQ ID NO 419
<211> LENGTH: 5
<212> TYPE: PRT
<213> ORGANISM: Oryctolagus cuniculus

<400> SEQUENCE: 419

Arg Tyr Ala Met Ile
1 5

<210> SEQ ID NO 420
<211> LENGTH: 6
<212> TYPE: PRT
<213> ORGANISM: Oryctolagus cuniculus

<400> SEQUENCE: 420

Asn Asn Tyr Trp Ile Cys
1 5

<210> SEQ ID NO 421
<211> LENGTH: 6
<212> TYPE: PRT
<213> ORGANISM: Oryctolagus cuniculus

<400> SEQUENCE: 421

Thr Tyr Tyr Tyr Met Cys
1 5

<210> SEQ ID NO 422
<211> LENGTH: 5
<212> TYPE: PRT
<213> ORGANISM: Oryctolagus cuniculus

<400> SEQUENCE: 422

Ser Tyr Trp Met Ser
1 5

<210> SEQ ID NO 423
<211> LENGTH: 5
<212> TYPE: PRT
<213> ORGANISM: Oryctolagus cuniculus

<400> SEQUENCE: 423

Arg Asn Ala Ala Ser
1 5

<210> SEQ ID NO 424
<211> LENGTH: 5
<212> TYPE: PRT
<213> ORGANISM: Oryctolagus cuniculus

<400> SEQUENCE: 424

Asn Tyr Ala Met Thr
1 5

<210> SEQ ID NO 425
<211> LENGTH: 5
<212> TYPE: PRT
<213> ORGANISM: Oryctolagus cuniculus

<400> SEQUENCE: 425

Ser Asn Ala Ile Ser
1 5

<210> SEQ ID NO 426
<211> LENGTH: 6
<212> TYPE: PRT
<213> ORGANISM: Oryctolagus cuniculus

<400> SEQUENCE: 426

Val Gly Tyr Tyr Met Cys
1 5

<210> SEQ ID NO 427
<211> LENGTH: 6
<212> TYPE: PRT
<213> ORGANISM: Oryctolagus cuniculus

<400> SEQUENCE: 427

Ser Ser Tyr Trp Ile Cys
1 5

<210> SEQ ID NO 428
<211> LENGTH: 6
<212> TYPE: PRT
<213> ORGANISM: Oryctolagus cuniculus

<400> SEQUENCE: 428

Ser Ser Tyr Tyr Met Cys
1 5

<210> SEQ ID NO 429
<211> LENGTH: 5
<212> TYPE: PRT
<213> ORGANISM: Oryctolagus cuniculus

<400> SEQUENCE: 429

Asn Tyr His Met Thr
1 5

<210> SEQ ID NO 430
<211> LENGTH: 5
<212> TYPE: PRT
<213> ORGANISM: Oryctolagus cuniculus

<400> SEQUENCE: 430

Ser Tyr Asp Met Thr
1 5

<210> SEQ ID NO 431

<211> LENGTH: 6
<212> TYPE: PRT
<213> ORGANISM: Oryctolagus cuniculus

<400> SEQUENCE: 431

Ser Ser Tyr Cys Val Cys
1 5

<210> SEQ ID NO 432
<211> LENGTH: 5
<212> TYPE: PRT
<213> ORGANISM: Oryctolagus cuniculus

<400> SEQUENCE: 432

Ser Asn Ala Met Cys
1 5

<210> SEQ ID NO 433
<211> LENGTH: 6
<212> TYPE: PRT
<213> ORGANISM: Oryctolagus cuniculus

<400> SEQUENCE: 433

Gly Asn Tyr Tyr Met Cys
1 5

<210> SEQ ID NO 434
<211> LENGTH: 5
<212> TYPE: PRT
<213> ORGANISM: Oryctolagus cuniculus

<400> SEQUENCE: 434

Ser Tyr His Met Asn
1 5

<210> SEQ ID NO 435
<211> LENGTH: 6
<212> TYPE: PRT
<213> ORGANISM: Oryctolagus cuniculus

<400> SEQUENCE: 435

Ser Ser Tyr Tyr Met Cys
1 5

<210> SEQ ID NO 436
<211> LENGTH: 5
<212> TYPE: PRT
<213> ORGANISM: Oryctolagus cuniculus

<400> SEQUENCE: 436

Ser Tyr Pro Val Asn
1 5

<210> SEQ ID NO 437
<211> LENGTH: 5
<212> TYPE: PRT
<213> ORGANISM: Oryctolagus cuniculus

<400> SEQUENCE: 437

Ser Tyr Asp Met Ser
1 5

<210> SEQ ID NO 438
<211> LENGTH: 5
<212> TYPE: PRT

<213> ORGANISM: Oryctolagus cuniculus

<400> SEQUENCE: 438

Asn Tyr Gly Met Thr
1 5

<210> SEQ ID NO 439
<211> LENGTH: 5
<212> TYPE: PRT
<213> ORGANISM: Oryctolagus cuniculus

<400> SEQUENCE: 439

Thr Tyr Trp Met Ser
1 5

<210> SEQ ID NO 440
<211> LENGTH: 5
<212> TYPE: PRT
<213> ORGANISM: Oryctolagus cuniculus

<400> SEQUENCE: 440

Ser Tyr Ala Met Gly
1 5

<210> SEQ ID NO 441
<211> LENGTH: 6
<212> TYPE: PRT
<213> ORGANISM: Oryctolagus cuniculus

<400> SEQUENCE: 441

Ser Ser Tyr Tyr Met Cys
1 5

<210> SEQ ID NO 442
<211> LENGTH: 6
<212> TYPE: PRT
<213> ORGANISM: Oryctolagus cuniculus

<400> SEQUENCE: 442

Ser Gly Gln Asp Met Cys
1 5

<210> SEQ ID NO 443
<211> LENGTH: 5
<212> TYPE: PRT
<213> ORGANISM: Oryctolagus cuniculus

<400> SEQUENCE: 443

Ser Tyr Asn Met Gly
1 5

<210> SEQ ID NO 444
<211> LENGTH: 6
<212> TYPE: PRT
<213> ORGANISM: Oryctolagus cuniculus

<400> SEQUENCE: 444

Ser Ser Tyr Tyr Met Cys
1 5

<210> SEQ ID NO 445
<211> LENGTH: 16
<212> TYPE: PRT
<213> ORGANISM: Oryctolagus cuniculus

<400> SEQUENCE: 445

Gly Ile Ala Asn Asn Gly Pro Thr Tyr Tyr Ala Asn Trp Ala Lys Gly
1 5 10 15

<210> SEQ ID NO 446
<211> LENGTH: 16
<212> TYPE: PRT
<213> ORGANISM: Oryctolagus cuniculus

<400> SEQUENCE: 446

Met Ile Tyr Pro Asn Ser Gly Thr Asn Tyr Ala Thr Trp Ala Lys Gly
1 5 10 15

<210> SEQ ID NO 447
<211> LENGTH: 16
<212> TYPE: PRT
<213> ORGANISM: Oryctolagus cuniculus

<400> SEQUENCE: 447

Gly Ile Ser Asn Ser Gly Thr Thr Tyr Tyr Ala Ser Trp Ala Lys Gly
1 5 10 15

<210> SEQ ID NO 448
<211> LENGTH: 16
<212> TYPE: PRT
<213> ORGANISM: Oryctolagus cuniculus

<400> SEQUENCE: 448

Val Ile Gly Lys Ser Gly Asn Thr Tyr Tyr Ala Ser Trp Ala Lys Gly
1 5 10 15

<210> SEQ ID NO 449
<211> LENGTH: 18
<212> TYPE: PRT
<213> ORGANISM: Oryctolagus cuniculus

<400> SEQUENCE: 449

Cys Ile Tyr Ala Gly Ser Ser Gly Ser Thr Tyr Tyr Ala Ser Trp Ala
1 5 10 15

Lys Gly

<210> SEQ ID NO 450
<211> LENGTH: 16
<212> TYPE: PRT
<213> ORGANISM: Oryctolagus cuniculus

<400> SEQUENCE: 450

Gly Ile Gly Asn Asn Gly Ile Ile His Tyr Ala Asn Trp Ala Lys Gly
1 5 10 15

<210> SEQ ID NO 451
<211> LENGTH: 18
<212> TYPE: PRT
<213> ORGANISM: Oryctolagus cuniculus

<400> SEQUENCE: 451

Cys Ile Tyr Gly Gly Ser Ser Gly Lys Thr Trp Tyr Ala Ser Trp Ala
1 5 10 15

Lys Gly

<210> SEQ ID NO 452
<211> LENGTH: 16
<212> TYPE: PRT

<213> ORGANISM: Oryctolagus cuniculus

<400> SEQUENCE: 452

Gly Ile Ala Asn Asn Gly Pro Thr Tyr Tyr Ala Ser Trp Ala Lys Gly
1 5 10 15

<210> SEQ ID NO 453
<211> LENGTH: 17
<212> TYPE: PRT
<213> ORGANISM: Oryctolagus cuniculus

<400> SEQUENCE: 453

Cys Ile Tyr Ala Asp Asp Ala Thr Thr Tyr Tyr Ala Thr Trp Ala Lys
1 5 10 15

Gly

<210> SEQ ID NO 454
<211> LENGTH: 16
<212> TYPE: PRT
<213> ORGANISM: Oryctolagus cuniculus

<400> SEQUENCE: 454

Ile Ile Arg Asn Thr Gly Thr Thr Trp Tyr Ala Ser Trp Ala Lys Gly
1 5 10 15

<210> SEQ ID NO 455
<211> LENGTH: 17
<212> TYPE: PRT
<213> ORGANISM: Oryctolagus cuniculus

<400> SEQUENCE: 455

Cys Ile Tyr Val Gly Ser Gly Ser Thr Tyr Tyr Ala Ser Trp Ala Gln
1 5 10 15

Gly

<210> SEQ ID NO 456
<211> LENGTH: 17
<212> TYPE: PRT
<213> ORGANISM: Oryctolagus cuniculus

<400> SEQUENCE: 456

Cys Ile Tyr Thr Ser Ser Gly Ser Thr Tyr Tyr Ala Ser Trp Ala Lys
1 5 10 15

Gly

<210> SEQ ID NO 457
<211> LENGTH: 18
<212> TYPE: PRT
<213> ORGANISM: Oryctolagus cuniculus

<400> SEQUENCE: 457

Cys Ile Tyr Ala Gly Ser Ser Gly Ser Thr Tyr Tyr Ala Ser Trp Ala
1 5 10 15

Lys Gly

<210> SEQ ID NO 458
<211> LENGTH: 18
<212> TYPE: PRT
<213> ORGANISM: Oryctolagus cuniculus

<400> SEQUENCE: 458

Cys Ile Tyr Ala Gly Ser Ser Asp Ser Thr Tyr Tyr Ala Ser Trp Ala

```
1               5                   10                  15

Lys Gly


<210> SEQ ID NO 459
<211> LENGTH: 18
<212> TYPE: PRT
<213> ORGANISM: Oryctolagus cuniculus

<400> SEQUENCE: 459

Cys Ile Tyr Thr Gly Ser Ser Gly Lys Thr His Tyr Ala Ser Trp Ala
1               5                   10                  15

Lys Gly


<210> SEQ ID NO 460
<211> LENGTH: 16
<212> TYPE: PRT
<213> ORGANISM: Oryctolagus cuniculus

<400> SEQUENCE: 460

Ile Ile Tyr Asp Ser Gly Ser Thr Tyr Tyr Ala Asn Trp Ala Lys Gly
1               5                   10                  15


<210> SEQ ID NO 461
<211> LENGTH: 17
<212> TYPE: PRT
<213> ORGANISM: Oryctolagus cuniculus

<400> SEQUENCE: 461

Cys Ile Ala Ala Gly Ser Gly Ser Thr Tyr Tyr Ala Ser Trp Ala Lys
1               5                   10                  15

Gly


<210> SEQ ID NO 462
<211> LENGTH: 18
<212> TYPE: PRT
<213> ORGANISM: Oryctolagus cuniculus

<400> SEQUENCE: 462

Cys Ile Tyr Ala Gly Ser Ser Gly Ser Thr Tyr Tyr Ala Ser Trp Ala
1               5                   10                  15

Lys Gly


<210> SEQ ID NO 463
<211> LENGTH: 17
<212> TYPE: PRT
<213> ORGANISM: Oryctolagus cuniculus

<400> SEQUENCE: 463

Cys Ile Tyr Thr Gly Pro Gly Gly Thr Phe Tyr Ala Ser Trp Ala Lys
1               5                   10                  15

Gly


<210> SEQ ID NO 464
<211> LENGTH: 16
<212> TYPE: PRT
<213> ORGANISM: Oryctolagus cuniculus

<400> SEQUENCE: 464

Ile Ile His Tyr Ser Gly Tyr Thr Ala Tyr Ala Ser Trp Ala Lys Gly
1               5                   10                  15
```

<210> SEQ ID NO 465
<211> LENGTH: 16
<212> TYPE: PRT
<213> ORGANISM: Oryctolagus cuniculus

<400> SEQUENCE: 465

Phe Ile Lys Ala Asp Gly Ser Ala Tyr Tyr Ala Asn Trp Ala Lys Gly
1 5 10 15

<210> SEQ ID NO 466
<211> LENGTH: 16
<212> TYPE: PRT
<213> ORGANISM: Oryctolagus cuniculus

<400> SEQUENCE: 466

Gly Ile Ala Thr Asn Gly Ile Ile His Tyr Ala Ser Trp Val Lys Gly
1 5 10 15

<210> SEQ ID NO 467
<211> LENGTH: 16
<212> TYPE: PRT
<213> ORGANISM: Oryctolagus cuniculus

<400> SEQUENCE: 467

Met Ile Tyr Pro Asn Ser Gly Thr Asn Tyr Ala Ser Trp Ala Lys Gly
1 5 10 15

<210> SEQ ID NO 468
<211> LENGTH: 16
<212> TYPE: PRT
<213> ORGANISM: Oryctolagus cuniculus

<400> SEQUENCE: 468

Met Ile Tyr Pro Asn Gly Gly Thr Asn Tyr Ala Thr Trp Ala Lys Gly
1 5 10 15

<210> SEQ ID NO 469
<211> LENGTH: 16
<212> TYPE: PRT
<213> ORGANISM: Oryctolagus cuniculus

<400> SEQUENCE: 469

Ile Ile Tyr Ala Ser Asp Ser Thr Tyr Tyr Ala Thr Trp Ala Lys Gly
1 5 10 15

<210> SEQ ID NO 470
<211> LENGTH: 16
<212> TYPE: PRT
<213> ORGANISM: Oryctolagus cuniculus

<400> SEQUENCE: 470

Gly Ile Ala Thr His Gly Ile Ile His Tyr Ala Ser Trp Val Lys Gly
1 5 10 15

<210> SEQ ID NO 471
<211> LENGTH: 16
<212> TYPE: PRT
<213> ORGANISM: Oryctolagus cuniculus

<400> SEQUENCE: 471

Ile Ile Ser Ser Ser Gly Ser Thr Tyr Tyr Ala Ser Trp Ala Lys Gly
1 5 10 15

<210> SEQ ID NO 472
<211> LENGTH: 17

<212> TYPE: PRT
<213> ORGANISM: Oryctolagus cuniculus

<400> SEQUENCE: 472

Cys Ile Val Thr Gly Arg Gly Asn Thr Tyr Tyr Ala Asn Trp Ala Lys
1 5 10 15

Gly

<210> SEQ ID NO 473
<211> LENGTH: 16
<212> TYPE: PRT
<213> ORGANISM: Oryctolagus cuniculus

<400> SEQUENCE: 473

Phe Ile Asn Ile Ile His Gly Ala Tyr Tyr Ala Ser Trp Ala Lys Gly
1 5 10 15

<210> SEQ ID NO 474
<211> LENGTH: 16
<212> TYPE: PRT
<213> ORGANISM: Oryctolagus cuniculus

<400> SEQUENCE: 474

Phe Ile Lys Thr Gly Gly Ser Ala Tyr Tyr Ala Ser Trp Ala Lys Gly
1 5 10 15

<210> SEQ ID NO 475
<211> LENGTH: 16
<212> TYPE: PRT
<213> ORGANISM: Oryctolagus cuniculus

<400> SEQUENCE: 475

Tyr Ile Asn Thr Gly Gly Ser Ala Ser Tyr Ala Thr Trp Ala Lys Gly
1 5 10 15

<210> SEQ ID NO 476
<211> LENGTH: 18
<212> TYPE: PRT
<213> ORGANISM: Oryctolagus cuniculus

<400> SEQUENCE: 476

Cys Ile Tyr Thr Gly Ser Thr Gly Ser Thr Tyr Tyr Ala Ser Trp Ala
1 5 10 15

Lys Gly

<210> SEQ ID NO 477
<211> LENGTH: 16
<212> TYPE: PRT
<213> ORGANISM: Oryctolagus cuniculus

<400> SEQUENCE: 477

Ile Ile Ser Asn Ser Gly Ala Thr Ala Tyr Ala Ser Trp Ala Lys Gly
1 5 10 15

<210> SEQ ID NO 478
<211> LENGTH: 17
<212> TYPE: PRT
<213> ORGANISM: Oryctolagus cuniculus

<400> SEQUENCE: 478

Cys Ile Gly Thr Ser Ser Thr Ile Ser Tyr Tyr Ala Ser Trp Ala Lys
1 5 10 15

Gly

<210> SEQ ID NO 479
<211> LENGTH: 16
<212> TYPE: PRT
<213> ORGANISM: Oryctolagus cuniculus

<400> SEQUENCE: 479

Ile Ile His Tyr Ser Gly Tyr Ile Ala Tyr Ala Asn Trp Ala Lys Gly
1 5 10 15

<210> SEQ ID NO 480
<211> LENGTH: 16
<212> TYPE: PRT
<213> ORGANISM: Oryctolagus cuniculus

<400> SEQUENCE: 480

Phe Ile Lys Pro Gly Gly Ser Ala Tyr Tyr Ala Ser Trp Ala Lys Gly
1 5 10 15

<210> SEQ ID NO 481
<211> LENGTH: 18
<212> TYPE: PRT
<213> ORGANISM: Oryctolagus cuniculus

<400> SEQUENCE: 481

Cys Ile Asp Gly Gly Ser Ser Gly Ile Thr Gly Tyr Ala Asn Trp Ala
1 5 10 15

Lys Gly

<210> SEQ ID NO 482
<211> LENGTH: 16
<212> TYPE: PRT
<213> ORGANISM: Oryctolagus cuniculus

<400> SEQUENCE: 482

Phe Ile Asn Thr Gly Gly Ser Ala Tyr Tyr Ala Ser Trp Ala Lys Gly
1 5 10 15

<210> SEQ ID NO 483
<211> LENGTH: 18
<212> TYPE: PRT
<213> ORGANISM: Oryctolagus cuniculus

<400> SEQUENCE: 483

Cys Ile Tyr Ala Gly Ser Ser Gly Ser Thr Tyr Tyr Ala Ser Trp Ala
1 5 10 15

Lys Gly

<210> SEQ ID NO 484
<211> LENGTH: 18
<212> TYPE: PRT
<213> ORGANISM: Oryctolagus cuniculus

<400> SEQUENCE: 484

Cys Ile Tyr Thr Gly Ser Ser Gly Ser Thr Tyr Tyr Ala Ser Trp Ala
1 5 10 15

Lys Gly

<210> SEQ ID NO 485
<211> LENGTH: 18
<212> TYPE: PRT
<213> ORGANISM: Oryctolagus cuniculus -continued

<400> SEQUENCE: 485

Cys Ile His Ala Gly Ser Ser Gly Ala Ala Tyr Tyr Ala Thr Trp Ala
1 5 10 15

Lys Gly

<210> SEQ ID NO 486
<211> LENGTH: 16
<212> TYPE: PRT
<213> ORGANISM: Oryctolagus cuniculus

<400> SEQUENCE: 486

Ile Ile Thr Thr Ser Gly Asn Thr Tyr Tyr Ala Ser Trp Ala Lys Gly
1 5 10 15

<210> SEQ ID NO 487
<211> LENGTH: 18
<212> TYPE: PRT
<213> ORGANISM: Oryctolagus cuniculus

<400> SEQUENCE: 487

Cys Ile Tyr Thr Gly Ser Ser Gly Gly Thr Tyr Tyr Ala Ser Trp Ala
1 5 10 15

Lys Gly

<210> SEQ ID NO 488
<211> LENGTH: 17
<212> TYPE: PRT
<213> ORGANISM: Oryctolagus cuniculus

<400> SEQUENCE: 488

Cys Ile Tyr Thr Val Asn Asp Asn Thr Trp Tyr Ala Ser Trp Ala Lys
1 5 10 15

Gly

<210> SEQ ID NO 489
<211> LENGTH: 18
<212> TYPE: PRT
<213> ORGANISM: Oryctolagus cuniculus

<400> SEQUENCE: 489

Cys Ile Val Asp Gly Ser Ser Gly Asn Thr Tyr Tyr Ala Ser Trp Ala
1 5 10 15

Lys Gly

<210> SEQ ID NO 490
<211> LENGTH: 16
<212> TYPE: PRT
<213> ORGANISM: Oryctolagus cuniculus

<400> SEQUENCE: 490

Tyr Ile Ser Thr Ser Gly Thr Pro Tyr Tyr Ala Ser Trp Val Asn Gly
1 5 10 15

<210> SEQ ID NO 491
<211> LENGTH: 16
<212> TYPE: PRT
<213> ORGANISM: Oryctolagus cuniculus

<400> SEQUENCE: 491

Ile Ile Tyr Asn Ser Gly Thr Thr Tyr Tyr Ala Asn Trp Ala Lys Gly
1 5 10 15

<210> SEQ ID NO 492
<211> LENGTH: 18
<212> TYPE: PRT
<213> ORGANISM: Oryctolagus cuniculus

<400> SEQUENCE: 492

Cys Ile Tyr Thr Asp Ser Ser Thr Ser Thr Tyr Tyr Ala Ser Trp Ala
1 5 10 15

Lys Gly

<210> SEQ ID NO 493
<211> LENGTH: 18
<212> TYPE: PRT
<213> ORGANISM: Oryctolagus cuniculus

<400> SEQUENCE: 493

Cys Ile Val Gly Gly Gly Gly Val Asn Thr Tyr Tyr Ala Asn Trp Ala
1 5 10 15

Lys Gly

<210> SEQ ID NO 494
<211> LENGTH: 17
<212> TYPE: PRT
<213> ORGANISM: Oryctolagus cuniculus

<400> SEQUENCE: 494

Phe Ile Tyr Pro Gly Val Gly Ile Thr His Tyr Ala His Ser Val Lys
1 5 10 15

Gly

<210> SEQ ID NO 495
<211> LENGTH: 16
<212> TYPE: PRT
<213> ORGANISM: Oryctolagus cuniculus

<400> SEQUENCE: 495

Gly Val Ala Asn Asn Gly Ile Thr Asn Tyr Ala Ser Trp Ala Arg Gly
1 5 10 15

<210> SEQ ID NO 496
<211> LENGTH: 16
<212> TYPE: PRT
<213> ORGANISM: Oryctolagus cuniculus

<400> SEQUENCE: 496

Tyr Ile Ser Thr Gly Gly Ser Ala Tyr Tyr Ala Thr Trp Val Asn Gly
1 5 10 15

<210> SEQ ID NO 497
<211> LENGTH: 16
<212> TYPE: PRT
<213> ORGANISM: Oryctolagus cuniculus

<400> SEQUENCE: 497

Ile Ile Tyr Asp Ser Gly Ser Thr Tyr Tyr Ala Ser Trp Ala Lys Gly
1 5 10 15

<210> SEQ ID NO 498
<211> LENGTH: 16
<212> TYPE: PRT
<213> ORGANISM: Oryctolagus cuniculus

<400> SEQUENCE: 498

Val Ile Ser Ser Asn Gly Gly Thr Val Tyr Ala Asn Trp Ala Lys Gly
1 5 10 15

<210> SEQ ID NO 499
<211> LENGTH: 16
<212> TYPE: PRT
<213> ORGANISM: Oryctolagus cuniculus

<400> SEQUENCE: 499

Ile Ile Thr Phe Ser Gly Asn Thr Tyr Tyr Ala Ser Trp Ala Lys Gly
1 5 10 15

<210> SEQ ID NO 500
<211> LENGTH: 16
<212> TYPE: PRT
<213> ORGANISM: Oryctolagus cuniculus

<400> SEQUENCE: 500

Tyr Ile Asn Ile Tyr Gly Arg Thr Tyr Tyr Ala Asn Trp Ala Lys Ser
1 5 10 15

<210> SEQ ID NO 501
<211> LENGTH: 16
<212> TYPE: PRT
<213> ORGANISM: Oryctolagus cuniculus

<400> SEQUENCE: 501

Gly Ile Ala Asn Asn Gly Pro Thr Tyr Tyr Ala Ser Trp Ala Lys Gly
1 5 10 15

<210> SEQ ID NO 502
<211> LENGTH: 16
<212> TYPE: PRT
<213> ORGANISM: Oryctolagus cuniculus

<400> SEQUENCE: 502

Ile Ile Ser Ser Ser Gly Asn Ser Tyr Tyr Ala Ser Trp Ala Lys Gly
1 5 10 15

<210> SEQ ID NO 503
<211> LENGTH: 15
<212> TYPE: PRT
<213> ORGANISM: Oryctolagus cuniculus

<400> SEQUENCE: 503

Ile Ile Ser Ser Gly Leu Thr Tyr Tyr Ala Ser Trp Ala Lys Gly
1 5 10 15

<210> SEQ ID NO 504
<211> LENGTH: 18
<212> TYPE: PRT
<213> ORGANISM: Oryctolagus cuniculus

<400> SEQUENCE: 504

Cys Ile Asn Phe Gly Arg Ser Gly Asn Ile Tyr Tyr Ala Arg Trp Ala
1 5 10 15

Lys Gly

<210> SEQ ID NO 505
<211> LENGTH: 16
<212> TYPE: PRT
<213> ORGANISM: Oryctolagus cuniculus

<400> SEQUENCE: 505

Phe Ile Asp Pro Tyr Ser Ser Pro Tyr Tyr Ala Ser Trp Ala Lys Gly
1 5 10 15

<210> SEQ ID NO 506
<211> LENGTH: 16
<212> TYPE: PRT
<213> ORGANISM: Oryctolagus cuniculus

<400> SEQUENCE: 506

Val Ile Tyr Gly Ser Gly Ser Ala Trp Tyr Ala Ser Trp Ala Lys Gly
1 5 10 15

<210> SEQ ID NO 507
<211> LENGTH: 17
<212> TYPE: PRT
<213> ORGANISM: Oryctolagus cuniculus

<400> SEQUENCE: 507

Cys Ile Tyr Pro Asp Tyr Gly Asp Thr Phe Tyr Ala Thr Trp Ala Lys
1 5 10 15

Gly

<210> SEQ ID NO 508
<211> LENGTH: 17
<212> TYPE: PRT
<213> ORGANISM: Oryctolagus cuniculus

<400> SEQUENCE: 508

Cys Ile Phe Gly Ser Ser Gly Ser Ile Ala Tyr Ala Thr Trp Ala Lys
1 5 10 15

Gly

<210> SEQ ID NO 509
<211> LENGTH: 16
<212> TYPE: PRT
<213> ORGANISM: Oryctolagus cuniculus

<400> SEQUENCE: 509

Phe Ile Thr Thr Thr Gly Gly Ser Tyr Tyr Ala Ser Trp Ala Arg Gly
1 5 10 15

<210> SEQ ID NO 510
<211> LENGTH: 18
<212> TYPE: PRT
<213> ORGANISM: Oryctolagus cuniculus

<400> SEQUENCE: 510

Cys Ile Asp Thr Gly Ser Arg Gly Phe Thr Tyr Tyr Pro Ser Trp Ala
1 5 10 15

Lys Gly

<210> SEQ ID NO 511
<211> LENGTH: 16
<212> TYPE: PRT
<213> ORGANISM: Oryctolagus cuniculus

<400> SEQUENCE: 511

Phe Met Asn Ser Gly Gly Ser Thr Tyr Tyr Ala Ser Trp Val Asn Gly
1 5 10 15

<210> SEQ ID NO 512
<211> LENGTH: 16

<212> TYPE: PRT
<213> ORGANISM: Oryctolagus cuniculus

<400> SEQUENCE: 512

Met Ile Arg Ser Ser Gly Ile Thr Trp Tyr Ala Ser Trp Ala Lys Gly
1 5 10 15

<210> SEQ ID NO 513
<211> LENGTH: 18
<212> TYPE: PRT
<213> ORGANISM: Oryctolagus cuniculus

<400> SEQUENCE: 513

Cys Ile Tyr Ala Gly Ser Arg Gly Ser Ala Tyr Tyr Ala Ser Trp Val
1 5 10 15

Asn Gly

<210> SEQ ID NO 514
<211> LENGTH: 16
<212> TYPE: PRT
<213> ORGANISM: Oryctolagus cuniculus

<400> SEQUENCE: 514

Ile Ile Thr Trp Ser Ala Asp Thr Tyr Tyr Thr Ser Trp Ala Lys Gly
1 5 10 15

<210> SEQ ID NO 515
<211> LENGTH: 16
<212> TYPE: PRT
<213> ORGANISM: Oryctolagus cuniculus

<400> SEQUENCE: 515

Ile Asn Gly Val Ser Gly Thr Thr Tyr Tyr Ala Thr Trp Ala Asn Gly
1 5 10 15

<210> SEQ ID NO 516
<211> LENGTH: 18
<212> TYPE: PRT
<213> ORGANISM: Oryctolagus cuniculus

<400> SEQUENCE: 516

Cys Ile Asp Gly Glu Gly Ser Gly Asn Thr Tyr Tyr Ala Ser Trp Val
1 5 10 15

Asn Gly

<210> SEQ ID NO 517
<211> LENGTH: 17
<212> TYPE: PRT
<213> ORGANISM: Oryctolagus cuniculus

<400> SEQUENCE: 517

Cys Ile Asp Thr Gly Asp Gly Ser Thr Tyr Tyr Ala Ser Trp Val Asn
1 5 10 15

Gly

<210> SEQ ID NO 518
<211> LENGTH: 16
<212> TYPE: PRT
<213> ORGANISM: Oryctolagus cuniculus

<400> SEQUENCE: 518

Ser Ile Ser Asn Ser Gly Gly Thr Tyr Tyr Ala Ser Trp Ala Lys Gly
1 5 10 15

<210> SEQ ID NO 519
<211> LENGTH: 18
<212> TYPE: PRT
<213> ORGANISM: Oryctolagus cuniculus

<400> SEQUENCE: 519

Cys Ile Asp Ala Gly Ser Val Gly Asp Thr Ser Tyr Ala Thr Trp Ala
1               5                   10                  15

Lys Gly

<210> SEQ ID NO 520
<211> LENGTH: 17
<212> TYPE: PRT
<213> ORGANISM: Oryctolagus cuniculus

<400> SEQUENCE: 520

Cys Ile Tyr Asn Gly Asp Gly Ser Thr Tyr Tyr Ala Ser Trp Val Asn
1               5                   10                  15

Gly

<210> SEQ ID NO 521
<211> LENGTH: 16
<212> TYPE: PRT
<213> ORGANISM: Oryctolagus cuniculus

<400> SEQUENCE: 521

Ile Ile Ser Asn Ser Gly Ala Thr Ala Tyr Ala Ser Trp Ala Lys Gly
1               5                   10                  15

<210> SEQ ID NO 522
<211> LENGTH: 16
<212> TYPE: PRT
<213> ORGANISM: Oryctolagus cuniculus

<400> SEQUENCE: 522

Tyr Ile Phe Thr Gly Gly Asn Thr Tyr Tyr Ala Ser Trp Ala Lys Gly
1               5                   10                  15

<210> SEQ ID NO 523
<211> LENGTH: 18
<212> TYPE: PRT
<213> ORGANISM: Oryctolagus cuniculus

<400> SEQUENCE: 523

Cys Ile Tyr Val Gly Ile Thr Gly Ser Thr Tyr Tyr Ala Ser Trp Ala
1               5                   10                  15

Lys Gly

<210> SEQ ID NO 524
<211> LENGTH: 18
<212> TYPE: PRT
<213> ORGANISM: Oryctolagus cuniculus

<400> SEQUENCE: 524

Cys Lys His Gly Gly Ala Ser Gly Thr Thr Tyr Tyr Ala Thr Trp Ala
1               5                   10                  15

Lys Gly

<210> SEQ ID NO 525
<211> LENGTH: 18
<212> TYPE: PRT

<213> ORGANISM: Oryctolagus cuniculus

<400> SEQUENCE: 525

Cys Ser Tyr Ala Gly Gly Ser Gly Gly Thr Tyr Tyr Ala Ser Trp Ala
1 5 10 15

Lys Gly

<210> SEQ ID NO 526
<211> LENGTH: 17
<212> TYPE: PRT
<213> ORGANISM: Oryctolagus cuniculus

<400> SEQUENCE: 526

Cys Thr Asp Gly Thr Gly Gly Ile Thr Tyr Tyr Ala Ser Trp Ala Lys
1 5 10 15

Gly

<210> SEQ ID NO 527
<211> LENGTH: 18
<212> TYPE: PRT
<213> ORGANISM: Oryctolagus cuniculus

<400> SEQUENCE: 527

Tyr Ile Asn Thr Gly Ser Ser Gly Thr Thr Tyr Tyr Ala Ser Trp Ala
1 5 10 15

Lys Gly

<210> SEQ ID NO 528
<211> LENGTH: 18
<212> TYPE: PRT
<213> ORGANISM: Oryctolagus cuniculus

<400> SEQUENCE: 528

Cys Ile Tyr Ala Gly Ser Ser Gly Ser Thr Tyr Tyr Ala Ser Trp Ala
1 5 10 15

Lys Gly

<210> SEQ ID NO 529
<211> LENGTH: 16
<212> TYPE: PRT
<213> ORGANISM: Oryctolagus cuniculus

<400> SEQUENCE: 529

Phe Ile Asn Ile Ile Asp Ser Thr Tyr Tyr Thr Asn Trp Ala Lys Gly
1 5 10 15

<210> SEQ ID NO 530
<211> LENGTH: 16
<212> TYPE: PRT
<213> ORGANISM: Oryctolagus cuniculus

<400> SEQUENCE: 530

Val Ile Asn Ala Gly Gly Ser Ala Tyr Tyr Ala Thr Trp Ala Lys Gly
1 5 10 15

<210> SEQ ID NO 531
<211> LENGTH: 18
<212> TYPE: PRT
<213> ORGANISM: Oryctolagus cuniculus

<400> SEQUENCE: 531

Cys Ile Tyr Ala Asp Ser Ser Gly Ser Thr Tyr Tyr Ala Ser Trp Ala 1 5 10 15

Lys Gly

<210> SEQ ID NO 532
<211> LENGTH: 17
<212> TYPE: PRT
<213> ORGANISM: Oryctolagus cuniculus

<400> SEQUENCE: 532

Cys Ile Asp Ala Gly Asp Gly Ser Thr Asp Tyr Ala Arg Trp Ala Lys
1 5 10 15

Gly

<210> SEQ ID NO 533
<211> LENGTH: 16
<212> TYPE: PRT
<213> ORGANISM: Oryctolagus cuniculus

<400> SEQUENCE: 533

Thr Ile Phe Asp Thr Tyr Leu Thr Tyr Asn Ala Asn Trp Ala Lys Gly
1 5 10 15

<210> SEQ ID NO 534
<211> LENGTH: 16
<212> TYPE: PRT
<213> ORGANISM: Oryctolagus cuniculus

<400> SEQUENCE: 534

Phe Ile Arg Thr Asp Gly Ser Ala Phe Tyr Ala Thr Trp Ala Lys Gly
1 5 10 15

<210> SEQ ID NO 535
<211> LENGTH: 16
<212> TYPE: PRT
<213> ORGANISM: Oryctolagus cuniculus

<400> SEQUENCE: 535

Tyr Ile Asn Asn Asn Gly Arg Thr Tyr Tyr Ala Ser Arg Ala Lys Gly
1 5 10 15

<210> SEQ ID NO 536
<211> LENGTH: 18
<212> TYPE: PRT
<213> ORGANISM: Oryctolagus cuniculus

<400> SEQUENCE: 536

Cys Val Tyr Ala Gly Ser Ser Gly Ser Thr Tyr Tyr Ala Ser Trp Ala
1 5 10 15

Lys Gly

<210> SEQ ID NO 537
<211> LENGTH: 16
<212> TYPE: PRT
<213> ORGANISM: Oryctolagus cuniculus

<400> SEQUENCE: 537

Ile Ile Asp Ala Ser Val Thr Thr Tyr Tyr Ala Ser Trp Ala Lys Gly
1 5 10 15

<210> SEQ ID NO 538
<211> LENGTH: 17
<212> TYPE: PRT
<213> ORGANISM: Oryctolagus cuniculus

<400> SEQUENCE: 538

Tyr Ile Asp Pro Val Phe Arg Ser Ala Tyr Tyr Ala Ser Trp Val Asn
1 5 10 15

Gly

<210> SEQ ID NO 539
<211> LENGTH: 17
<212> TYPE: PRT
<213> ORGANISM: Oryctolagus cuniculus

<400> SEQUENCE: 539

Cys Ile Gly Gly Asn Ser Gly Asn Ile Tyr Tyr Ala Arg Trp Ala Lys
1 5 10 15

Gly

<210> SEQ ID NO 540
<211> LENGTH: 17
<212> TYPE: PRT
<213> ORGANISM: Oryctolagus cuniculus

<400> SEQUENCE: 540

Cys Ile Tyr Ser Ser Asn Gly Leu Thr Trp Tyr Ala Thr Trp Ala Lys
1 5 10 15

Gly

<210> SEQ ID NO 541
<211> LENGTH: 17
<212> TYPE: PRT
<213> ORGANISM: Oryctolagus cuniculus

<400> SEQUENCE: 541

Cys Ile Val Thr Gly Ser Gly Ser Thr Tyr Tyr Ala Ser Trp Ala Lys
1 5 10 15

Gly

<210> SEQ ID NO 542
<211> LENGTH: 17
<212> TYPE: PRT
<213> ORGANISM: Oryctolagus cuniculus

<400> SEQUENCE: 542

Gly Val Asp Gly Ser Gly Gly Ile Lys Trp Tyr Ala Asn Trp Ala Lys
1 5 10 15

Gly

<210> SEQ ID NO 543
<211> LENGTH: 17
<212> TYPE: PRT
<213> ORGANISM: Oryctolagus cuniculus

<400> SEQUENCE: 543

Cys Phe His Ala Gly Ser Gly Ser Thr Tyr Tyr Ala Ser Trp Val Asn
1 5 10 15

Gly

<210> SEQ ID NO 544
<211> LENGTH: 16
<212> TYPE: PRT
<213> ORGANISM: Oryctolagus cuniculus

<400> SEQUENCE: 544

Trp Ile Ser Ser Ser Gly Ser Ala Tyr Tyr Ala Thr Trp Ala Lys Gly
1 5 10 15

<210> SEQ ID NO 545
<211> LENGTH: 18
<212> TYPE: PRT
<213> ORGANISM: Oryctolagus cuniculus

<400> SEQUENCE: 545

Cys Ile Tyr Thr Gly Ser Thr Gly Ser Thr Tyr Tyr Ala Asn Trp Ala
1 5 10 15

Lys Gly

<210> SEQ ID NO 546
<211> LENGTH: 18
<212> TYPE: PRT
<213> ORGANISM: Oryctolagus cuniculus

<400> SEQUENCE: 546

Cys Ile Tyr Ala Gly Ser Ser Gly Ser Ser Tyr Tyr Ala Ser Trp Ala
1 5 10 15

Lys Gly

<210> SEQ ID NO 547
<211> LENGTH: 16
<212> TYPE: PRT
<213> ORGANISM: Oryctolagus cuniculus

<400> SEQUENCE: 547

Ile Ile Arg Arg Ser Gly Ala Thr Trp Tyr Ala Asn Trp Ala Arg Gly
1 5 10 15

<210> SEQ ID NO 548
<211> LENGTH: 18
<212> TYPE: PRT
<213> ORGANISM: Oryctolagus cuniculus

<400> SEQUENCE: 548

Cys Ile Tyr Asp Gly Ser Ser Asp Ser Ala Tyr Tyr Ala Thr Trp Ala
1 5 10 15

Lys Gly

<210> SEQ ID NO 549
<211> LENGTH: 16
<212> TYPE: PRT
<213> ORGANISM: Oryctolagus cuniculus

<400> SEQUENCE: 549

Ile Ile Thr Tyr Gly Gly Ser Thr Tyr Tyr Ala Ser Trp Ala Lys Gly
1 5 10 15

<210> SEQ ID NO 550
<211> LENGTH: 18
<212> TYPE: PRT
<213> ORGANISM: Oryctolagus cuniculus

<400> SEQUENCE: 550

Cys Ile Ala Val Tyr Ser Ser Gly Ser Thr Tyr Tyr Ala Ser Trp Ala
1 5 10 15

Lys Gly

<210> SEQ ID NO 551
<211> LENGTH: 16
<212> TYPE: PRT
<213> ORGANISM: Oryctolagus cuniculus

<400> SEQUENCE: 551

Val Val Ser Trp Asn Gly Asn Thr Tyr Tyr Ala Ser Trp Ala Lys Gly
1 5 10 15

<210> SEQ ID NO 552
<211> LENGTH: 16
<212> TYPE: PRT
<213> ORGANISM: Oryctolagus cuniculus

<400> SEQUENCE: 552

Phe Ile Lys Ser Gly Gly Ser Thr Tyr Tyr Ala Ser Trp Ala Lys Gly
1 5 10 15

<210> SEQ ID NO 553
<211> LENGTH: 18
<212> TYPE: PRT
<213> ORGANISM: Oryctolagus cuniculus

<400> SEQUENCE: 553

Cys Ile Asp Ala Gly Ser Asn Gly Ser Thr Tyr Tyr Ala Ser Trp Ala
1 5 10 15

Arg Gly

<210> SEQ ID NO 554
<211> LENGTH: 16
<212> TYPE: PRT
<213> ORGANISM: Oryctolagus cuniculus

<400> SEQUENCE: 554

Val Ile Asn Thr Gly Gly Ser Ala Tyr Tyr Ala Ser Trp Ala Lys Gly
1 5 10 15

<210> SEQ ID NO 555
<211> LENGTH: 16
<212> TYPE: PRT
<213> ORGANISM: Oryctolagus cuniculus

<400> SEQUENCE: 555

Phe Ile Lys Ala Asp Gly Asn Thr Tyr Tyr Ala Thr Trp Ala Lys Gly
1 5 10 15

<210> SEQ ID NO 556
<211> LENGTH: 18
<212> TYPE: PRT
<213> ORGANISM: Oryctolagus cuniculus

<400> SEQUENCE: 556

Cys Ile Gly Ala Gly Ser Ser Asn Asp Thr Tyr Tyr Ala Ser Trp Ala
1 5 10 15

Lys Gly

<210> SEQ ID NO 557
<211> LENGTH: 18
<212> TYPE: PRT
<213> ORGANISM: Oryctolagus cuniculus

<400> SEQUENCE: 557

Cys Ile Ser Val Gly Ser Ser Gly Ser Thr Tyr Tyr Ala Asn Trp Ala

-continued 1 5 10 15

Lys Gly

<210> SEQ ID NO 558
<211> LENGTH: 16
<212> TYPE: PRT
<213> ORGANISM: Oryctolagus cuniculus

<400> SEQUENCE: 558

Ile Ile Arg Arg Ser Gly Phe Thr Tyr Tyr Ala Ser Trp Ala Arg Gly
1 5 10 15

<210> SEQ ID NO 559
<211> LENGTH: 16
<212> TYPE: PRT
<213> ORGANISM: Oryctolagus cuniculus

<400> SEQUENCE: 559

Leu Ile Ser Arg Ser Gly Arg Thr Tyr Tyr Ala Thr Trp Ala Lys Gly
1 5 10 15

<210> SEQ ID NO 560
<211> LENGTH: 18
<212> TYPE: PRT
<213> ORGANISM: Oryctolagus cuniculus

<400> SEQUENCE: 560

Cys Ile Tyr Thr Gly Thr Thr Gly Ser Thr Tyr Tyr Ala Ser Trp Ala
1 5 10 15

Lys Tyr

<210> SEQ ID NO 561
<211> LENGTH: 17
<212> TYPE: PRT
<213> ORGANISM: Oryctolagus cuniculus

<400> SEQUENCE: 561

Cys Ile Ala Ile Ile Asn Ser Ile Thr Tyr Tyr Ala Asn Trp Ala Lys
1 5 10 15

Gly

<210> SEQ ID NO 562
<211> LENGTH: 18
<212> TYPE: PRT
<213> ORGANISM: Oryctolagus cuniculus

<400> SEQUENCE: 562

Cys Ile Tyr Ser Asp Gly Ser Gly Ser Thr Tyr Tyr Ala Asn Trp Ala
1 5 10 15

Lys Gly

<210> SEQ ID NO 563
<211> LENGTH: 16
<212> TYPE: PRT
<213> ORGANISM: Oryctolagus cuniculus

<400> SEQUENCE: 563

Phe Ile Val Gly Thr Gly Asp Thr Tyr Tyr Ala Ser Trp Ala Lys Gly
1 5 10 15

<210> SEQ ID NO 564
<211> LENGTH: 16

<212> TYPE: PRT
<213> ORGANISM: Oryctolagus cuniculus

<400> SEQUENCE: 564

Val Ile Gly Lys Ser Gly Ser Thr Tyr Tyr Ala Ser Trp Ala Lys Gly
1 5 10 15

<210> SEQ ID NO 565
<211> LENGTH: 17
<212> TYPE: PRT
<213> ORGANISM: Oryctolagus cuniculus

<400> SEQUENCE: 565

Ser Ile Val Ser Gly Ser Gly Ser Thr Tyr Tyr Ala Ser Trp Ala Lys
1 5 10 15

Gly

<210> SEQ ID NO 566
<211> LENGTH: 18
<212> TYPE: PRT
<213> ORGANISM: Oryctolagus cuniculus

<400> SEQUENCE: 566

Cys Ile Tyr Ala Gly Ser Ser Gly Ser Thr Tyr Tyr Ala Ser Trp Ala
1 5 10 15

Lys Gly

<210> SEQ ID NO 567
<211> LENGTH: 16
<212> TYPE: PRT
<213> ORGANISM: Oryctolagus cuniculus

<400> SEQUENCE: 567

Ile Ile Asp Ile Arg Gly Thr Thr Tyr Tyr Ala Ser Trp Ala Lys Gly
1 5 10 15

<210> SEQ ID NO 568
<211> LENGTH: 18
<212> TYPE: PRT
<213> ORGANISM: Oryctolagus cuniculus

<400> SEQUENCE: 568

Cys Ile Val Ala Gly Ser Ser Gly Arg Thr Tyr Tyr Ala Asn Trp Ala
1 5 10 15

Lys Gly

<210> SEQ ID NO 569
<211> LENGTH: 18
<212> TYPE: PRT
<213> ORGANISM: Oryctolagus cuniculus

<400> SEQUENCE: 569

Cys Ile His Ala Gly Ser Ser Gly Ser Thr Tyr Tyr Ala Ser Trp Ala
1 5 10 15

Lys Gly

<210> SEQ ID NO 570
<211> LENGTH: 17
<212> TYPE: PRT
<213> ORGANISM: Oryctolagus cuniculus

<400> SEQUENCE: 570

Thr Ile Asn Ala Ala Ser Gly Ala Thr Trp Tyr Ala Ser Trp Ala Lys
1 5 10 15

Gly

<210> SEQ ID NO 571
<211> LENGTH: 16
<212> TYPE: PRT
<213> ORGANISM: Oryctolagus cuniculus

<400> SEQUENCE: 571

Ile Ile Ser Thr Gly Gly Ser Thr Tyr Tyr Ala Thr Trp Ala Lys Gly
1 5 10 15

<210> SEQ ID NO 572
<211> LENGTH: 16
<212> TYPE: PRT
<213> ORGANISM: Oryctolagus cuniculus

<400> SEQUENCE: 572

Ile Ile Ile Asn Thr Gly Tyr Thr Tyr Tyr Ala Ser Trp Ala Lys Gly
1 5 10 15

<210> SEQ ID NO 573
<211> LENGTH: 16
<212> TYPE: PRT
<213> ORGANISM: Oryctolagus cuniculus

<400> SEQUENCE: 573

His Ser Asp Ile Arg Gly Ser Ala Tyr Tyr Ala Ser Trp Ala Lys Gly
1 5 10 15

<210> SEQ ID NO 574
<211> LENGTH: 18
<212> TYPE: PRT
<213> ORGANISM: Oryctolagus cuniculus

<400> SEQUENCE: 574

Cys Ile Tyr Ala Gly Ser Asn Gly Ser Thr Tyr Tyr Ala Ser Trp Ala
1 5 10 15

Lys Gly

<210> SEQ ID NO 575
<211> LENGTH: 18
<212> TYPE: PRT
<213> ORGANISM: Oryctolagus cuniculus

<400> SEQUENCE: 575

Cys Ile Tyr Ala Asp Gly Ser Gly Ser Ile Tyr Cys Ala Thr Trp Ala
1 5 10 15

Lys Gly

<210> SEQ ID NO 576
<211> LENGTH: 17
<212> TYPE: PRT
<213> ORGANISM: Oryctolagus cuniculus

<400> SEQUENCE: 576

Cys Ile Tyr Ile Gly Asp Gly Asn Thr Tyr Tyr Ala Ser Trp Ala Lys
1 5 10 15

Gly

<210> SEQ ID NO 577

<211> LENGTH: 16
<212> TYPE: PRT
<213> ORGANISM: Oryctolagus cuniculus

<400> SEQUENCE: 577

Phe Ile Lys Ala Gly Gly Ser Ala Gly Tyr Ala Ser Trp Ala Lys Gly
1 5 10 15

<210> SEQ ID NO 578
<211> LENGTH: 16
<212> TYPE: PRT
<213> ORGANISM: Oryctolagus cuniculus

<400> SEQUENCE: 578

Val Ile Ser Ser Ser Asp Ser Thr Tyr Tyr Ala Ser Trp Ala Lys Gly
1 5 10 15

<210> SEQ ID NO 579
<211> LENGTH: 18
<212> TYPE: PRT
<213> ORGANISM: Oryctolagus cuniculus

<400> SEQUENCE: 579

Cys Ile Tyr Gly Gly Ser Ser Gly Gly Thr Tyr Tyr Ala Ser Trp Ala
1 5 10 15

Lys Gly

<210> SEQ ID NO 580
<211> LENGTH: 18
<212> TYPE: PRT
<213> ORGANISM: Oryctolagus cuniculus

<400> SEQUENCE: 580

Cys Ile Tyr Thr Ser Ser Ser Gly Ser Thr Tyr Tyr Ala Ser Trp Val
1 5 10 15

Asn Gly

<210> SEQ ID NO 581
<211> LENGTH: 18
<212> TYPE: PRT
<213> ORGANISM: Oryctolagus cuniculus

<400> SEQUENCE: 581

Cys Ile Tyr Ala Asp Asn Ser Gly Ser Thr Tyr Tyr Ala Ser Trp Ala
1 5 10 15

Lys Gly

<210> SEQ ID NO 582
<211> LENGTH: 16
<212> TYPE: PRT
<213> ORGANISM: Oryctolagus cuniculus

<400> SEQUENCE: 582

Val Ile Tyr Gly Ser Gly Ser Thr Asp Tyr Ala Ser Trp Ala Lys Gly
1 5 10 15

<210> SEQ ID NO 583
<211> LENGTH: 18
<212> TYPE: PRT
<213> ORGANISM: Oryctolagus cuniculus

<400> SEQUENCE: 583

Cys Ile Tyr Ser Asp Ser Ser Gly Ser Thr Tyr Asn Ala Asn Trp Val 1 5 10 15

Lys Gly

<210> SEQ ID NO 584
<211> LENGTH: 16
<212> TYPE: PRT
<213> ORGANISM: Oryctolagus cuniculus

<400> SEQUENCE: 584

Val Ile Gly Asn Arg Gly Ser Thr Asp Tyr Ala Ser Trp Ala Lys Gly
1 5 10 15

<210> SEQ ID NO 585
<211> LENGTH: 16
<212> TYPE: PRT
<213> ORGANISM: Oryctolagus cuniculus

<400> SEQUENCE: 585

Thr Ile Tyr Asp Gly Gly Ser Thr Tyr Tyr Ala Ser Trp Thr Lys Gly
1 5 10 15

<210> SEQ ID NO 586
<211> LENGTH: 16
<212> TYPE: PRT
<213> ORGANISM: Oryctolagus cuniculus

<400> SEQUENCE: 586

Ile Ile Asn Ile Ile Asp Asn Thr Tyr Tyr Ala Ser Trp Ala Lys Gly
1 5 10 15

<210> SEQ ID NO 587
<211> LENGTH: 16
<212> TYPE: PRT
<213> ORGANISM: Oryctolagus cuniculus

<400> SEQUENCE: 587

Thr Ile Ser Thr Gly Gly Ser Ala Tyr Tyr Ala Ser Trp Ala Lys Ser
1 5 10 15

<210> SEQ ID NO 588
<211> LENGTH: 15
<212> TYPE: PRT
<213> ORGANISM: Oryctolagus cuniculus

<400> SEQUENCE: 588

Tyr Ile Asn Arg Gly Asn Thr Tyr Tyr Ala Asn Trp Ala Lys Gly
1 5 10 15

<210> SEQ ID NO 589
<211> LENGTH: 18
<212> TYPE: PRT
<213> ORGANISM: Oryctolagus cuniculus

<400> SEQUENCE: 589

Cys Ile His Ala Gly Ser Ser Gly Ser Ala Tyr Tyr Ala Ser Trp Ala
1 5 10 15

Lys Gly

<210> SEQ ID NO 590
<211> LENGTH: 17
<212> TYPE: PRT
<213> ORGANISM: Oryctolagus cuniculus

<400> SEQUENCE: 590

Cys Ile Tyr Gly Gly Asp Gly Asn Thr Tyr Tyr Ala Ser Trp Ala Lys
1 5 10 15

Gly

<210> SEQ ID NO 591
<211> LENGTH: 16
<212> TYPE: PRT
<213> ORGANISM: Oryctolagus cuniculus

<400> SEQUENCE: 591

Tyr Ile Trp Ser Gly Gly Ser Ala Tyr Tyr Ala Ser Trp Ala Lys Gly
1 5 10 15

<210> SEQ ID NO 592
<211> LENGTH: 18
<212> TYPE: PRT
<213> ORGANISM: Oryctolagus cuniculus

<400> SEQUENCE: 592

Cys Ile Tyr Ala Gly Ser Ser Gly Ser Thr Tyr Tyr Ala Ser Trp Ala
1 5 10 15

Lys Gly

<210> SEQ ID NO 593
<211> LENGTH: 14
<212> TYPE: PRT
<213> ORGANISM: Oryctolagus cuniculus

<400> SEQUENCE: 593

Phe Pro Pro Gly Thr Asn Gly Gly Thr Asp Tyr Phe Asn Ile
1 5 10

<210> SEQ ID NO 594
<211> LENGTH: 9
<212> TYPE: PRT
<213> ORGANISM: Oryctolagus cuniculus

<400> SEQUENCE: 594

Asp Ser Gly Trp Gly Ala Phe Asp Pro
1 5

<210> SEQ ID NO 595
<211> LENGTH: 14
<212> TYPE: PRT
<213> ORGANISM: Oryctolagus cuniculus

<400> SEQUENCE: 595

Phe Pro Pro Gly Ser Asn Ser Gly Thr Asp Tyr Phe Asn Ile
1 5 10

<210> SEQ ID NO 596
<211> LENGTH: 7
<212> TYPE: PRT
<213> ORGANISM: Oryctolagus cuniculus

<400> SEQUENCE: 596

Asn Ile Ser Gly Ser Ala Val
1 5

<210> SEQ ID NO 597
<211> LENGTH: 17
<212> TYPE: PRT
<213> ORGANISM: Oryctolagus cuniculus

<400> SEQUENCE: 597

Asp Leu Gly Ala Gly Tyr Ala Gly Tyr Gly Tyr Ala Ser Asp Phe Asn
1 5 10 15

Leu

<210> SEQ ID NO 598
<211> LENGTH: 14
<212> TYPE: PRT
<213> ORGANISM: Oryctolagus cuniculus

<400> SEQUENCE: 598

Phe Pro Pro Gly Ser Asn Ser Gly Thr Asp Tyr Phe Asn Ile
1 5 10

<210> SEQ ID NO 599
<211> LENGTH: 9
<212> TYPE: PRT
<213> ORGANISM: Oryctolagus cuniculus

<400> SEQUENCE: 599

Asp Asn Tyr Asp Trp Tyr Phe Asn Leu
1 5

<210> SEQ ID NO 600
<211> LENGTH: 14
<212> TYPE: PRT
<213> ORGANISM: Oryctolagus cuniculus

<400> SEQUENCE: 600

Phe Pro Pro Gly Ser Asn Ser Gly Thr Asp Tyr Phe Asn Ile
1 5 10

<210> SEQ ID NO 601
<211> LENGTH: 16
<212> TYPE: PRT
<213> ORGANISM: Oryctolagus cuniculus

<400> SEQUENCE: 601

Arg Asp Ala Asp Tyr Val Gly Phe Ile Trp Ala Tyr Tyr Phe Asn Leu
1 5 10 15

<210> SEQ ID NO 602
<211> LENGTH: 8
<212> TYPE: PRT
<213> ORGANISM: Oryctolagus cuniculus

<400> SEQUENCE: 602

Gly Asn Pro Gly Trp Ala Ser Thr
1 5

<210> SEQ ID NO 603
<211> LENGTH: 15
<212> TYPE: PRT
<213> ORGANISM: Oryctolagus cuniculus

<400> SEQUENCE: 603

Gly Val Val Ile Gly Asn Ala Tyr Ser Met Ala His Phe Ser Leu
1 5 10 15

<210> SEQ ID NO 604
<211> LENGTH: 17
<212> TYPE: PRT
<213> ORGANISM: Oryctolagus cuniculus

<400> SEQUENCE: 604

Arg Leu Asn Tyr Val Thr Tyr Pro Ala Tyr Gly Tyr Gly Tyr Phe Asn
1 5 10 15

Leu

<210> SEQ ID NO 605
<211> LENGTH: 11
<212> TYPE: PRT
<213> ORGANISM: Oryctolagus cuniculus

<400> SEQUENCE: 605

Asp Lys Pro Ala Gly Gly Ser Ser Tyr Thr Leu
1 5 10

<210> SEQ ID NO 606
<211> LENGTH: 10
<212> TYPE: PRT
<213> ORGANISM: Oryctolagus cuniculus

<400> SEQUENCE: 606

Gly Gly Gly Ile Ile Tyr Thr Gln Asn Leu
1 5 10

<210> SEQ ID NO 607
<211> LENGTH: 15
<212> TYPE: PRT
<213> ORGANISM: Oryctolagus cuniculus

<400> SEQUENCE: 607

Ala Gly Ser Val Gly Tyr Gly Tyr Asp Thr Ala Tyr Phe Asn Leu
1 5 10 15

<210> SEQ ID NO 608
<211> LENGTH: 9
<212> TYPE: PRT
<213> ORGANISM: Oryctolagus cuniculus

<400> SEQUENCE: 608

Thr Leu Asn Thr Leu Pro Phe Asn Ile
1 5

<210> SEQ ID NO 609
<211> LENGTH: 11
<212> TYPE: PRT
<213> ORGANISM: Oryctolagus cuniculus

<400> SEQUENCE: 609

Asp Leu Gly Asp Asp Gly Tyr Ala Tyr Gly Leu
1 5 10

<210> SEQ ID NO 610
<211> LENGTH: 11
<212> TYPE: PRT
<213> ORGANISM: Oryctolagus cuniculus

<400> SEQUENCE: 610

Gly Thr Gly Ser Ser His Tyr Thr Ser Asn Leu
1 5 10

<210> SEQ ID NO 611
<211> LENGTH: 11
<212> TYPE: PRT
<213> ORGANISM: Oryctolagus cuniculus

<400> SEQUENCE: 611

Asp Leu Asn Gly Ala Asp Ser Gly Ser Ala Leu
1 5 10

<210> SEQ ID NO 612
<211> LENGTH: 11
<212> TYPE: PRT
<213> ORGANISM: Oryctolagus cuniculus

<400> SEQUENCE: 612

Gly Gly Asp Ala Asp Asn Phe Tyr Tyr Asn Ile
1 5 10

<210> SEQ ID NO 613
<211> LENGTH: 14
<212> TYPE: PRT
<213> ORGANISM: Oryctolagus cuniculus

<400> SEQUENCE: 613

Asp Phe Tyr Ala Gly Ser Ser Gly Asn Val Asn Gly Asp Ile
1 5 10

<210> SEQ ID NO 614
<211> LENGTH: 14
<212> TYPE: PRT
<213> ORGANISM: Oryctolagus cuniculus

<400> SEQUENCE: 614

Phe Pro Pro Gly Ser Asn Gly Gly Thr Ala Tyr Phe Asn Ile
1 5 10

<210> SEQ ID NO 615
<211> LENGTH: 9
<212> TYPE: PRT
<213> ORGANISM: Oryctolagus cuniculus

<400> SEQUENCE: 615

Asp Ser Gly Trp Gly Ala Phe Asp Pro
1 5

<210> SEQ ID NO 616
<211> LENGTH: 9
<212> TYPE: PRT
<213> ORGANISM: Oryctolagus cuniculus

<400> SEQUENCE: 616

Asp Ser Gly Trp Gly Ala Phe Asp Pro
1 5

<210> SEQ ID NO 617
<211> LENGTH: 7
<212> TYPE: PRT
<213> ORGANISM: Oryctolagus cuniculus

<400> SEQUENCE: 617

Gly Tyr Ser Asp Ile Asp Ile
1 5

<210> SEQ ID NO 618
<211> LENGTH: 14
<212> TYPE: PRT
<213> ORGANISM: Oryctolagus cuniculus

<400> SEQUENCE: 618

```
Phe Pro Pro Gly Ser Asn Gly Gly Thr Ala Tyr Phe Asn Ile
1               5                   10


<210> SEQ ID NO 619
<211> LENGTH: 15
<212> TYPE: PRT
<213> ORGANISM: Oryctolagus cuniculus

<400> SEQUENCE: 619

Gly Leu Gly Arg Gly Glu Tyr Thr Ser Asn Asp Ala Phe Asp Pro
1               5                   10                  15


<210> SEQ ID NO 620
<211> LENGTH: 10
<212> TYPE: PRT
<213> ORGANISM: Oryctolagus cuniculus

<400> SEQUENCE: 620

Gly Ser Ser Asp Glu Ile Ala Leu Asp Leu
1               5                   10


<210> SEQ ID NO 621
<211> LENGTH: 13
<212> TYPE: PRT
<213> ORGANISM: Oryctolagus cuniculus

<400> SEQUENCE: 621

Gly Pro Tyr Tyr Val Gly Ser Glu Tyr Val Phe Asp Pro
1               5                   10


<210> SEQ ID NO 622
<211> LENGTH: 13
<212> TYPE: PRT
<213> ORGANISM: Oryctolagus cuniculus

<400> SEQUENCE: 622

Met Phe Tyr Ala Gly Asp Ser Gly His Tyr Leu His Leu
1               5                   10


<210> SEQ ID NO 623
<211> LENGTH: 3
<212> TYPE: PRT
<213> ORGANISM: Oryctolagus cuniculus

<400> SEQUENCE: 623

Asn Asn Leu
1


<210> SEQ ID NO 624
<211> LENGTH: 11
<212> TYPE: PRT
<213> ORGANISM: Oryctolagus cuniculus

<400> SEQUENCE: 624

Gly Gly Tyr Ser Tyr Gly Gly Ala Val Ser Leu
1               5                   10


<210> SEQ ID NO 625
<211> LENGTH: 11
<212> TYPE: PRT
<213> ORGANISM: Oryctolagus cuniculus

<400> SEQUENCE: 625

Gly Arg Ser Gly Gly Trp Asp Ala Leu Asp Pro
```

1 5 10

<210> SEQ ID NO 626
<211> LENGTH: 13
<212> TYPE: PRT
<213> ORGANISM: Oryctolagus cuniculus

<400> SEQUENCE: 626

Glu Asp Tyr Ala Gly Gly Thr Asp Tyr Tyr Phe Arg Leu
1 5 10

<210> SEQ ID NO 627
<211> LENGTH: 11
<212> TYPE: PRT
<213> ORGANISM: Oryctolagus cuniculus

<400> SEQUENCE: 627

Gly Gly Asp Ala Asp Asn Phe Tyr Tyr Asn Ile
1 5 10

<210> SEQ ID NO 628
<211> LENGTH: 14
<212> TYPE: PRT
<213> ORGANISM: Oryctolagus cuniculus

<400> SEQUENCE: 628

Asp Phe Tyr Ala Gly Ser Ser Gly Asn Val Asn Gly Asp Ile
1 5 10

<210> SEQ ID NO 629
<211> LENGTH: 7
<212> TYPE: PRT
<213> ORGANISM: Oryctolagus cuniculus

<400> SEQUENCE: 629

Glu Leu Asp Tyr Phe Asn Leu
1 5

<210> SEQ ID NO 630
<211> LENGTH: 14
<212> TYPE: PRT
<213> ORGANISM: Oryctolagus cuniculus

<400> SEQUENCE: 630

Asp Phe Tyr Ala Gly Ser Ser Gly Asn Val Asn Gly Asp Ile
1 5 10

<210> SEQ ID NO 631
<211> LENGTH: 10
<212> TYPE: PRT
<213> ORGANISM: Oryctolagus cuniculus

<400> SEQUENCE: 631

Gly Ala Gly Ser Asn Gly Asp Phe Asn Leu
1 5 10

<210> SEQ ID NO 632
<211> LENGTH: 11
<212> TYPE: PRT
<213> ORGANISM: Oryctolagus cuniculus

<400> SEQUENCE: 632

Gly Ala Gly Ser Tyr Gly Gly Ala Val Arg Leu
1 5 10

<210> SEQ ID NO 633
<211> LENGTH: 12
<212> TYPE: PRT
<213> ORGANISM: Oryctolagus cuniculus

<400> SEQUENCE: 633

Asp Gly Tyr Asp Asp Tyr Gly Asp Pro Phe Asn Leu
1 5 10

<210> SEQ ID NO 634
<211> LENGTH: 13
<212> TYPE: PRT
<213> ORGANISM: Oryctolagus cuniculus

<400> SEQUENCE: 634

Ile Ser Ala Gly Ser Asp Ser Tyr Ile Ile Asp Asn Ile
1 5 10

<210> SEQ ID NO 635
<211> LENGTH: 11
<212> TYPE: PRT
<213> ORGANISM: Oryctolagus cuniculus

<400> SEQUENCE: 635

Asp Ala Gly Asn Ser Gly Tyr Tyr Ile Asn Leu
1 5 10

<210> SEQ ID NO 636
<211> LENGTH: 4
<212> TYPE: PRT
<213> ORGANISM: Oryctolagus cuniculus

<400> SEQUENCE: 636

Leu Tyr Lys Leu
1

<210> SEQ ID NO 637
<211> LENGTH: 11
<212> TYPE: PRT
<213> ORGANISM: Oryctolagus cuniculus

<400> SEQUENCE: 637

Pro Tyr Val Gly Tyr Gly Tyr Ala Thr Asp Leu
1 5 10

<210> SEQ ID NO 638
<211> LENGTH: 11
<212> TYPE: PRT
<213> ORGANISM: Oryctolagus cuniculus

<400> SEQUENCE: 638

Asp Ser Tyr Ala Gly Asp Tyr Ala Phe Asn Leu
1 5 10

<210> SEQ ID NO 639
<211> LENGTH: 9
<212> TYPE: PRT
<213> ORGANISM: Oryctolagus cuniculus

<400> SEQUENCE: 639

Thr His Asn Thr Leu Pro Phe Tyr Ile
1 5

<210> SEQ ID NO 640

<211> LENGTH: 10
<212> TYPE: PRT
<213> ORGANISM: Oryctolagus cuniculus

<400> SEQUENCE: 640

Gly Ser Gly Gly Ser Asp Tyr Phe Asn Leu
1 5 10

<210> SEQ ID NO 641
<211> LENGTH: 11
<212> TYPE: PRT
<213> ORGANISM: Oryctolagus cuniculus

<400> SEQUENCE: 641

Asp Leu Gly Ala Asp Gly Tyr Ala Tyr His Leu
1 5 10

<210> SEQ ID NO 642
<211> LENGTH: 13
<212> TYPE: PRT
<213> ORGANISM: Oryctolagus cuniculus

<400> SEQUENCE: 642

Asp Pro Ile Tyr Asp Asp Tyr Gly Gly Arg Leu Asp Leu
1 5 10

<210> SEQ ID NO 643
<211> LENGTH: 14
<212> TYPE: PRT
<213> ORGANISM: Oryctolagus cuniculus

<400> SEQUENCE: 643

Phe Pro Pro Gly Ser Asn Gly Gly Thr Asp Tyr Phe Asn Ile
1 5 10

<210> SEQ ID NO 644
<211> LENGTH: 11
<212> TYPE: PRT
<213> ORGANISM: Oryctolagus cuniculus

<400> SEQUENCE: 644

Asp Ser Tyr Ala Gly Asp Tyr Ala Phe Asn Leu
1 5 10

<210> SEQ ID NO 645
<211> LENGTH: 9
<212> TYPE: PRT
<213> ORGANISM: Oryctolagus cuniculus

<400> SEQUENCE: 645

Ala Arg Asn Thr Leu Pro Phe Asn Ile
1 5

<210> SEQ ID NO 646
<211> LENGTH: 14
<212> TYPE: PRT
<213> ORGANISM: Oryctolagus cuniculus

<400> SEQUENCE: 646

Gly Leu Tyr Ser Ala Ser Gly Trp Ser Tyr Cys Phe Asp Ile
1 5 10

<210> SEQ ID NO 647
<211> LENGTH: 13
<212> TYPE: PRT

<213> ORGANISM: Oryctolagus cuniculus

<400> SEQUENCE: 647

Phe Asp Phe Leu Val Gly Leu Thr Tyr Ala Gly Val Leu
1 5 10

<210> SEQ ID NO 648
<211> LENGTH: 13
<212> TYPE: PRT
<213> ORGANISM: Oryctolagus cuniculus

<400> SEQUENCE: 648

Asn Gly Ala Ser Gly Thr Tyr Tyr Ser Ser Leu Tyr Ile
1 5 10

<210> SEQ ID NO 649
<211> LENGTH: 14
<212> TYPE: PRT
<213> ORGANISM: Oryctolagus cuniculus

<400> SEQUENCE: 649

Phe Pro Pro Gly Ser Asn Ser Gly Thr Asp Tyr Phe Asn Ile
1 5 10

<210> SEQ ID NO 650
<211> LENGTH: 6
<212> TYPE: PRT
<213> ORGANISM: Oryctolagus cuniculus

<400> SEQUENCE: 650

Gly Ser Gly Trp Asp Leu
1 5

<210> SEQ ID NO 651
<211> LENGTH: 11
<212> TYPE: PRT
<213> ORGANISM: Oryctolagus cuniculus

<400> SEQUENCE: 651

Gly Leu Gly Ala Ala Ser Ala Thr Trp Asp Ile
1 5 10

<210> SEQ ID NO 652
<211> LENGTH: 11
<212> TYPE: PRT
<213> ORGANISM: Oryctolagus cuniculus

<400> SEQUENCE: 652

Asp Lys Ala Gly Asp Ser Tyr Tyr Phe Asn Leu
1 5 10

<210> SEQ ID NO 653
<211> LENGTH: 7
<212> TYPE: PRT
<213> ORGANISM: Oryctolagus cuniculus

<400> SEQUENCE: 653

Gly Val Ala Val Gly Asp Ile
1 5

<210> SEQ ID NO 654
<211> LENGTH: 7
<212> TYPE: PRT
<213> ORGANISM: Oryctolagus cuniculus

<400> SEQUENCE: 654

Gly Ile Leu Val Ser Asp Leu
1               5

<210> SEQ ID NO 655
<211> LENGTH: 13
<212> TYPE: PRT
<213> ORGANISM: Oryctolagus cuniculus

<400> SEQUENCE: 655

Gly Pro Ile Met Val Val Ser Pro Ser Tyr Phe Asn Phe
1               5                   10

<210> SEQ ID NO 656
<211> LENGTH: 15
<212> TYPE: PRT
<213> ORGANISM: Oryctolagus cuniculus

<400> SEQUENCE: 656

Ser Tyr Tyr Ser Gly Gly Tyr Lys Tyr Val Tyr Val Phe Asp Leu
1               5                   10                  15

<210> SEQ ID NO 657
<211> LENGTH: 7
<212> TYPE: PRT
<213> ORGANISM: Oryctolagus cuniculus

<400> SEQUENCE: 657

Gly Ile Ala Val Ala Ser Leu
1               5

<210> SEQ ID NO 658
<211> LENGTH: 9
<212> TYPE: PRT
<213> ORGANISM: Oryctolagus cuniculus

<400> SEQUENCE: 658

Leu Asp Thr Tyr Asp Asp Tyr Asp Leu
1               5

<210> SEQ ID NO 659
<211> LENGTH: 13
<212> TYPE: PRT
<213> ORGANISM: Oryctolagus cuniculus

<400> SEQUENCE: 659

Met Phe Tyr Ala Gly Asp Ser Gly His Tyr Phe Asp Leu
1               5                   10

<210> SEQ ID NO 660
<211> LENGTH: 16
<212> TYPE: PRT
<213> ORGANISM: Oryctolagus cuniculus

<400> SEQUENCE: 660

Asp Ser Asp Tyr Asp Asp Tyr Gly Asn Ser Tyr Tyr Gly Met Asp Pro
1               5                   10                  15

<210> SEQ ID NO 661
<211> LENGTH: 11
<212> TYPE: PRT
<213> ORGANISM: Oryctolagus cuniculus

<400> SEQUENCE: 661

Glu Tyr Val Gly Ser Gln Gly Tyr Phe Asn Leu
1 5 10

<210> SEQ ID NO 662
<211> LENGTH: 13
<212> TYPE: PRT
<213> ORGANISM: Oryctolagus cuniculus

<400> SEQUENCE: 662

Phe Asp Tyr Leu Val Gly Gly Thr Trp Ala Gly Val Leu
1 5 10

<210> SEQ ID NO 663
<211> LENGTH: 12
<212> TYPE: PRT
<213> ORGANISM: Oryctolagus cuniculus

<400> SEQUENCE: 663

Gly Val Gly Asp Thr Thr Asp Thr Gln Leu Asp Leu
1 5 10

<210> SEQ ID NO 664
<211> LENGTH: 10
<212> TYPE: PRT
<213> ORGANISM: Oryctolagus cuniculus

<400> SEQUENCE: 664

Asp Pro Ser Ala Trp Gly Gly Leu Asp Leu
1 5 10

<210> SEQ ID NO 665
<211> LENGTH: 10
<212> TYPE: PRT
<213> ORGANISM: Oryctolagus cuniculus

<400> SEQUENCE: 665

Tyr Asn Asn Gly Trp Asp Tyr Phe Asn Leu
1 5 10

<210> SEQ ID NO 666
<211> LENGTH: 3
<212> TYPE: PRT
<213> ORGANISM: Oryctolagus cuniculus

<400> SEQUENCE: 666

Gly Ser Leu
1

<210> SEQ ID NO 667
<211> LENGTH: 14
<212> TYPE: PRT
<213> ORGANISM: Oryctolagus cuniculus

<400> SEQUENCE: 667

Arg Tyr Gly Ala Gly Ser Gly Tyr Phe Ile Ser Pro Asn Leu
1 5 10

<210> SEQ ID NO 668
<211> LENGTH: 11
<212> TYPE: PRT
<213> ORGANISM: Oryctolagus cuniculus

<400> SEQUENCE: 668

Glu Tyr Val Asp Ser Gln Gly Tyr Phe Asn Leu
1 5 10

<210> SEQ ID NO 669
<211> LENGTH: 11
<212> TYPE: PRT
<213> ORGANISM: Oryctolagus cuniculus

<400> SEQUENCE: 669

Gly Arg Ser Gly Gly Trp Asp Ala Phe Asp Pro
1 5 10

<210> SEQ ID NO 670
<211> LENGTH: 3
<212> TYPE: PRT
<213> ORGANISM: Oryctolagus cuniculus

<400> SEQUENCE: 670

Phe Asp Ile
1

<210> SEQ ID NO 671
<211> LENGTH: 11
<212> TYPE: PRT
<213> ORGANISM: Oryctolagus cuniculus

<400> SEQUENCE: 671

Asp Thr Gly Asn Ser Asn Tyr Gln Phe Asn Leu
1 5 10

<210> SEQ ID NO 672
<211> LENGTH: 17
<212> TYPE: PRT
<213> ORGANISM: Oryctolagus cuniculus

<400> SEQUENCE: 672

Asp Asp Val Ser Val Gly Asp Ala Asn Tyr Pro Tyr Thr Ala Phe Asp
1 5 10 15

Leu

<210> SEQ ID NO 673
<211> LENGTH: 12
<212> TYPE: PRT
<213> ORGANISM: Oryctolagus cuniculus

<400> SEQUENCE: 673

Glu Ala Tyr Ser Ser Ala Asn Ser Tyr Tyr Asp Leu
1 5 10

<210> SEQ ID NO 674
<211> LENGTH: 12
<212> TYPE: PRT
<213> ORGANISM: Oryctolagus cuniculus

<400> SEQUENCE: 674

Asp Pro Thr Ala Ala Gly Gly Val Tyr Phe Asp Leu
1 5 10

<210> SEQ ID NO 675
<211> LENGTH: 9
<212> TYPE: PRT
<213> ORGANISM: Oryctolagus cuniculus

<400> SEQUENCE: 675

Gly Ser Gly Tyr Ser Lys Phe Arg Leu
1 5

<210> SEQ ID NO 676
<211> LENGTH: 9
<212> TYPE: PRT
<213> ORGANISM: Oryctolagus cuniculus

<400> SEQUENCE: 676

Asp Arg Gly Asp Thr Asp Ile Ser Leu
1               5

<210> SEQ ID NO 677
<211> LENGTH: 13
<212> TYPE: PRT
<213> ORGANISM: Oryctolagus cuniculus

<400> SEQUENCE: 677

Gly Pro Tyr Tyr Val Asn Asn Glu Asn Val Phe Asp Pro
1               5                   10

<210> SEQ ID NO 678
<211> LENGTH: 11
<212> TYPE: PRT
<213> ORGANISM: Oryctolagus cuniculus

<400> SEQUENCE: 678

Ser Tyr Ala Gly Asn Arg Tyr Asp Phe Ala Ile
1               5                   10

<210> SEQ ID NO 679
<211> LENGTH: 7
<212> TYPE: PRT
<213> ORGANISM: Oryctolagus cuniculus

<400> SEQUENCE: 679

Gly Pro Tyr Ser Phe Asp Phe
1               5

<210> SEQ ID NO 680
<211> LENGTH: 12
<212> TYPE: PRT
<213> ORGANISM: Oryctolagus cuniculus

<400> SEQUENCE: 680

Gly Asp Ala Tyr Arg Asp Asp Tyr Ala Ser Asp Leu
1               5                   10

<210> SEQ ID NO 681
<211> LENGTH: 12
<212> TYPE: PRT
<213> ORGANISM: Oryctolagus cuniculus

<400> SEQUENCE: 681

Tyr Ile Gly Ser Val Gly Tyr Arg Arg Met Asp Ile
1               5                   10

<210> SEQ ID NO 682
<211> LENGTH: 13
<212> TYPE: PRT
<213> ORGANISM: Oryctolagus cuniculus

<400> SEQUENCE: 682

Met Phe Tyr Ala Gly Asp Ser Gly His Tyr Phe Asp Leu
1               5                   10

<210> SEQ ID NO 683
<211> LENGTH: 13
<212> TYPE: PRT
<213> ORGANISM: Oryctolagus cuniculus

<400> SEQUENCE: 683

Asn Gly Ala Gly Gly Tyr Tyr Tyr Ser Ser Leu Tyr Ile
1 5 10

<210> SEQ ID NO 684
<211> LENGTH: 9
<212> TYPE: PRT
<213> ORGANISM: Oryctolagus cuniculus

<400> SEQUENCE: 684

Asp Arg Gly Gly Thr Asp Ile Ser Leu
1 5

<210> SEQ ID NO 685
<211> LENGTH: 11
<212> TYPE: PRT
<213> ORGANISM: Oryctolagus cuniculus

<400> SEQUENCE: 685

Ser Ser Ser Thr Tyr Ala Tyr Gly Phe Asp Pro
1 5 10

<210> SEQ ID NO 686
<211> LENGTH: 9
<212> TYPE: PRT
<213> ORGANISM: Oryctolagus cuniculus

<400> SEQUENCE: 686

Lys Gly Tyr Phe His Tyr Phe Asn Leu
1 5

<210> SEQ ID NO 687
<211> LENGTH: 11
<212> TYPE: PRT
<213> ORGANISM: Oryctolagus cuniculus

<400> SEQUENCE: 687

Asp Arg Ala Gly Asn Ser Tyr Tyr Phe Asn Leu
1 5 10

<210> SEQ ID NO 688
<211> LENGTH: 4
<212> TYPE: PRT
<213> ORGANISM: Oryctolagus cuniculus

<400> SEQUENCE: 688

Val Trp Ser Leu
1

<210> SEQ ID NO 689
<211> LENGTH: 11
<212> TYPE: PRT
<213> ORGANISM: Oryctolagus cuniculus

<400> SEQUENCE: 689

Gly Tyr Asp Gly Tyr Gly Tyr Val Leu Val Leu
1 5 10

<210> SEQ ID NO 690
<211> LENGTH: 12

<212> TYPE: PRT
<213> ORGANISM: Oryctolagus cuniculus

<400> SEQUENCE: 690

Asp Pro Thr Ala Ala Gly Gly Val Tyr Phe Asp Leu
1 5 10

<210> SEQ ID NO 691
<211> LENGTH: 14
<212> TYPE: PRT
<213> ORGANISM: Oryctolagus cuniculus

<400> SEQUENCE: 691

Gly Ser Gly Ser Ile Tyr Tyr Thr Pro Ser Tyr Phe Asp Leu
1 5 10

<210> SEQ ID NO 692
<211> LENGTH: 3
<212> TYPE: PRT
<213> ORGANISM: Oryctolagus cuniculus

<400> SEQUENCE: 692

Ser Asp Ile
1

<210> SEQ ID NO 693
<211> LENGTH: 10
<212> TYPE: PRT
<213> ORGANISM: Oryctolagus cuniculus

<400> SEQUENCE: 693

Asp Asp Lys Val Glu His Gly Tyr Gly Leu
1 5 10

<210> SEQ ID NO 694
<211> LENGTH: 19
<212> TYPE: PRT
<213> ORGANISM: Oryctolagus cuniculus

<400> SEQUENCE: 694

Ser Met Glu Ala Tyr Gly Tyr Ala Gly Tyr Ala Met Pro Gly Tyr Tyr
1 5 10 15

Phe Asn Leu

<210> SEQ ID NO 695
<211> LENGTH: 16
<212> TYPE: PRT
<213> ORGANISM: Oryctolagus cuniculus

<400> SEQUENCE: 695

Asp Ser Asp Tyr Asp Asp Tyr Gly Asp Ser Tyr Tyr Gly Met Asp Pro
1 5 10 15

<210> SEQ ID NO 696
<211> LENGTH: 18
<212> TYPE: PRT
<213> ORGANISM: Oryctolagus cuniculus

<400> SEQUENCE: 696

Asp Tyr Asp Thr Tyr Asp Tyr Asp Gly Tyr Thr Tyr Ala Ala Gly Phe
1 5 10 15

Asp Leu

<210> SEQ ID NO 697
<211> LENGTH: 11
<212> TYPE: PRT
<213> ORGANISM: Oryctolagus cuniculus

<400> SEQUENCE: 697

Gly Leu Gly Gly Ala Ser Thr Thr Trp Asp Ile
1 5 10

<210> SEQ ID NO 698
<211> LENGTH: 14
<212> TYPE: PRT
<213> ORGANISM: Oryctolagus cuniculus

<400> SEQUENCE: 698

Asp Ile Ile Thr Asp Ser Val Trp Ile Thr Arg Leu Asp Leu
1 5 10

<210> SEQ ID NO 699
<211> LENGTH: 13
<212> TYPE: PRT
<213> ORGANISM: Oryctolagus cuniculus

<400> SEQUENCE: 699

Phe Asp Tyr Leu Val Gly Asp Thr Tyr Ala Gly Val Leu
1 5 10

<210> SEQ ID NO 700
<211> LENGTH: 14
<212> TYPE: PRT
<213> ORGANISM: Oryctolagus cuniculus

<400> SEQUENCE: 700

Met Phe Tyr Ala Gly Asp Ser Ser Gly Asn Tyr Leu His Leu
1 5 10

<210> SEQ ID NO 701
<211> LENGTH: 12
<212> TYPE: PRT
<213> ORGANISM: Oryctolagus cuniculus

<400> SEQUENCE: 701

Glu Gly Ser Ser Ala Tyr Pro Ser Tyr Phe Asn Phe
1 5 10

<210> SEQ ID NO 702
<211> LENGTH: 11
<212> TYPE: PRT
<213> ORGANISM: Oryctolagus cuniculus

<400> SEQUENCE: 702

Ser Tyr Gly Gly Asn Arg Tyr Asp Phe Asn Ile
1 5 10

<210> SEQ ID NO 703
<211> LENGTH: 14
<212> TYPE: PRT
<213> ORGANISM: Oryctolagus cuniculus

<400> SEQUENCE: 703

Met Phe Tyr Ala Gly His Thr Ser Gly His Tyr Phe Asp Leu
1 5 10

<210> SEQ ID NO 704
<211> LENGTH: 21

<212> TYPE: PRT
<213> ORGANISM: Oryctolagus cuniculus

<400> SEQUENCE: 704

Gly Phe Asp Tyr Thr Tyr Gly Asp Ala Gly Tyr Thr Tyr Ser Thr Ser
1 5 10 15

His Tyr Phe Asn Leu
20

<210> SEQ ID NO 705
<211> LENGTH: 11
<212> TYPE: PRT
<213> ORGANISM: Oryctolagus cuniculus

<400> SEQUENCE: 705

Glu Gly Ala Asp Tyr Gln Gly His Phe Asn Leu
1 5 10

<210> SEQ ID NO 706
<211> LENGTH: 16
<212> TYPE: PRT
<213> ORGANISM: Oryctolagus cuniculus

<400> SEQUENCE: 706

Asp Ser Asp Tyr Asp Asp Tyr Gly Asn Ser Tyr Tyr Gly Met Asp Pro
1 5 10 15

<210> SEQ ID NO 707
<211> LENGTH: 14
<212> TYPE: PRT
<213> ORGANISM: Oryctolagus cuniculus

<400> SEQUENCE: 707

Glu Ile Gly Ser Gly Tyr Asp Ala Pro Tyr Tyr Phe Asn Leu
1 5 10

<210> SEQ ID NO 708
<211> LENGTH: 10
<212> TYPE: PRT
<213> ORGANISM: Oryctolagus cuniculus

<400> SEQUENCE: 708

Asp Asp Arg Val Glu His Gly Tyr Gly Leu
1 5 10

<210> SEQ ID NO 709
<211> LENGTH: 11
<212> TYPE: PRT
<213> ORGANISM: Oryctolagus cuniculus

<400> SEQUENCE: 709

Asp Leu Ser Ser Ser Ile Tyr Asp Met Asp Leu
1 5 10

<210> SEQ ID NO 710
<211> LENGTH: 12
<212> TYPE: PRT
<213> ORGANISM: Oryctolagus cuniculus

<400> SEQUENCE: 710

Val Leu Asn Gly Trp Gly Glu Tyr Tyr Phe Asn Leu
1 5 10

<210> SEQ ID NO 711

-continued

<211> LENGTH: 7
<212> TYPE: PRT
<213> ORGANISM: Oryctolagus cuniculus

<400> SEQUENCE: 711

Gly Val Ala Ala Gly Asp Ile
1 5

<210> SEQ ID NO 712
<211> LENGTH: 7
<212> TYPE: PRT
<213> ORGANISM: Oryctolagus cuniculus

<400> SEQUENCE: 712

Asn Ile Ser Gly Ser Ala Val
1 5

<210> SEQ ID NO 713
<211> LENGTH: 11
<212> TYPE: PRT
<213> ORGANISM: Oryctolagus cuniculus

<400> SEQUENCE: 713

Gly Gly Asp Gly Tyr Gly Tyr Val Leu Val Leu
1 5 10

<210> SEQ ID NO 714
<211> LENGTH: 7
<212> TYPE: PRT
<213> ORGANISM: Oryctolagus cuniculus

<400> SEQUENCE: 714

Gly Ile Ser Tyr Ala Leu Leu
1 5

<210> SEQ ID NO 715
<211> LENGTH: 10
<212> TYPE: PRT
<213> ORGANISM: Oryctolagus cuniculus

<400> SEQUENCE: 715

Gly Gly Val Gly His Glu Val Asn Asn Leu
1 5 10

<210> SEQ ID NO 716
<211> LENGTH: 12
<212> TYPE: PRT
<213> ORGANISM: Oryctolagus cuniculus

<400> SEQUENCE: 716

Lys Leu Ser Asp Trp Asp Tyr Gly Tyr Phe Asn Leu
1 5 10

<210> SEQ ID NO 717
<211> LENGTH: 18
<212> TYPE: PRT
<213> ORGANISM: Oryctolagus cuniculus

<400> SEQUENCE: 717

Gly Tyr Ala Gly Tyr Tyr Gly Tyr Gly Tyr Pro Thr Pro Ser Trp Leu
1 5 10 15

Asp Leu

<210> SEQ ID NO 718

<211> LENGTH: 13
<212> TYPE: PRT
<213> ORGANISM: Oryctolagus cuniculus

<400> SEQUENCE: 718

Gly Gly Thr Thr Gly Ser Asn Tyr Tyr Gly Met Asp Pro
1 5 10

<210> SEQ ID NO 719
<211> LENGTH: 4
<212> TYPE: PRT
<213> ORGANISM: Oryctolagus cuniculus

<400> SEQUENCE: 719

Gly Ile Arg Phe
1

<210> SEQ ID NO 720
<211> LENGTH: 17
<212> TYPE: PRT
<213> ORGANISM: Oryctolagus cuniculus

<400> SEQUENCE: 720

Val Leu Gly Ala Gly Ser Ser Tyr Tyr Thr Ser Tyr Asp Arg Leu Asp
1 5 10 15

Leu

<210> SEQ ID NO 721
<211> LENGTH: 10
<212> TYPE: PRT
<213> ORGANISM: Oryctolagus cuniculus

<400> SEQUENCE: 721

Ile Ala Asp Val Asn Thr Gln Leu Asp Leu
1 5 10

<210> SEQ ID NO 722
<211> LENGTH: 11
<212> TYPE: PRT
<213> ORGANISM: Oryctolagus cuniculus

<400> SEQUENCE: 722

Gly Ala Gly Tyr Ala Gly Tyr Gly Phe Asn Leu
1 5 10

<210> SEQ ID NO 723
<211> LENGTH: 15
<212> TYPE: PRT
<213> ORGANISM: Oryctolagus cuniculus

<400> SEQUENCE: 723

Gly Asn Ala Gly Ser Tyr Trp Asp Ile Tyr Tyr Gly Met Asp Leu
1 5 10 15

<210> SEQ ID NO 724
<211> LENGTH: 10
<212> TYPE: PRT
<213> ORGANISM: Oryctolagus cuniculus

<400> SEQUENCE: 724

Gly Ser Gly Gly Tyr Phe Val Asp Asn Leu
1 5 10

<210> SEQ ID NO 725

<211> LENGTH: 13
<212> TYPE: PRT
<213> ORGANISM: Oryctolagus cuniculus

<400> SEQUENCE: 725

Met Phe Tyr Ala Gly Asp Ser Gly His Tyr Phe Asp Leu
1 5 10

<210> SEQ ID NO 726
<211> LENGTH: 12
<212> TYPE: PRT
<213> ORGANISM: Oryctolagus cuniculus

<400> SEQUENCE: 726

Asp His Pro Ala Phe Ser Thr Val Asp Leu Asp Ile
1 5 10

<210> SEQ ID NO 727
<211> LENGTH: 11
<212> TYPE: PRT
<213> ORGANISM: Oryctolagus cuniculus

<400> SEQUENCE: 727

Asp Ala Gly Ser Ser Gly Tyr Tyr Ile Asn Leu
1 5 10

<210> SEQ ID NO 728
<211> LENGTH: 10
<212> TYPE: PRT
<213> ORGANISM: Oryctolagus cuniculus

<400> SEQUENCE: 728

Tyr Asn Asn Gly Trp Asp Tyr Phe Asn Leu
1 5 10

<210> SEQ ID NO 729
<211> LENGTH: 11
<212> TYPE: PRT
<213> ORGANISM: Oryctolagus cuniculus

<400> SEQUENCE: 729

His Lys Pro Ala Gly Gly Ser Ser Tyr Ile Leu
1 5 10

<210> SEQ ID NO 730
<211> LENGTH: 7
<212> TYPE: PRT
<213> ORGANISM: Oryctolagus cuniculus

<400> SEQUENCE: 730

Gly Ile Leu Val Ser Asn Leu
1 5

<210> SEQ ID NO 731
<211> LENGTH: 7
<212> TYPE: PRT
<213> ORGANISM: Oryctolagus cuniculus

<400> SEQUENCE: 731

Gly Thr Tyr Pro Phe Thr Leu
1 5

<210> SEQ ID NO 732
<211> LENGTH: 13
<212> TYPE: PRT

<213> ORGANISM: Oryctolagus cuniculus

<400> SEQUENCE: 732

Gly Ser Gly Tyr Gly Thr Gly Trp Asp Ala Phe Asp Pro
1 5 10

<210> SEQ ID NO 733
<211> LENGTH: 9
<212> TYPE: PRT
<213> ORGANISM: Oryctolagus cuniculus

<400> SEQUENCE: 733

Gly Ser Thr Asn Met Glu Phe Trp Phe
1 5

<210> SEQ ID NO 734
<211> LENGTH: 14
<212> TYPE: PRT
<213> ORGANISM: Oryctolagus cuniculus

<400> SEQUENCE: 734

Ala Asp Tyr Tyr Pro Asp Thr Thr Gly Trp Tyr Leu Asn Ile
1 5 10

<210> SEQ ID NO 735
<211> LENGTH: 8
<212> TYPE: PRT
<213> ORGANISM: Oryctolagus cuniculus

<400> SEQUENCE: 735

Asp Gly Asp Ser Tyr Phe Lys Leu
1 5

<210> SEQ ID NO 736
<211> LENGTH: 11
<212> TYPE: PRT
<213> ORGANISM: Oryctolagus cuniculus

<400> SEQUENCE: 736

Asp Ser Tyr Gly Gly Asp Tyr Ala Phe Asn Leu
1 5 10

<210> SEQ ID NO 737
<211> LENGTH: 12
<212> TYPE: PRT
<213> ORGANISM: Oryctolagus cuniculus

<400> SEQUENCE: 737

Asp Gly Tyr Asp Asp Tyr Gly Asp Pro Phe Asn Leu
1 5 10

<210> SEQ ID NO 738
<211> LENGTH: 18
<212> TYPE: PRT
<213> ORGANISM: Oryctolagus cuniculus

<400> SEQUENCE: 738

Leu His Tyr Ser Pro Tyr Gly Asp Ala Gly Tyr Pro Tyr Val Ser Phe
1 5 10 15

Asn Leu

<210> SEQ ID NO 739
<211> LENGTH: 9
<212> TYPE: PRT

<213> ORGANISM: Oryctolagus cuniculus

<400> SEQUENCE: 739

Asn Gly Ala Ser Gly Thr Phe Asp Ile
1 5

<210> SEQ ID NO 740
<211> LENGTH: 11
<212> TYPE: PRT
<213> ORGANISM: Oryctolagus cuniculus

<400> SEQUENCE: 740

Gly Gly Gly Ser Gly Gly Val Asp Asn Asn Leu
1 5 10

<210> SEQ ID NO 741
<211> LENGTH: 13
<212> TYPE: PRT
<213> ORGANISM: Oryctolagus cuniculus

<400> SEQUENCE: 741

Gln Ala Ser Gln Ser Leu Tyr Asn Asn Lys Asn Leu Ala
1 5 10

<210> SEQ ID NO 742
<211> LENGTH: 13
<212> TYPE: PRT
<213> ORGANISM: Oryctolagus cuniculus

<400> SEQUENCE: 742

Gln Ser Ser Gln Ser Val Tyr Asp Lys Lys Trp Leu Gly
1 5 10

<210> SEQ ID NO 743
<211> LENGTH: 13
<212> TYPE: PRT
<213> ORGANISM: Oryctolagus cuniculus

<400> SEQUENCE: 743

Gln Ala Ser Gln Ser Leu Tyr Asn Asn Lys Asn Leu Ala
1 5 10

<210> SEQ ID NO 744
<211> LENGTH: 13
<212> TYPE: PRT
<213> ORGANISM: Oryctolagus cuniculus

<400> SEQUENCE: 744

Gln Ser Ser Glu Ser Val Tyr Asn Asn Asn Leu Leu Ser
1 5 10

<210> SEQ ID NO 745
<211> LENGTH: 11
<212> TYPE: PRT
<213> ORGANISM: Oryctolagus cuniculus

<400> SEQUENCE: 745

Gln Ala Ser Gln Ser Val Ser Asn Leu Leu Ala
1 5 10

<210> SEQ ID NO 746
<211> LENGTH: 13
<212> TYPE: PRT
<213> ORGANISM: Oryctolagus cuniculus

<400> SEQUENCE: 746

Gln Ala Ser Gln Ser Leu Tyr Asn Asn Lys Asn Leu Ala
1 5 10

<210> SEQ ID NO 747
<211> LENGTH: 11
<212> TYPE: PRT
<213> ORGANISM: Oryctolagus cuniculus

<400> SEQUENCE: 747

Gln Ala Ser Glu Asp Ile Glu Ser Tyr Leu Ala
1 5 10

<210> SEQ ID NO 748
<211> LENGTH: 13
<212> TYPE: PRT
<213> ORGANISM: Oryctolagus cuniculus

<400> SEQUENCE: 748

Gln Ala Ser Gln Ser Leu Tyr Asn Asn Lys Asn Leu Gly
1 5 10

<210> SEQ ID NO 749
<211> LENGTH: 11
<212> TYPE: PRT
<213> ORGANISM: Oryctolagus cuniculus

<400> SEQUENCE: 749

Gln Ala Ser Gln Thr Ile Ser Ser Tyr Leu Ala
1 5 10

<210> SEQ ID NO 750
<211> LENGTH: 13
<212> TYPE: PRT
<213> ORGANISM: Oryctolagus cuniculus

<400> SEQUENCE: 750

Gln Ser Ser Gln Ser Val Tyr Asp Asn Asn Ala Leu Ala
1 5 10

<210> SEQ ID NO 751
<211> LENGTH: 13
<212> TYPE: PRT
<213> ORGANISM: Oryctolagus cuniculus

<400> SEQUENCE: 751

Gln Ser Ser Gln Asn Val Asp Arg Asn Asn Arg Leu Ala
1 5 10

<210> SEQ ID NO 752
<211> LENGTH: 11
<212> TYPE: PRT
<213> ORGANISM: Oryctolagus cuniculus

<400> SEQUENCE: 752

Gln Ala Ser Gln Ser Ile Gly Ser Asn Leu Ala
1 5 10

<210> SEQ ID NO 753
<211> LENGTH: 11
<212> TYPE: PRT
<213> ORGANISM: Oryctolagus cuniculus

<400> SEQUENCE: 753

Gln Ala Ser Glu Asp Ile Glu Ser Tyr Leu Ala
1 5 10

<210> SEQ ID NO 754
<211> LENGTH: 11
<212> TYPE: PRT
<213> ORGANISM: Oryctolagus cuniculus

<400> SEQUENCE: 754

Gln Ala Ser Glu Asp Ile Glu Ser Tyr Leu Ala
1 5 10

<210> SEQ ID NO 755
<211> LENGTH: 11
<212> TYPE: PRT
<213> ORGANISM: Oryctolagus cuniculus

<400> SEQUENCE: 755

Gln Ala Ser Gln Asn Ile Tyr Asp Asn Leu Ala
1 5 10

<210> SEQ ID NO 756
<211> LENGTH: 13
<212> TYPE: PRT
<213> ORGANISM: Oryctolagus cuniculus

<400> SEQUENCE: 756

Gln Ser Ser Pro Ser Val Tyr Asn Asn Asn Arg Leu Ser
1 5 10

<210> SEQ ID NO 757
<211> LENGTH: 11
<212> TYPE: PRT
<213> ORGANISM: Oryctolagus cuniculus

<400> SEQUENCE: 757

Gln Ala Ser Gln Asn Ile Gly Asn Asn Leu Ala
1 5 10

<210> SEQ ID NO 758
<211> LENGTH: 11
<212> TYPE: PRT
<213> ORGANISM: Oryctolagus cuniculus

<400> SEQUENCE: 758

Gln Ala Ser Glu Asp Ile Glu Ser Tyr Leu Ala
1 5 10

<210> SEQ ID NO 759
<211> LENGTH: 11
<212> TYPE: PRT
<213> ORGANISM: Oryctolagus cuniculus

<400> SEQUENCE: 759

Gln Ala Ser Gln Asn Ile Asn Ser Trp Leu Ser
1 5 10

<210> SEQ ID NO 760
<211> LENGTH: 13
<212> TYPE: PRT
<213> ORGANISM: Oryctolagus cuniculus

<400> SEQUENCE: 760

Gln Ser Ser Gln Ser Val Tyr Ser Asn Asn His Leu Ala
1 5 10

<210> SEQ ID NO 761
<211> LENGTH: 13
<212> TYPE: PRT
<213> ORGANISM: Oryctolagus cuniculus

<400> SEQUENCE: 761

Gln Ser Ser Gln Ile Val His Asn Asn Asn Asn Leu Ala
1 5 10

<210> SEQ ID NO 762
<211> LENGTH: 13
<212> TYPE: PRT
<213> ORGANISM: Oryctolagus cuniculus

<400> SEQUENCE: 762

Gln Ala Ser Gln Ser Leu Tyr Asn Lys Lys Asn Leu Ala
1 5 10

<210> SEQ ID NO 763
<211> LENGTH: 13
<212> TYPE: PRT
<213> ORGANISM: Oryctolagus cuniculus

<400> SEQUENCE: 763

Gln Ser Ser Gln Ser Val Tyr Asp Asn Lys Trp Leu Gly
1 5 10

<210> SEQ ID NO 764
<211> LENGTH: 13
<212> TYPE: PRT
<213> ORGANISM: Oryctolagus cuniculus

<400> SEQUENCE: 764

Gln Ser Ser Gln Ser Val Tyr Asp Asn Lys Trp Leu Gly
1 5 10

<210> SEQ ID NO 765
<211> LENGTH: 13
<212> TYPE: PRT
<213> ORGANISM: Oryctolagus cuniculus

<400> SEQUENCE: 765

Gln Ser Ser Lys Ser Val Phe Asp Asn Asn Trp Leu Ser
1 5 10

<210> SEQ ID NO 766
<211> LENGTH: 13
<212> TYPE: PRT
<213> ORGANISM: Oryctolagus cuniculus

<400> SEQUENCE: 766

Gln Ala Ser Gln Ser Leu Tyr Asn Lys Lys Asn Leu Ala
1 5 10

<210> SEQ ID NO 767
<211> LENGTH: 11
<212> TYPE: PRT
<213> ORGANISM: Oryctolagus cuniculus

<400> SEQUENCE: 767

Gln Ala Ser Glu Thr Ile Tyr Ser Tyr Leu Asn
1 5 10

<210> SEQ ID NO 768
<211> LENGTH: 13
<212> TYPE: PRT
<213> ORGANISM: Oryctolagus cuniculus

<400> SEQUENCE: 768

Gln Ser Ser Gln Asn Ile Tyr Asn Lys Asn Gln Leu Ser
1 5 10

<210> SEQ ID NO 769
<211> LENGTH: 11
<212> TYPE: PRT
<213> ORGANISM: Oryctolagus cuniculus

<400> SEQUENCE: 769

Gln Ala Ser Gln Ser Ile Gly Gly Ser Leu Ala
1 5 10

<210> SEQ ID NO 770
<211> LENGTH: 13
<212> TYPE: PRT
<213> ORGANISM: Oryctolagus cuniculus

<400> SEQUENCE: 770

Gln Ser Ser Gln Ser Val Asn Asn Asn Lys Asn Leu Ala
1 5 10

<210> SEQ ID NO 771
<211> LENGTH: 11
<212> TYPE: PRT
<213> ORGANISM: Oryctolagus cuniculus

<400> SEQUENCE: 771

Gln Ala Ser Gln Asn Ile Gly Ser Thr Leu Ala
1 5 10

<210> SEQ ID NO 772
<211> LENGTH: 11
<212> TYPE: PRT
<213> ORGANISM: Oryctolagus cuniculus

<400> SEQUENCE: 772

Gln Ala Ser Glu Asp Ile Glu Thr Tyr Leu Ala
1 5 10

<210> SEQ ID NO 773
<211> LENGTH: 11
<212> TYPE: PRT
<213> ORGANISM: Oryctolagus cuniculus

<400> SEQUENCE: 773

Gln Ala Ser Glu Asp Ile Glu Asn Tyr Leu Ala
1 5 10

<210> SEQ ID NO 774
<211> LENGTH: 12
<212> TYPE: PRT
<213> ORGANISM: Oryctolagus cuniculus

<400> SEQUENCE: 774

Gln Ser Ser Gln Ser Val Asp Asn Asn Trp Leu Ser
1 5 10

<210> SEQ ID NO 775
<211> LENGTH: 13

<212> TYPE: PRT
<213> ORGANISM: Oryctolagus cuniculus

<400> SEQUENCE: 775

Gln Ser Ser Gln Ser Val Tyr Ser Asn Asn His Leu Ala
1 5 10

<210> SEQ ID NO 776
<211> LENGTH: 13
<212> TYPE: PRT
<213> ORGANISM: Oryctolagus cuniculus

<400> SEQUENCE: 776

Gln Ser Ser Gln Ser Val His Asn Asn Asn Asn Leu Ala
1 5 10

<210> SEQ ID NO 777
<211> LENGTH: 11
<212> TYPE: PRT
<213> ORGANISM: Oryctolagus cuniculus

<400> SEQUENCE: 777

Gln Ala Ser Glu Asp Ile Ser Ser Ser Leu Ala
1 5 10

<210> SEQ ID NO 778
<211> LENGTH: 13
<212> TYPE: PRT
<213> ORGANISM: Oryctolagus cuniculus

<400> SEQUENCE: 778

Gln Ala Ser Gln Ser Val His Asn Asn Asn Asn Leu Ala
1 5 10

<210> SEQ ID NO 779
<211> LENGTH: 11
<212> TYPE: PRT
<213> ORGANISM: Oryctolagus cuniculus

<400> SEQUENCE: 779

Gln Ala Ser Glu Asp Ile Glu Ser Tyr Leu Ala
1 5 10

<210> SEQ ID NO 780
<211> LENGTH: 11
<212> TYPE: PRT
<213> ORGANISM: Oryctolagus cuniculus

<400> SEQUENCE: 780

Gln Ala Thr Glu Asp Ile Glu Ser Phe Leu Ala
1 5 10

<210> SEQ ID NO 781
<211> LENGTH: 11
<212> TYPE: PRT
<213> ORGANISM: Oryctolagus cuniculus

<400> SEQUENCE: 781

Arg Ala Ser Glu Asp Ile Lys Ser Tyr Leu Ala
1 5 10

<210> SEQ ID NO 782
<211> LENGTH: 13
<212> TYPE: PRT
<213> ORGANISM: Oryctolagus cuniculus

<400> SEQUENCE: 782

Gln Ala Ser Gln Ser Val Tyr Asn His Lys Asn Leu Ala
1 5 10

<210> SEQ ID NO 783
<211> LENGTH: 11
<212> TYPE: PRT
<213> ORGANISM: Oryctolagus cuniculus

<400> SEQUENCE: 783

Gln Ala Ser Gln Ser Ile Gly Ser Ser Leu Ala
1 5 10

<210> SEQ ID NO 784
<211> LENGTH: 13
<212> TYPE: PRT
<213> ORGANISM: Oryctolagus cuniculus

<400> SEQUENCE: 784

Gln Ser Ser Gln Ser Val Tyr Gly Val Asn Glu Leu Ser
1 5 10

<210> SEQ ID NO 785
<211> LENGTH: 11
<212> TYPE: PRT
<213> ORGANISM: Oryctolagus cuniculus

<400> SEQUENCE: 785

Gln Ala Ser Gln Ser Ile Ser Asn Leu Leu Ala
1 5 10

<210> SEQ ID NO 786
<211> LENGTH: 13
<212> TYPE: PRT
<213> ORGANISM: Oryctolagus cuniculus

<400> SEQUENCE: 786

Gln Ser Ser Lys Ser Val Tyr Asn Asn Asn Trp Leu Ser
1 5 10

<210> SEQ ID NO 787
<211> LENGTH: 13
<212> TYPE: PRT
<213> ORGANISM: Oryctolagus cuniculus

<400> SEQUENCE: 787

Gln Ser Ser Pro Ser Val Tyr Asn Asn Asn Arg Leu Ser
1 5 10

<210> SEQ ID NO 788
<211> LENGTH: 11
<212> TYPE: PRT
<213> ORGANISM: Oryctolagus cuniculus

<400> SEQUENCE: 788

Gln Ala Ser Gln Ser Ile Gly Ser Tyr Leu Ser
1 5 10

<210> SEQ ID NO 789
<211> LENGTH: 11
<212> TYPE: PRT
<213> ORGANISM: Oryctolagus cuniculus

<400> SEQUENCE: 789

Gln Ala Ser Gln Asn Ile Gly Asn Asn Leu Ala
1 5 10

<210> SEQ ID NO 790
<211> LENGTH: 11
<212> TYPE: PRT
<213> ORGANISM: Oryctolagus cuniculus

<400> SEQUENCE: 790

Gln Ala Ser Glu Asp Ile Tyr Ser Asn Leu Ala
1 5 10

<210> SEQ ID NO 791
<211> LENGTH: 13
<212> TYPE: PRT
<213> ORGANISM: Oryctolagus cuniculus

<400> SEQUENCE: 791

Gln Ala Ser Gln Ser Leu Tyr Asn Asn Lys Asn Leu Ala
1 5 10

<210> SEQ ID NO 792
<211> LENGTH: 13
<212> TYPE: PRT
<213> ORGANISM: Oryctolagus cuniculus

<400> SEQUENCE: 792

Gln Ser Ser Lys Thr Val Tyr Asn Asn Asn Trp Leu Ala
1 5 10

<210> SEQ ID NO 793
<211> LENGTH: 13
<212> TYPE: PRT
<213> ORGANISM: Oryctolagus cuniculus

<400> SEQUENCE: 793

Gln Ser Ser Pro Ser Val Tyr Asn Asn Val Arg Leu Ser
1 5 10

<210> SEQ ID NO 794
<211> LENGTH: 12
<212> TYPE: PRT
<213> ORGANISM: Oryctolagus cuniculus

<400> SEQUENCE: 794

Gln Ser Ser Gln Ser Val Tyr Ser Thr Asn Leu Ala
1 5 10

<210> SEQ ID NO 795
<211> LENGTH: 11
<212> TYPE: PRT
<213> ORGANISM: Oryctolagus cuniculus

<400> SEQUENCE: 795

Gln Ala Ser Glu Asn Ile Ala Asn His Leu Ala
1 5 10

<210> SEQ ID NO 796
<211> LENGTH: 13
<212> TYPE: PRT
<213> ORGANISM: Oryctolagus cuniculus

<400> SEQUENCE: 796

Gln Ser Ser Gln Ser Val Tyr Gly Asn Asn Glu Leu Ser 1 5 10

<210> SEQ ID NO 797
<211> LENGTH: 13
<212> TYPE: PRT
<213> ORGANISM: Oryctolagus cuniculus

<400> SEQUENCE: 797

Gln Ala Ser Gln Ser Leu Tyr Asn Lys Lys Asn Leu Ala
1 5 10

<210> SEQ ID NO 798
<211> LENGTH: 13
<212> TYPE: PRT
<213> ORGANISM: Oryctolagus cuniculus

<400> SEQUENCE: 798

Gln Ser Ser Gln Ser Val Tyr Gly Ser Asp Ala Leu Ala
1 5 10

<210> SEQ ID NO 799
<211> LENGTH: 11
<212> TYPE: PRT
<213> ORGANISM: Oryctolagus cuniculus

<400> SEQUENCE: 799

Gln Ala Ser Gln Ser Ile Ser Ser Asn Leu Ala
1 5 10

<210> SEQ ID NO 800
<211> LENGTH: 11
<212> TYPE: PRT
<213> ORGANISM: Oryctolagus cuniculus

<400> SEQUENCE: 800

Gln Ala Ser Glu Asn Ile Tyr Ser Phe Leu Ala
1 5 10

<210> SEQ ID NO 801
<211> LENGTH: 11
<212> TYPE: PRT
<213> ORGANISM: Oryctolagus cuniculus

<400> SEQUENCE: 801

Gln Ala Ser Gln Ser Ile Ser Asp Tyr Leu Ser
1 5 10

<210> SEQ ID NO 802
<211> LENGTH: 11
<212> TYPE: PRT
<213> ORGANISM: Oryctolagus cuniculus

<400> SEQUENCE: 802

Gln Ala Ser Gln Ser Ile Ser Ser Tyr Leu Ser
1 5 10

<210> SEQ ID NO 803
<211> LENGTH: 11
<212> TYPE: PRT
<213> ORGANISM: Oryctolagus cuniculus

<400> SEQUENCE: 803

Gln Ala Ser Gln Asn Ile Asn Asn Leu Leu Ala
1 5 10

<210> SEQ ID NO 804
<211> LENGTH: 13
<212> TYPE: PRT
<213> ORGANISM: Oryctolagus cuniculus

<400> SEQUENCE: 804

Gln Ala Ser Gln Ser Val Tyr Ala Asn Asn Tyr Leu Ala
1 5 10

<210> SEQ ID NO 805
<211> LENGTH: 11
<212> TYPE: PRT
<213> ORGANISM: Oryctolagus cuniculus

<400> SEQUENCE: 805

Gln Ala Ser Glu Ser Ile Ser Asn Tyr Leu Ser
1 5 10

<210> SEQ ID NO 806
<211> LENGTH: 13
<212> TYPE: PRT
<213> ORGANISM: Oryctolagus cuniculus

<400> SEQUENCE: 806

Gln Ser Ser Gln Ser Val Tyr Asn Asn Asn Trp Leu Ser
1 5 10

<210> SEQ ID NO 807
<211> LENGTH: 13
<212> TYPE: PRT
<213> ORGANISM: Oryctolagus cuniculus

<400> SEQUENCE: 807

Gln Ala Ser Gln Ser Val His Lys His Lys Asn Leu Ala
1 5 10

<210> SEQ ID NO 808
<211> LENGTH: 11
<212> TYPE: PRT
<213> ORGANISM: Oryctolagus cuniculus

<400> SEQUENCE: 808

Gln Ala Ser Gln Ser Ile Ser Ser Tyr Leu Ser
1 5 10

<210> SEQ ID NO 809
<211> LENGTH: 11
<212> TYPE: PRT
<213> ORGANISM: Oryctolagus cuniculus

<400> SEQUENCE: 809

Gln Ala Ser Gln Asn Ile Asn Asn Glu Leu Ser
1 5 10

<210> SEQ ID NO 810
<211> LENGTH: 11
<212> TYPE: PRT
<213> ORGANISM: Oryctolagus cuniculus

<400> SEQUENCE: 810

Arg Ala Ser Glu Asp Ile Glu Ser Tyr Leu Ala
1 5 10

<210> SEQ ID NO 811

<211> LENGTH: 13
<212> TYPE: PRT
<213> ORGANISM: Oryctolagus cuniculus

<400> SEQUENCE: 811

Gln Ser Ser Gln Ser Val Tyr Asn Asp Asn Asp Leu Ala
1 5 10

<210> SEQ ID NO 812
<211> LENGTH: 11
<212> TYPE: PRT
<213> ORGANISM: Oryctolagus cuniculus

<400> SEQUENCE: 812

Gln Ala Ser Glu Ser Ile Tyr Ser Gly Leu Ala
1 5 10

<210> SEQ ID NO 813
<211> LENGTH: 11
<212> TYPE: PRT
<213> ORGANISM: Oryctolagus cuniculus

<400> SEQUENCE: 813

Gln Ala Ser Gln Ser Ile Ser Tyr Tyr Leu Asn
1 5 10

<210> SEQ ID NO 814
<211> LENGTH: 13
<212> TYPE: PRT
<213> ORGANISM: Oryctolagus cuniculus

<400> SEQUENCE: 814

Gln Ala Ser Gln Ser Val Tyr Lys Asn Asn Tyr Leu Ala
1 5 10

<210> SEQ ID NO 815
<211> LENGTH: 13
<212> TYPE: PRT
<213> ORGANISM: Oryctolagus cuniculus

<400> SEQUENCE: 815

Gln Ser Ser Gln Ser Val Tyr Asn Asn Asn Trp Leu Gly
1 5 10

<210> SEQ ID NO 816
<211> LENGTH: 11
<212> TYPE: PRT
<213> ORGANISM: Oryctolagus cuniculus

<400> SEQUENCE: 816

Gln Ala Ser Glu Asp Ile Tyr Asn Leu Leu Ala
1 5 10

<210> SEQ ID NO 817
<211> LENGTH: 11
<212> TYPE: PRT
<213> ORGANISM: Oryctolagus cuniculus

<400> SEQUENCE: 817

Gln Ala Ser Glu Asp Ile Glu Ser Tyr Leu Ala
1 5 10

<210> SEQ ID NO 818
<211> LENGTH: 13
<212> TYPE: PRT

<213> ORGANISM: Oryctolagus cuniculus

<400> SEQUENCE: 818

Gln Ala Ser Gln Ser Val Tyr Ser Asn Asn Tyr Leu Ser
1 5 10

<210> SEQ ID NO 819
<211> LENGTH: 11
<212> TYPE: PRT
<213> ORGANISM: Oryctolagus cuniculus

<400> SEQUENCE: 819

Gln Ala Ser Glu Ser Ile Asp Ser Tyr Leu Asn
1 5 10

<210> SEQ ID NO 820
<211> LENGTH: 11
<212> TYPE: PRT
<213> ORGANISM: Oryctolagus cuniculus

<400> SEQUENCE: 820

Gln Ala Ser Gln Asn Ile Tyr Ser Ser Leu Ala
1 5 10

<210> SEQ ID NO 821
<211> LENGTH: 11
<212> TYPE: PRT
<213> ORGANISM: Oryctolagus cuniculus

<400> SEQUENCE: 821

Gln Ala Ser Gln Ser Ile Ser Tyr Tyr Leu Ala
1 5 10

<210> SEQ ID NO 822
<211> LENGTH: 11
<212> TYPE: PRT
<213> ORGANISM: Oryctolagus cuniculus

<400> SEQUENCE: 822

Gln Ala Ser Gln Asn Ile Tyr Ser Arg Leu Ala
1 5 10

<210> SEQ ID NO 823
<211> LENGTH: 12
<212> TYPE: PRT
<213> ORGANISM: Oryctolagus cuniculus

<400> SEQUENCE: 823

Gln Ser Ser Gln Ser Val Thr Asp Asn Phe Leu Ser
1 5 10

<210> SEQ ID NO 824
<211> LENGTH: 11
<212> TYPE: PRT
<213> ORGANISM: Oryctolagus cuniculus

<400> SEQUENCE: 824

Gln Ala Ser Glu Asp Ile Glu Ser Tyr Leu Ala
1 5 10

<210> SEQ ID NO 825
<211> LENGTH: 11
<212> TYPE: PRT
<213> ORGANISM: Oryctolagus cuniculus

<400> SEQUENCE: 825

Gln Ala Ser Gln Ser Ile Gly Ser Ser Leu Ala
1 5 10

<210> SEQ ID NO 826
<211> LENGTH: 11
<212> TYPE: PRT
<213> ORGANISM: Oryctolagus cuniculus

<400> SEQUENCE: 826

Gln Ala Ser Gln Ser Ile Ser Ser Tyr Leu Ala
1 5 10

<210> SEQ ID NO 827
<211> LENGTH: 11
<212> TYPE: PRT
<213> ORGANISM: Oryctolagus cuniculus

<400> SEQUENCE: 827

Gln Ala Ser Gln Asn Ile Gly Ser Asp Leu Ala
1 5 10

<210> SEQ ID NO 828
<211> LENGTH: 11
<212> TYPE: PRT
<213> ORGANISM: Oryctolagus cuniculus

<400> SEQUENCE: 828

Gln Ala Ser Gln Ser Ile Ser Ser Tyr Leu Ala
1 5 10

<210> SEQ ID NO 829
<211> LENGTH: 13
<212> TYPE: PRT
<213> ORGANISM: Oryctolagus cuniculus

<400> SEQUENCE: 829

Gln Ala Ser Glu Ser Val Val Gly Lys Asn Glu Leu Ser
1 5 10

<210> SEQ ID NO 830
<211> LENGTH: 13
<212> TYPE: PRT
<213> ORGANISM: Oryctolagus cuniculus

<400> SEQUENCE: 830

Gln Ala Ser Gln Ser Val His Asn Asn Lys Asn Leu Ala
1 5 10

<210> SEQ ID NO 831
<211> LENGTH: 13
<212> TYPE: PRT
<213> ORGANISM: Oryctolagus cuniculus

<400> SEQUENCE: 831

Gln Ser Ser Gln Ser Val Tyr Arg Asn Asn Glu Leu Ser
1 5 10

<210> SEQ ID NO 832
<211> LENGTH: 11
<212> TYPE: PRT
<213> ORGANISM: Oryctolagus cuniculus

<400> SEQUENCE: 832

Gln Ala Ser Glu Asp Ile Glu Ser Phe Leu Ala
1 5 10

<210> SEQ ID NO 833
<211> LENGTH: 11
<212> TYPE: PRT
<213> ORGANISM: Oryctolagus cuniculus

<400> SEQUENCE: 833

Gln Ala Ser Glu Asp Ile Ser Ser Arg Leu Ala
1 5 10

<210> SEQ ID NO 834
<211> LENGTH: 11
<212> TYPE: PRT
<213> ORGANISM: Oryctolagus cuniculus

<400> SEQUENCE: 834

Gln Ala Ser Gln Asn Ile Tyr Ser Asn Leu Ala
1 5 10

<210> SEQ ID NO 835
<211> LENGTH: 11
<212> TYPE: PRT
<213> ORGANISM: Oryctolagus cuniculus

<400> SEQUENCE: 835

Gln Ala Ser Glu Asn Ile Tyr Ser Phe Leu Ala
1 5 10

<210> SEQ ID NO 836
<211> LENGTH: 13
<212> TYPE: PRT
<213> ORGANISM: Oryctolagus cuniculus

<400> SEQUENCE: 836

Gln Ser Ser Gln Ser Val Ala Asp Asn Asn Leu Leu Ala
1 5 10

<210> SEQ ID NO 837
<211> LENGTH: 13
<212> TYPE: PRT
<213> ORGANISM: Oryctolagus cuniculus

<400> SEQUENCE: 837

Gln Ala Ser Gln Ser Val Tyr Gly Thr Asn Arg Leu Ala
1 5 10

<210> SEQ ID NO 838
<211> LENGTH: 11
<212> TYPE: PRT
<213> ORGANISM: Oryctolagus cuniculus

<400> SEQUENCE: 838

Gln Ala Ser Gln Asn Ile Tyr Ser Lys Phe Ala
1 5 10

<210> SEQ ID NO 839
<211> LENGTH: 11
<212> TYPE: PRT
<213> ORGANISM: Oryctolagus cuniculus

<400> SEQUENCE: 839

Gln Ala Ser Gln Ser Ile Gly Val Ser Leu Ala
1 5 10

<210> SEQ ID NO 840
<211> LENGTH: 13
<212> TYPE: PRT
<213> ORGANISM: Oryctolagus cuniculus

<400> SEQUENCE: 840

Gln Ala Ser Gln Ser Val Tyr Asn Asn Asn Tyr Leu Gly
1 5 10

<210> SEQ ID NO 841
<211> LENGTH: 11
<212> TYPE: PRT
<213> ORGANISM: Oryctolagus cuniculus

<400> SEQUENCE: 841

Gln Ala Ser Glu Ser Ile Asp Asn Trp Leu Ala
1 5 10

<210> SEQ ID NO 842
<211> LENGTH: 13
<212> TYPE: PRT
<213> ORGANISM: Oryctolagus cuniculus

<400> SEQUENCE: 842

Gln Ser Ser Gln Ser Val Tyr Ser Asn Asn Asn Leu Ala
1 5 10

<210> SEQ ID NO 843
<211> LENGTH: 11
<212> TYPE: PRT
<213> ORGANISM: Oryctolagus cuniculus

<400> SEQUENCE: 843

Gln Ala Ser Gln Ser Ile Ser Ser Tyr Leu Ser
1 5 10

<210> SEQ ID NO 844
<211> LENGTH: 11
<212> TYPE: PRT
<213> ORGANISM: Oryctolagus cuniculus

<400> SEQUENCE: 844

Gln Ala Ser Gln Ser Ile Arg Ser Tyr Leu Ala
1 5 10

<210> SEQ ID NO 845
<211> LENGTH: 11
<212> TYPE: PRT
<213> ORGANISM: Oryctolagus cuniculus

<400> SEQUENCE: 845

Gln Ala Ser Glu Ser Ile Ser Val Asn Leu Ala
1 5 10

<210> SEQ ID NO 846
<211> LENGTH: 13
<212> TYPE: PRT
<213> ORGANISM: Oryctolagus cuniculus

<400> SEQUENCE: 846

Gln Ser Ser Glu Ser Ile Tyr Lys Asn Asn Tyr Leu Ala
1 5 10

<210> SEQ ID NO 847
<211> LENGTH: 11
<212> TYPE: PRT
<213> ORGANISM: Oryctolagus cuniculus

<400> SEQUENCE: 847

Gln Ala Ser Gln Asn Ile Tyr Ser Asp Phe Ala
1 5 10

<210> SEQ ID NO 848
<211> LENGTH: 13
<212> TYPE: PRT
<213> ORGANISM: Oryctolagus cuniculus

<400> SEQUENCE: 848

Gln Ala Ser Gln Ser Val Tyr Asn His Lys Asn Leu Ala
1 5 10

<210> SEQ ID NO 849
<211> LENGTH: 11
<212> TYPE: PRT
<213> ORGANISM: Oryctolagus cuniculus

<400> SEQUENCE: 849

Gln Ala Ser Gln Ser Ile Ser Ala Tyr Leu Ser
1 5 10

<210> SEQ ID NO 850
<211> LENGTH: 11
<212> TYPE: PRT
<213> ORGANISM: Oryctolagus cuniculus

<400> SEQUENCE: 850

Gln Ala Ser Gln Thr Ile Thr Ser Tyr Leu Ala
1 5 10

<210> SEQ ID NO 851
<211> LENGTH: 13
<212> TYPE: PRT
<213> ORGANISM: Oryctolagus cuniculus

<400> SEQUENCE: 851

Gln Ala Ser Gln Ser Val Tyr Asn Asn Lys Asn Leu Ala
1 5 10

<210> SEQ ID NO 852
<211> LENGTH: 11
<212> TYPE: PRT
<213> ORGANISM: Oryctolagus cuniculus

<400> SEQUENCE: 852

Gln Ala Ser Glu Asn Ile Tyr Ser Leu Leu Ala
1 5 10

<210> SEQ ID NO 853
<211> LENGTH: 11
<212> TYPE: PRT
<213> ORGANISM: Oryctolagus cuniculus

<400> SEQUENCE: 853

Gln Ala Ser Glu Asp Ile Tyr Ser Leu Leu Ala
1 5 10

<210> SEQ ID NO 854
<211> LENGTH: 11

<212> TYPE: PRT
<213> ORGANISM: Oryctolagus cuniculus

<400> SEQUENCE: 854

Gln Ala Ser Gln Ser Ile Ser Thr Tyr Leu Ser
1 5 10

<210> SEQ ID NO 855
<211> LENGTH: 11
<212> TYPE: PRT
<213> ORGANISM: Oryctolagus cuniculus

<400> SEQUENCE: 855

Gln Ala Ser Glu Asn Ile Tyr Ser Ser Leu Ala
1 5 10

<210> SEQ ID NO 856
<211> LENGTH: 11
<212> TYPE: PRT
<213> ORGANISM: Oryctolagus cuniculus

<400> SEQUENCE: 856

Gln Ala Ser Glu Ser Ile Gly Ser Trp Leu Ala
1 5 10

<210> SEQ ID NO 857
<211> LENGTH: 13
<212> TYPE: PRT
<213> ORGANISM: Oryctolagus cuniculus

<400> SEQUENCE: 857

Gln Ser Ser Gln Ser Val Tyr Asn Asn Asn Arg Leu Ser
1 5 10

<210> SEQ ID NO 858
<211> LENGTH: 13
<212> TYPE: PRT
<213> ORGANISM: Oryctolagus cuniculus

<400> SEQUENCE: 858

Gln Ala Ser Gln Ser Val Tyr Asn Asn Asn Asn Leu Ala
1 5 10

<210> SEQ ID NO 859
<211> LENGTH: 11
<212> TYPE: PRT
<213> ORGANISM: Oryctolagus cuniculus

<400> SEQUENCE: 859

Gln Ala Ser Gln Ser Ile Gly Ser Tyr Leu Ser
1 5 10

<210> SEQ ID NO 860
<211> LENGTH: 13
<212> TYPE: PRT
<213> ORGANISM: Oryctolagus cuniculus

<400> SEQUENCE: 860

Gln Ser Ser Glu Ser Val Tyr Asn Asn Asn Leu Leu Ser
1 5 10

<210> SEQ ID NO 861
<211> LENGTH: 12
<212> TYPE: PRT
<213> ORGANISM: Oryctolagus cuniculus

<400> SEQUENCE: 861

Gln Ala Ser Gln Ser Val Tyr Asn Asn Arg Leu Ala
1 5 10

<210> SEQ ID NO 862
<211> LENGTH: 11
<212> TYPE: PRT
<213> ORGANISM: Oryctolagus cuniculus

<400> SEQUENCE: 862

Gln Ala Ser Gln Ser Ile Ser Thr Tyr Ser Ser
1 5 10

<210> SEQ ID NO 863
<211> LENGTH: 13
<212> TYPE: PRT
<213> ORGANISM: Oryctolagus cuniculus

<400> SEQUENCE: 863

Gln Ser Ser Gln Ser Val Tyr Ala Ser Val Trp Leu Gly
1 5 10

<210> SEQ ID NO 864
<211> LENGTH: 11
<212> TYPE: PRT
<213> ORGANISM: Oryctolagus cuniculus

<400> SEQUENCE: 864

Gln Ala Ser Gln Ser Ile Tyr Asn Tyr Leu Ser
1 5 10

<210> SEQ ID NO 865
<211> LENGTH: 11
<212> TYPE: PRT
<213> ORGANISM: Oryctolagus cuniculus

<400> SEQUENCE: 865

Gln Ala Ser Gln Asn Ile Tyr Ser Tyr Leu Ala
1 5 10

<210> SEQ ID NO 866
<211> LENGTH: 11
<212> TYPE: PRT
<213> ORGANISM: Oryctolagus cuniculus

<400> SEQUENCE: 866

Gln Ala Ser Gln Ser Ile Tyr Ser Tyr Leu Ala
1 5 10

<210> SEQ ID NO 867
<211> LENGTH: 11
<212> TYPE: PRT
<213> ORGANISM: Oryctolagus cuniculus

<400> SEQUENCE: 867

Gln Ala Ser Glu Ser Ile Gly Ser Val Leu Ala
1 5 10

<210> SEQ ID NO 868
<211> LENGTH: 11
<212> TYPE: PRT
<213> ORGANISM: Oryctolagus cuniculus

<400> SEQUENCE: 868

Gln Ala Ser Gln Asn Ile Tyr Ser Asn Leu Ala
1 5 10

<210> SEQ ID NO 869
<211> LENGTH: 13
<212> TYPE: PRT
<213> ORGANISM: Oryctolagus cuniculus

<400> SEQUENCE: 869

Gln Ser Asn Lys Asn Val Tyr Asp Asn Asn Ala Leu Ser
1 5 10

<210> SEQ ID NO 870
<211> LENGTH: 11
<212> TYPE: PRT
<213> ORGANISM: Oryctolagus cuniculus

<400> SEQUENCE: 870

Gln Ala Ser Gln Ser Ile Ile Asn Tyr Leu Ser
1 5 10

<210> SEQ ID NO 871
<211> LENGTH: 11
<212> TYPE: PRT
<213> ORGANISM: Oryctolagus cuniculus

<400> SEQUENCE: 871

Gln Ala Ser Gln Ser Ile Tyr Ser Tyr Leu Ser
1 5 10

<210> SEQ ID NO 872
<211> LENGTH: 11
<212> TYPE: PRT
<213> ORGANISM: Oryctolagus cuniculus

<400> SEQUENCE: 872

Gln Ala Ser Gln Ser Ile Ser Ser Trp Leu Ala
1 5 10

<210> SEQ ID NO 873
<211> LENGTH: 13
<212> TYPE: PRT
<213> ORGANISM: Oryctolagus cuniculus

<400> SEQUENCE: 873

Gln Ser Ser Gln Ser Val Asn Asn Ala Lys Asn Leu Ala
1 5 10

<210> SEQ ID NO 874
<211> LENGTH: 13
<212> TYPE: PRT
<213> ORGANISM: Oryctolagus cuniculus

<400> SEQUENCE: 874

Gln Ser Ser Lys Ser Val Tyr Asp Asn Asn Trp Leu Ser
1 5 10

<210> SEQ ID NO 875
<211> LENGTH: 11
<212> TYPE: PRT
<213> ORGANISM: Oryctolagus cuniculus

<400> SEQUENCE: 875

Gln Ala Ser Gln Ser Ile Gly Ser Ser Leu Ala 1 5 10

<210> SEQ ID NO 876
<211> LENGTH: 11
<212> TYPE: PRT
<213> ORGANISM: Oryctolagus cuniculus

<400> SEQUENCE: 876

Gln Ala Ser Glu Asn Ile Tyr Arg Asn Leu Ala
1 5 10

<210> SEQ ID NO 877
<211> LENGTH: 11
<212> TYPE: PRT
<213> ORGANISM: Oryctolagus cuniculus

<400> SEQUENCE: 877

Gln Ala Ser Glu Asp Ile Glu Ser Tyr Leu Ala
1 5 10

<210> SEQ ID NO 878
<211> LENGTH: 11
<212> TYPE: PRT
<213> ORGANISM: Oryctolagus cuniculus

<400> SEQUENCE: 878

Gln Ala Ser Gln Ser Ile Ser Ser Trp Leu Ser
1 5 10

<210> SEQ ID NO 879
<211> LENGTH: 11
<212> TYPE: PRT
<213> ORGANISM: Oryctolagus cuniculus

<400> SEQUENCE: 879

Gln Ala Ser Gln Ser Ile Gly Ser Asp Leu Ala
1 5 10

<210> SEQ ID NO 880
<211> LENGTH: 11
<212> TYPE: PRT
<213> ORGANISM: Oryctolagus cuniculus

<400> SEQUENCE: 880

Gln Gly Ser Gln Ser Ile Ser Ser Tyr Leu Ser
1 5 10

<210> SEQ ID NO 881
<211> LENGTH: 12
<212> TYPE: PRT
<213> ORGANISM: Oryctolagus cuniculus

<400> SEQUENCE: 881

Gln Ser Ser Pro Ser Val Tyr Ser Val Tyr Leu Ser
1 5 10

<210> SEQ ID NO 882
<211> LENGTH: 13
<212> TYPE: PRT
<213> ORGANISM: Oryctolagus cuniculus

<400> SEQUENCE: 882

Gln Ser Ser Lys Ser Val Tyr Asn Asn Lys Trp Leu Ser
1 5 10

<210> SEQ ID NO 883
<211> LENGTH: 11
<212> TYPE: PRT
<213> ORGANISM: Oryctolagus cuniculus

<400> SEQUENCE: 883

Gln Ala Ser Glu Ser Val Gly Asp Ala Leu Ala
1 5 10

<210> SEQ ID NO 884
<211> LENGTH: 13
<212> TYPE: PRT
<213> ORGANISM: Oryctolagus cuniculus

<400> SEQUENCE: 884

Gln Ser Ser Lys Thr Ile Tyr Asn Asp Asn Trp Leu Ser
1 5 10

<210> SEQ ID NO 885
<211> LENGTH: 11
<212> TYPE: PRT
<213> ORGANISM: Oryctolagus cuniculus

<400> SEQUENCE: 885

Arg Ala Ser Glu Asp Ile Lys Ser Tyr Leu Ala
1 5 10

<210> SEQ ID NO 886
<211> LENGTH: 11
<212> TYPE: PRT
<213> ORGANISM: Oryctolagus cuniculus

<400> SEQUENCE: 886

Gln Ala Ser Gln Ser Ile Tyr Ser Asn Leu Ala
1 5 10

<210> SEQ ID NO 887
<211> LENGTH: 13
<212> TYPE: PRT
<213> ORGANISM: Oryctolagus cuniculus

<400> SEQUENCE: 887

Gln Ala Ser Gln Ser Val Tyr Asn Asn Asn Tyr Leu Ala
1 5 10

<210> SEQ ID NO 888
<211> LENGTH: 11
<212> TYPE: PRT
<213> ORGANISM: Oryctolagus cuniculus

<400> SEQUENCE: 888

Arg Ala Ser Glu Asp Ile Glu Arg Phe Leu Ala
1 5 10

<210> SEQ ID NO 889
<211> LENGTH: 7
<212> TYPE: PRT
<213> ORGANISM: Oryctolagus cuniculus

<400> SEQUENCE: 889

Asp Val Ser Thr Leu Ala Ser
1 5

<210> SEQ ID NO 890

<211> LENGTH: 7
<212> TYPE: PRT
<213> ORGANISM: Oryctolagus cuniculus

<400> SEQUENCE: 890

Lys Ala Ser Thr Leu Ala Ser
1 5

<210> SEQ ID NO 891
<211> LENGTH: 7
<212> TYPE: PRT
<213> ORGANISM: Oryctolagus cuniculus

<400> SEQUENCE: 891

Asp Val Ser Thr Leu Ala Ser
1 5

<210> SEQ ID NO 892
<211> LENGTH: 7
<212> TYPE: PRT
<213> ORGANISM: Oryctolagus cuniculus

<400> SEQUENCE: 892

Thr Thr Ser Ser Leu Ala Ser
1 5

<210> SEQ ID NO 893
<211> LENGTH: 7
<212> TYPE: PRT
<213> ORGANISM: Oryctolagus cuniculus

<400> SEQUENCE: 893

Gly Ala Ser Asn Leu Glu Ser
1 5

<210> SEQ ID NO 894
<211> LENGTH: 7
<212> TYPE: PRT
<213> ORGANISM: Oryctolagus cuniculus

<400> SEQUENCE: 894

Asp Ala Ser Thr Leu Ala Ser
1 5

<210> SEQ ID NO 895
<211> LENGTH: 7
<212> TYPE: PRT
<213> ORGANISM: Oryctolagus cuniculus

<400> SEQUENCE: 895

Asp Ala Ser Asp Leu Ala Ser
1 5

<210> SEQ ID NO 896
<211> LENGTH: 7
<212> TYPE: PRT
<213> ORGANISM: Oryctolagus cuniculus

<400> SEQUENCE: 896

Asp Val Ser Thr Leu Ala Ser
1 5

<210> SEQ ID NO 897
<211> LENGTH: 7
<212> TYPE: PRT

<213> ORGANISM: Oryctolagus cuniculus

<400> SEQUENCE: 897

Gly Ala Ser Thr Leu Ala Ser
1 5

<210> SEQ ID NO 898
<211> LENGTH: 7
<212> TYPE: PRT
<213> ORGANISM: Oryctolagus cuniculus

<400> SEQUENCE: 898

Glu Thr Ser Thr Leu Ala Ser
1 5

<210> SEQ ID NO 899
<211> LENGTH: 7
<212> TYPE: PRT
<213> ORGANISM: Oryctolagus cuniculus

<400> SEQUENCE: 899

Tyr Ala Ser Ile Leu Ala Ser
1 5

<210> SEQ ID NO 900
<211> LENGTH: 7
<212> TYPE: PRT
<213> ORGANISM: Oryctolagus cuniculus

<400> SEQUENCE: 900

Lys Ala Ser Thr Leu Ala Ser
1 5

<210> SEQ ID NO 901
<211> LENGTH: 7
<212> TYPE: PRT
<213> ORGANISM: Oryctolagus cuniculus

<400> SEQUENCE: 901

Gln Ala Ser Lys Leu Ala Ser
1 5

<210> SEQ ID NO 902
<211> LENGTH: 7
<212> TYPE: PRT
<213> ORGANISM: Oryctolagus cuniculus

<400> SEQUENCE: 902

Ser Ala Ser Thr Leu Ala Ser
1 5

<210> SEQ ID NO 903
<211> LENGTH: 7
<212> TYPE: PRT
<213> ORGANISM: Oryctolagus cuniculus

<400> SEQUENCE: 903

Gly Ala Ser Asn Leu Glu Ser
1 5

<210> SEQ ID NO 904
<211> LENGTH: 7
<212> TYPE: PRT
<213> ORGANISM: Oryctolagus cuniculus

<400> SEQUENCE: 904

Tyr Ala Ser Thr Leu Ala Ser
1 5

<210> SEQ ID NO 905
<211> LENGTH: 7
<212> TYPE: PRT
<213> ORGANISM: Oryctolagus cuniculus

<400> SEQUENCE: 905

Tyr Ala Ser Thr Leu Ala Ser
1 5

<210> SEQ ID NO 906
<211> LENGTH: 7
<212> TYPE: PRT
<213> ORGANISM: Oryctolagus cuniculus

<400> SEQUENCE: 906

Gly Ala Ser Asn Leu Ala Ser
1 5

<210> SEQ ID NO 907
<211> LENGTH: 7
<212> TYPE: PRT
<213> ORGANISM: Oryctolagus cuniculus

<400> SEQUENCE: 907

Lys Ala Ser Thr Leu Ala Ser
1 5

<210> SEQ ID NO 908
<211> LENGTH: 7
<212> TYPE: PRT
<213> ORGANISM: Oryctolagus cuniculus

<400> SEQUENCE: 908

Arg Ala Ser Lys Leu Ala Ser
1 5

<210> SEQ ID NO 909
<211> LENGTH: 7
<212> TYPE: PRT
<213> ORGANISM: Oryctolagus cuniculus

<400> SEQUENCE: 909

Gln Ala Ser Thr Leu Ala Ser
1 5

<210> SEQ ID NO 910
<211> LENGTH: 7
<212> TYPE: PRT
<213> ORGANISM: Oryctolagus cuniculus

<400> SEQUENCE: 910

Asp Ala Ser Thr Leu Thr Ser
1 5

<210> SEQ ID NO 911
<211> LENGTH: 7
<212> TYPE: PRT
<213> ORGANISM: Oryctolagus cuniculus

<400> SEQUENCE: 911

-continued

Ser Ala Ser Thr Leu Ala Ser
1 5

<210> SEQ ID NO 912
<211> LENGTH: 7
<212> TYPE: PRT
<213> ORGANISM: Oryctolagus cuniculus

<400> SEQUENCE: 912

Lys Ala Ser Thr Leu Ala Ser
1 5

<210> SEQ ID NO 913
<211> LENGTH: 7
<212> TYPE: PRT
<213> ORGANISM: Oryctolagus cuniculus

<400> SEQUENCE: 913

Lys Ala Ser Thr Leu Ala Ser
1 5

<210> SEQ ID NO 914
<211> LENGTH: 7
<212> TYPE: PRT
<213> ORGANISM: Oryctolagus cuniculus

<400> SEQUENCE: 914

Asp Ala Ser Thr Leu Ala Ser
1 5

<210> SEQ ID NO 915
<211> LENGTH: 7
<212> TYPE: PRT
<213> ORGANISM: Oryctolagus cuniculus

<400> SEQUENCE: 915

Ser Ala Ser Thr Leu Ala Ser
1 5

<210> SEQ ID NO 916
<211> LENGTH: 7
<212> TYPE: PRT
<213> ORGANISM: Oryctolagus cuniculus

<400> SEQUENCE: 916

Glu Ala Ser Lys Leu Ala Ser
1 5

<210> SEQ ID NO 917
<211> LENGTH: 7
<212> TYPE: PRT
<213> ORGANISM: Oryctolagus cuniculus

<400> SEQUENCE: 917

Ser Ala Ser Asn Leu Ala Ser
1 5

<210> SEQ ID NO 918
<211> LENGTH: 7
<212> TYPE: PRT
<213> ORGANISM: Oryctolagus cuniculus

<400> SEQUENCE: 918

Asp Thr Ser Thr Leu Ala Ser
1 5

<210> SEQ ID NO 919
<211> LENGTH: 7
<212> TYPE: PRT
<213> ORGANISM: Oryctolagus cuniculus

<400> SEQUENCE: 919

Gly Ala Ser Thr Leu Ser Ser
1 5

<210> SEQ ID NO 920
<211> LENGTH: 7
<212> TYPE: PRT
<213> ORGANISM: Oryctolagus cuniculus

<400> SEQUENCE: 920

Arg Ala Ser Thr Leu Ala Ser
1 5

<210> SEQ ID NO 921
<211> LENGTH: 7
<212> TYPE: PRT
<213> ORGANISM: Oryctolagus cuniculus

<400> SEQUENCE: 921

Ser Ala Ser Thr Leu Ala Ser
1 5

<210> SEQ ID NO 922
<211> LENGTH: 7
<212> TYPE: PRT
<213> ORGANISM: Oryctolagus cuniculus

<400> SEQUENCE: 922

Thr Thr Ser Lys Leu Ala Ser
1 5

<210> SEQ ID NO 923
<211> LENGTH: 7
<212> TYPE: PRT
<213> ORGANISM: Oryctolagus cuniculus

<400> SEQUENCE: 923

Arg Ala Ser Lys Leu Ala Ser
1 5

<210> SEQ ID NO 924
<211> LENGTH: 7
<212> TYPE: PRT
<213> ORGANISM: Oryctolagus cuniculus

<400> SEQUENCE: 924

Gln Ala Ser Thr Leu Ala Ser
1 5

<210> SEQ ID NO 925
<211> LENGTH: 7
<212> TYPE: PRT
<213> ORGANISM: Oryctolagus cuniculus

<400> SEQUENCE: 925

Arg Ala Ser Asn Leu Ala Ser
1 5

<210> SEQ ID NO 926
<211> LENGTH: 7
<212> TYPE: PRT
<213> ORGANISM: Oryctolagus cuniculus

<400> SEQUENCE: 926

Gln Ala Ser Thr Leu Ala Ser
1               5

<210> SEQ ID NO 927
<211> LENGTH: 7
<212> TYPE: PRT
<213> ORGANISM: Oryctolagus cuniculus

<400> SEQUENCE: 927

Arg Ala Ser Thr Leu Ala Ser
1               5

<210> SEQ ID NO 928
<211> LENGTH: 7
<212> TYPE: PRT
<213> ORGANISM: Oryctolagus cuniculus

<400> SEQUENCE: 928

Arg Ala Ser Thr Leu Glu Ser
1               5

<210> SEQ ID NO 929
<211> LENGTH: 7
<212> TYPE: PRT
<213> ORGANISM: Oryctolagus cuniculus

<400> SEQUENCE: 929

Asp Ala Ser Asp Leu Ala Ser
1               5

<210> SEQ ID NO 930
<211> LENGTH: 7
<212> TYPE: PRT
<213> ORGANISM: Oryctolagus cuniculus

<400> SEQUENCE: 930

Asp Thr Ser Thr Leu Ala Ser
1               5

<210> SEQ ID NO 931
<211> LENGTH: 7
<212> TYPE: PRT
<213> ORGANISM: Oryctolagus cuniculus

<400> SEQUENCE: 931

Tyr Val Ser Asn Leu Glu Ser
1               5

<210> SEQ ID NO 932
<211> LENGTH: 7
<212> TYPE: PRT
<213> ORGANISM: Oryctolagus cuniculus

<400> SEQUENCE: 932

Lys Ala Ala Thr Leu Ala Ser
1               5

<210> SEQ ID NO 933
<211> LENGTH: 7

<212> TYPE: PRT
<213> ORGANISM: Oryctolagus cuniculus

<400> SEQUENCE: 933

Asp Ala Ser Asp Leu Ala Ser
1 5

<210> SEQ ID NO 934
<211> LENGTH: 7
<212> TYPE: PRT
<213> ORGANISM: Oryctolagus cuniculus

<400> SEQUENCE: 934

Gly Ala Ser Thr Leu Ala Ser
1 5

<210> SEQ ID NO 935
<211> LENGTH: 7
<212> TYPE: PRT
<213> ORGANISM: Oryctolagus cuniculus

<400> SEQUENCE: 935

Tyr Ala Ser Thr Leu Ala Ser
1 5

<210> SEQ ID NO 936
<211> LENGTH: 7
<212> TYPE: PRT
<213> ORGANISM: Oryctolagus cuniculus

<400> SEQUENCE: 936

Asp Ala Ser Thr Leu Ala Ser
1 5

<210> SEQ ID NO 937
<211> LENGTH: 7
<212> TYPE: PRT
<213> ORGANISM: Oryctolagus cuniculus

<400> SEQUENCE: 937

Asp Ala Ser Asp Leu Ala Ser
1 5

<210> SEQ ID NO 938
<211> LENGTH: 7
<212> TYPE: PRT
<213> ORGANISM: Oryctolagus cuniculus

<400> SEQUENCE: 938

Ser Ala Ser Thr Leu Ala Ser
1 5

<210> SEQ ID NO 939
<211> LENGTH: 7
<212> TYPE: PRT
<213> ORGANISM: Oryctolagus cuniculus

<400> SEQUENCE: 939

Asp Val Ser Thr Leu Ala Ser
1 5

<210> SEQ ID NO 940
<211> LENGTH: 7
<212> TYPE: PRT
<213> ORGANISM: Oryctolagus cuniculus

<400> SEQUENCE: 940

Gly Ala Ser Thr Leu Ala Ser
1 5

<210> SEQ ID NO 941
<211> LENGTH: 7
<212> TYPE: PRT
<213> ORGANISM: Oryctolagus cuniculus

<400> SEQUENCE: 941

Ser Ala Ser Thr Leu Ala Ser
1 5

<210> SEQ ID NO 942
<211> LENGTH: 7
<212> TYPE: PRT
<213> ORGANISM: Oryctolagus cuniculus

<400> SEQUENCE: 942

Tyr Ala Ser Thr Leu Ala Ser
1 5

<210> SEQ ID NO 943
<211> LENGTH: 7
<212> TYPE: PRT
<213> ORGANISM: Oryctolagus cuniculus

<400> SEQUENCE: 943

Ser Ala Ser Ala Leu Ala Ser
1 5

<210> SEQ ID NO 944
<211> LENGTH: 7
<212> TYPE: PRT
<213> ORGANISM: Oryctolagus cuniculus

<400> SEQUENCE: 944

Asp Ala Ser Lys Leu Ala Ser
1 5

<210> SEQ ID NO 945
<211> LENGTH: 7
<212> TYPE: PRT
<213> ORGANISM: Oryctolagus cuniculus

<400> SEQUENCE: 945

Asp Val Ser Thr Leu Ala Ser
1 5

<210> SEQ ID NO 946
<211> LENGTH: 7
<212> TYPE: PRT
<213> ORGANISM: Oryctolagus cuniculus

<400> SEQUENCE: 946

Gly Ala Ser Thr Leu Ala Ser
1 5

<210> SEQ ID NO 947
<211> LENGTH: 7
<212> TYPE: PRT
<213> ORGANISM: Oryctolagus cuniculus

<400> SEQUENCE: 947

Leu Ala Ser Thr Leu Ala Ser
1 5

<210> SEQ ID NO 948
<211> LENGTH: 7
<212> TYPE: PRT
<213> ORGANISM: Oryctolagus cuniculus

<400> SEQUENCE: 948

Ser Ala Ser Thr Leu Glu Ser
1 5

<210> SEQ ID NO 949
<211> LENGTH: 7
<212> TYPE: PRT
<213> ORGANISM: Oryctolagus cuniculus

<400> SEQUENCE: 949

Arg Ala Ser Asn Leu Ala Ser
1 5

<210> SEQ ID NO 950
<211> LENGTH: 7
<212> TYPE: PRT
<213> ORGANISM: Oryctolagus cuniculus

<400> SEQUENCE: 950

Asp Ala Ser Asp Leu Ala Ser
1 5

<210> SEQ ID NO 951
<211> LENGTH: 7
<212> TYPE: PRT
<213> ORGANISM: Oryctolagus cuniculus

<400> SEQUENCE: 951

Lys Ala Ser Thr Leu Ala Ser
1 5

<210> SEQ ID NO 952
<211> LENGTH: 7
<212> TYPE: PRT
<213> ORGANISM: Oryctolagus cuniculus

<400> SEQUENCE: 952

Lys Ala Ser Thr Leu Ala Ser
1 5

<210> SEQ ID NO 953
<211> LENGTH: 7
<212> TYPE: PRT
<213> ORGANISM: Oryctolagus cuniculus

<400> SEQUENCE: 953

Tyr Asp Ser Thr Leu Glu Ser
1 5

<210> SEQ ID NO 954
<211> LENGTH: 7
<212> TYPE: PRT
<213> ORGANISM: Oryctolagus cuniculus

<400> SEQUENCE: 954

Gly Ala Ser Thr Leu Ala Ser 1 5

<210> SEQ ID NO 955
<211> LENGTH: 7
<212> TYPE: PRT
<213> ORGANISM: Oryctolagus cuniculus

<400> SEQUENCE: 955

Glu Ala Ser Lys Leu Ala Ser
1 5

<210> SEQ ID NO 956
<211> LENGTH: 7
<212> TYPE: PRT
<213> ORGANISM: Oryctolagus cuniculus

<400> SEQUENCE: 956

Arg Ala Ser Ser Leu Lys Ser
1 5

<210> SEQ ID NO 957
<211> LENGTH: 7
<212> TYPE: PRT
<213> ORGANISM: Oryctolagus cuniculus

<400> SEQUENCE: 957

Lys Ala Ser Thr Leu Ala Ser
1 5

<210> SEQ ID NO 958
<211> LENGTH: 7
<212> TYPE: PRT
<213> ORGANISM: Oryctolagus cuniculus

<400> SEQUENCE: 958

Ser Ala Ser Ser Leu Ala Ser
1 5

<210> SEQ ID NO 959
<211> LENGTH: 7
<212> TYPE: PRT
<213> ORGANISM: Oryctolagus cuniculus

<400> SEQUENCE: 959

Gly Ala Ser Thr Leu Ala Ser
1 5

<210> SEQ ID NO 960
<211> LENGTH: 7
<212> TYPE: PRT
<213> ORGANISM: Oryctolagus cuniculus

<400> SEQUENCE: 960

Arg Ala Ser Thr Leu Glu Ser
1 5

<210> SEQ ID NO 961
<211> LENGTH: 7
<212> TYPE: PRT
<213> ORGANISM: Oryctolagus cuniculus

<400> SEQUENCE: 961

Arg Ala Ser Thr Leu Ala Ser
1 5

<210> SEQ ID NO 962
<211> LENGTH: 7
<212> TYPE: PRT
<213> ORGANISM: Oryctolagus cuniculus

<400> SEQUENCE: 962

Ser Ala Ser Thr Leu Asp Ser
1               5

<210> SEQ ID NO 963
<211> LENGTH: 7
<212> TYPE: PRT
<213> ORGANISM: Oryctolagus cuniculus

<400> SEQUENCE: 963

Ser Ala Ser Thr Leu Ala Ser
1               5

<210> SEQ ID NO 964
<211> LENGTH: 7
<212> TYPE: PRT
<213> ORGANISM: Oryctolagus cuniculus

<400> SEQUENCE: 964

Gly Ala Ser Thr Leu Ala Ser
1               5

<210> SEQ ID NO 965
<211> LENGTH: 7
<212> TYPE: PRT
<213> ORGANISM: Oryctolagus cuniculus

<400> SEQUENCE: 965

Gly Ala Ser Thr Leu Ala Ser
1               5

<210> SEQ ID NO 966
<211> LENGTH: 7
<212> TYPE: PRT
<213> ORGANISM: Oryctolagus cuniculus

<400> SEQUENCE: 966

Asp Ala Ser Asp Leu Ala Ser
1               5

<210> SEQ ID NO 967
<211> LENGTH: 7
<212> TYPE: PRT
<213> ORGANISM: Oryctolagus cuniculus

<400> SEQUENCE: 967

Gly Ala Ser Thr Leu Ala Ser
1               5

<210> SEQ ID NO 968
<211> LENGTH: 7
<212> TYPE: PRT
<213> ORGANISM: Oryctolagus cuniculus

<400> SEQUENCE: 968

Gly Ala Ser Asn Leu Glu Ser
1               5

<210> SEQ ID NO 969

<211> LENGTH: 7
<212> TYPE: PRT
<213> ORGANISM: Oryctolagus cuniculus

<400> SEQUENCE: 969

Arg Ala Ser Thr Leu Ala Ser
1 5

<210> SEQ ID NO 970
<211> LENGTH: 7
<212> TYPE: PRT
<213> ORGANISM: Oryctolagus cuniculus

<400> SEQUENCE: 970

Ala Ala Ser Thr Leu Ala Ser
1 5

<210> SEQ ID NO 971
<211> LENGTH: 7
<212> TYPE: PRT
<213> ORGANISM: Oryctolagus cuniculus

<400> SEQUENCE: 971

Gly Ala Ser Thr Leu Ala Ser
1 5

<210> SEQ ID NO 972
<211> LENGTH: 7
<212> TYPE: PRT
<213> ORGANISM: Oryctolagus cuniculus

<400> SEQUENCE: 972

Ser Ala Ser Thr Leu Ala Ser
1 5

<210> SEQ ID NO 973
<211> LENGTH: 7
<212> TYPE: PRT
<213> ORGANISM: Oryctolagus cuniculus

<400> SEQUENCE: 973

Ser Ala Ser Asn Leu Ala Ser
1 5

<210> SEQ ID NO 974
<211> LENGTH: 7
<212> TYPE: PRT
<213> ORGANISM: Oryctolagus cuniculus

<400> SEQUENCE: 974

Arg Thr Ser Ile Leu Glu Ser
1 5

<210> SEQ ID NO 975
<211> LENGTH: 7
<212> TYPE: PRT
<213> ORGANISM: Oryctolagus cuniculus

<400> SEQUENCE: 975

Asp Ala Ser Ala Leu Ala Ser
1 5

<210> SEQ ID NO 976
<211> LENGTH: 7
<212> TYPE: PRT

<213> ORGANISM: Oryctolagus cuniculus

<400> SEQUENCE: 976

Arg Ala Ser Thr Leu Ala Ser
1 5

<210> SEQ ID NO 977
<211> LENGTH: 7
<212> TYPE: PRT
<213> ORGANISM: Oryctolagus cuniculus

<400> SEQUENCE: 977

Gly Thr Ser Thr Leu Ala Ser
1 5

<210> SEQ ID NO 978
<211> LENGTH: 7
<212> TYPE: PRT
<213> ORGANISM: Oryctolagus cuniculus

<400> SEQUENCE: 978

Asp Val Ser Thr Val Ala Ser
1 5

<210> SEQ ID NO 979
<211> LENGTH: 7
<212> TYPE: PRT
<213> ORGANISM: Oryctolagus cuniculus

<400> SEQUENCE: 979

Asp Ala Ser Asn Leu Ala Ser
1 5

<210> SEQ ID NO 980
<211> LENGTH: 7
<212> TYPE: PRT
<213> ORGANISM: Oryctolagus cuniculus

<400> SEQUENCE: 980

Ser Ala Ser Thr Leu Ala Ser
1 5

<210> SEQ ID NO 981
<211> LENGTH: 7
<212> TYPE: PRT
<213> ORGANISM: Oryctolagus cuniculus

<400> SEQUENCE: 981

Arg Ala Ser Thr Leu Ala Ser
1 5

<210> SEQ ID NO 982
<211> LENGTH: 7
<212> TYPE: PRT
<213> ORGANISM: Oryctolagus cuniculus

<400> SEQUENCE: 982

Gly Ala Ser Asn Leu Glu Ser
1 5

<210> SEQ ID NO 983
<211> LENGTH: 7
<212> TYPE: PRT
<213> ORGANISM: Oryctolagus cuniculus

<400> SEQUENCE: 983

Asp Ser Ser Thr Leu Ala Ser
1 5

<210> SEQ ID NO 984
<211> LENGTH: 7
<212> TYPE: PRT
<213> ORGANISM: Oryctolagus cuniculus

<400> SEQUENCE: 984

Lys Ala Ser Thr Leu Ala Ser
1 5

<210> SEQ ID NO 985
<211> LENGTH: 7
<212> TYPE: PRT
<213> ORGANISM: Oryctolagus cuniculus

<400> SEQUENCE: 985

Asp Ala Ser Thr Leu Ala Ser
1 5

<210> SEQ ID NO 986
<211> LENGTH: 7
<212> TYPE: PRT
<213> ORGANISM: Oryctolagus cuniculus

<400> SEQUENCE: 986

Ser Ala Ser Thr Leu Ala Ser
1 5

<210> SEQ ID NO 987
<211> LENGTH: 7
<212> TYPE: PRT
<213> ORGANISM: Oryctolagus cuniculus

<400> SEQUENCE: 987

Ser Ala Ser Thr Leu Ala Ser
1 5

<210> SEQ ID NO 988
<211> LENGTH: 7
<212> TYPE: PRT
<213> ORGANISM: Oryctolagus cuniculus

<400> SEQUENCE: 988

Ser Ala Ser Lys Leu Glu Ser
1 5

<210> SEQ ID NO 989
<211> LENGTH: 7
<212> TYPE: PRT
<213> ORGANISM: Oryctolagus cuniculus

<400> SEQUENCE: 989

Ser Ala Ser Asn Leu Ala Ser
1 5

<210> SEQ ID NO 990
<211> LENGTH: 7
<212> TYPE: PRT
<213> ORGANISM: Oryctolagus cuniculus

<400> SEQUENCE: 990

Asp Ala Ser Asn Leu Ala Ser
1 5

<210> SEQ ID NO 991
<211> LENGTH: 7
<212> TYPE: PRT
<213> ORGANISM: Oryctolagus cuniculus

<400> SEQUENCE: 991

Arg Ala Ser Ser Leu Glu Ser
1 5

<210> SEQ ID NO 992
<211> LENGTH: 7
<212> TYPE: PRT
<213> ORGANISM: Oryctolagus cuniculus

<400> SEQUENCE: 992

Arg Ala Ser Thr Leu Glu Ser
1 5

<210> SEQ ID NO 993
<211> LENGTH: 7
<212> TYPE: PRT
<213> ORGANISM: Oryctolagus cuniculus

<400> SEQUENCE: 993

Leu Ala Ser Thr Leu Ala Ser
1 5

<210> SEQ ID NO 994
<211> LENGTH: 7
<212> TYPE: PRT
<213> ORGANISM: Oryctolagus cuniculus

<400> SEQUENCE: 994

Arg Ala Ser Thr Leu Thr Ser
1 5

<210> SEQ ID NO 995
<211> LENGTH: 7
<212> TYPE: PRT
<213> ORGANISM: Oryctolagus cuniculus

<400> SEQUENCE: 995

Ser Ala Ser Ala Leu Ala Ser
1 5

<210> SEQ ID NO 996
<211> LENGTH: 7
<212> TYPE: PRT
<213> ORGANISM: Oryctolagus cuniculus

<400> SEQUENCE: 996

Ser Ala Ser Ser Leu Ala Ser
1 5

<210> SEQ ID NO 997
<211> LENGTH: 7
<212> TYPE: PRT
<213> ORGANISM: Oryctolagus cuniculus

<400> SEQUENCE: 997

Asp Ala Ser Asp Leu Ala Ser
1 5

<210> SEQ ID NO 998
<211> LENGTH: 7
<212> TYPE: PRT
<213> ORGANISM: Oryctolagus cuniculus

<400> SEQUENCE: 998

Arg Ala Ser Ile Leu Glu Ser
1               5

<210> SEQ ID NO 999
<211> LENGTH: 7
<212> TYPE: PRT
<213> ORGANISM: Oryctolagus cuniculus

<400> SEQUENCE: 999

Asp Ala Ser Lys Leu Ala Ser
1               5

<210> SEQ ID NO 1000
<211> LENGTH: 7
<212> TYPE: PRT
<213> ORGANISM: Oryctolagus cuniculus

<400> SEQUENCE: 1000

Arg Ala Ser Thr Leu Ala Ser
1               5

<210> SEQ ID NO 1001
<211> LENGTH: 7
<212> TYPE: PRT
<213> ORGANISM: Oryctolagus cuniculus

<400> SEQUENCE: 1001

Ala Ala Ser Thr Leu Ala Ser
1               5

<210> SEQ ID NO 1002
<211> LENGTH: 7
<212> TYPE: PRT
<213> ORGANISM: Oryctolagus cuniculus

<400> SEQUENCE: 1002

Arg Ala Thr Thr Leu Glu Ser
1               5

<210> SEQ ID NO 1003
<211> LENGTH: 7
<212> TYPE: PRT
<213> ORGANISM: Oryctolagus cuniculus

<400> SEQUENCE: 1003

Asp Ala Ser Asp Leu Ala Ser
1               5

<210> SEQ ID NO 1004
<211> LENGTH: 7
<212> TYPE: PRT
<213> ORGANISM: Oryctolagus cuniculus

<400> SEQUENCE: 1004

Ser Ala Ser Ser Leu Ala Ser
1               5

<210> SEQ ID NO 1005
<211> LENGTH: 7
<212> TYPE: PRT
<213> ORGANISM: Oryctolagus cuniculus

<400> SEQUENCE: 1005

Arg Ser Ser Thr Leu Ala Ser
1               5

<210> SEQ ID NO 1006
<211> LENGTH: 7
<212> TYPE: PRT
<213> ORGANISM: Oryctolagus cuniculus

<400> SEQUENCE: 1006

Thr Ala Ser Ser Leu Ala Ser
1               5

<210> SEQ ID NO 1007
<211> LENGTH: 7
<212> TYPE: PRT
<213> ORGANISM: Oryctolagus cuniculus

<400> SEQUENCE: 1007

Tyr Ala Ser Asp Leu Glu Ser
1               5

<210> SEQ ID NO 1008
<211> LENGTH: 7
<212> TYPE: PRT
<213> ORGANISM: Oryctolagus cuniculus

<400> SEQUENCE: 1008

Lys Ala Ser Thr Leu Asp Ser
1               5

<210> SEQ ID NO 1009
<211> LENGTH: 7
<212> TYPE: PRT
<213> ORGANISM: Oryctolagus cuniculus

<400> SEQUENCE: 1009

Glu Ala Ser Thr Leu Thr Ser
1               5

<210> SEQ ID NO 1010
<211> LENGTH: 7
<212> TYPE: PRT
<213> ORGANISM: Oryctolagus cuniculus

<400> SEQUENCE: 1010

Tyr Ala Ser Asp Leu Glu Ser
1               5

<210> SEQ ID NO 1011
<211> LENGTH: 7
<212> TYPE: PRT
<213> ORGANISM: Oryctolagus cuniculus

<400> SEQUENCE: 1011

Ala Ala Ser Thr Leu Ala Ser
1               5

<210> SEQ ID NO 1012
<211> LENGTH: 7

<212> TYPE: PRT
<213> ORGANISM: Oryctolagus cuniculus

<400> SEQUENCE: 1012

Gly Ala Ser Asp Leu Ala Ser
1 5

<210> SEQ ID NO 1013
<211> LENGTH: 7
<212> TYPE: PRT
<213> ORGANISM: Oryctolagus cuniculus

<400> SEQUENCE: 1013

Asp Ala Ser Asp Leu Glu Ser
1 5

<210> SEQ ID NO 1014
<211> LENGTH: 7
<212> TYPE: PRT
<213> ORGANISM: Oryctolagus cuniculus

<400> SEQUENCE: 1014

Gly Ala Ser Thr Leu Ala Ser
1 5

<210> SEQ ID NO 1015
<211> LENGTH: 7
<212> TYPE: PRT
<213> ORGANISM: Oryctolagus cuniculus

<400> SEQUENCE: 1015

Ser Ala Ser Thr Leu Ala Ser
1 5

<210> SEQ ID NO 1016
<211> LENGTH: 7
<212> TYPE: PRT
<213> ORGANISM: Oryctolagus cuniculus

<400> SEQUENCE: 1016

Gly Ala Ser Asp Leu Glu Ser
1 5

<210> SEQ ID NO 1017
<211> LENGTH: 7
<212> TYPE: PRT
<213> ORGANISM: Oryctolagus cuniculus

<400> SEQUENCE: 1017

Arg Ala Ser Thr Leu Ala Ser
1 5

<210> SEQ ID NO 1018
<211> LENGTH: 7
<212> TYPE: PRT
<213> ORGANISM: Oryctolagus cuniculus

<400> SEQUENCE: 1018

Arg Ala Ser Thr Leu Glu Ser
1 5

<210> SEQ ID NO 1019
<211> LENGTH: 7
<212> TYPE: PRT
<213> ORGANISM: Oryctolagus cuniculus

<400> SEQUENCE: 1019

Gln Ala Ser Ile Leu Ala Ser
1 5

<210> SEQ ID NO 1020
<211> LENGTH: 7
<212> TYPE: PRT
<213> ORGANISM: Oryctolagus cuniculus

<400> SEQUENCE: 1020

Arg Ala Ser Thr Leu Glu Ser
1 5

<210> SEQ ID NO 1021
<211> LENGTH: 7
<212> TYPE: PRT
<213> ORGANISM: Oryctolagus cuniculus

<400> SEQUENCE: 1021

Asp Ala Ser Thr Leu Ala Ser
1 5

<210> SEQ ID NO 1022
<211> LENGTH: 7
<212> TYPE: PRT
<213> ORGANISM: Oryctolagus cuniculus

<400> SEQUENCE: 1022

Gln Ala Ser Thr Leu Ala Ser
1 5

<210> SEQ ID NO 1023
<211> LENGTH: 7
<212> TYPE: PRT
<213> ORGANISM: Oryctolagus cuniculus

<400> SEQUENCE: 1023

Tyr Thr Ser Thr Leu Ala Ser
1 5

<210> SEQ ID NO 1024
<211> LENGTH: 7
<212> TYPE: PRT
<213> ORGANISM: Oryctolagus cuniculus

<400> SEQUENCE: 1024

Lys Ala Ser Thr Leu Ala Ser
1 5

<210> SEQ ID NO 1025
<211> LENGTH: 7
<212> TYPE: PRT
<213> ORGANISM: Oryctolagus cuniculus

<400> SEQUENCE: 1025

Ser Ala Ser Thr Leu Ala Ser
1 5

<210> SEQ ID NO 1026
<211> LENGTH: 7
<212> TYPE: PRT
<213> ORGANISM: Oryctolagus cuniculus

<400> SEQUENCE: 1026

Asp Ala Ser Asp Leu Ala Ser
1 5

<210> SEQ ID NO 1027
<211> LENGTH: 7
<212> TYPE: PRT
<213> ORGANISM: Oryctolagus cuniculus

<400> SEQUENCE: 1027

Asp Ala Ser Ser Leu Glu Ser
1 5

<210> SEQ ID NO 1028
<211> LENGTH: 7
<212> TYPE: PRT
<213> ORGANISM: Oryctolagus cuniculus

<400> SEQUENCE: 1028

Gly Ala Ser Thr Leu Ala Ser
1 5

<210> SEQ ID NO 1029
<211> LENGTH: 7
<212> TYPE: PRT
<213> ORGANISM: Oryctolagus cuniculus

<400> SEQUENCE: 1029

Arg Ala Ser Thr Leu Ala Ser
1 5

<210> SEQ ID NO 1030
<211> LENGTH: 7
<212> TYPE: PRT
<213> ORGANISM: Oryctolagus cuniculus

<400> SEQUENCE: 1030

Gly Ala Phe Thr Leu Ala Ser
1 5

<210> SEQ ID NO 1031
<211> LENGTH: 7
<212> TYPE: PRT
<213> ORGANISM: Oryctolagus cuniculus

<400> SEQUENCE: 1031

Arg Ala Ser Thr Leu Glu Ser
1 5

<210> SEQ ID NO 1032
<211> LENGTH: 7
<212> TYPE: PRT
<213> ORGANISM: Oryctolagus cuniculus

<400> SEQUENCE: 1032

Gly Ala Ser Thr Leu Ala Ser
1 5

<210> SEQ ID NO 1033
<211> LENGTH: 7
<212> TYPE: PRT
<213> ORGANISM: Oryctolagus cuniculus

<400> SEQUENCE: 1033

Asp Ala Ser Asp Leu Ala Ser 1 5

<210> SEQ ID NO 1034
<211> LENGTH: 7
<212> TYPE: PRT
<213> ORGANISM: Oryctolagus cuniculus

<400> SEQUENCE: 1034

Gly Ala Ser Asn Leu Glu Ser
1 5

<210> SEQ ID NO 1035
<211> LENGTH: 7
<212> TYPE: PRT
<213> ORGANISM: Oryctolagus cuniculus

<400> SEQUENCE: 1035

Leu Ala Ser Thr Leu Ala Ser
1 5

<210> SEQ ID NO 1036
<211> LENGTH: 7
<212> TYPE: PRT
<213> ORGANISM: Oryctolagus cuniculus

<400> SEQUENCE: 1036

Lys Ala Ser Thr Leu Ala Ser
1 5

<210> SEQ ID NO 1037
<211> LENGTH: 13
<212> TYPE: PRT
<213> ORGANISM: Oryctolagus cuniculus

<400> SEQUENCE: 1037

Gln Gly Glu Phe Ser Cys Ser Ser Gly Asp Cys Tyr Ala
1 5 10

<210> SEQ ID NO 1038
<211> LENGTH: 10
<212> TYPE: PRT
<213> ORGANISM: Oryctolagus cuniculus

<400> SEQUENCE: 1038

Ala Gly Gly Tyr Ser Gly Asn Ile Trp Ser
1 5 10

<210> SEQ ID NO 1039
<211> LENGTH: 13
<212> TYPE: PRT
<213> ORGANISM: Oryctolagus cuniculus

<400> SEQUENCE: 1039

Gln Gly Glu Phe Ser Cys Ser Ser Gly Asp Cys Tyr Ala
1 5 10

<210> SEQ ID NO 1040
<211> LENGTH: 10
<212> TYPE: PRT
<213> ORGANISM: Oryctolagus cuniculus

<400> SEQUENCE: 1040

Gln Gly Gly Tyr Thr Asp Ala Thr Tyr Ala
1 5 10

<210> SEQ ID NO 1041
<211> LENGTH: 6
<212> TYPE: PRT
<213> ORGANISM: Oryctolagus cuniculus

<400> SEQUENCE: 1041

Gln Ser Gly Tyr Tyr Thr
1 5

<210> SEQ ID NO 1042
<211> LENGTH: 13
<212> TYPE: PRT
<213> ORGANISM: Oryctolagus cuniculus

<400> SEQUENCE: 1042

Gln Gly Glu Phe Ser Cys Gly Ser Gly Asp Cys Tyr Ala
1 5 10

<210> SEQ ID NO 1043
<211> LENGTH: 12
<212> TYPE: PRT
<213> ORGANISM: Oryctolagus cuniculus

<400> SEQUENCE: 1043

Gln Ser Tyr Tyr Tyr Gly Ser Ser Tyr Val Val Ala
1 5 10

<210> SEQ ID NO 1044
<211> LENGTH: 13
<212> TYPE: PRT
<213> ORGANISM: Oryctolagus cuniculus

<400> SEQUENCE: 1044

Gln Gly Glu Phe Ser Cys Ser Ser Gly Asp Cys Tyr Ala
1 5 10

<210> SEQ ID NO 1045
<211> LENGTH: 13
<212> TYPE: PRT
<213> ORGANISM: Oryctolagus cuniculus

<400> SEQUENCE: 1045

Leu Tyr Ser Tyr Tyr Thr Ser Asn Ser Ala Asp Asn Thr
1 5 10

<210> SEQ ID NO 1046
<211> LENGTH: 11
<212> TYPE: PRT
<213> ORGANISM: Oryctolagus cuniculus

<400> SEQUENCE: 1046

Ala Gly Gly Tyr Asn Ser Gly Ser Asp Ala Ala
1 5 10

<210> SEQ ID NO 1047
<211> LENGTH: 10
<212> TYPE: PRT
<213> ORGANISM: Oryctolagus cuniculus

<400> SEQUENCE: 1047

Gln Gly Tyr Tyr Ser Gly Asp Ile Asn Val
1 5 10

<210> SEQ ID NO 1048

<211> LENGTH: 13
<212> TYPE: PRT
<213> ORGANISM: Oryctolagus cuniculus

<400> SEQUENCE: 1048

Gln Ser Tyr Tyr Gly Thr Ser Asn Ser Tyr Gly Asp Ala
1 5 10

<210> SEQ ID NO 1049
<211> LENGTH: 13
<212> TYPE: PRT
<213> ORGANISM: Oryctolagus cuniculus

<400> SEQUENCE: 1049

Gln Cys Thr Leu Tyr Gly Val Asn Phe Val Pro Asn Val
1 5 10

<210> SEQ ID NO 1050
<211> LENGTH: 13
<212> TYPE: PRT
<213> ORGANISM: Oryctolagus cuniculus

<400> SEQUENCE: 1050

Gln Cys Ile Leu Tyr Gly Val Asn Phe Val Pro Asn Thr
1 5 10

<210> SEQ ID NO 1051
<211> LENGTH: 13
<212> TYPE: PRT
<213> ORGANISM: Oryctolagus cuniculus

<400> SEQUENCE: 1051

Gln Cys Ser Tyr Asp Gly Gly Ser Tyr Val Pro Asn Ala
1 5 10

<210> SEQ ID NO 1052
<211> LENGTH: 11
<212> TYPE: PRT
<213> ORGANISM: Oryctolagus cuniculus

<400> SEQUENCE: 1052

Ala Gly Gly Tyr Ser Thr Ile Ser Asp Asn Ala
1 5 10

<210> SEQ ID NO 1053
<211> LENGTH: 12
<212> TYPE: PRT
<213> ORGANISM: Oryctolagus cuniculus

<400> SEQUENCE: 1053

Gln Cys Thr Phe Tyr Gly Ser Gly Tyr Val Ala Ala
1 5 10

<210> SEQ ID NO 1054
<211> LENGTH: 13
<212> TYPE: PRT
<213> ORGANISM: Oryctolagus cuniculus

<400> SEQUENCE: 1054

Gln Cys Gly Ile Tyr Gly Val Asn Phe Val Pro Asn Val
1 5 10

<210> SEQ ID NO 1055
<211> LENGTH: 12
<212> TYPE: PRT

<213> ORGANISM: Oryctolagus cuniculus

<400> SEQUENCE: 1055

Gln Gln Gly Ala Gly Trp Asn Asn Leu Asp Asn Ala
1 5 10

<210> SEQ ID NO 1056
<211> LENGTH: 11
<212> TYPE: PRT
<213> ORGANISM: Oryctolagus cuniculus

<400> SEQUENCE: 1056

Leu Gly Val Tyr Asp Asp Asp Ala Asp Asn Ala
1 5 10

<210> SEQ ID NO 1057
<211> LENGTH: 12
<212> TYPE: PRT
<213> ORGANISM: Oryctolagus cuniculus

<400> SEQUENCE: 1057

Ala Gly Gly Tyr Ser Thr Asn Thr Asp Thr Tyr Ile
1 5 10

<210> SEQ ID NO 1058
<211> LENGTH: 13
<212> TYPE: PRT
<213> ORGANISM: Oryctolagus cuniculus

<400> SEQUENCE: 1058

Gln Gly Glu Phe Ser Cys Ser Ala Gly Asp Cys Tyr Ala
1 5 10

<210> SEQ ID NO 1059
<211> LENGTH: 10
<212> TYPE: PRT
<213> ORGANISM: Oryctolagus cuniculus

<400> SEQUENCE: 1059

Ala Gly Gly Tyr Ser Gly Asn Ile Trp Ser
1 5 10

<210> SEQ ID NO 1060
<211> LENGTH: 10
<212> TYPE: PRT
<213> ORGANISM: Oryctolagus cuniculus

<400> SEQUENCE: 1060

Ala Gly Gly Tyr Ser Gly Asn Ile Trp Ser
1 5 10

<210> SEQ ID NO 1061
<211> LENGTH: 11
<212> TYPE: PRT
<213> ORGANISM: Oryctolagus cuniculus

<400> SEQUENCE: 1061

Ala Gly Ile Tyr Ser Ser Asp Ser Asp Asn Ala
1 5 10

<210> SEQ ID NO 1062
<211> LENGTH: 13
<212> TYPE: PRT
<213> ORGANISM: Oryctolagus cuniculus

<400> SEQUENCE: 1062

Gln Gly Glu Phe Ser Cys Ser Ser Gly Asp Cys Tyr Ala
1 5 10

<210> SEQ ID NO 1063
<211> LENGTH: 12
<212> TYPE: PRT
<213> ORGANISM: Oryctolagus cuniculus

<400> SEQUENCE: 1063

Gln Gln Gly Tyr Ser Gly Arg Asn Val Glu Asn Thr
1 5 10

<210> SEQ ID NO 1064
<211> LENGTH: 11
<212> TYPE: PRT
<213> ORGANISM: Oryctolagus cuniculus

<400> SEQUENCE: 1064

Leu Gly Gly Tyr Ile Ser Ser Ser Asp Thr Thr
1 5 10

<210> SEQ ID NO 1065
<211> LENGTH: 12
<212> TYPE: PRT
<213> ORGANISM: Oryctolagus cuniculus

<400> SEQUENCE: 1065

Gln Cys Thr Tyr Tyr Asp Asp Ser Tyr Asp Val Pro
1 5 10

<210> SEQ ID NO 1066
<211> LENGTH: 12
<212> TYPE: PRT
<213> ORGANISM: Oryctolagus cuniculus

<400> SEQUENCE: 1066

Ala Gly Gly Tyr Ser Ser Ser Ala Asp Thr Phe Ala
1 5 10

<210> SEQ ID NO 1067
<211> LENGTH: 14
<212> TYPE: PRT
<213> ORGANISM: Oryctolagus cuniculus

<400> SEQUENCE: 1067

Gln Ser Asn Tyr Gly Ser Asn Ser Gly Gly Tyr Val Phe Pro
1 5 10

<210> SEQ ID NO 1068
<211> LENGTH: 13
<212> TYPE: PRT
<213> ORGANISM: Oryctolagus cuniculus

<400> SEQUENCE: 1068

Gln Cys Thr Leu Tyr Gly Val Asn Phe Val Ala Asn Ala
1 5 10

<210> SEQ ID NO 1069
<211> LENGTH: 11
<212> TYPE: PRT
<213> ORGANISM: Oryctolagus cuniculus

<400> SEQUENCE: 1069

-continued

Gln Ser Tyr Tyr Asp Gly Ala Val Thr Phe Thr
1 5 10

<210> SEQ ID NO 1070
<211> LENGTH: 13
<212> TYPE: PRT
<213> ORGANISM: Oryctolagus cuniculus

<400> SEQUENCE: 1070

Leu Gly Gly Tyr Asp Ser Met Ser Ala Asp Cys Phe Ala
1 5 10

<210> SEQ ID NO 1071
<211> LENGTH: 11
<212> TYPE: PRT
<213> ORGANISM: Oryctolagus cuniculus

<400> SEQUENCE: 1071

Leu Gly Val Tyr Asp Asp Asp Ala Asp Asn Ala
1 5 10

<210> SEQ ID NO 1072
<211> LENGTH: 12
<212> TYPE: PRT
<213> ORGANISM: Oryctolagus cuniculus

<400> SEQUENCE: 1072

Ala Gly Gly Tyr Ser Thr Asn Thr Asp Thr Phe Thr
1 5 10

<210> SEQ ID NO 1073
<211> LENGTH: 14
<212> TYPE: PRT
<213> ORGANISM: Oryctolagus cuniculus

<400> SEQUENCE: 1073

Gln Ala Tyr Tyr Tyr Ser Ile Ser Asp Asp Leu Tyr Asn Ala
1 5 10

<210> SEQ ID NO 1074
<211> LENGTH: 12
<212> TYPE: PRT
<213> ORGANISM: Oryctolagus cuniculus

<400> SEQUENCE: 1074

Ala Gly Gly Tyr Ser Thr Asn Thr Asp Thr Phe Thr
1 5 10

<210> SEQ ID NO 1075
<211> LENGTH: 13
<212> TYPE: PRT
<213> ORGANISM: Oryctolagus cuniculus

<400> SEQUENCE: 1075

Gln Cys Thr Ile Tyr Gly Val Asn Phe Val Pro Asn Ala
1 5 10

<210> SEQ ID NO 1076
<211> LENGTH: 13
<212> TYPE: PRT
<213> ORGANISM: Oryctolagus cuniculus

<400> SEQUENCE: 1076

Gln Cys Thr Val Tyr Gly Val Asn Phe Val Ala Asn Ala
1 5 10

<210> SEQ ID NO 1077
<211> LENGTH: 10
<212> TYPE: PRT
<213> ORGANISM: Oryctolagus cuniculus

<400> SEQUENCE: 1077

Gln Ser Val Trp Tyr Ala Gly Gly Ala Ala
1               5                   10

<210> SEQ ID NO 1078
<211> LENGTH: 13
<212> TYPE: PRT
<213> ORGANISM: Oryctolagus cuniculus

<400> SEQUENCE: 1078

Ala Gly Glu Phe Ser Cys Ala Ser Ala Asp Cys Phe Ala
1               5                   10

<210> SEQ ID NO 1079
<211> LENGTH: 12
<212> TYPE: PRT
<213> ORGANISM: Oryctolagus cuniculus

<400> SEQUENCE: 1079

Gln Ser Tyr Gly Tyr Gly Ser Gly Tyr Val Phe Ala
1               5                   10

<210> SEQ ID NO 1080
<211> LENGTH: 13
<212> TYPE: PRT
<213> ORGANISM: Oryctolagus cuniculus

<400> SEQUENCE: 1080

Leu Gly Asn Tyr Asp Cys Glu Ser Asp Asp Cys Tyr Ala
1               5                   10

<210> SEQ ID NO 1081
<211> LENGTH: 15
<212> TYPE: PRT
<213> ORGANISM: Oryctolagus cuniculus

<400> SEQUENCE: 1081

Gln Cys Thr Tyr Gly Ser Ser Ser Ser Ser Ala Tyr Gly Trp Ala
1               5                   10                  15

<210> SEQ ID NO 1082
<211> LENGTH: 11
<212> TYPE: PRT
<213> ORGANISM: Oryctolagus cuniculus

<400> SEQUENCE: 1082

Leu Gly Ser Tyr Ile Ser Ser Ser Asp Asn Ala
1               5                   10

<210> SEQ ID NO 1083
<211> LENGTH: 11
<212> TYPE: PRT
<213> ORGANISM: Oryctolagus cuniculus

<400> SEQUENCE: 1083

Ala Gly Gly Tyr Ser Ser Ile Ser Asp Asn Gly
1               5                   10

<210> SEQ ID NO 1084
<211> LENGTH: 14
<212> TYPE: PRT
<213> ORGANISM: Oryctolagus cuniculus

<400> SEQUENCE: 1084

Gln Gly Tyr Tyr Tyr Tyr Ile Ser Asn Thr Tyr Gly Tyr Pro
1               5                   10

<210> SEQ ID NO 1085
<211> LENGTH: 12
<212> TYPE: PRT
<213> ORGANISM: Oryctolagus cuniculus

<400> SEQUENCE: 1085

Gln Cys Thr Tyr Gly Tyr Ser Gly Tyr Val Ser Ala
1               5                   10

<210> SEQ ID NO 1086
<211> LENGTH: 12
<212> TYPE: PRT
<213> ORGANISM: Oryctolagus cuniculus

<400> SEQUENCE: 1086

Leu Gly Val Tyr Thr Tyr Ile Ser Ala Asp Asn Ala
1               5                   10

<210> SEQ ID NO 1087
<211> LENGTH: 13
<212> TYPE: PRT
<213> ORGANISM: Oryctolagus cuniculus

<400> SEQUENCE: 1087

Gln Gly Glu Phe Ser Cys Ser Ser Gly Asp Cys Tyr Ala
1               5                   10

<210> SEQ ID NO 1088
<211> LENGTH: 11
<212> TYPE: PRT
<213> ORGANISM: Oryctolagus cuniculus

<400> SEQUENCE: 1088

Leu Gly Ser Tyr Ile Ser Ser Ser Asp Asn Gly
1               5                   10

<210> SEQ ID NO 1089
<211> LENGTH: 11
<212> TYPE: PRT
<213> ORGANISM: Oryctolagus cuniculus

<400> SEQUENCE: 1089

Ala Gly Gly Tyr Ser Asp Ile Ser Asp Asn Ala
1               5                   10

<210> SEQ ID NO 1090
<211> LENGTH: 13
<212> TYPE: PRT
<213> ORGANISM: Oryctolagus cuniculus

<400> SEQUENCE: 1090

Gln Gly Glu Phe Asn Cys Gly Ser Gly Asp Cys Ser Thr
1               5                   10

<210> SEQ ID NO 1091
<211> LENGTH: 12

<212> TYPE: PRT
<213> ORGANISM: Oryctolagus cuniculus

<400> SEQUENCE: 1091

Gln Cys Thr Phe Trp Asp Ile Asn Asn Phe Gly Gly
1 5 10

<210> SEQ ID NO 1092
<211> LENGTH: 11
<212> TYPE: PRT
<213> ORGANISM: Oryctolagus cuniculus

<400> SEQUENCE: 1092

Leu Gly Gly Tyr Asp Ala Asp Ala Asp Asn Ala
1 5 10

<210> SEQ ID NO 1093
<211> LENGTH: 13
<212> TYPE: PRT
<213> ORGANISM: Oryctolagus cuniculus

<400> SEQUENCE: 1093

Gln Gly Glu Phe Ser Cys Ser Ser Gly Asp Cys Tyr Ala
1 5 10

<210> SEQ ID NO 1094
<211> LENGTH: 10
<212> TYPE: PRT
<213> ORGANISM: Oryctolagus cuniculus

<400> SEQUENCE: 1094

Ala Gly Ala Tyr Ser Gly Asn Val Gly Thr
1 5 10

<210> SEQ ID NO 1095
<211> LENGTH: 12
<212> TYPE: PRT
<213> ORGANISM: Oryctolagus cuniculus

<400> SEQUENCE: 1095

Gln Gln Thr Tyr Ser Gly Ser Asn Val Glu Asn Ser
1 5 10

<210> SEQ ID NO 1096
<211> LENGTH: 13
<212> TYPE: PRT
<213> ORGANISM: Oryctolagus cuniculus

<400> SEQUENCE: 1096

Gln Gln Thr Tyr Ile Tyr Asn Asn Ala Glu Asp Asn Thr
1 5 10

<210> SEQ ID NO 1097
<211> LENGTH: 14
<212> TYPE: PRT
<213> ORGANISM: Oryctolagus cuniculus

<400> SEQUENCE: 1097

Gln Cys Thr Phe Gly Ala Thr Asn Asp Asp Tyr Gly Asn Ala
1 5 10

<210> SEQ ID NO 1098
<211> LENGTH: 15
<212> TYPE: PRT
<213> ORGANISM: Oryctolagus cuniculus

<400> SEQUENCE: 1098

Gln Cys Thr Val Gly Ser Ser Gly Val Thr Gly Tyr Gly Asn Ala
1 5 10 15

<210> SEQ ID NO 1099
<211> LENGTH: 14
<212> TYPE: PRT
<213> ORGANISM: Oryctolagus cuniculus

<400> SEQUENCE: 1099

Gln Asn Tyr Tyr Gly Tyr Gly Leu Ser Thr Asn Tyr Val Val
1 5 10

<210> SEQ ID NO 1100
<211> LENGTH: 13
<212> TYPE: PRT
<213> ORGANISM: Oryctolagus cuniculus

<400> SEQUENCE: 1100

Gln Gly Glu Phe Ser Cys Ser Ser Gly Asp Cys Thr Ala
1 5 10

<210> SEQ ID NO 1101
<211> LENGTH: 14
<212> TYPE: PRT
<213> ORGANISM: Oryctolagus cuniculus

<400> SEQUENCE: 1101

Gln Cys Thr Ala Gly Ser Ile Asn Val Ser Tyr Gly Asn Ala
1 5 10

<210> SEQ ID NO 1102
<211> LENGTH: 13
<212> TYPE: PRT
<213> ORGANISM: Oryctolagus cuniculus

<400> SEQUENCE: 1102

Leu Gly Ser Tyr Asp Cys Ser Ser Val Asp Cys Asn Ala
1 5 10

<210> SEQ ID NO 1103
<211> LENGTH: 12
<212> TYPE: PRT
<213> ORGANISM: Oryctolagus cuniculus

<400> SEQUENCE: 1103

Ala Gly Gly Tyr Asp Ser Thr Ile Asp Thr Phe Thr
1 5 10

<210> SEQ ID NO 1104
<211> LENGTH: 15
<212> TYPE: PRT
<213> ORGANISM: Oryctolagus cuniculus

<400> SEQUENCE: 1104

Gln Cys Thr Tyr Gly Ser Ser Thr Ser Ser Arg Ser Gly Asn Ala
1 5 10 15

<210> SEQ ID NO 1105
<211> LENGTH: 15
<212> TYPE: PRT
<213> ORGANISM: Oryctolagus cuniculus

<400> SEQUENCE: 1105

Gln Ser Tyr Tyr Tyr Gly Ile Ser Ser Thr Tyr Ala Phe Tyr Thr
1 5 10 15

<210> SEQ ID NO 1106
<211> LENGTH: 12
<212> TYPE: PRT
<213> ORGANISM: Oryctolagus cuniculus

<400> SEQUENCE: 1106

Gln Cys Thr Tyr Trp Asp Ser Ser Thr Val Gly Ala
1 5 10

<210> SEQ ID NO 1107
<211> LENGTH: 11
<212> TYPE: PRT
<213> ORGANISM: Oryctolagus cuniculus

<400> SEQUENCE: 1107

Ser Gly Gly Tyr Ile Ser Ser Ser Asp Asn Ala
1 5 10

<210> SEQ ID NO 1108
<211> LENGTH: 11
<212> TYPE: PRT
<213> ORGANISM: Oryctolagus cuniculus

<400> SEQUENCE: 1108

Gln Ser Thr Tyr Tyr Gly Ser Ser Gly Asn Ala
1 5 10

<210> SEQ ID NO 1109
<211> LENGTH: 13
<212> TYPE: PRT
<213> ORGANISM: Oryctolagus cuniculus

<400> SEQUENCE: 1109

Leu Tyr Gly Tyr Val Thr Ser Ser Asn Ala Asp Phe Ala
1 5 10

<210> SEQ ID NO 1110
<211> LENGTH: 13
<212> TYPE: PRT
<213> ORGANISM: Oryctolagus cuniculus

<400> SEQUENCE: 1110

Leu Gly Thr Tyr Asp Cys Val Ser Ala Asp Cys Gly Ala
1 5 10

<210> SEQ ID NO 1111
<211> LENGTH: 12
<212> TYPE: PRT
<213> ORGANISM: Oryctolagus cuniculus

<400> SEQUENCE: 1111

Gln Gly Thr Tyr Ser Asn Asn Gly Trp Tyr Phe Ala
1 5 10

<210> SEQ ID NO 1112
<211> LENGTH: 15
<212> TYPE: PRT
<213> ORGANISM: Oryctolagus cuniculus

<400> SEQUENCE: 1112

Gln Ser Tyr Tyr Tyr Gly Ile Ser Ser Thr Tyr Ala Phe Tyr Thr 1 5 10 15

<210> SEQ ID NO 1113
<211> LENGTH: 11
<212> TYPE: PRT
<213> ORGANISM: Oryctolagus cuniculus

<400> SEQUENCE: 1113

Gln Thr Tyr Tyr Gly Gly Ile Asn Ile Phe Thr
1 5 10

<210> SEQ ID NO 1114
<211> LENGTH: 13
<212> TYPE: PRT
<213> ORGANISM: Oryctolagus cuniculus

<400> SEQUENCE: 1114

Leu Gly Thr Tyr Asp Cys Ser Ser Thr Asp Cys Tyr Ala
1 5 10

<210> SEQ ID NO 1115
<211> LENGTH: 13
<212> TYPE: PRT
<213> ORGANISM: Oryctolagus cuniculus

<400> SEQUENCE: 1115

Gln Cys Thr Val Tyr Gly Val Asn Phe Val Pro Asn Ala
1 5 10

<210> SEQ ID NO 1116
<211> LENGTH: 12
<212> TYPE: PRT
<213> ORGANISM: Oryctolagus cuniculus

<400> SEQUENCE: 1116

Gln Gly Gly Tyr Tyr Ile Ser Ser Thr Asp Asn Ala
1 5 10

<210> SEQ ID NO 1117
<211> LENGTH: 12
<212> TYPE: PRT
<213> ORGANISM: Oryctolagus cuniculus

<400> SEQUENCE: 1117

Gln Gln Gly Tyr Ser Ser Ser Asn Val Asp Asn Ala
1 5 10

<210> SEQ ID NO 1118
<211> LENGTH: 12
<212> TYPE: PRT
<213> ORGANISM: Oryctolagus cuniculus

<400> SEQUENCE: 1118

Gln Gly Gly Tyr Tyr Gly Ser Ser Asp Thr Val Thr
1 5 10

<210> SEQ ID NO 1119
<211> LENGTH: 12
<212> TYPE: PRT
<213> ORGANISM: Oryctolagus cuniculus

<400> SEQUENCE: 1119

Ala Gly Gly Tyr Ser Gly Ser Ser Asp Val Phe Ala
1 5 10

<210> SEQ ID NO 1120
<211> LENGTH: 13
<212> TYPE: PRT
<213> ORGANISM: Oryctolagus cuniculus

<400> SEQUENCE: 1120

Gln Cys Thr Val Tyr Gly Val Asn Tyr Val Pro Asn Ala
1 5 10

<210> SEQ ID NO 1121
<211> LENGTH: 12
<212> TYPE: PRT
<213> ORGANISM: Oryctolagus cuniculus

<400> SEQUENCE: 1121

Gln Cys Thr Tyr Tyr Gly Gly Ser Gly Asp Val Pro
1 5 10

<210> SEQ ID NO 1122
<211> LENGTH: 14
<212> TYPE: PRT
<213> ORGANISM: Oryctolagus cuniculus

<400> SEQUENCE: 1122

Gln Cys Thr Tyr Gly Thr Thr Asn Thr Gly His Tyr Val Gly
1 5 10

<210> SEQ ID NO 1123
<211> LENGTH: 11
<212> TYPE: PRT
<213> ORGANISM: Oryctolagus cuniculus

<400> SEQUENCE: 1123

Gln Cys Thr Tyr Tyr Ser Gly Ser Pro His Thr
1 5 10

<210> SEQ ID NO 1124
<211> LENGTH: 16
<212> TYPE: PRT
<213> ORGANISM: Oryctolagus cuniculus

<400> SEQUENCE: 1124

Gln Ser Asn Tyr Gly Ser Ser Ser Ile Ser Asn Tyr Gly Gly Gly Ala
1 5 10 15

<210> SEQ ID NO 1125
<211> LENGTH: 10
<212> TYPE: PRT
<213> ORGANISM: Oryctolagus cuniculus

<400> SEQUENCE: 1125

Ala Gly Gly Tyr Ser Gly Asn Met Tyr Val
1 5 10

<210> SEQ ID NO 1126
<211> LENGTH: 12
<212> TYPE: PRT
<213> ORGANISM: Oryctolagus cuniculus

<400> SEQUENCE: 1126

Ala Gly Gly Tyr Gly Ser Tyr Thr Asp Thr Phe Ala
1 5 10

<210> SEQ ID NO 1127

<211> LENGTH: 11
<212> TYPE: PRT
<213> ORGANISM: Oryctolagus cuniculus

<400> SEQUENCE: 1127

Leu Gly Gly Tyr Asp Asp Asp Ala Asp Asn Thr
1 5 10

<210> SEQ ID NO 1128
<211> LENGTH: 13
<212> TYPE: PRT
<213> ORGANISM: Oryctolagus cuniculus

<400> SEQUENCE: 1128

Gln Cys Thr Ile Tyr Gly Val Asn Phe Val Pro Asn Ala
1 5 10

<210> SEQ ID NO 1129
<211> LENGTH: 12
<212> TYPE: PRT
<213> ORGANISM: Oryctolagus cuniculus

<400> SEQUENCE: 1129

Gln Ser Asn Tyr Ala Ile Ile Ser Cys Gly Ala Ala
1 5 10

<210> SEQ ID NO 1130
<211> LENGTH: 12
<212> TYPE: PRT
<213> ORGANISM: Oryctolagus cuniculus

<400> SEQUENCE: 1130

Gln Ser Ala Tyr Tyr Ser Ser Ser Ala Val Tyr Ala
1 5 10

<210> SEQ ID NO 1131
<211> LENGTH: 13
<212> TYPE: PRT
<213> ORGANISM: Oryctolagus cuniculus

<400> SEQUENCE: 1131

Gln Gln Thr Tyr Ile Tyr Asn Asn Ala Glu Ser Asn Ala
1 5 10

<210> SEQ ID NO 1132
<211> LENGTH: 10
<212> TYPE: PRT
<213> ORGANISM: Oryctolagus cuniculus

<400> SEQUENCE: 1132

Val Gly Gly Tyr Ser Thr Ser Gly Tyr Ala
1 5 10

<210> SEQ ID NO 1133
<211> LENGTH: 13
<212> TYPE: PRT
<213> ORGANISM: Oryctolagus cuniculus

<400> SEQUENCE: 1133

Gln Gly Glu Phe Ser Cys Ser Asn Gly Asp Cys Ile Ala
1 5 10

<210> SEQ ID NO 1134
<211> LENGTH: 12
<212> TYPE: PRT

<213> ORGANISM: Oryctolagus cuniculus

<400> SEQUENCE: 1134

Gln Gly Gly Tyr Tyr Gly Ser Ser Asp Thr Val Thr
1 5 10

<210> SEQ ID NO 1135
<211> LENGTH: 12
<212> TYPE: PRT
<213> ORGANISM: Oryctolagus cuniculus

<400> SEQUENCE: 1135

Gln Gln Gly Tyr Thr Ser Ser Asn Val Asp Asn Val
1 5 10

<210> SEQ ID NO 1136
<211> LENGTH: 13
<212> TYPE: PRT
<213> ORGANISM: Oryctolagus cuniculus

<400> SEQUENCE: 1136

Leu Gly Ser Tyr Asp Cys Ser Ser Ala Asp Cys Asn Val
1 5 10

<210> SEQ ID NO 1137
<211> LENGTH: 13
<212> TYPE: PRT
<213> ORGANISM: Oryctolagus cuniculus

<400> SEQUENCE: 1137

Gln Ser Thr Phe Tyr Gly Val Asn Pro Val Pro Asn Ala
1 5 10

<210> SEQ ID NO 1138
<211> LENGTH: 11
<212> TYPE: PRT
<213> ORGANISM: Oryctolagus cuniculus

<400> SEQUENCE: 1138

Leu Gly Val Tyr Asp Asp Asp Ala Asp Asn Ala
1 5 10

<210> SEQ ID NO 1139
<211> LENGTH: 15
<212> TYPE: PRT
<213> ORGANISM: Oryctolagus cuniculus

<400> SEQUENCE: 1139

Gln Cys Thr Tyr Gly Ser Ser Thr Ser Ser Arg Ser Gly Asn Ala
1 5 10 15

<210> SEQ ID NO 1140
<211> LENGTH: 13
<212> TYPE: PRT
<213> ORGANISM: Oryctolagus cuniculus

<400> SEQUENCE: 1140

Gln Cys Thr Tyr Gly Ser Ser Gly Ser Ser Phe Leu Ala
1 5 10

<210> SEQ ID NO 1141
<211> LENGTH: 12
<212> TYPE: PRT
<213> ORGANISM: Oryctolagus cuniculus

<400> SEQUENCE: 1141

Gln Gln Thr Tyr Ser Gly Ser Asn Val Glu Asn Ser
1 5 10

<210> SEQ ID NO 1142
<211> LENGTH: 11
<212> TYPE: PRT
<213> ORGANISM: Oryctolagus cuniculus

<400> SEQUENCE: 1142

Ala Gly Asp Tyr Ser Ser Ser Ser Asp Asn Thr
1 5 10

<210> SEQ ID NO 1143
<211> LENGTH: 12
<212> TYPE: PRT
<213> ORGANISM: Oryctolagus cuniculus

<400> SEQUENCE: 1143

Gln Ser Thr Tyr Trp Glu Ser Asn Asn Ile Gly Thr
1 5 10

<210> SEQ ID NO 1144
<211> LENGTH: 12
<212> TYPE: PRT
<213> ORGANISM: Oryctolagus cuniculus

<400> SEQUENCE: 1144

Ala Gly Gly Tyr Ser Gly Ser Ala Asp Thr Phe Ala
1 5 10

<210> SEQ ID NO 1145
<211> LENGTH: 11
<212> TYPE: PRT
<213> ORGANISM: Oryctolagus cuniculus

<400> SEQUENCE: 1145

Gln Ser Tyr Ala Gly Ile Ser Ser Gly Val Ala
1 5 10

<210> SEQ ID NO 1146
<211> LENGTH: 14
<212> TYPE: PRT
<213> ORGANISM: Oryctolagus cuniculus

<400> SEQUENCE: 1146

Gln Cys Thr Tyr Gly Thr Thr Asn Thr Gly His Tyr Val Gly
1 5 10

<210> SEQ ID NO 1147
<211> LENGTH: 12
<212> TYPE: PRT
<213> ORGANISM: Oryctolagus cuniculus

<400> SEQUENCE: 1147

Ala Gly Gly Tyr Asp Ser Ser Val Asp Thr Phe Ala
1 5 10

<210> SEQ ID NO 1148
<211> LENGTH: 15
<212> TYPE: PRT
<213> ORGANISM: Oryctolagus cuniculus

<400> SEQUENCE: 1148

Gln Ser His Tyr Cys Cys Ser Ser Asn Tyr Asp Tyr Ile Tyr Ala
1 5 10 15

<210> SEQ ID NO 1149
<211> LENGTH: 14
<212> TYPE: PRT
<213> ORGANISM: Oryctolagus cuniculus

<400> SEQUENCE: 1149

Gln Ser Tyr Tyr Tyr Ser Ile Ser Asp Ser Val Asp Tyr Pro
1 5 10

<210> SEQ ID NO 1150
<211> LENGTH: 15
<212> TYPE: PRT
<213> ORGANISM: Oryctolagus cuniculus

<400> SEQUENCE: 1150

Gln Cys Thr Tyr Gly Ser Ser Ala Ser Ser Ser Tyr Gly Asn Ala
1 5 10 15

<210> SEQ ID NO 1151
<211> LENGTH: 11
<212> TYPE: PRT
<213> ORGANISM: Oryctolagus cuniculus

<400> SEQUENCE: 1151

Gln Thr Tyr Tyr Pro Ser Ser Val Thr Tyr Ala
1 5 10

<210> SEQ ID NO 1152
<211> LENGTH: 13
<212> TYPE: PRT
<213> ORGANISM: Oryctolagus cuniculus

<400> SEQUENCE: 1152

Gln Ser Thr Phe Tyr Gly Val Asn Pro Val Pro Thr Ala
1 5 10

<210> SEQ ID NO 1153
<211> LENGTH: 11
<212> TYPE: PRT
<213> ORGANISM: Oryctolagus cuniculus

<400> SEQUENCE: 1153

Ala Gly Gly Tyr Ser Ser Ser Ser Asp Asn Ala
1 5 10

<210> SEQ ID NO 1154
<211> LENGTH: 10
<212> TYPE: PRT
<213> ORGANISM: Oryctolagus cuniculus

<400> SEQUENCE: 1154

Gln Gly Tyr Tyr Ser Gly Tyr Ile Asn Ala
1 5 10

<210> SEQ ID NO 1155
<211> LENGTH: 14
<212> TYPE: PRT
<213> ORGANISM: Oryctolagus cuniculus

<400> SEQUENCE: 1155

Gln Cys Thr Tyr Gly Ser Ile Ser Ser Ser Ala Gly Asn Ala
1 5 10

<210> SEQ ID NO 1156
<211> LENGTH: 10
<212> TYPE: PRT
<213> ORGANISM: Oryctolagus cuniculus

<400> SEQUENCE: 1156

Gln Gly Gly Tyr Thr Asp Ala Thr Tyr Ala
1 5 10

<210> SEQ ID NO 1157
<211> LENGTH: 13
<212> TYPE: PRT
<213> ORGANISM: Oryctolagus cuniculus

<400> SEQUENCE: 1157

Gln Gly Glu Phe Ser Cys Ser Asn Gly Asp Cys Ile Ala
1 5 10

<210> SEQ ID NO 1158
<211> LENGTH: 14
<212> TYPE: PRT
<213> ORGANISM: Oryctolagus cuniculus

<400> SEQUENCE: 1158

Gln Cys Thr Tyr Gly Ser Ile Ser Ser Ser Ser Gly Asn Ala
1 5 10

<210> SEQ ID NO 1159
<211> LENGTH: 10
<212> TYPE: PRT
<213> ORGANISM: Oryctolagus cuniculus

<400> SEQUENCE: 1159

Ala Gly Gly Tyr Ile Gly Asp Ile Tyr Ala
1 5 10

<210> SEQ ID NO 1160
<211> LENGTH: 15
<212> TYPE: PRT
<213> ORGANISM: Oryctolagus cuniculus

<400> SEQUENCE: 1160

Gln Cys Thr Tyr Gly Ser Ser Arg Val Ser Ser Tyr Gly Asp Ala
1 5 10 15

<210> SEQ ID NO 1161
<211> LENGTH: 10
<212> TYPE: PRT
<213> ORGANISM: Oryctolagus cuniculus

<400> SEQUENCE: 1161

Gln Ser Tyr Tyr Gly Ile Ser Ala Tyr Ala
1 5 10

<210> SEQ ID NO 1162
<211> LENGTH: 13
<212> TYPE: PRT
<213> ORGANISM: Oryctolagus cuniculus

<400> SEQUENCE: 1162

Gln Asp Asn Tyr Gly Ser Ser Thr Thr Tyr Gly Asn Ser
1 5 10

<210> SEQ ID NO 1163
<211> LENGTH: 15
<212> TYPE: PRT
<213> ORGANISM: Oryctolagus cuniculus

<400> SEQUENCE: 1163

Gln Ser Tyr Tyr His Ser Thr Ser Gly Ser Ser Tyr Gly Asn Thr
1 5 10 15

<210> SEQ ID NO 1164
<211> LENGTH: 13
<212> TYPE: PRT
<213> ORGANISM: Oryctolagus cuniculus

<400> SEQUENCE: 1164

Gln Ser Thr Tyr Tyr Asn Ile Ser Ala Asp Phe Tyr Ala
1 5 10

<210> SEQ ID NO 1165
<211> LENGTH: 11
<212> TYPE: PRT
<213> ORGANISM: Oryctolagus cuniculus

<400> SEQUENCE: 1165

Ala Gly Asp Tyr Ile Ser Asp Ser Asp Asn Thr
1 5 10

<210> SEQ ID NO 1166
<211> LENGTH: 15
<212> TYPE: PRT
<213> ORGANISM: Oryctolagus cuniculus

<400> SEQUENCE: 1166

Gln Cys Thr Tyr Gly Ser Ser Ser Gly Ser Tyr Gly Gly Trp Ala
1 5 10 15

<210> SEQ ID NO 1167
<211> LENGTH: 12
<212> TYPE: PRT
<213> ORGANISM: Oryctolagus cuniculus

<400> SEQUENCE: 1167

Gln Ser Asn Tyr Gly Phe Ser Ser Gly Ser Tyr Ala
1 5 10

<210> SEQ ID NO 1168
<211> LENGTH: 14
<212> TYPE: PRT
<213> ORGANISM: Oryctolagus cuniculus

<400> SEQUENCE: 1168

Gln Cys Thr Tyr Gly Ser Leu Ser Ser Thr Tyr Gly Trp Ala
1 5 10

<210> SEQ ID NO 1169
<211> LENGTH: 12
<212> TYPE: PRT
<213> ORGANISM: Oryctolagus cuniculus

<400> SEQUENCE: 1169

Ala Gly Gly Tyr Asp Arg Phe Ile Asp Thr Phe Ala
1 5 10

<210> SEQ ID NO 1170
<211> LENGTH: 11

<212> TYPE: PRT
<213> ORGANISM: Oryctolagus cuniculus

<400> SEQUENCE: 1170

Ala Gly Gly Tyr Ile Thr Asn Ser Asp Asn Gly
1 5 10

<210> SEQ ID NO 1171
<211> LENGTH: 12
<212> TYPE: PRT
<213> ORGANISM: Oryctolagus cuniculus

<400> SEQUENCE: 1171

Gln Ser Tyr Gly Tyr Gly Ser Gly Tyr Val Phe Ala
1 5 10

<210> SEQ ID NO 1172
<211> LENGTH: 13
<212> TYPE: PRT
<213> ORGANISM: Oryctolagus cuniculus

<400> SEQUENCE: 1172

Leu Tyr Ser Tyr Tyr Ile Asp Ser Asn Val Asp Phe Ala
1 5 10

<210> SEQ ID NO 1173
<211> LENGTH: 13
<212> TYPE: PRT
<213> ORGANISM: Oryctolagus cuniculus

<400> SEQUENCE: 1173

Gln Cys Thr Leu Tyr Gly Val Asn Phe Val Pro Asn Val
1 5 10

<210> SEQ ID NO 1174
<211> LENGTH: 15
<212> TYPE: PRT
<213> ORGANISM: Oryctolagus cuniculus

<400> SEQUENCE: 1174

Gln Cys Thr Val Gly Ser Ser Gly Val Thr Gly Tyr Gly Asn Ala
1 5 10 15

<210> SEQ ID NO 1175
<211> LENGTH: 11
<212> TYPE: PRT
<213> ORGANISM: Oryctolagus cuniculus

<400> SEQUENCE: 1175

Gln Cys Thr Tyr Tyr Gly Gly Ser Pro Asn Val
1 5 10

<210> SEQ ID NO 1176
<211> LENGTH: 12
<212> TYPE: PRT
<213> ORGANISM: Oryctolagus cuniculus

<400> SEQUENCE: 1176

Gln Gln Gly Tyr Thr Thr Ser Asn Val Asp Asn Thr
1 5 10

<210> SEQ ID NO 1177
<211> LENGTH: 11
<212> TYPE: PRT
<213> ORGANISM: Oryctolagus cuniculus

<400> SEQUENCE: 1177

Ala Gly Ala Tyr Val Gly Ser Ser Asp Asn Thr
1 5 10

<210> SEQ ID NO 1178
<211> LENGTH: 11
<212> TYPE: PRT
<213> ORGANISM: Oryctolagus cuniculus

<400> SEQUENCE: 1178

Ala Gly Asp Tyr Ser Ser Asn Ser Asp Asp Ala
1 5 10

<210> SEQ ID NO 1179
<211> LENGTH: 14
<212> TYPE: PRT
<213> ORGANISM: Oryctolagus cuniculus

<400> SEQUENCE: 1179

Gln Ser Tyr Trp Tyr Thr Met Gly Asn Ser Tyr Gly Asn Thr
1 5 10

<210> SEQ ID NO 1180
<211> LENGTH: 11
<212> TYPE: PRT
<213> ORGANISM: Oryctolagus cuniculus

<400> SEQUENCE: 1180

Leu Gly Ser Tyr Ile Asn Ser Ser Asp Asn Ala
1 5 10

<210> SEQ ID NO 1181
<211> LENGTH: 13
<212> TYPE: PRT
<213> ORGANISM: Oryctolagus cuniculus

<400> SEQUENCE: 1181

Gln Ser Ala Tyr Tyr Ser Ser Ser Thr Asp Gly Gly Ala
1 5 10

<210> SEQ ID NO 1182
<211> LENGTH: 13
<212> TYPE: PRT
<213> ORGANISM: Oryctolagus cuniculus

<400> SEQUENCE: 1182

Gln Gly Tyr Tyr Tyr Ala Asp Ser Asp Asp Asn Ile Ala
1 5 10

<210> SEQ ID NO 1183
<211> LENGTH: 10
<212> TYPE: PRT
<213> ORGANISM: Oryctolagus cuniculus

<400> SEQUENCE: 1183

Gln Gly Tyr Tyr Ser Thr Gly Met Phe Ala
1 5 10

<210> SEQ ID NO 1184
<211> LENGTH: 13
<212> TYPE: PRT
<213> ORGANISM: Oryctolagus cuniculus

<400> SEQUENCE: 1184

```
Gln Cys Thr Leu Tyr Gly Val Asn Phe Val Pro Asn Ala
1               5                   10


<210> SEQ ID NO 1185
<211> LENGTH: 117
<212> TYPE: PRT
<213> ORGANISM: Artificial Sequence
<220> FEATURE:
<223> OTHER INFORMATION: MAB-17-0119 HC VR

<400> SEQUENCE: 1185

Glu Val Gln Leu Glu Glu Ser Gly Gly Arg Leu Val Gln Pro Gly Thr
1               5                   10                  15

Ser Leu Arg Leu Ser Cys Ala Val Ser Gly Phe Ser Leu Asn Ser Tyr
            20                  25                  30

Asp Met Ser Trp Val Arg Gln Ala Pro Gly Lys Gly Leu Glu Tyr Val
        35                  40                  45

Gly Ile Ile Tyr Asn Ser Gly Thr Thr Tyr Tyr Ala Asn Trp Ala Lys
    50                  55                  60

Gly Arg Phe Thr Ile Ser Lys Asp Thr Ser Lys Thr Thr Leu Tyr Leu
65                  70                  75                  80

Gln Met Asn Ser Leu Arg Ala Glu Asp Thr Ala Thr Tyr Phe Cys Ala
                85                  90                  95

Arg Thr His Asn Thr Leu Pro Phe Tyr Ile Trp Gly Gln Gly Thr Leu
            100                 105                 110

Val Thr Val Ser Ser
        115


<210> SEQ ID NO 1186
<211> LENGTH: 122
<212> TYPE: PRT
<213> ORGANISM: Artificial Sequence
<220> FEATURE:
<223> OTHER INFORMATION: MAB-17-0127 HC VR

<400> SEQUENCE: 1186

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Ser
            20                  25                  30

Tyr Tyr Met Cys Trp Val Arg Gln Ala Pro Gly Lys Gly Leu Glu Trp
        35                  40                  45

Val Ala Cys Ile Tyr Ala Gly Ser Ser Gly Ser Thr Tyr Tyr Ala Ser
    50                  55                  60

Trp Ala Lys Gly Arg Phe Thr Ile Ser Lys Asp Ile Ser Lys Thr Thr
65                  70                  75                  80

Leu Tyr Leu Gln Met Asn Ser Leu Arg Ala Glu Asp Thr Ala Val Tyr
                85                  90                  95

Phe Cys Ala Arg Gly Gly Gly Ser Gly Gly Val Asp Asn Asn Leu Trp
            100                 105                 110

Gly Gln Gly Thr Leu Val Thr Val Ser Ser
        115                 120


<210> SEQ ID NO 1187
<211> LENGTH: 121
<212> TYPE: PRT
<213> ORGANISM: Artificial Sequence
<220> FEATURE:
<223> OTHER INFORMATION: MAB-17-0193 HC VR
```

<400> SEQUENCE: 1187

Glu Val Gln Leu Glu Glu Ser Gly Gly Gly Leu Val Gln Pro Gly Gly
1 5 10 15

Ser Leu Arg Leu Ser Cys Ala Ala Ser Gly Phe Ser Phe Asn Asn Asn
20 25 30

Tyr Tyr Met Cys Trp Val Arg Gln Ala Pro Gly Lys Gly Leu Glu Trp
35 40 45

Val Ala Cys Ile Tyr Thr Gly Ser Thr Gly Ser Thr Tyr Tyr Ala Asn
50 55 60

Trp Ala Lys Gly Arg Phe Thr Ile Ser Lys Asp Leu Ser Lys Thr Thr
65 70 75 80

Leu Tyr Leu Gln Met Asn Ser Leu Arg Ala Glu Asp Thr Ala Thr Tyr
85 90 95

Phe Cys Ala Arg Asp Asp Lys Val Glu His Gly Tyr Gly Leu Trp Gly
100 105 110

Gln Gly Thr Leu Val Thr Val Ser Ser
115 120

<210> SEQ ID NO 1188
<211> LENGTH: 123
<212> TYPE: PRT
<213> ORGANISM: Artificial Sequence
<220> FEATURE:
<223> OTHER INFORMATION: MAB-17-0200 HC VR

<400> SEQUENCE: 1188

Glu Val Gln Leu Glu Glu Ser Gly Gly Arg Leu Val Gln Pro Gly Thr
1 5 10 15

Ser Leu Arg Leu Ser Cys Ala Ala Ser Gly Phe Ser Leu Ser Ser Asn
20 25 30

Ser Ile Ser Trp Val Arg Gln Ala Pro Gly Lys Gly Leu Glu Trp Val
35 40 45

Gly Ile Ile Ser Ser Ser Gly Ser Thr Tyr Tyr Ala Ser Trp Ala Lys
50 55 60

Gly Arg Phe Thr Ile Ser Lys Asp Ala Ser Lys Thr Thr Leu Tyr Leu
65 70 75 80

Gln Met Asn Ser Leu Arg Ala Glu Asp Thr Ala Thr Tyr Phe Cys Ala
85 90 95

Lys Gly Leu Gly Arg Gly Glu Tyr Thr Ser Asn Asp Ala Phe Asp Pro
100 105 110

Trp Gly Gln Gly Thr Leu Val Thr Val Ser Ser
115 120

<210> SEQ ID NO 1189
<211> LENGTH: 122
<212> TYPE: PRT
<213> ORGANISM: Artificial Sequence
<220> FEATURE:
<223> OTHER INFORMATION: MAB-17-0201 HC VR

<400> SEQUENCE: 1189

Glu Val Gln Leu Glu Glu Ser Gly Gly Asp Leu Val Gln Pro Gly Gly
1 5 10 15

Ser Leu Arg Leu Ser Cys Ala Ala Ser Gly Phe Ser Phe Asn Gly Asn
20 25 30

Tyr Tyr Ile Cys Trp Val Arg Gln Ala Pro Gly Lys Gly Leu Glu Trp
35 40 45

```
Val Ala Cys Ile Tyr Ala Gly Ser Ser Gly Ser Thr Tyr Tyr Ala Ser
    50                  55                  60

Trp Ala Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Phe Cys Val Arg Asp Lys Pro Ala Gly Gly Ser Ser Tyr Thr Leu Trp
            100                 105                 110

Gly Gln Gly Thr Leu Val Thr Val Ser Ser
        115                 120


<210> SEQ ID NO 1190
<211> LENGTH: 122
<212> TYPE: PRT
<213> ORGANISM: Artificial Sequence
<220> FEATURE:
<223> OTHER INFORMATION: MAB-17-0212 HC VR

<400> SEQUENCE: 1190

Glu Val Gln Leu Glu Glu Ser Gly Gly Asp Leu Val Gln Pro Gly Gly
1               5                   10                  15

Ser Leu Arg Leu Ser Cys Ala Ala Ser Gly Phe Asp Phe Ser Ser Asn
            20                  25                  30

Tyr Tyr Met Cys Trp Val Arg Gln Ala Pro Gly Lys Gly Leu Glu Trp
        35                  40                  45

Val Ala Cys Ile Tyr Thr Gly Ser Ser Gly Ser Thr Tyr Tyr Ala Ser
    50                  55                  60

Trp Ala Lys Gly Arg Phe Thr Ile Ser Lys Asp Thr Ser Lys Asn Thr
65                  70                  75                  80

Leu Tyr Leu Gln Met Asn Ser Leu Arg Ala Glu Asp Thr Ala Val Tyr
                85                  90                  95

Phe Cys Ala Arg Gly Ala Gly Ser Tyr Gly Gly Ala Val Arg Leu Trp
            100                 105                 110

Gly Gln Gly Thr Leu Val Thr Val Ser Ser
        115                 120


<210> SEQ ID NO 1191
<211> LENGTH: 121
<212> TYPE: PRT
<213> ORGANISM: Artificial Sequence
<220> FEATURE:
<223> OTHER INFORMATION: MAB-17-0218 HC VR

<400> SEQUENCE: 1191

Glu Val Gln Leu Glu Glu Ser Gly Gly Asp Leu Val Gln Pro Gly Gly
1               5                   10                  15

Ser Leu Arg Leu Ser Cys Ala Ala Ser Gly Phe Ser Phe Ser Arg Ser
            20                  25                  30

Tyr Tyr Met Cys Trp Val Arg Gln Ala Pro Gly Lys Gly Leu Glu Trp
        35                  40                  45

Val Ala Cys Ile Tyr Ala Gly Ser Ser Asp Ser Thr Tyr Tyr Ala Ser
    50                  55                  60

Trp Ala Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Phe Cys Ala Arg Gly Gly Gly Ile Ile Tyr Thr Gln Asn Leu Trp Gly
```

```
            100                 105                 110

Gln Gly Thr Leu Val Thr Val Ser Ser
        115                 120


<210> SEQ ID NO 1192
<211> LENGTH: 121
<212> TYPE: PRT
<213> ORGANISM: Artificial Sequence
<220> FEATURE:
<223> OTHER INFORMATION: MAB-17-0223 HC VR

<400> SEQUENCE: 1192

Glu Val Gln Leu Glu Glu Ser Gly Gly Asp Leu Val Gln Pro Gly Gly
1               5                   10                  15

Ser Leu Arg Leu Ser Cys Ala Ala Ser Gly Phe Ser Phe Ser Ser Ser
            20                  25                  30

Tyr Tyr Met Cys Trp Val Arg Gln Ala Pro Gly Lys Gly Leu Glu Trp
        35                  40                  45

Val Ala Cys Ile Tyr Ala Gly Ser Ser Gly Ser Thr Tyr Tyr Ala Ser
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Phe Cys Ala Arg Gly Ala Gly Ser Asn Gly Asp Phe Asn Leu Trp Gly
            100                 105                 110

Gln Gly Thr Leu Val Thr Val Ser Ser
        115                 120


<210> SEQ ID NO 1193
<211> LENGTH: 120
<212> TYPE: PRT
<213> ORGANISM: Artificial Sequence
<220> FEATURE:
<223> OTHER INFORMATION: MAB-17-0225 HC VR

<400> SEQUENCE: 1193

Glu Val Gln Leu Glu Glu Ser Gly Gly Asp Leu Val Gln Pro Gly Gly
1               5                   10                  15

Ser Leu Arg Leu Ser Cys Ala Ala Ser Gly Phe Ser Phe Ser Ser Ser
            20                  25                  30

Tyr Tyr Met Cys Trp Val Arg Gln Ala Pro Gly Lys Gly Leu Glu Trp
        35                  40                  45

Val Ala Cys Val Tyr Ala Gly Ser Ser Gly Ser Thr Tyr Tyr Ala Ser
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Phe Cys Ala Arg Asp Arg Gly Gly Thr Asp Ile Ser Leu Trp Gly Gln
            100                 105                 110

Gly Thr Leu Val Thr Val Ser Ser
        115                 120


<210> SEQ ID NO 1194
<211> LENGTH: 111
<212> TYPE: PRT
<213> ORGANISM: Artificial Sequence
<220> FEATURE:
```

<223> OTHER INFORMATION: MAB-17-0119 LC VR

<400> SEQUENCE: 1194

Asp Ile Val Met Thr Gln Ser Pro Ser Ser Leu Ser Ala Ser Val Gly
1 5 10 15

Asp Arg Val Thr Ile Thr Cys Gln Ser Ser Pro Ser Val Tyr Asn Asn
20 25 30

Asn Arg Leu Ser Trp Phe Gln Gln Lys Pro Gly Gln Ala Pro Lys Leu
35 40 45

Leu Ile Tyr Tyr Ala Ser Thr Leu Ala Ser Gly Val Pro Ser Arg Phe
50 55 60

Ser Gly Ser Gly Ser Gly Thr Asp Phe Thr Leu Thr Ile Ser Ser Leu
65 70 75 80

Gln Pro Glu Asp Phe Ala Thr Tyr Tyr Cys Ala Gly Gly Tyr Ser Ser
85 90 95

Ile Ser Asp Asn Gly Phe Gly Gln Gly Thr Lys Val Val Ile Lys
100 105 110

<210> SEQ ID NO 1195
<211> LENGTH: 111
<212> TYPE: PRT
<213> ORGANISM: Artificial Sequence
<220> FEATURE:
<223> OTHER INFORMATION: MAB-17-0127 LC VR

<400> SEQUENCE: 1195

Asp Ile Gln Met Thr Gln Ser Pro Ser Ser Leu Ser Ala Ser Val Gly
1 5 10 15

Asp Arg Val Thr Ile Thr Cys Arg Ala Ser Glu Asp Ile Glu Arg Phe
20 25 30

Leu Ala Trp Tyr Gln Gln Lys Pro Gly Gln Ala Pro Lys Leu Leu Ile
35 40 45

Tyr Lys Ala Ser Thr Leu Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Cys Thr Leu Tyr Gly Val Asn
85 90 95

Phe Val Pro Asn Ala Phe Gly Gly Gly Thr Lys Val Val Ile Lys
100 105 110

<210> SEQ ID NO 1196
<211> LENGTH: 111
<212> TYPE: PRT
<213> ORGANISM: Artificial Sequence
<220> FEATURE:
<223> OTHER INFORMATION: MAB-17-0193 LC VR

<400> SEQUENCE: 1196

Asp Ile Gln Met Thr Gln Ser Pro Ser Ser Leu Ser Ala Ser Val Gly
1 5 10 15

Asp Arg Val Thr Ile Thr Cys Gln Ala Ser Glu Ser Ile Asp Asn Trp
20 25 30

Leu Ala Trp Tyr Gln Gln Lys Pro Gly Gln Ala Pro Lys Leu Leu Ile
35 40 45

Tyr Ser Ala Ser Asn Leu Ala Ser Gly Val Pro Ser Arg Phe Ser Gly
50 55 60

Ser Gly Ser Gly Thr Asp Phe Thr Leu Thr Ile Ser Ser Leu Gln Pro

```
65                  70                  75                  80

Glu Asp Phe Ala Thr Tyr Tyr Cys Gln Ser Thr Phe Tyr Gly Val Asn
                85                  90                  95

Pro Val Pro Asn Ala Phe Gly Gln Gly Thr Lys Val Val Ile Lys
            100                 105                 110


<210> SEQ ID NO 1197
<211> LENGTH: 110
<212> TYPE: PRT
<213> ORGANISM: Artificial Sequence
<220> FEATURE:
<223> OTHER INFORMATION: MAB-17-0200 LC VR

<400> SEQUENCE: 1197

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Thr Ile Tyr Ser Tyr
            20                  25                  30

Leu Asn Trp Tyr Gln Gln Lys Pro Gly Gln Ala Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Gly Arg Asn
                85                  90                  95

Val Glu Asn Thr Phe Gly Gln Gly Thr Lys Val Val Ile Lys
            100                 105                 110


<210> SEQ ID NO 1198
<211> LENGTH: 111
<212> TYPE: PRT
<213> ORGANISM: Artificial Sequence
<220> FEATURE:
<223> OTHER INFORMATION: MAB-17-0201 LC VR

<400> SEQUENCE: 1198

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Glu Ser Tyr
            20                  25                  30

Leu Ala Trp Tyr Gln Gln Lys Pro Gly Gln Ala Pro Lys Leu Leu Ile
        35                  40                  45

Tyr Gln Ala Ser Lys Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Thr Leu Tyr Gly Val Asn
                85                  90                  95

Phe Val Pro Asn Val Phe Gly Gly Gly Thr Lys Val Val Ile Lys
            100                 105                 110


<210> SEQ ID NO 1199
<211> LENGTH: 111
<212> TYPE: PRT
<213> ORGANISM: Artificial Sequence
<220> FEATURE:
<223> OTHER INFORMATION: MAB-17-0212 LC VR

<400> SEQUENCE: 1199
```

Asp Ile Gln Met Thr Gln Ser Pro Ser Ser Leu Ser Ala Ser Val Gly
1 5 10 15

Asp Arg Val Thr Ile Thr Cys Gln Ala Thr Glu Asp Ile Glu Ser Phe
20 25 30

Leu Ala Trp Tyr Gln Gln Lys Pro Gly Gln Ala Pro Lys Leu Leu Ile
35 40 45

Tyr Arg Ala Ser Thr Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Cys Thr Val Tyr Gly Val Asn
85 90 95

Phe Val Ala Asn Ala Phe Gly Gly Gly Thr Lys Val Val Ile Lys
100 105 110

<210> SEQ ID NO 1200
<211> LENGTH: 111
<212> TYPE: PRT
<213> ORGANISM: Artificial Sequence
<220> FEATURE:
<223> OTHER INFORMATION: MAB-17-0218 LC VR

<400> SEQUENCE: 1200

Asp Ile Gln Met Thr Gln Ser Pro Ser Ser Leu Ser Ala Ser Val Gly
1 5 10 15

Asp Arg Val Thr Ile Thr Cys Gln Ala Ser Glu Asp Ile Glu Ser Tyr
20 25 30

Leu Ala Trp Tyr Gln Gln Lys Pro Gly Gln Ala Pro Lys Leu Leu Ile
35 40 45

Tyr Ser Ala Ser Thr Leu Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Cys Ile Leu Tyr Gly Val Asn
85 90 95

Phe Val Pro Asn Thr Phe Gly Gly Gly Thr Lys Val Val Ile Lys
100 105 110

<210> SEQ ID NO 1201
<211> LENGTH: 111
<212> TYPE: PRT
<213> ORGANISM: Artificial Sequence
<220> FEATURE:
<223> OTHER INFORMATION: MAB-17-0223 LC VR

<400> SEQUENCE: 1201

Asp Ile Gln Met Thr Gln Ser Pro Ser Ser Leu Ser Ala Ser Val Gly
1 5 10 15

Asp Arg Val Thr Ile Thr Cys Gln Ala Ser Glu Asp Ile Glu Ser Tyr
20 25 30

Leu Ala Trp Tyr Gln Gln Lys Pro Gly Gln Ala Pro Lys Leu Leu Ile
35 40 45

Tyr Arg Ala Ser Thr Leu Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Cys Thr Ile Tyr Gly Val Asn

```
                85                  90                  95

Phe Val Pro Asn Ala Phe Gly Gly Gly Thr Lys Val Val Ile Lys
            100                 105                 110


<210> SEQ ID NO 1202
<211> LENGTH: 111
<212> TYPE: PRT
<213> ORGANISM: Artificial Sequence
<220> FEATURE:
<223> OTHER INFORMATION: MAB-17-0225 LC VR

<400> SEQUENCE: 1202

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Glu Ser Phe
            20                  25                  30

Leu Ala Trp Tyr Gln Gln Lys Pro Gly Gln Ala Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Cys Thr Ile Tyr Gly Val Asn
                85                  90                  95

Phe Val Pro Asn Ala Phe Gly Gly Gly Thr Lys Val Val Ile Lys
            100                 105                 110


<210> SEQ ID NO 1203
<211> LENGTH: 111
<212> TYPE: PRT
<213> ORGANISM: Artificial Sequence
<220> FEATURE:
<223> OTHER INFORMATION: MAB-17-0545 LC VR

<400> SEQUENCE: 1203

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Glu Ser Tyr
            20                  25                  30

Leu Ala Trp Tyr Gln Gln Lys Pro Gly Gln Ala Pro Lys Leu Leu Ile
        35                  40                  45

Tyr Gln Ala Ser Lys Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Thr Leu Tyr Gly Val Asn
                85                  90                  95

Phe Val Pro Asn Val Phe Gly Gly Gly Thr Lys Val Val Ile Lys
            100                 105                 110


<210> SEQ ID NO 1204
<211> LENGTH: 111
<212> TYPE: PRT
<213> ORGANISM: Artificial Sequence
<220> FEATURE:
<223> OTHER INFORMATION: MAB-17-0547 LC VR

<400> SEQUENCE: 1204

Asp Ile Gln Met Thr Gln Ser Pro Ser Ser Leu Ser Ala Ser Val Gly
1               5                   10                  15
```

-continued

```
Asp Arg Val Thr Ile Thr Cys Gln Ala Ser Glu Asp Ile Glu Ser Tyr
            20                  25                  30

Leu Ala Trp Tyr Gln Gln Lys Pro Gly Gln Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Thr Ile Tyr Gly Val Asn
                85                  90                  95

Phe Val Pro Asn Ala Phe Gly Gly Gly Thr Lys Val Val Ile Lys
            100                 105                 110


<210> SEQ ID NO 1205
<211> LENGTH: 13
<212> TYPE: PRT
<213> ORGANISM: Artificial Sequence
<220> FEATURE:
<223> OTHER INFORMATION: MAB-17-0545 CDR H3

<400> SEQUENCE: 1205

Gln Ser Thr Leu Tyr Gly Val Asn Phe Val Pro Asn Val
1               5                   10


<210> SEQ ID NO 1206
<211> LENGTH: 13
<212> TYPE: PRT
<213> ORGANISM: Artificial Sequence
<220> FEATURE:
<223> OTHER INFORMATION: MAB-17-0547 CDR H3

<400> SEQUENCE: 1206

Gln Ser Thr Ile Tyr Gly Val Asn Phe Val Pro Asn Ala
1               5                   10
```